US012559738B2

(12) United States Patent
Tang et al.

(10) Patent No.: US 12,559,738 B2
(45) Date of Patent: *Feb. 24, 2026

(54) GLUCOAMYLASE AND METHODS OF USE THEREOF

(71) Applicant: DANISCO US INC., Palo Alto, CA (US)

(72) Inventors: Zhongmei Tang, Shanghai (CN); Zhenghong Zhang, Shanghai (CN); Jing Ge, Shanghai (CN); Lilia Babe, Emerald Hills, CA (US); Xingxiang Xi, Shanghai (CN); Helong Hao, Shanghai (CN); Chao Huang, Shanghai (CN)

(73) Assignee: DANISCO US INC., Palo Alto, CA (US)

( * ) Notice: Subject to any disclaimer, the term of this patent is extended or adjusted under 35 U.S.C. 154(b) by 675 days.

This patent is subject to a terminal disclaimer.

(21) Appl. No.: 17/719,518

(22) Filed: Apr. 13, 2022

(65) Prior Publication Data

US 2022/0396783 A1      Dec. 15, 2022

Related U.S. Application Data

(63) Continuation of application No. PCT/US2021/027894, filed on Apr. 19, 2021.

(51) Int. Cl.
| | |
|---|---|
| *C12N 9/34* | (2006.01) |
| *A23L 2/38* | (2021.01) |
| *A23L 29/00* | (2016.01) |
| *A23L 29/30* | (2016.01) |
| *C12N 1/16* | (2006.01) |
| *C12N 15/81* | (2006.01) |
| *C12P 19/02* | (2006.01) |
| *C12P 19/14* | (2006.01) |

(52) U.S. Cl.
CPC ............ *C12N 9/2428* (2013.01); *A23L 2/382* (2013.01); *A23L 29/06* (2016.08); *A23L 29/35* (2016.08); *C12N 1/16* (2013.01); *C12N 15/81* (2013.01); *C12P 19/02* (2013.01); *C12P 19/14* (2013.01); *C12Y 302/01003* (2013.01)

(58) Field of Classification Search
CPC ........ C12N 9/2428; C12N 1/16; C12N 15/81; A23L 2/382; A23L 29/06; A23L 29/35; C12P 19/02; C12P 19/14; C12Y 302/01003; Y02E 50/10
See application file for complete search history.

(56) References Cited

U.S. PATENT DOCUMENTS

| | | | |
|---|---|---|---|
| 5,084,385 A | 1/1992 | Ashikari et al. | |
| 5,223,409 A | 6/1993 | Lander et al. | |
| 6,022,725 A | 2/2000 | Fowler et al. | |
| 11,421,212 B2 * | 8/2022 | Miller | ................. C12N 9/2428 |

| | | | |
|---|---|---|---|
| 2011/0020899 A1 | 1/2011 | Aehle et al. | |
| 2013/0323798 A1 | 12/2013 | Ge et al. | |
| 2022/0396783 A1 | 12/2022 | Tang | |
| 2023/0340444 A1 * | 10/2023 | Tang | ...................... A23L 29/06 |

FOREIGN PATENT DOCUMENTS

| | | | |
|---|---|---|---|
| RU | 2394101 C2 | 7/2010 | |
| RU | 2439153 C2 | 1/2012 | |
| WO | 199117243 A1 | 11/1991 | |
| WO | 199206204 A1 | 4/1992 | |
| WO | 1992012645 A1 | 8/1992 | |
| WO | 199517413 A1 | 6/1995 | |
| WO | 199522625 A1 | 8/1995 | |
| WO | 1997016076 A1 | 5/1997 | |
| WO | 2007044968 A2 | 4/2007 | |
| WO | 2012019169 A1 | 2/2012 | |
| WO | 2013169645 A1 | 11/2013 | |
| WO | 2014099415 A1 | 6/2014 | |
| WO | 2016138315 A1 | 9/2016 | |
| WO | 2017112635 A1 | 6/2017 | |
| WO | 2018027131 A1 | 2/2018 | |
| WO | 2019173424 A1 | 9/2019 | |
| WO | 2019191263 A1 | 10/2019 | |
| WO | PCT/CN2020/085393 | * 12/2021 | ........... C12N 9/2428 |

OTHER PUBLICATIONS

Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
GenPept: Glucoamylase, intracellular sporulation-specific [Apophysomyces ossiformis]; GenBank: KAF7727643.1, Oct. 2, 2020, 2 pages.
Whisstock, J.C. et al., Prediction of protein function from protein sequence and structure. Quarterly Reviews of Biophysics 36, 3 2003, p. 307-340.
Witkowski, A et al., Conversion of a B-Ketoacyl Synthase to a Malonyl Decarboxylase by Replacement of the Active-Site Cysteine with Glutamine Biochemistry, 1999, 38, 11643-11650.
Seffernick, J. L. et al., Melamine Deaminase and Atrazine Chlorohydrolase: 98 Percent Identical but Functionally Different. Journal of Bacteriology, 2001, v.183, No. 8, p. 2405-2410.
Broun et al., Catalytic Plasticity of Fatty Acid Modification Enzymes Underlying Chemical Diversity of Plant Lipids. SCIENCE, 1998, v.282, p. 1315-1317.

(Continued)

*Primary Examiner* — Ganapathirama Raghu

(57) ABSTRACT

Described are a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

7 Claims, 20 Drawing Sheets

Specification includes a Sequence Listing.

(56) References Cited

OTHER PUBLICATIONS

Wishart et al., A single mutation converts a novel phospholyrosine binding domain into a dual-specificity phophatase, J.Biol. Chem., 1995, vol. 270(45): 26782-26785 (Year 1995).

Yang et al., Heterologous expression and efficient ethanol production of aglucoamylase gene in; Molecular Biology Reports: An International Journal on Molecular and Cellular Biology, Kluwer Academic Publishers, vol. 38, No. 1, Mar. 18, 2010, pp. 59-64.

Ashikari et al., High expression and efficient secretion ofglucoamylase in the yeast, Applied Microbiology and Biotechnology, Spring, Berlin, DE, vol. 30, No. 5, May 1, 1989, pp. 515-520.

Carroll et al., Comprehensive analysis of fungal diversity and enzyme activity in nuruk, a Korean fermenting starter, for acquiring useful fungi, J. of Microbiology, vol. 55, No. 5, Mar. 20, 2017, pp. 357-365.

Kumar et al., Purification and kinetics of a raw starch-hydrolyzing, thermostable, and neutral glucoamylase of the thermophilic mold thermomucor indicae-seudaticae, Biotechol. Prog. 2003, vol. 19, p. 936-944.

* cited by examiner

```
                1         10        20        30        40        50        60
                :         :         :         :         :         :         :
       AnGA     WLSNEATVARTAILNNIGADGAWVSGADSGIVVASPSTDNPDYFYTWTRDSGLVLKTLVD
       AfuGA    WLGTETTVALNGILANIGADGAYAKSAKPGIIIASPSTSEPDYYYTWTRDAALVTKVLVD
       FraGA1   YIASESPVAKAGVLANIGTEGSLSSGAYSGVVIASPSTVNPDYLYTWVRDSSLTFQALID
       FveABC11 FISKEADISIKGVLANIGADGKRAQGAAPGAVVASPSRTDPDYWYTWTRDSALTYKVLVE
       GtGA     YVGSEGPIAKAGVLANIGPNGSKASGAAAGVVVASPSKSDPDYWYTWTRDSSLVFKSLID
       PoxGA    FIHKEGERSLQGILDNLGGRGKKTPGTAAGLFIASPNTENPNYYYTWTRDSALTAKCLID
       TrGA     FISTETPIALNNLLCNVGPDGCRAFGTSAGAVIASPSTIDPDYYMWTRDSALVFKNLID
       WcoGA1   YIASESPIAKAGVLANIGADGSLSSGAYSGIVIASPSTVNPNYLYTWTRDSSLTFMELIN
       SvaGA1   WVSKQEDISFSEMLRNVNP-----EGTAKGFVAASLSTAGPDYFYTWTRDAALVSRVIAY
       BciGA1   WSPSQHSISLYAMLRNINP-----PGSAAGFISASLSTSGPDYYYSWTRDSALVAHVIVN
       BciGA2   WIKGQEDTSRSVMLGNINP-----PGSATGFISASLSTSGPDYYYHWTRDAALVAHVIVN
       BpoGA1   WLKSQIGISRYAMLRNINP-----AGSAVGFIAASLSTANPDYYYAWTRDSALTSYVIAN
       CcuGA1   WIDKQIDISRSAMLRNINP-----AGTVKGFIAASLSTSNPDYFYAWTRDAALVAHVVAN
       RstGA1   WIKRQEKISRFAMLRNINP-----PGSAAGFIAASLSTSGPDYYYSWTRDSALTSNLIAY
       MciGA5   WIDGQTSVSRYAMLRNINP-----AGAVSGFIAASMSTSGPDYFYAWTRDSALTSHVVAY
       DelGA1   WADSQHKISWKAMLANINP-----PGSATGFIAASLSTSGPDYYYAWTRDAAMVAHVIVN
       FspGA3   WVNDQLEISWPSLLKNVNP-----SGAVTGFIAASLSTNDPDYFYCWTRDAALVARVMVY
       GpeGA1   WLKGQIETSRFAMLRNINP-----AGTVKGFIAASLSTANPDYFYAWTRDAALVGHVIAN
       MciGA3   WIDGQTSVSRYAMLRNINP-----AGAVTGFIAASMSTSGPDYFYAWTRDSALTSHVVAY
       CumGA1   WVNKQLKISWSDLLQNVNP-----SGTVTGFIAASLSTSNPDYFYCWTRDAAMVARVMTY
       McoGA1   WLKSQEDISRGAMLRNINP-----PGAATGFIAASLSTSGPDYYYAWTRDSALTSHVIAH
       ParGA1   WVNTQFAISWPTLLKNVNP-----SGTVKGFIAASLSTNNPDYFYSWTRDSALVAHTMTY
       RmiGA1   WIKNQEEISRFAMLRNINP-----PGSATGFIAASLSTAGPDYYYSWTRDSALTANVIAY
       SfuGA2   WGSKQDGISFSTMLGNINP-----PGSSKGFIAASLSTAGPNYYYSWTRDSALVARAITY
       SraGA1   WAKSQKDISWKTLLTSLNP-----SGTAKGFIAASLSTSNPDYYYAWTRDSALVARTMVN
       SraGA3   WVKKQEAISWTDLKTNVNP-----EGAAKGFIAASLSTSEPDYYYAWTRDSALVARVMVN
       TinGA1   WIQEQLAISWNTMLTSVNP-----VGAVTGFIAASLSTANPDYYCWTRDAALVARVMTF
       ZmeGA1   WASAQLDISWPNLMMNVNP-----SGAVTGSIVASLSTSNPDYFYIWTRDAAMVARVMVY
       GAN00808.1 WIDGQTSVSRYAMLRNINP-----AGTVTGFIAASMSTSGPDYFYAWTRDSALTSHVVAY
       ORE14155.1 WIKKQEEISRFAMLRNINP-----PGSATGFIAASLSTAGPDYYYSWTRDSALTANVIAY
       RCH88939.1 WIKNQEEISRFAMLRNINP-----PGSATGFIAASLSTAGPDYYYSWTRDSALTANVIAY
```

FIG. 1A

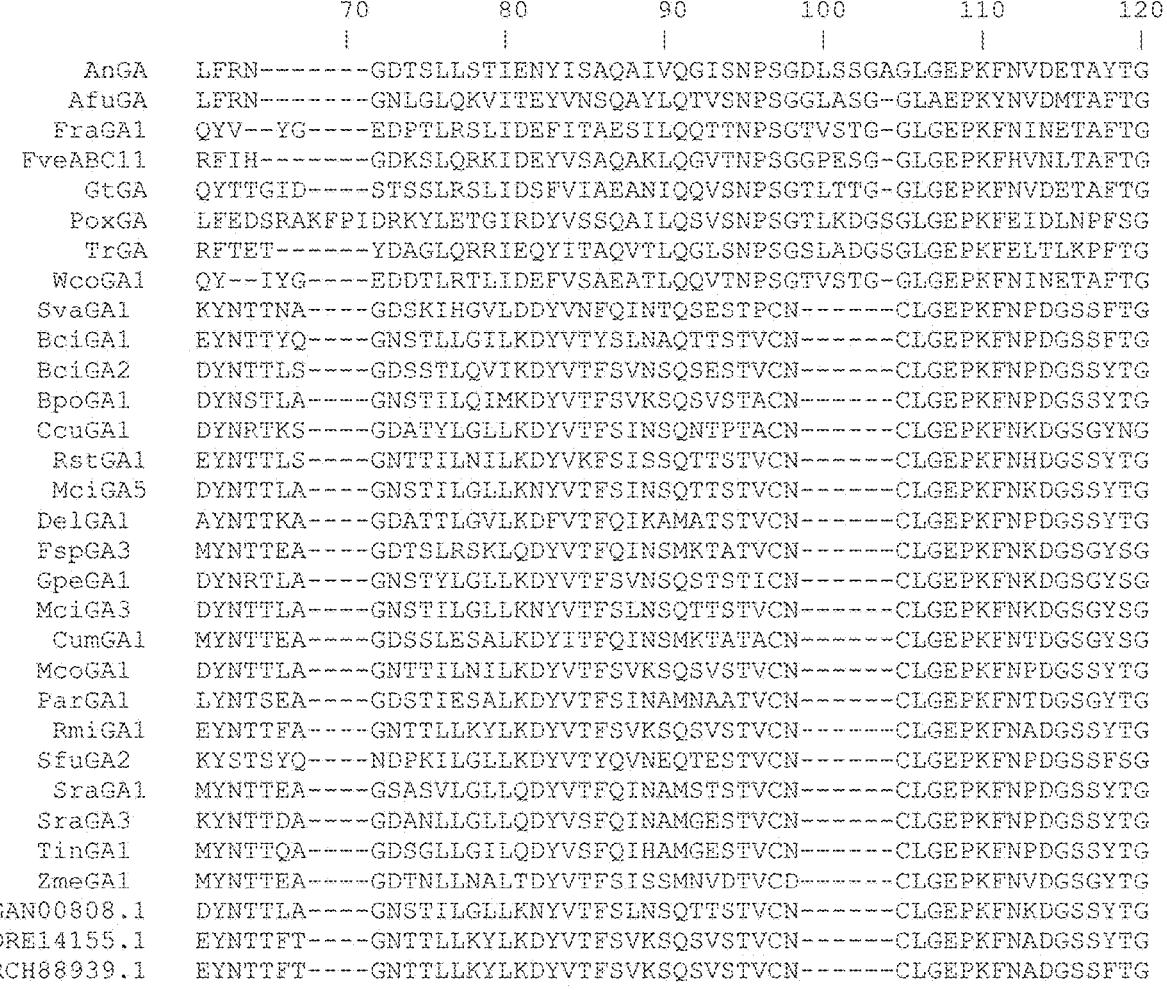

```
                    70        80        90        100       110       120
                    |         |         |         |         |         |
        AnGA   LFRN-------GDTSLLSTIENYISAQAIVQGISNPSGDLSSGAGLGEPKFNVDETAYTG
        AfuGA  LFRN-------GNLGLQKVITEYVNSQAYLQTVSNPSGGLASG-GLAEPKYNVDMTAFTG
        FraGA1 QYV--YG----EDPTLRSLIDEFITAESILQQTTNPSGTVSTG-GLGEPKFNINETAFTG
        FveABC11 RFIH-------GDKSLQRKIDEYVSAQAKLQGVTNPSGGPESG-GLGEPKFHVNLTAFTG
        GtGA   QYTTGID----STSSLRSLIDSFVIAEANIQQVSNPSGTLTTG-GLGEPKFNVDETAFTG
        PoxGA  LFEDSRAKFPIDRKYLETGIRDYVSSQAILQSVSNPSGTLKDGSGLGEPKFEIDLNPFSG
        TrGA   RFTET------YDAGLQRRIEQYITAQVTLQGLSNPSGSLADGSGLGEPKFELTLKPFTG
        WcoGA1 QY--IYG----EDDTLRTLIDEFVSAEATLQQVTNPSGTVSTG-GLGEPKFNINETAFTG
        SvaGA1 KYNTTNA----GDSKIHGVLDDYVNFQINTQSESTPCN------CLGEPKFNPDGSSFTG
        BciGA1 EYNTTYQ----GNSTLLGILKDYVTYSLNAQTTSTVCN------CLGEPKFNPDGSSFTG
        BciGA2 DYNTTLS----GDSSTLQVIKDYVTFSVNSQSESTVCN------CLGEPKFNPDGSSYTG
        BpoGA1 DYNSTLA----GNSTILQIMKDYVTFSVKSQSVSTACN------CLGEPKFNPDGSSYTG
        CcuGA1 DYNRTKS----GDATYLGLLKDYVTFSINSQNTPTACN------CLGEPKFNKDGSGYNG
        RstGA1 EYNTTLS----GNTTILNILKDYVKFSISSQTTSTVCN------CLGEPKFNHDGSSYTG
        MciGA5 DYNTTLA----GNSTILGLLKNYVTFSINSQTTSTVCN------CLGEPKFNKDGSSYTG
        DelGA1 AYNTTKA----GDATTLGVLKDFVTFQIKAMATSTVCN------CLGEPKFNPDGSSYTG
        FspGA3 MYNTTEA----GDTSLRSKLQDYVTFQINSMKTATVCN------CLGEPKFNKDGSGYSG
        GpeGA1 DYNRTLA----GNSTYLGLLKDYVTFSVNSQSTSTICN------CLGEPKFNKDGSGYSG
        MciGA3 DYNTTLA----GNSTILGLLKNYVTFSLNSQTTSTVCN------CLGEPKFNKDGSGYSG
        CumGA1 MYNTTEA----GDSSLESALKDYITFQINSMKTATACN------CLGEPKFNTDGSGYSG
        McoGA1 DYNTTLA----GNTTILNILKDYVTFSVKSQSVSTVCN------CLGEPKFNPDGSSYTG
        ParGA1 LYNTSEA----GDSTIESALKDYVTFSINAMNAATVCN------CLGEPKFNTDGSGYTG
        RmiGA1 EYNTTFA----GNTLLLKYLKDYVTFSVKSQSVSTVCN------CLGEPKFNADGSSYTG
        SfuGA2 KYSTSYQ----NDPKILGLLKDYVTYQVNEQTESTVCN------CLGEPKFNPDGSSFSG
        SraGA1 MYNTTEA----GSASVLGLLQDYVTFQINAMSTSTVCN------CLGEPKFNPDGSSYTG
        SraGA3 KYNTTDA----GDANLLGLLQDYVSFQINAMGESTVCN------CLGEPKFNPDGSSYTG
        TinGA1 MYNTTQA----GDSGLLGILQDYVSFQIHAMGESTVCN------CLGEPKFNPDGSSYTG
        ZmeGA1 MYNTTEA----GDTNLLNALTDYVTFSISSMNVDTVCD------CLGEPKFNVDGSGYTG
     GAN00808.1 DYNTTLA----GNSTILGLLKNYVTFSLNSQTTSTVCN------CLGEPKFNKDGSSYTG
     ORE14155.1 EYNTTFT----GNTLLLKYLKDYVTFSVKSQSVSTVCN------CLGEPKFNADGSSYTG
     RCH88939.1 EYNTTFT----GNTLLLKYLKDYVTFSVKSQSVSTVCN------CLGEPKFNADGSSFTG
```

FIG. 1B

```
               130        140        150        160        170        180
                |          |          |          |          |          |
      AnGA    SWGRPQRDGPALRATAMIGFGQWLLDN--GYTSTATDIVWPLVRNDLSYVAQYWNQTGYD
      AfuGA   AWGRPQRDGPALRATALIDFGNWLIDN--GYSSYAVNNIWPIVRNDLSYVSQYWSQSGFD
      FraGA1  PWGRPQRDGPALRSTAIITYATYLWNS--GNTSYVSDSLWPIIELDLNYIATYWNFSTFD
      FveABC11 SWGRPQRDGPPLRATALTLYANWLVSH--GDRSKAVNKVWPVIEKDLAYTVKFWNRTGYD
      GtGA    AWGRPQRDGPALRATALITYGNWLLSN--GNTTWVTSTLWPIIQNDLNYVVQYWNQTTFD
      PoxGA   AWGRPQRDGPALRATAMITYANYLISH--GQKSDVSQVMWPIIANDLAYVGQYWNNTGFD
      TrGA    NWGRPQRDGPALRAIALIGYSKWLINN--NYQSTVSNVIWPIVRNDLNYVAQYWNQTGFD
      WcoGA1  PWGRPQRDGPALRATAIMAYATYLYEN--GNTSYVTDTLWPIIELDLGYVAEYWNESTFD
      SvaGA1  PWGRPQNDGPAERASSFMLIADSFLSQ-TKNASYFTNTLKPAIYKDLDYVVDTWSNPCFD
      BciGA1  AWGRPQNDGPAERAVSFIYFADSYLTQ-TSDSSYVTGTLAPAIYKDLDYVVSVWSNGCFD
      BciGA2  AWGRPQNDGPAERATTFIFFADTYLAQ-GGDSSYVTGTLAPAIYADLDYVVNNWSTGCYD
      BpoGA1  AWGRPQNDGPAERATTFILFADSYLKQ-TGDASYVTGTLKPAIFKDLDYVVNTWTNGCFD
      CcuGA1  PWGRPQNDGPAERADTFVLIADSILTQ-TKDVSYVTGTLRPAIYTDLDYVVRTWSNGCFD
      RstGA1  AWGRPQNDGPAERANTFILFADSYLDQ-TKDASYVTGTLKPAIFKDLDYVVNVWSNGCYD
      MciGA5  AWGRPQNDGPASRADTFILIADSILKQ-TGDATYVTGTLAPAIYKDLDYVVSTWSNGCFD
      DelGA1  PWGRPQNDGPAERATTFILFADSYLSQ-TGDAAYVT-TLKRAIFTDLDYVVTTWQDNCFD
      FspGA3  AWGRPQNDGPADRAITLILFADSFIAQ-GGDVSYITNTLKPAIYTNLDYVVNTWSNVCFD
      GpeGA1  AWGRPQNDGPAERADTFILIADSILKQ-TGDATYVTGTLRPAIYKDLDYVVNVWSNGCFD
      MciGA3  AWGRPQNDGPASRADTFILIADSILKQ-TGDATYVTGTLAPAIYKDLDYVVSTWSNGCFD
      CumGA1  PWGRPQNDGPAERATTMILFADSYLAQ-GGDTSYVTNTLKPAIYTNLDYVVGTWSNNCFD
      McoGA1  AWGRPQNDGPAERASTFILFGDSYLKQ-TGDATYVTGTLAPAIYKDLDYVVNTWSNGCFD
      ParGA1  AWGRPQNDGPASRATTMILFADSFLAQ-GGDVSYVINTLKPAIYKDLDYVVSTWSNTCYD
      RmiGA1  PWGRPQNDGPAERAVTFMLIADSYLTQ-TKDASYVTGTLKPAIFKDLDYVVSVWSNGCYD
      SfuGA2  PWGRPQNDGPAERASTMILFAKSYYAQ-TNDVGYVSNTLKPAIYKDLDYIVNVWGNNCFD
      SraGA1  AWGRPQNDGPAERASTFILFADSYIAQ-GGQLSYVTGTLAPAIYKDLNYVVSTWSNNCFD
      SraGA3  AWGRPQNDGPAERASTFILLADSMIAQKSANGSYVSDTLAPAIYKDLAYVASTWENACYD
      TinGA1  AWGRPQNDGPAERASTFIKIADSYLTQ-TGDVSYVTNTLKPAIYEDLDYIVNVWQNTCFD
      ZmeGA1  AWGRPQNDGPAERASTMILIADSYIAQ-GGDVSYVTDTLKPAIYTDLDYVVDTWSNVCFD
  GAN00808.1  AWGRPQNDGPASRADTFILIADSILKQ-TGDATYVTGTLAPAIYKDLDYVVSTWSNGCFD
  ORE14155.1  PWGRPQNDGPAERAVTFMLIADSYLTQ-TKDASYVTGTLKPAIFKDLDYVVSVWSNGCYD
  RCH88939.1  PWGRPQNDGPAERAVTFMLIADSYLTQ-TKDASYVTGTLKPAIFKDLDYVVSVWSNGCYD
```

FIG. 1C

```
                     190        200        210        220        230        240
                      |          |          |          |          |          |
       AnGA   LWEEVNGSSFFTIAVQHRALVEGSAFATAVGSSC--SWCDSQAPEILCYLQSFW---TGSF
      AfuGA   LWEEVNSMSFFTVAVQHRALVEGSTFAKRVGASC--SWCDSQAPQILCYMQSFW---TGSY
      FraGA1  LWEEIDSSSFWTTAVQHRALRQGITFANLIGQTSPVSNYETQAGDILCFLQTYWNPTGNY
      FveABC11 LWEEVNGSSFFTLSASHRALVEGAALAKKLGKSC--SDCATNAPRVLCFMQSFW---TGSY
       GtGA   LWEEVNSSSFFTTAVQHRALREGAAFATKIGQTSSVSSYTTQAANLLCFLQSYWNPTSGY
      PoxGA   LWEEVDGSSFFTIAVQHRALVEGSQLAKKLGKSC--DACDSQPPQILCFLQSFW---NGKY
       TrGA   LWEEVNGSSFFTVANQHRALVEGATLAATLGQSG--SAYSSVAPQVLCFLQRFWVSSGGY
      WcoGA1  LWEEIDSSSFFTTAVQHRALRAGVTFANLIGETSDVSNYQENADDLLCFLQSYWNPTGSY
      SvaGA1  LWEEVNGIHFYTLMVMRRSLLDGANFATRNGDNSKASTYSGVAAKIQARLNSFWDAGKNY
      BciGA1  LWEEVNGIHFYTLMFMRRGLLDGANFASRNGDSTRASTYTSTAASIKTKIDGFWVSSGNY
      BciGA2  LWEEVNGIHFYTLMVMRRGLIDGASFASRNGDSTRSSSYTSTAKSIATKIDSFWSASNNY
      BpoGA1  LWEEVNGVHFYTLMVMRKGLIRGANFATRNGDSTRASTYTNTAASIKTKMDSFWSSGNNY
      CcuGA1  LWEEVNGVHFYTLMVMRRALLVGANFASRNGDSARASNYNNAANSIKSKIDSFWSSNNNY
      RstGA1  LWEEVNGVHFYTLMVMRKGLLLGADFAKRNGDSTRASTYTNTASTIATKISSFWVSSSNW
      MciGA5  LWEEVNGVHFYTLMVMRRGLIKGANFASRNGDNTRANTYTNTAASIKTKIDSFWNSNGNY
      DelGA1  LWEEVNGLHMYTLAVMRRSLVDGASFAARNGDNTRASTYTNTAKSIETKLASFYNSSSNY
      FspGA3  LWEEVNGVHIYTLSVMRKGLLEGADFASRNGDSTRANTYRSTASSIKTRLESFWSSSNNY
      GpeGA1  LWEEVNGVHFYTLMVMRRSLILGANFASRNGDSTRASTYTNTANSIKTKIDTFWSSSNNY
      MciGA3  LWEEVNGVHFYTLMVMRRGLVKGANFASRNGDSTRATTYTNTAASIKTKIDSFWNSNGQY
      CumGA1  LWEEVNGVHIFTLAVMRKSLLDGADFAARNGDTSRVSGYQSTASSIKTKLESFWSSSNNY
      McoGA1  LWEEVNGVHFYTLMSMRRGLLDGANFAKRNGDTTRATTYTNTAASIATKIDTFWVSSGNY
      ParGA1  LWEEVNGVHIYTLSVMRRALIDGANFAQRNGDTSRVSGYTSTATTIKTRLESFWSDSNNY
      RmiGA1  LWEEVNGVHFYTLMVMRKGLILGADFAARNGDSSRASTYKNTASTMESKISSFWSDSNNY
      SfuGA2  LWEEVNGVHFYTLMMMRHGLVQGSIFANTLGDSTRANTYKTAAQNIKNRIDTFWESGSNY
      SraGA1  LWEEVNGRHMFTLAVMRRALLDGVNFASRIGDTTYSSTWSSTASSIQSTLSGYYLSSGNY
      SraGA3  LWEEVNGKHMYTLSVMRRALLDGADFASRQGQTANVTSWKSTADKIKSSLEGFFSSDNGY
      TinGA1  LWEEVYGMHMYTLAVMRRGLLDGADFATRNGDTDKASTYTSTATSIQTRLATFWSDSNGY
      ZmeGA1  LWEEVNGIHMYTLSVMRKALLDGANFATRNGDTSRVSGYESTASSIKTRLESFWSSSNNY
   GAN00808.1 LWEEVNGVHFYTLMVMPRGLVKGASFASRNGDSTRANTYTNTAASIKTKIDSFWNSNGQY
   ORE14155.1 LWEEVNGVHFYTLMVMRKGLILGADFAARNGDSSRASTYKKTASTMESKISSFWSDSNNY
   RCH88939.1 LWEEVNGVHFYTLMVMRKGLILGADFAARNGDSSRASTYKKTASTMESKISSFWSDSNNY
```

FIG. 1D

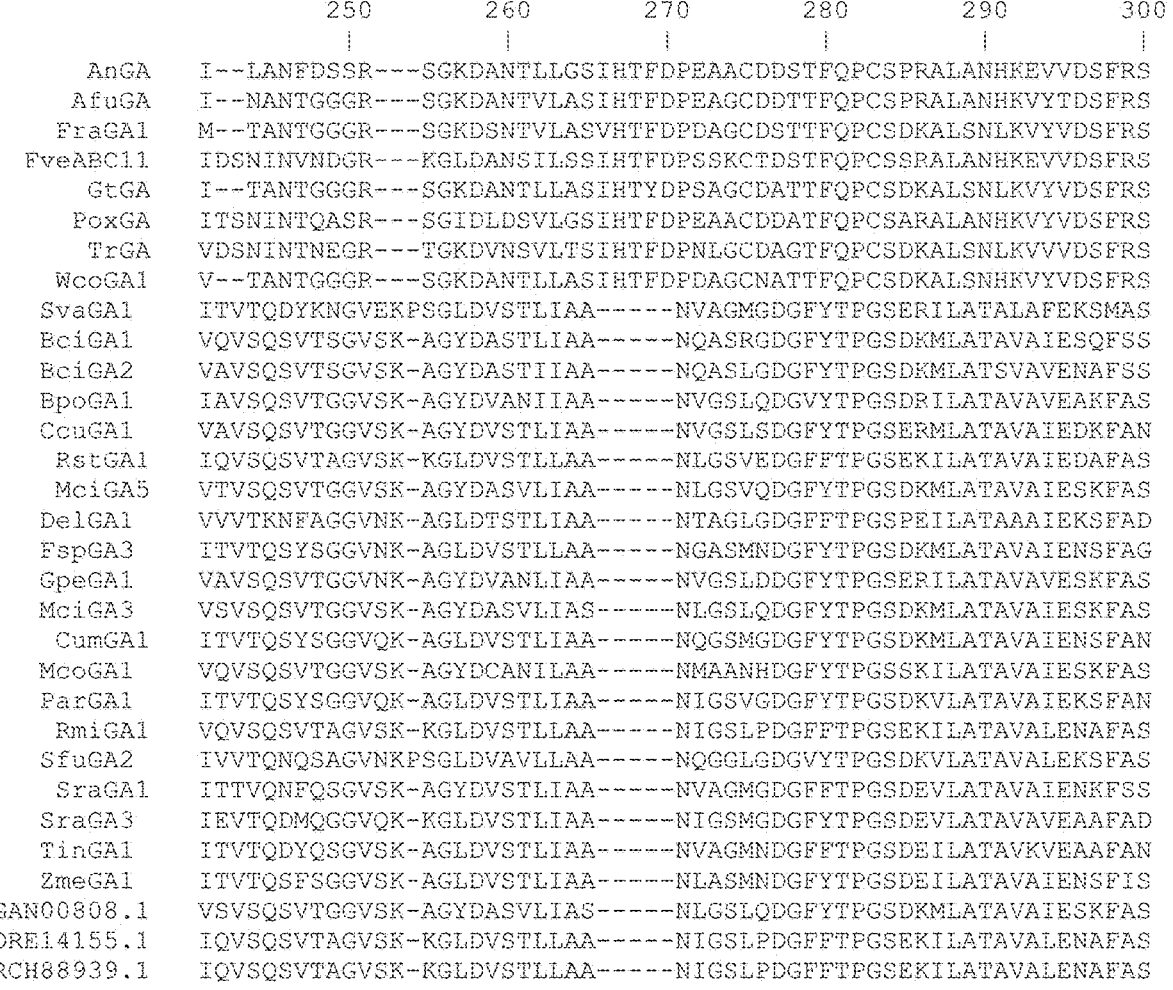

```
                  250       260       270       280       290       300
                   |         |         |         |         |         |
      AnGA  I--LANFDSSR---SGKDANTLLGSIHTFDPEAACDDSTFQPCSPRALANHKEVVDSFRS
     AfuGA  I--NANTGGGR---SGKDANTVLASIHTFDPEAGCDDTTFQPCSPRALANHKVYTDSFRS
     FraGA1 M--TANTGGGR---SGKDSNTVLASVHTFDPDAGCDSTTFQPCSDKALSNLKVYVDSFRS
   FveABC11 IDSNINVNDGR---KGLDANSILSSIHTFDPSSKCTDSTFQPCSSRALANHKEVVDSFRS
      GtGA  I--TANTGGGR---SGKDANTLLASIHTYDPSAGCDATTFQPCSDKALSNLKVYVDSFRS
     PoxGA  ITSNINTQASR---SGIDLDSVLGSIHTFDPEAACDDATFQPCSARALANHKVYVDSFRS
      TrGA  VDSNINTNEGR---TGKDVNSVLTSIHTFDPNLGCDAGTFQPCSDKALSNLKVVVDSFRS
     WcoGA1 V--TANTGGGR---SGKDANTLLASIHTFDPDAGCNATTFQPCSDKALSNHKVYVDSFRS
     SvaGA1 ITVTQDYKNGVEKPSGLDVSTLIAA-----NVAGMGDGFYTPGSERILATALAFEKSMAS
     BciGA1 VQVSQSVTSGVSK-AGYDASTLIAA-----NQASRGDGFYTPGSDKMLATAVAIESQFSS
     BciGA2 VAVSQSVTSGVSK-AGYDASTIIAA-----NQASLGDGFYTPGSDKMLATSVAVENAFSS
     BpoGA1 IAVSQSVTGGVSK-AGYDVANIIAA-----NVGSLQDGVYTPGSDRILATAVAVEAKFAS
     CcuGA1 VAVSQSVTGGVSK-AGYDVSTLIAA-----NVGSLSDGFYTPGSERMLATAVAIEDKFAN
     RstGA1 IQVSQSVTAGVSK-KGLDVSTLLAA-----NLGSVEDGFFTPGSEKILATAVAIEDAFAS
     MciGA5 VTVSQSVTGGVSK-AGYDASVLIAA-----NLGSVQDGFYTPGSDKMLATAVAIESKFAS
      DelGA1 VVVTKNFAGGVNK-AGLDTSTLIAA-----NTAGLGDGFFTPGSPEILATAAAIEKSFAD
     FspGA3 ITVTQSYSGGVNK-AGLDVSTLLAA-----NGASMNDGFYTPGSDKMLATAVAIENSFAG
     GpeGA1 VAVSQSVTGGVNK-AGYDVANLIAA-----NVGSLDDGFYTPGSERILATAVAVESKFAS
     MciGA3 VSVSQSVTGGVSK-AGYDASVLIAS-----NLGSLQDGFYTPGSDKMLATAVAIESKFAS
     CumGA1 ITVTQSYSGGVQK-AGLDVSTLIAA-----NQGSMGDGFYTPGSDKMLATAVAIENSFAN
     McoGA1 VQVSQSVTGGVSK-AGYDCANILAA-----NMAANHDGFYTPGSSKILATAVAIESKFAS
     ParGA1 ITVTQSYSGGVQK-AGLDVSTLIAA-----NIGSVGDGFYTPGSDKVLATAVAIEKSFAN
     RmiGA1 VQVSQSVTAGVSK-KGLDVSTLLAA-----NIGSLPDGFFTPGSEKILATAVALENAFAS
     SfuGA2 IVVTQNQSAGVNKPSGLDVAVLLAA-----NQGGLGDGVYTPGSDKVLATAVALEKSFAS
     SraGA1 ITTVQNFQSGVSK-AGYDVSTLIAA-----NVAGMGDGFFTPGSDEVLATAVAIENKFSS
     SraGA3 IEVTQDMQGGVQK-KGLDVSTLIAA-----NIGSMGDGFYTPGSDEVLATAVAVEAAFAD
     TinGA1 ITVTQDYQSGVSK-AGLDVSTLIAA-----NVAGMNDGFFTPGSDEILATAVKVEAAFAN
     ZmeGA1 ITVTQSFSGGVSK-AGLDVSTLIAA-----NLASMNDGFYTPGSDEILATAVAIENSFIS
  GAN00808.1 VSVSQSVTGGVSK-AGYDASVLIAS-----NLGSLQDGFYTPGSDKMLATAVAIESKFAS
  ORE14155.1 IQVSQSVTAGVSK-KGLDVSTLLAA-----NIGSLPDGFFTPGSEKILATAVALENAFAS
  RCH88939.1 IQVSQSVTAGVSK-KGLDVSTLLAA-----NIGSLPDGFFTPGSEKILATAVALENAFAS
```

FIG. 1E

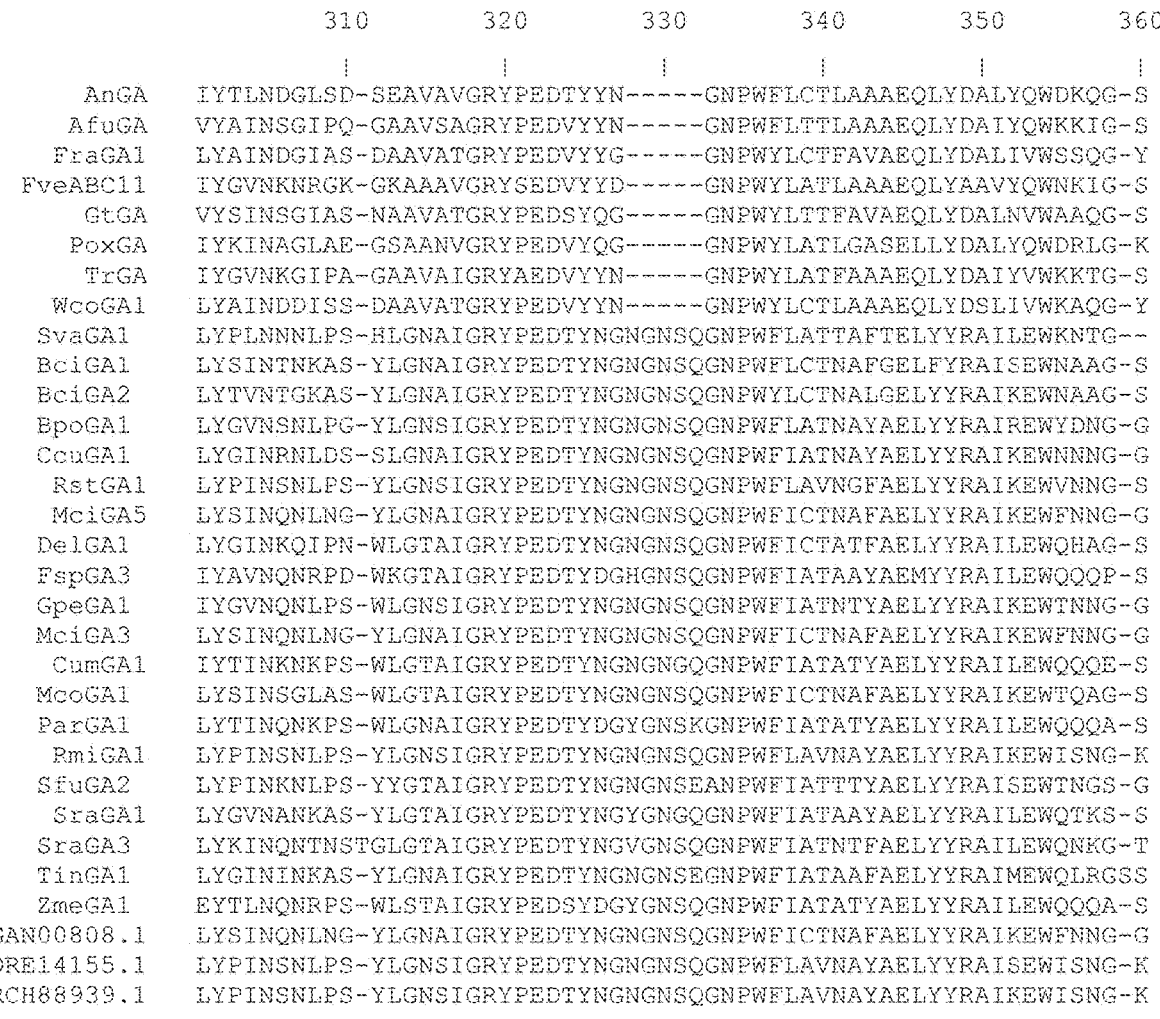

```
                    310         320         330         340         350         360
                     |           |           |           |           |           |
       AnGA    IYTLNDGLSD-SEAVAVGRYPEDTYYN-----GNPWFLCTLAAAEQLYDALYQWDKQG-S
      AfuGA    VYAINSGIPQ-GAAVSAGRYPEDVYYN-----GNPWFLTTLAAAEQLYDAIYQWKKIG-S
      FraGA1   LYAINDGIAS-DAAVATGRYPEDVYYG-----GNPWYLCTFAVAEQLYDALIVWSSQG-Y
    FveABC11   IYGVNKNRGK-GKAAAVGRYSEDVYYD-----GNPWYLATLAAAEQLYAAVYQWNKIG-S
        GtGA   VYSINSGIAS-NAAVATGRYPEDSYQG-----GNPWYLTTFAVAEQLYDALNVWAAQG-S
       PoxGA   IYKINAGLAE-GSAANVGRYPEDVYQG-----GNPWYLATLGASELLYDALYQWDRLG-K
        TrGA   IYGVNKGIPA-GAAVAIGRYAEDVYYN-----GNPWYLATFAAAEQLYDAIYVWKKTG-S
      WcoGA1   LYAINDDISS-DAAVATGRYPEDVYYN-----GNPWYLCTLAAAEQLYDSLIVWKAQG-Y
      SvaGA1   LYPLNNNLPS-HLGNAIGRYPEDTYNGNGNSQGNPWFLATTAFTELYYRAILEWKNTG--
      BciGA1   LYSINTNKAS-YLGNAIGRYPEDTYNGNGNSQGNPWFLCTNAFGELFYRAISEWNAAG-S
      BciGA2   LYTVNTGKAS-YLGNAIGRYPEDTYNGNGNSQGNPWYLCTNALGELYYRAIKEWNAAG-S
      BpoGA1   LYGVNSNLPG-YLGNSIGRYPEDTYNGNGNSQGNPWFLATNAYAELYYRAIREWYDNG-G
      CcuGA1   LYGINRNLDS-SLGNAIGRYPEDTYNGNGNSQGNPWFIATNAYAELYYRAIKEWNNNG-G
      RstGA1   LYPINSNLPS-YLGNSIGRYPEDTYNGNGNSQGNPWFLAVNGFAELYYRAIKEWVNNG-S
      MciGA5   LYSINQNLNG-YLGNAIGRYPEDTYNGNGNSQGNPWFICTNAFAELYYRAIKEWFNNG-G
      DelGA1   LYGINKQIPN-WLGTAIGRYPEDTYNGNGNSQGNPWFICTATFAELYYRAILEWQHAG-S
      FspGA3   IYAVNQNRPD-WKGTAIGRYPEDTYDGHGNSQGNPWFIATAAYAEMYYRAILEWQQQP-S
      GpeGA1   IYGVNQNLPS-WLGNSIGRYPEDTYNGNGNSQGNPWFIATNTYAELYYRAIKEWTNNG-G
      MciGA3   LYSINQNLNG-YLGNAIGRYPEDTYNGNGNSQGNPWFICTNAFAELYYRAIKEWFNNG-G
      CumGA1   IYTINKNKPS-WLGTAIGRYPEDTYNGNGNGQGNPWFIATATYAELYYRAILEWQQQE-S
      McoGA1   LYSINSGLAS-WLGTAIGRYPEDTYNGNGNSQGNPWFICTNAFAELYYRAIKEWTQAG-S
      ParGA1   LYTINQNKPS-WLGNAIGRYPEDTYDGYGNSKGNPWFIATATYAELYYRAILEWQQQA-S
      RmiGA1   LYPINSNLPS-YLGNSIGRYPEDTYNGNGNSQGNPWFLAVNAYAELYYRAIKEWISNG-K
      SfuGA2   LYPINKNLPS-YYGTAIGRYPEDTYNGNGNSEANPWFIATTTYAELYYRAISEWTNGS-G
      SraGA1   LYGVNANKAS-YLGTAIGRYPEDTYNGYGNGQGNPWFIATAAYAELYYRAILEWQTKS-S
      SraGA3   LYKINQNTNSTGLGTAIGRYPEDTYNGVGNSQGNPWFIATNTFAELYYRAILEWQNKG-T
      TinGA1   LYGININKAS-YLGNAIGRYPEDTYNGNGNSEGNPWFIATAAFAELYYRAIMEWQLRGSS
      ZmeGA1   EYTLNQNRPS-WLSTAIGRYPEDSYDGYGNSQGNPWFIATATYAELYYRAILEWQQQA-S
    GAN00808.1 LYSINQNLNG-YLGNAIGRYPEDTYNGNGNSQGNPWFICTNAFAELYYRAIKEWFNNG-G
    ORE14155.1 LYPINSNLPS-YLGNSIGRYPEDTYNGNGNSQGNPWFLAVNAYAELYYRAISEWISNG-K
    RCH88939.1 LYPINSNLPS-YLGNSIGRYPEDTYNGNGNSQGNPWFLAVNAYAELYYRAIKEWISNG-K
```

FIG. 1F

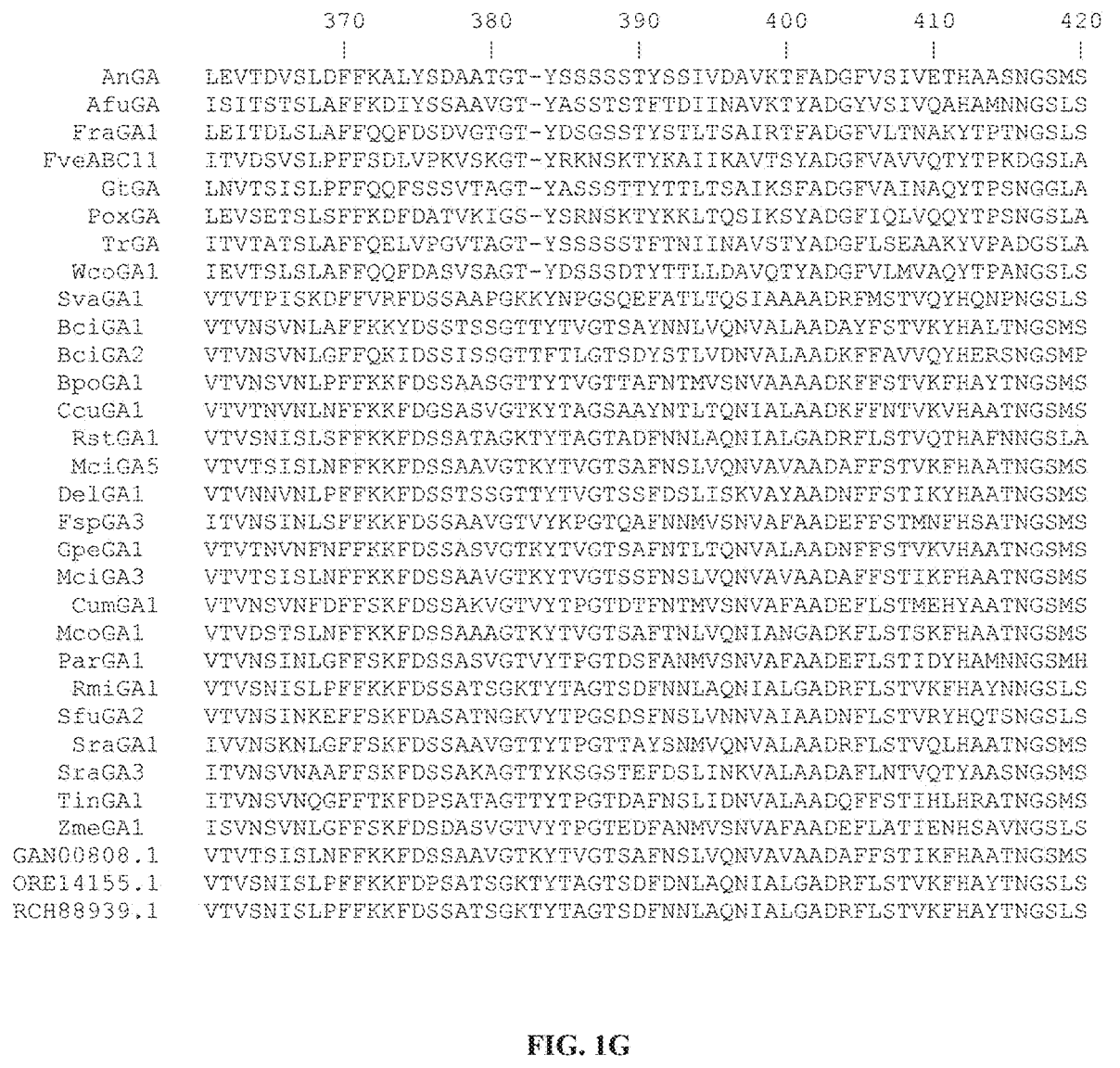

```
              370        380        390        400        410        420
               |          |          |          |          |          |
      AnGA  LEVTDVSLDFFKALYSDAATGT-YSSSSSTYSSIVDAVKTFADGFVSIVETHAASNGSMS
      AfuGA ISITSTSLAFFKDIYSSAAVGT-YASSTSTFTDIINAVKTYADGYVSIVQAHAMNNGSLS
     FraGA1 LEITDLSLAFFQQFDSDVGTGT-YDSGSSTYSTLTSAIRTFADGFVLTNAKYTPTNGSLS
    FveABC11 ITVDSVSLPFFSDLVPKVSKGT-YRKNSKTYKAIIKAVTSYADGFVAVVQTYTPKDGSLA
       GtGA  LNVTSISLPFFQQFSSSVTAGT-YASSSTTYTTLTSAIKSFADGFVAINAQYTPSNGGLA
      PoxGA  LEVSETSLSFFKDFDATVKIGS-YSRNSKTYKKLTQSIKSYADGFIQLVQQYTPSNGSLA
       TrGA  ITVTATSLAFFQELVPGVTAGT-YSSSSSTFTNIINAVSTYADGFLSEAAKYVPADGSLA
      WcoGA1 IEVTSLSLAFFQQFDASVSAGT-YDSSSDTYTTLLDAVQTYADGFVLMVAQYTPANGSLS
      SvaGA1 VTVTPISKDFFVRFDSSAAPGKKYNPGSQEFATLTQSIAAAADRFMSTVQYHQNPNGSLS
      BciGA1 VTVNSVNLAFFKKYDSSTSSGTTYTVGTSAYNNLVQNVALAADAYFSTVKYHALTNGSMS
      BciGA2 VTVNSVNLGFFQKIDSSISSGTTFTLGTSDYSTLVDNVALAADKFFAVVQYHERSNGSMP
      BpoGA1 VTVNSVNLPFFKKFDSSAASGTTYTVGTTAFNTMVSNVAAAADKFFSTVKFHAYTNGSMS
      CcuGA1 VTVTNVNLNFFKKFDGSASVGTKYTAGSAAYNTLTQNIALAADKFFNTVKVHAATNGSMS
      RstGA1 VTVSNISLSFFKKFDSSATAGKTYTAGTADFNNLAQNIALGADRFLSTVQTHAFNNGSLA
      MciGA5 VTVTSISLNFFKKFDSSAAVGTKYTVGTSAFNSLVQNVAVAADAFFSTVKFHAATNGSMS
      DelGA1 VTVNNVNLPFFKKFDSSTSSGTTYTVGTSSFDSLISKVAYAADNFFSTIKYHAATNGSMS
      FspGA3 ITVNSINLSFFKKFDSSAAVGTVYKPGTQAFNNMVSNVAFAADEFFSTMNFHSATNGSMS
      GpeGA1 VTVTNVNFNFFKKFDSSASVGTKYTVGTSAFNTLTQNVALAADNFFSTVKVHAATNGSMS
      MciGA3 VTVTSISLNFFKKFDSSAAVGTKYTVGTSSFNSLVQNVAVAADAFFSTIKFHAATNGSMS
      CumGA1 VTVNSVNFDFFSKFDSSAKVGTVYTPGTDTFNTMVSNVAFAADEFLSTMEHYAATNGSMS
      McoGA1 VTVDSTSLNFFKKFDSSAAAGTKYTVGTSAFTNLVQNIANGADKFLSTSKFHAATNGSMS
      ParGA1 VTVNSINLGFFSKFDSSASVGTVYTPGTDSFANMVSNVAFAADEFLSTIDYHAMNNGSMH
      RmiGA1 VTVSNISLPFFKKFDSSATSGKTYTAGTSDFNNLAQNIALGADRFLSTVKFHAYNNGSLS
      SfuGA2 VTVNSINKEFFSKFDASATNGKVYTPGSDSFNSLVNNVAIAADNFLSTVRYHQTSNGSLS
      SraGA1 IVVNSKNLGFFSKFDSSAAVGTTYTPGTTAYSNMVQNVALAADRFLSTVQLHAATNGSMS
      SraGA3 ITVNSVNAAFFSKFDSSAKAGTTYKSGSTEFDSLINKVALAADAFLNTVQTYAASNGSMS
      TinGA1 ITVNSVNQGFFTKFDPSATAGTTYTPGTDAFNSLIDNVALAADQFFSTIHLHRATNGSMS
      ZmeGA1 ISVNSVNLGFFSKFDSDASVGTVYTPGTEDFANMVSNVAFAADEFLATIENHSAVNGSLS
   GAN00808.1 VTVTSISLNFFKKFDSSAAVGTKYTVGTSAFNSLVQNVAVAADAFFSTIKFHAATNGSMS
   ORE14155.1 VTVSNISLPFFKKFDPSATSGKTYTAGTSDFDNLAQNIALGADRFLSTVKFHAYTNGSLS
   RCH88939.1 VTVSNISLPFFKKFDSSATSGKTYTAGTSDFNNLAQNIALGADRFLSTVKFHAYTNGSLS
```

FIG. 1G

```
            430         440         450         460         470         480
             |           |           |           |           |           |
    AnGA    EQYDKSDGEQLSARDLTWSYAALLTANNRRNSVVPASWGETSASSVPGTCAATSAIGTYS
   AfuGA    EQFDKSSGLSLSARDLTWSYAAFLTANMRRNGVVPAPWGAASANSVPSSCSMGSATGTYS
   FraGA1   EEYTSADGTPISAYDLTWSYASALTVFAAEAGTTYGSWGAAGL-TVPSTC----TSG----
  FveABC11  EQFDKSTGTPKSAVHLTWSYASFVGAAERRTGVVFPAWGESNANKVPAVCEAAPACDT--
    GtGA    EQFSRSNGAPVSAVDLTWSYASALTAFEARNNTQFAGWGAVGL-TVPTSCSSNSGGGG--
   PoxGA    EQYDPNTAAPLSANDLTWSFASFLTATQRRDAVVPPSWGAKSANKVPTTCSASPVVGTYK
    TrGA    EQFDRNSGTPLSALHLTWSYASFLTATARRAGIVPPSWANSSASTIPSTCSGASVVGSYS
   WcoGA1   EQYAKADGSPTSAYDLTWSFAAALTAFAARDGKTYGSWGAADL-S--STCSGSTDT----
   SvaGA1   EEFDRSSGYMTGARDLTWSHAAFITAAQARAG----------------------------
   BciGA1   EQYDRSSGMATGARDLTWSHAAMITALKAKSG----------------------------
   BciGA2   EQFGREDGLPTGARDLTWSHAAMISAARAKAG----------------------------
   BpoGA1   EQFGRNDGLCTGARDLTWSHASLISAALAKAG----------------------------
   CcuGA1   EQYHRDTGSMTGARDLTWSHASLITAALAKAG----------------------------
   RstGA1   EEYDRTTGVSTGARDLTWSHASLITAAYAKAG----------------------------
   MciGA5   EQYGRSDGLMTGARDLTWSHASLISASYAKAG----------------------------
   DelGA1   EQFNRDTGFMTGARDLTWSHAAFITAAKAKAG----------------------------
   FspGA3   EQYNRNTGIMQGARDLTWSHAAFITAAKAKLG----------------------------
   GpeGA1   EQFGRDSGVMTGARDLTWSHASLITAALAKTG----------------------------
   MciGA3   EQYGRTDGLMTGARDLTWSHASLISASYAKAG----------------------------
   CumGA1   EQFNRETGSLTGARDLTWSHAAFITAGKAKLG----------------------------
   McoGA1   EQYNRDSGLMTGARDLTWSHASLISASRAKAG----------------------------
   ParGA1   EQYNRDTGISQGARDLTWSHAAFITAAKAKLG----------------------------
   RmiGA1   EEYDRSTGMSTGARDLTWSHASLITAAYAKAG----------------------------
   SfuGA2   EQFNRYTGFMTGARDLTWSHAAMVTALAAKAG----------------------------
   SraGA1   EQFNRDTGVMQGARDLTWSHSAFITAARAKLG----------------------------
   SraGA3   EQYNRDTGALTGARDLTWSHASLITAANAKLG----------------------------
   TinGA1   EQYNRDTGFMQGARDLTWSHAAFITAAKAKQG----------------------------
   ZmeGA1   EQYNRDTGIMQGARDLTWSHAAFITAAKAKQG----------------------------
GAN00808.1  EQYGRTDGLMTGARDLTWSHASLISASYAKAG----------------------------
ORE14155.1  EEYDRSTGMSTGARDLTWSHASLITAAYAKAG----------------------------
RCH88939.1  EEYDRSTGMSTGARDLTWSHASLITAAYAKAG----------------------------
```

FIG. 1H

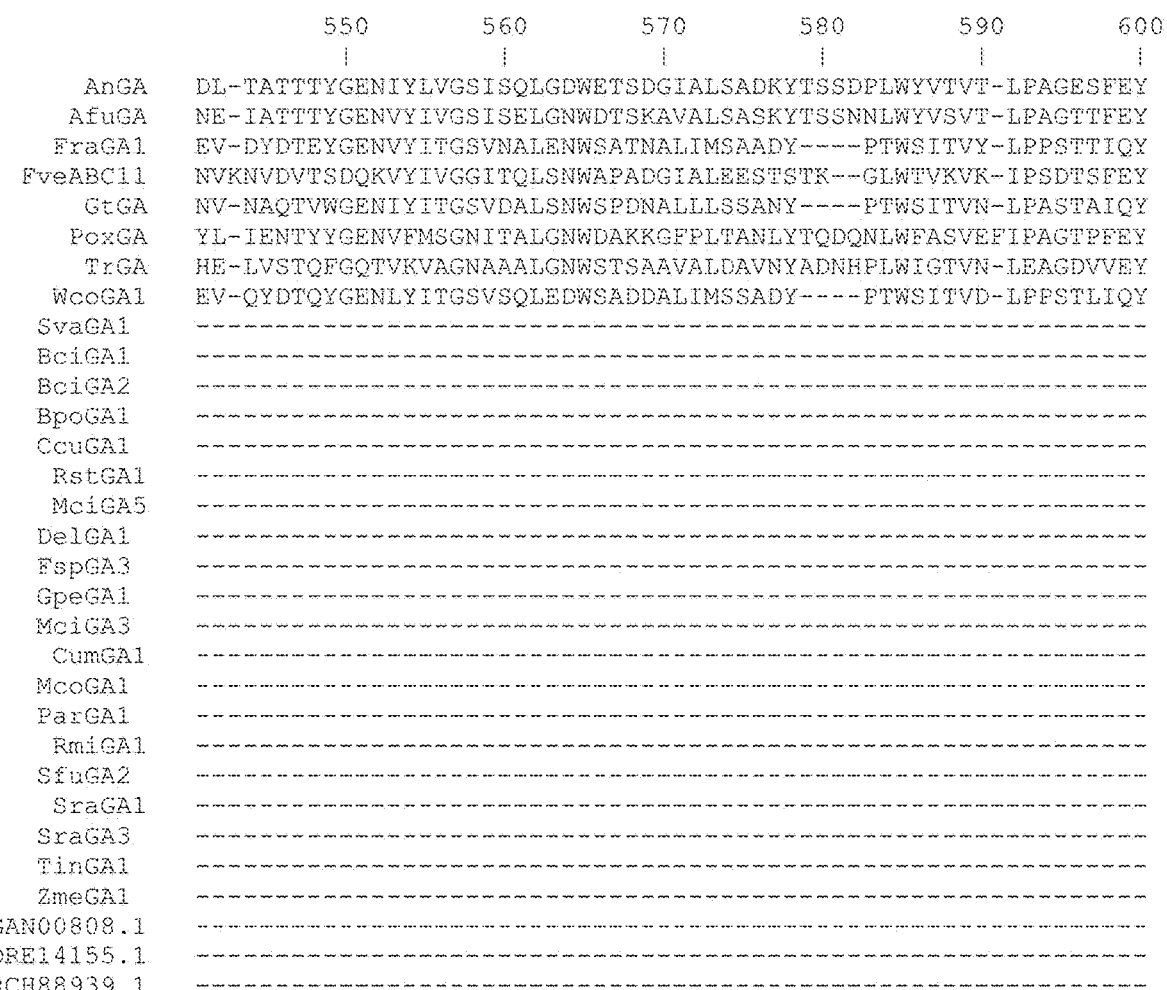

```
            550        560        570        580        590        600
             |          |          |          |          |          |
    AnGA    DL-TATTTYGENIYLVGSISQLGDWETSDGIALSADKYTSSDPLWYVTVT-LPAGESFEY
    AfuGA   NE-IATTTYGENVYIVGSISELGNWDTSKAVALSASKYTSSNNLWYVSVT-LPAGTTFEY
    FraGA1  EV-DYDTEYGENVYITGSVNALENWSATNALIMSAADY----PTWSITVY-LPPSTTIQY
    FveABC11 NVKNVDVTSDQKVYIVGGITQLSNWAPADGIALEESTSTK--GLWTVKVK-IPSDTSFEY
    GtGA    NV-NAQTVWGENIYITGSVDALSNWSPDNALLLSSANY----PTWSITVN-LPASTAIQY
    PoxGA   YL-IENTYYGENVFMSGNITALGNWDAKKGFPLTANLYTQDQNLWFASVEFIPAGTPFEY
    TrGA    HE-LVSTQFGQTVKVAGNAAALGNWSTSAAVALDAVNYADNHPLWIGTVN-LEAGDVVEY
    WcoGA1  EV-QYDTQYGENLYITGSVSQLEDWSADDALIMSSADY----PTWSITVD-LPPSTLIQY
    SvaGA1  ----------------------------------------------------------
    BciGA1  ----------------------------------------------------------
    BciGA2  ----------------------------------------------------------
    BpoGA1  ----------------------------------------------------------
    CcuGA1  ----------------------------------------------------------
    RstGA1  ----------------------------------------------------------
    MciGA5  ----------------------------------------------------------
    DelGA1  ----------------------------------------------------------
    FspGA3  ----------------------------------------------------------
    GpeGA1  ----------------------------------------------------------
    MciGA3  ----------------------------------------------------------
    CumGA1  ----------------------------------------------------------
    McoGA1  ----------------------------------------------------------
    ParGA1  ----------------------------------------------------------
    RmiGA1  ----------------------------------------------------------
    SfuGA2  ----------------------------------------------------------
    SraGA1  ----------------------------------------------------------
    SraGA3  ----------------------------------------------------------
    TinGA1  ----------------------------------------------------------
    ZmeGA1  ----------------------------------------------------------
GAN00808.1  ----------------------------------------------------------
ORE14155.1  ----------------------------------------------------------
RCH88939.1  ----------------------------------------------------------
```

FIG. 1J

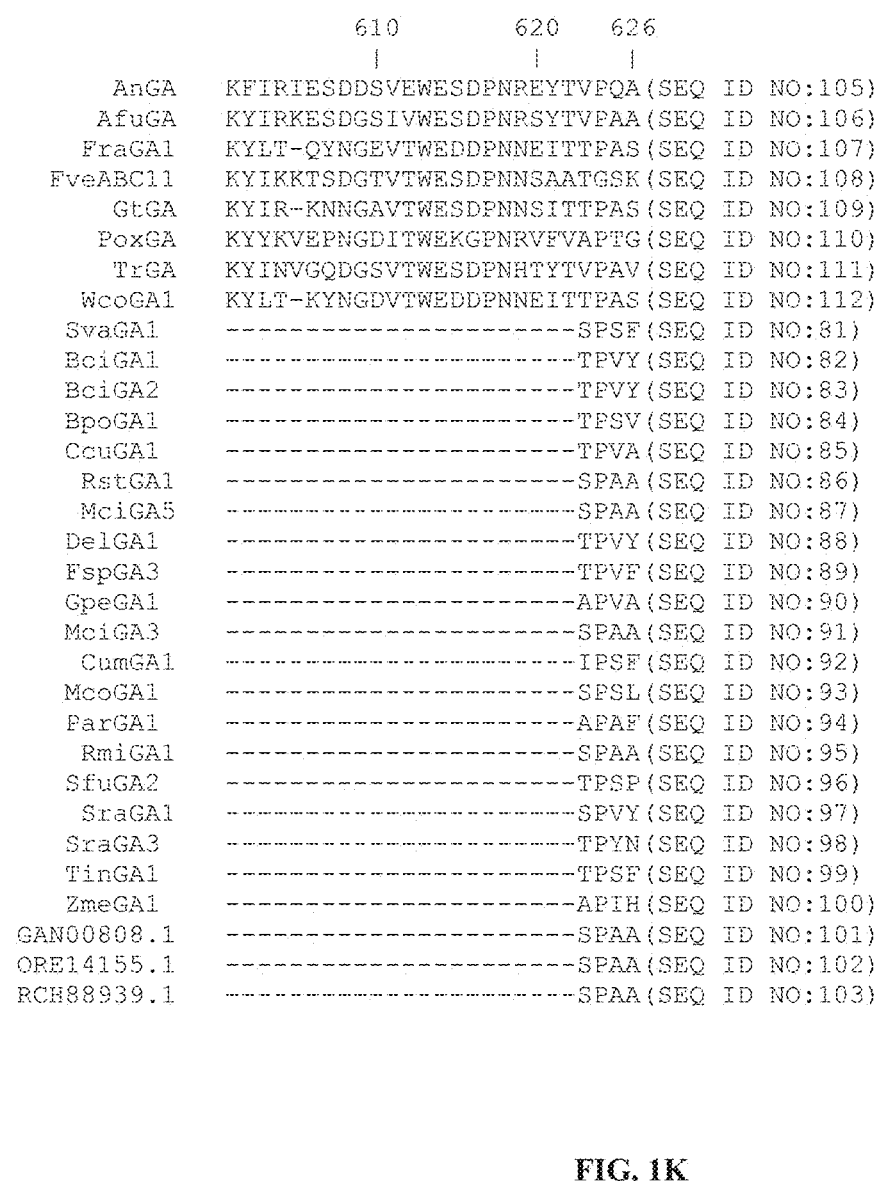

```
                       610        620    626
                        |          |      |
        AnGA    KFIRIESDDSVEWESDPNREYTVPQA(SEQ ID NO:105)
        AfuGA   KYIRKESDGSIVWESDPNRSYTVPAA(SEQ ID NO:106)
        FraGA1  KYLT-QYNGEVTWEDDPNNEITTPAS(SEQ ID NO:107)
      FveABC11  KYIKKTSDGTVTWESDPNNSAATGSK(SEQ ID NO:108)
         GtGA   KYIR-KNNGAVTWESDPNNSITTPAS(SEQ ID NO:109)
        PoxGA   KYYKVEPNGDITWEKGPNRVFVAPTG(SEQ ID NO:110)
         TrGA   KYINVGQDGSVTWESDPNHTYTVPAV(SEQ ID NO:111)
       WcoGA1   KYLT-KYNGDVTWEDDPNNEITTPAS(SEQ ID NO:112)
       SvaGA1   -------------------------SPSF(SEQ ID NO:81)
       BciGA1   -------------------------TPVY(SEQ ID NO:82)
       BciGA2   -------------------------TPVY(SEQ ID NO:83)
       BpoGA1   -------------------------TPSV(SEQ ID NO:84)
       CcuGA1   -------------------------TPVA(SEQ ID NO:85)
        RstGA1  -------------------------SPAA(SEQ ID NO:86)
        MciGA5  -------------------------SPAA(SEQ ID NO:87)
       DelGA1   -------------------------TPVY(SEQ ID NO:88)
       FspGA3   -------------------------TPVF(SEQ ID NO:89)
       GpeGA1   -------------------------APVA(SEQ ID NO:90)
       MciGA3   -------------------------SPAA(SEQ ID NO:91)
        CumGA1  -------------------------IPSF(SEQ ID NO:92)
       McoGA1   -------------------------SPSL(SEQ ID NO:93)
       ParGA1   -------------------------APAF(SEQ ID NO:94)
        RmiGA1  -------------------------SPAA(SEQ ID NO:95)
       SfuGA2   -------------------------TPSP(SEQ ID NO:96)
        SraGA1  -------------------------SPVY(SEQ ID NO:97)
        SraGA3  -------------------------TPYN(SEQ ID NO:98)
       TinGA1   -------------------------TPSF(SEQ ID NO:99)
       ZmeGA1   -------------------------APIH(SEQ ID NO:100)
    GAN00808.1  -------------------------SPAA(SEQ ID NO:101)
    ORE14155.1  -------------------------SPAA(SEQ ID NO:102)
    RCH88939.1  -------------------------SPAA(SEQ ID NO:103)
```

FIG. 1K

```
                      50          55          60          65          70
 1: SvaGA1...  S R V I A Y K Y N T T N A G D S K I H G V
                      50          55          60          65          70
 2: BciGA1...  A H V I V N E Y N T T Y Q G N S T L L G I
                      50          55          60          65          70
 3: BciGA2...  A H V I V N Q Y N T T L S G D S S T L Q V
                      50          55          60          65          70
 4: BpoGA1...  S Y V I A N Q Y N S T L A G N S T I L Q I
                      50          55          60          65          70
 5: CcuGA1...  A H V V A N Q Y N R T K S G D A T Y L G L
                      50          55          60          65          70
 6: RstGA1 ... S N L I A Y E Y N T T L S G N T T I L N I
                      50          55          60          65          70
 7: MciGA5 ... S H V V A Y Q Y N T T L A G N S T I L G L
                      50          55          60          65          70
 8: DeiGA1... A H V I V N A Y N T T K A G D A T T L G V
                      50          55          60          65          70
 9: FspGA3... A R V H V Y R Y N T T E A G D T S L R S K
                      50          55          60          65          70
10: GpeGA1... G H V I A N Q Y N R T L A G N S T Y L G L
                      50          55          60          65          70
11: MciGA3... S H V V A Y Q Y N T T L A G N S T I L G L
                      50          55          60          65          70
12: CumGA... A R V M T Y R Y N T T E A G D S S L E S A
                      50          55          60          65          70
13: McoGA1... S H V I A H Q Y N T T L A G N T T I L N I
                      50          55          60          65          70
14: ParGA1... A H T M T Y L Y N T S E A G D S T I E S A
                      50          55          60          65          70
15: RmiGA1 ... A N V I A Y E Y N T T F A G N T T L L K Y
                      50          55          60          65          70
    SfuGA2... A R A I T Y K Y S T S Y Q N D P K I L G L
                      50          55          60          65          70
17: SraGA1 ... A R T M V N R Y N T T E A G S A S V L G L
                      50          55          60          65          70
18: SraGA3... A R V H V N K Y N T T D A G D A N L L G L
                      50          55          60          65          70
19: TriGA1_... A R V M T F R Y N T T Q A G D S G L L G I
                      50          55          60          65          70
20: ZmeGA... A R V H V Y R Y N T T E A G D T N L L N A
```

*Mucorales*-clade GA motif 1A (SEQ ID NO: 114):

57Y-58N-59T-60T-61X-62A-63G-64D, wherein X is any amino acid

FIG. 3

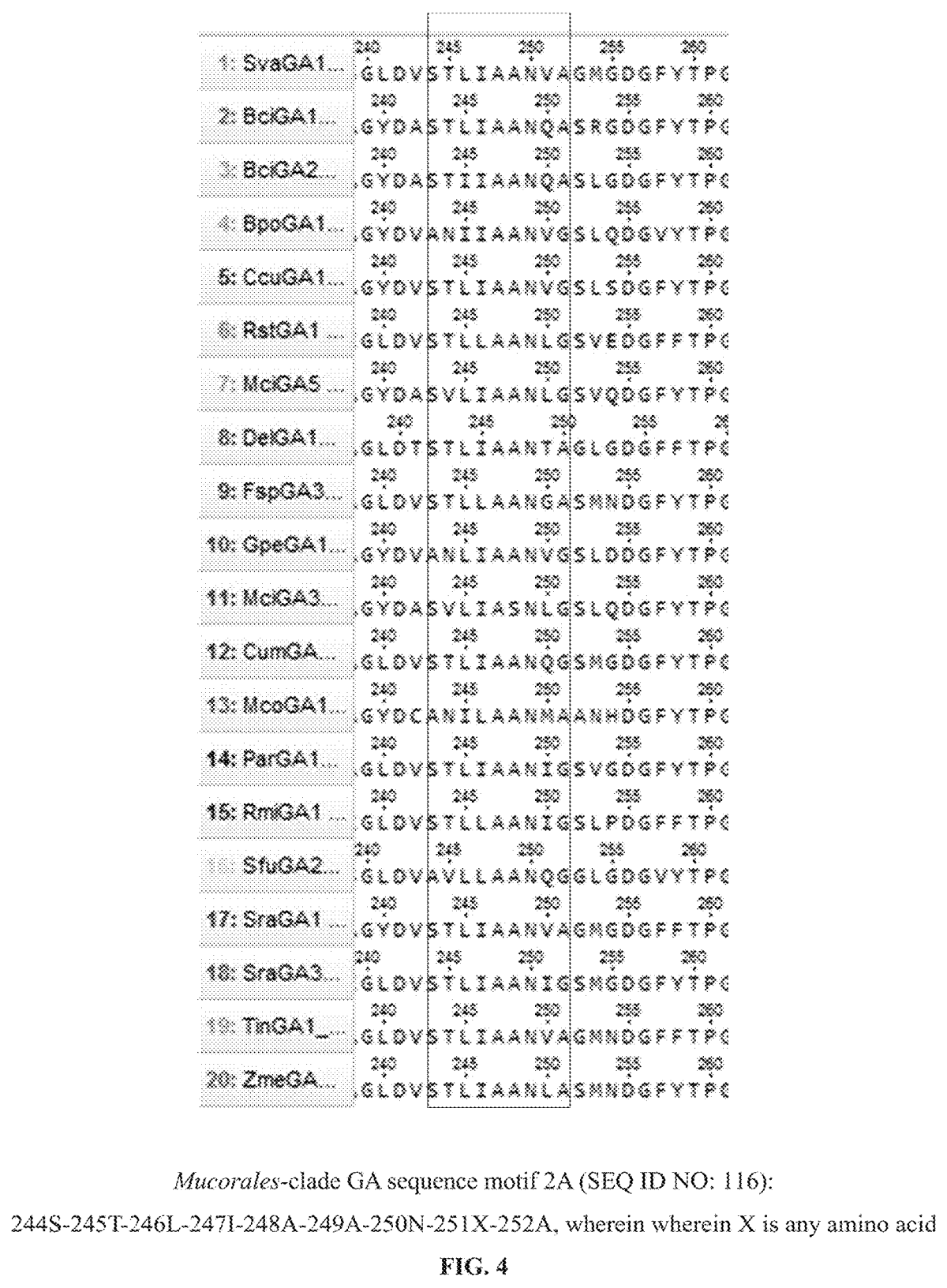

*Mucorales*-clade GA sequence motif 2A (SEQ ID NO: 116):

244S-245T-246L-247I-248A-249A-250N-251X-252A, wherein wherein X is any amino acid

FIG. 4

*Mucorales*-clade GA motif 3A (SEQ ID NO: 118):

```
                  10        20        30        40        50        60
AnGA       WLSNEATVARTAILNNIGADGAWVSGADSGIVVASPSTDNPDYFYTWTRDSGLVLKTLVD
AfuGA      WLGTETTVALNGILANIGADGAYAKSAKPGIIIASPSTSEPDYYYTWTRDAALVTKVLVD
FraGA1     YIASESPVAKAGVLANIGTEGSLSSGAYSGVVIASPSTVNPDYLYTWVRDSSLTFQALID
FveABC11   FISKEADISIKGVLANIGADGKRAQGAAPGAVVASPSRTDPDYWYTWTRDSALTYKVLVE
GtGA       YVGSEGPIAKAGVLANIGPNGSKASGAAAGVVVASPSKSDPDYWYTWTRDSSLVFKSLID
PoxGA      FIHKEGERSLQGILDNLGGRGKKTPGTAAGLFIASPNTENPNYYTWTRDSALTAKCLID
TrGA       FISTETPIALNNLLCNVGPDGCRAFGTSAGAVIASPSTIDPDYYMWTRDSALVFKNLID
WcoGA1     YIASESPIAKAGVLANIGADGSLSSGAYSGIVIASPSTVNPNYLYTWTRDSSLTFMELIN
SvaGA1     WVSKQEDISFSEMLRNVNP-----EGTAKGFVAASLSTAGPDYFYTWTRDAALVSRVIAY
SobGA1     WVSKQEGISFSEMLRNVNP-----PGTAKGFVAASLSTAGPDYFYTWTRDAALVSRVIAY
AosGA3     WVSSQEDISFSVMLGNINP-----PGTVKGFVAASLSTAGPDYFYSWVRDSALVSRVVTH
AelGA1     WVSSQEDISFSVMLGNINP-----PGTVKGFVAASLSTAGPDYFYSWVRDSALVSRVVTH
AvaGA1     WVSSQEDISFSVMLGNINP-----PGTVKGFVAASLSTAGPDYFYSWVRDSALVSRVVTH
AtrGA1     WVSSQEDISFSVMLGNINP-----PGTVKGFVAASLSTAGPDYFYSWVRDSALVSRVVTH 70        80        90       100       110       120
AnGA       LFRN----------GDTSLLSTIENYISAQAIVQGISNPSGDLSSGAGLGEPKFNVDETAYTG
AfuGA      LFRN----------GNLGLQKVITEYVNSQAYLQTVSNPSGGLASG-GLAEPKYNVDMTAFTG
FraGA1     QYVYG-------EDPTLRSLIDEFITAESILQQTTNPSGTVSTG-GLGEPKFNINETAFTG
FveABC11   RFIH-------GDKSLQRKIDEYVSAQAKLQGVTNPSGGPESG-GLGEPKFHVNLTAFTG
GtGA       QYTTGID----STSSLRSLIDSFVIAEANIQQVSNPSGTLTTG-GLGEPKFNVDETAFTG
PoxGA      LFEDSRAKFPIDRKYLETGIRDYVSSQAILQSVSNPSGTLKDGSGLGEPKFEIDLNPFSG
TrGA       RFTET-------YDAGLQRRIEQYITAQVTLQGLSNPSGSLADGSGLGEPKFELTLKPFTG
WcoGA1     QYIYG-------EDDTLRTLIDEFVSAEATLQQVTNPSGTVSTG-GLGEPKFNINETAFTG
SvaGA1     KYNTTNA----GDSKIHGVLDDYVNFQINTQSESTPCN------CLGEPKFNPDGSSFTG
SobGA1     KYNTTNA----GDNNIHGALQDYVTFQINTQTESTPCN------CLGEPKFNPDGSSFTG
AosGA3     KYNTTET----GNSTVAGFLEDYVHFQINTQTESTVCN------CLGEPKFNPDGSSYTG
AelGA1     KYNTTET----GNSTVAGFLQDYVHFQINTQTESTVCN------CLGEPKFNPDGSSYTG
AvaGA1     KYNTTET----GNSTVAGFLQDYVHFQINTQTESTVCN------CLGEPKFNPDGSSYTG
AtrGA1     KYNTTET----GNSTVAGFLQDYVHFQINTQTESTVCN------CLGEPKFNPDGSSYTG 130       140       150       160       170       180
AnGA       SWGRPQRDGPALRATAMIGFGQ-WLLDNGYTSTATDIVWPLVRNDLSYVAQYWNQTGYDL
AfuGA      AWGRPQRDGPALRATALIDFGN-WLIDNGYSSYAVNNIWPIVRNDLSYVSQYWSQSGFDL
FraGA1     PWGRPQRDGPALRSTAIITYAT-YLWNSGNTSYVSDSLWPIIELDLNYIATYWNFSTFDL
FveABC11   SWGRPQRDGPPLRATALTLYAN-WLVSHGDRSKAVNKVWPIIEKDLAYTVKFWNRTGYDL
GtGA       AWGRPQRDGPALRATALITYGN-WLLSNGNTTWVTSTLWPIIQNDLNYVVQYWNQTTFDL
PoxGA      AWGRPQRDGPALRATAMITYAN-YLISHGQKSDVSQVMWPIIANDLAYVGQYWNNTGFDL
TrGA       NWGRPQRDGPALRAIALIGYSK-WLINNNYQSTVSNVIWPIVRNDLNYVAQYWNQTGFDL
WcoGA1     PWGRPQRDGPALRATAIMAYAT-YLYENGNTSYVTDTLWPIIELDLGYVAEYWNESTFDL
SvaGA1     PWGRPQNDGPAERASSFMLIADSFLSQTKNASYFTNTLKPAIYKDLDYVVDTWSNPCFDL
SobGA1     PWGRPQNDGPAERASSMILIADSFLAQTKDTAYVTNTLKPAIYKDLDYVVNTWSNPCFDL
AosGA3     PWGRPQNDGPAERASTMILIADSFLTQTKNTSYVDNTLKPAIYKDLDYVVNTWSNPCFDL
AelGA1     PWGRPQNDGPAERASTMILIADSFLTQTKNTSYVDNTLKPAIYKDLDYVVNTWSNPCFDL
AvaGA1     PWGRPQNDGPAERASTMILIADSFLAQTKNTSYVDNTLKPAIYKDLDYVVNTWSNPCFDL
AtrGA1     PWGRPQNDGPAERASTMILIADSFLTQTKNTSYVDNTLKPAIYKDLDYVVNTWSNPCFDL
```

FIG. 6A

```
                 190       200       210       220       230       240
AnGA      WEEVNGSSFFTIAVQHRALVEGSAFATAVGSSC---SWCDSQAPEILCYLQSFW--TGSFI
AfuGA     WEEVNSMSFFTVAVQHRALVEGSTFAKRVGASC--SWCDSQAPQILCYMQSFW--TGSYI
FraGA1    WEEIDSSSFWTTAVQHRALRQGITFANLIGQTSPVSNYETQAGDILCFLQTYWNPTGNYM
FveABC11  WEEVNGSSFFTLSASHRALVEGAALAKKLGKSC--SDCATNAPRVLCFMQSFW--TGSYI
GtGA      WEEVNSSSFFTTAVQHRALREGAAFATKIGQTSSVSSYTTQAANLLCFLQSYWNPTSGYI
PoxGA     WEEVDGSSFFTIAVQHRALVEGSQLAKKLGKSC--DACDSQPPQILCFLQSFW--NGKYI
TrGA      WEEVNGSSFFTVANQHRALVEGATLAATLGQSG--SAYSSVAPQVLCFLQRFWVSSGGYV
WcoGA1    WEEIDSSSFFTTAVQHRALRAGVTFANLIGETSDVSNYQENADDLLCFLQSYWNPTGSYV
SvaGA1    WEEVNGIHFYTLMVMRRSLLDGANFATRNGDNSKASTYSGVAAKIQARLNSFWDAGKNYI
SobGA1    WEEVNGVHFYTLMVMRRGLLDGADFATRNGDASKASSYSDAASKIKTRLDSFWVSDKNYI
AosGA3    WEEVNGIHFYTLMVMRRGLLDGANFATRNGDTSKASSYSSTASQIQNKIDSFWSSNKNYI
AelGA1    WEEVNGIHFYTLMVMRRGLLDGANFATRNGDTSKASSYSSTASQIQNKIDSFWSSSKNYI
AvaGA1    WEEVNGIHFYTLMVMRRGLLDGANFATRNGDTSKASSYSSTASQIQNKIDSFWSSSKNYI
AtrGA1    WEEVNGIHFYTLMVMRRGLLDGANFATRNGDTSKASSYSSTASQIQNKIDSFWSSSKNYI 250       260       270       280       290       300
AnGA      --LANFDSS---RSGKDANTLLGSIHTFDPEAACDDSTFQPCSPRALANHKEVVDSFRSI
AfuGA     --NANTGGG---RSGKDANTVLASIHTFDPEAGCDDTTFQPCSPRALANHKVYTDSFRSV
FraGA1    --TANTGGG---RSGKDSNTVLASVHTFDPDAGCDSTTFQPCSDKALSNLKVYVDSFRSL
FveABC11  DSNINVNDG---RKGLDANSILSSIHTFDPSSKCTDSTFQPCSSRALANHKEVVDSFRSI
GtGA      --TANTGGG---RSGKDANTLLASIHTYDPSAGCDATTFQPCSDKALSNLKVYVDSFRSV
PoxGA     TSNINTQAS---RSGIDLDSVLGSIHTFDPEAACDDATFQPCSARALANHKVYVDSFRSI
TrGA      DSNINTNEG---RTGKDVNSVLTSIHTFDPNLGCDAGTFQPCSDKALSNLKVVVDSFRSI
WcoGA1    --TANTGGG---RSGKDANTLLASIHTFDPDAGCNATTFQPCSDKALSNHKVYVDSFRSL
SvaGA1    TVTQDYKNGVEKPSGLDVSTLIAA------NVAGMGDGFYTPGSERILATALAFEKSMASL
SobGA1    TVTQDYKEGVKKDTGLDVSTLIAA------NVAGKDDGFYTPGSDKILATAVAFENAMAKL
AosGA3    IVTQDYQNGVQKPSGLDISTLIAA------NVAGMNDGFYTPGSDKMLATAVAIENAMANL
AelGA1    MVTQDYQNGIQKPSGLDISTLIAA------NVAGMNDGFYTPGSDKMLATAVAIENAMANL
AvaGA1    MVTQDYQNGVQKPSGLDISTLIAA------NVAGMNDGFYTPGSDKMLATAVAIENAMANL
AtrGA1    IVTQDYQNGVQKPSGLDVSTLIAA------NVAGMNDGFYTPGSDKMLATAVAIENAMANL 310       320       330       340       350       360
AnGA      YTLNDGLSDSEAVAVGRYPEDTYYN-----GNPWFLCTLAAAEQLYDALYQWDKQGSLEV
AfuGA     YAINSGIPQGAAVSAGRYPEDVYYN-----GNPWFLTTLAAAEQLYDAIYQWKKIGSISI
FraGA1    YAINDGIASDAAVATGRYPEDVYYG------GNPWYLCTFAVAEQLYDALIVWSSQGYLEI
FveABC11  YGVNKNRGKGKAAAVGRYSEDVYYD-----GNPWYLATLAAAEQLYAAVYQWNKIGSITV
GtGA      YSINSGIASNAAVATGRYPEDSYQG-----GNPWYLTTFAVAEQLYDALNVWAAQGSLNV
PoxGA     YKINAGLAEGSAANVGRYPEDVYQG-----GNPWYLATLGASELLYDALYQWDRLGKLEV
TrGA      YGVNKGIPAGAAVAIGRYAEDVYYN-----GNPWYLATFAAAEQLYDAIYVWKKTGSITV
WcoGA1    YAINDDISSDAAVATGRYPEDVYYN------GNPWYLCTLAAAEQLYDSLIVWKAQGYIEV
SvaGA1    YPLNNNLPSHLGNAIGRYPEDTYNGNGNSQGNPWFLATTAFTELYYRAILEWKNTG-VTV
SobGA1    YPLNQNLDSHLGNSIGRYPEDTYNGNGNSQGNPWFLATTAFTELYYRAILEWKDSG-VTV
AosGA3    YPLNKNLPSYLGNAIGRYPEDTYNGDGNSQGNPWFLATTAFSELYYRALLEWQETG-VTV
AelGA1    YPLNKNLPSYLGNAIGRYPEDTYNGDGNSQGNPWFLATTAFSELYYRALLEWQETG-VTV
AvaGA1    YPLNKNLPSYLGNAIGRYPEDTYNGDGNSQGNPWFLATTAFSELYYRALLEWQETG-VTV
AtrGA1    YPLNKNLPSYLGNAIGRYPEDTYNGDGNSQGNPWFLATTAFSELYYRALLEWQETG-VTV
```

FIG. 6B

```
                    370        380        390        400        410        420
AnGA       TDVSLDFFKALYSDAATG-TYSSSSSTYSSIVDAVKTFADGFVSIVETHAASNGSMSEQY
AfuGA      TSTSLAFFKDIYSSAAVG-TYASSTSTFTDIINAVKTYADGYVSIVQAHAMNNGSLSEQF
FraGA1     TDLSLAFFQQFDSDVGTG-TYDSGSSTYSTLTSAIRTFADGFVLTNAKYTPTNGSLSEEY
FveABC11   DSVSLPFFSDLVPKVSKG-TYRKNSKTYKAIIKAVTSYADGFVAVVQTYTPKDGSLAEQF
GtGA       TSISLPFFQQFSSSVTAG-TYASSSTTYTTLTSAIKSFADGFVAINAQYTPSNGGLAEQF
PoxGA      SETSLSFFKDFDATVKIG-SYSRNSKTYKKLTQSIKSYADGFIQLVQQYTPSNGSLAEQY
TrGA       TATSLAFFQELVPGVTAG-TYSSSSSTFTNIINAVSTYADGFLSEAAKYVPADGSLAEQF
WcoGA1     TSLSLAFFQQFDASVSAG-TYDSSSDTYTTLLDAVQTYADGFVLMVAQYTPANGSLSEQY
SvaGA1     TPISKDFFVRFDSSAAPGKKYNPGSQEFATLTQSIAAAADRFMSTVQYHQNPNGSLSEEF
SobGA1     TPVSKDFFAKFDSNAVAGKKYSPNSEEFATLTANIAAAADRFMSTVKYHQNPNGSLSEQF
AosGA3     TSISKDFFSKFDPNASAGKKYSPGSNEFASLAQNIASAADRFLSTVNYHRNSNGSLSEEF
AelGA1     TSISKDFFSKFDPNASAGKKYSPGSDEFNSLAQNIASAADRFLSTVNYHRNSNGSLSEEY
AvaGA1     TSISKDFFSKFDPNASAGKKYSPGSDEFNSLAQNIASAADRFLSTVNYHRNSNGSLSEEY
AtrGA1     TSISKDFFSKFDPNASAGKKYSPGSNEYASLAQNIASAADRFLSTVNYHRNPNGSLSEEY 430        440        450        460        470        480
AnGA       DKSDGEQLSARDLTWSYAALLTANNRRNSVVPASWGETSASSVPGTCAATSAIGTYSSVT
AfuGA      DKSSGLSLSARDLTWSYAAFLTANMRRNGVVPAPWGAASANSVPSSCSMGSATGTYSTAT
FraGA1     TSADGTPISAYDLTWSYASALTVFAAEAGTTYGSWGAAGL-TVPSTCTSG----------
FveABC11   DKSTGTPKSAVHLTWSYASFVGAAERRTGVVPPAWGESNANKVPAVCEAAPACD-------
GtGA       SRSNGAPVSAVDLTWSYASALTAFEARNNTQFAGWGAVGL-TVPTSCSSNSGGGGGGST--
PoxGA      DRNTAAPLSANDLTWSFASFLTATQRRDAVVPPSWGAKSANKVPTTCSASPVVGTYKAPT
TrGA       DRNSGTPLSALHLTWSYASFLTATARRAGIVPPSWANSSASTIPSTCSGASVVGSYSRPT
WcoGA1     AKADGSPTSAYDLTWSFAAALTAFAARDGKTYGSWGAADL-S--STCSGSTDT-------
SvaGA1     DRSSGYMTGARDLTWSHAAFITAAQARAG-------------------------------
SobGA1     DRHSGYMTGARDLTWSHAAFITAAQARAG-------------------------------
AosGA3     DRNTGYMTGARDLTWSHAAFITAGLARAG-------------------------------
AelGA1     DRNSGYMTGARDLTWSHAAFITAGLARAG-------------------------------
AvaGA1     DRNSGYMTGARDLTWSHAAFITAGLARAG-------------------------------
AtrGA1     DRNTGYMTGARDLTWSHAAFITAGLARAG-------------------------------

490        500        510        520        530        540
AnGA       VTSWPSIVATGGTTTTATPTGSGSVTSTSKTTATASKTSTSTSSTSCTTPTAVAVTFDL-
AfuGA      ATSWPSTLTSG---------SPGSTTTVGTTTST---TSGTAAETACATPTAVAVTFNE-
FraGA1     -------------------------------------------------------VAVTFEV-
FveABC11   -------------------------------------------------------TTITFNVK
GtGA       -------------------------------------------------------VAVTFNV-
PoxGA      ATFSSKTKCV----------------------------------------PAKDIVPITFYL-
TrGA       ATSFPPSQTP----------KPGVP-----------SGTPYTPLPCATPTSVAVTFHE-
WcoGA1     --------------------------------------------------VAVTFEV-
SvaGA1     -----------------------------------------------------------
SobGA1     -----------------------------------------------------------
AosGA3     -----------------------------------------------------------
AelGA1     -----------------------------------------------------------
AvaGA1     -----------------------------------------------------------
AtrGA1     -----------------------------------------------------------
```

FIG. 6C

```
                    550       560       570       580       590       600
AnGA       TATTTYGENIYLVGSISQLGDWETSDGIALSADKYTSSDPLWYVTVT--LPAGESFEYKFI
AfuGA      IATTTYGENVYIVGSISELGNWDTSKAVALSASKYTSSNNLWYVSVT--LPAGTTFEYKYI
FraGA1     DYDTEYGENVYITGSVNALENWSATNALIMSAADY----PTWSITVY--LPPSTTIQYKYL
FveABC11   NVDVTSDQKVYIVGGITQLSNWAPADGIALEESTSTK--GLWTVKVK-IPSDTSFEYKYI
GtGA       NAQTVWGENIYITGSVDALSNWSPDNALLLSSANY----PTWSITVN-LPASTAIQYKYI
PoxGA      IENTYYGENVFMSGNITALGNWDAKKGFPLTANLYTQDQNLWFASVEFIPAGTPFEYKYY
TrGA       LVSTQFGQTVKVAGNAAALGNWSTSAAVALDAVNYADNHPLWIGTVN-LEAGDVVEYKYI
WcoGA1     QYDTQYGENLYITGSVSQLEDWSADDALIMSSADY----PTWSITVD-LPPSTLIQYKYL
SvaGA1     ------------------------------------------------------------
SobGA1     ------------------------------------------------------------
AosGA3     ------------------------------------------------------------
AelGA1     ------------------------------------------------------------
AvaGA1     ------------------------------------------------------------
AtrGA1     ------------------------------------------------------------

610       620
AnGA       RIESDDSVEWESDPNREYTVPQA(SEQ ID NO:105)
AfuGA      RKESDGSIVWESDPNRSYTVPAA(SEQ ID NO:106)
FraGA1     T-QYNGEVTWEDDPNNEITTPAS(SEQ ID NO:107)
FveABC11   KKTSDGTVTWESDPNNSAATGSK(SEQ ID NO:108)
GtGA       R-KNNGAVTWESDPNNSITTPAS(SEQ ID NO:109)
PoxGA      KVEPNGDITWEKGPNRVFVAPTG(SEQ ID NO:110)
TrGA       NVGQDGSVTWESDPNHTYTVPAV(SEQ ID NO:111)
WcoGA1     T-KYNGDVTWEDDPNNEITTPAS(SEQ ID NO:112)
SvaGA1     --------------------SPSF(SEQ ID NO:81)
SobGA1     --------------------TPSF(SEQ ID NO:126)
AosGA3     --------------------TPSF(SEQ ID NO:129)
AelGA1     --------------------TPS-(SEQ ID NO:132)
AvaGA1     --------------------TPSF(SEQ ID NO:135)
AtrGA1     --------------------TPSF(SEQ ID NO:138)
```

FIG. 6D

SEQUENCE LISTING

<160> NUMBER OF SEQ ID NOS: 142

<210> SEQ ID NO 1
<211> LENGTH: 1633
<212> TYPE: DNA
<213> ORGANISM: Saksenaea vasiformis

<400> SEQUENCE: 1
atgccatcct ggaaaaccct tttcttgctc cttgggccga ttgcgactgc agcagctgct          60
ccagtggaca agcagtctct tccaaccgga aattctacca ttagctcctg ggtatccaaa          120

-continued

```
caagaagata ttagctttc ggaaatgctt cgcaatgtaa accctgaggg aactgcaaaa      180
ggatttgtag ctgcatcttt atccaccgcc ggcccagatt acttctacac atggacacgc      240
gacgctgctt tggtttctcg ggtgattgct tacaagtaca acaccaccaa cgctggcgac      300
agtaagatcc acgggtcct tgatgattat gtcaacttcc aaatcaacac gcaatcggag      360 agtaccctt gcaattgcct tggcgaacca aaatttaatc ccgatggatc aagctttacg      420 ggccctggg gaaggtaata ctgacctcat tgtgcatggg aaagatacta aataattatt      480
tgttgaaact catcagacca caaaacgatg gtccagctga gcgagcttca agcttcatgt      540
tgattgccga tagcttcctg agccaaacaa aaaatgcgtc gtacttcacg aatacattaa      600
agccaggtac gtctaacctc tccggaaata cgttttcccc tttaatcacc gtctttatta      660
gctatctata aggatctcga ttacgtcgtc gatacctgga gcaatccatg cttcgatctg      720
tggtaagcac acacacttta aaaagttggc gaataaggcc tctaattata ttatagggag      780
gaggtcaatg gtatccattt ctataccttg atggtgatgc gacgtagcct cttggatggt      840
gcaaactttg ccacgcgtaa tggtgacaac tccaaggcca gtacctatag tggcgtcgct      900
gccaaaatcc aagcaagact taattccttc tgggacgctg gcaagaatta tattactgtc      960
acacaagact ataagaacgg tgtcgaaaag ccatctggat tggatgtctc tacattgatt     1020
gctgctaatg tagcaggcat gggcgatggt aacaataacg tagtaaagtc tccaacctta     1080
tactgacata ctattttgct taggcttcta cactcccgga tctgaaagaa ttctcgcaac     1140
tgctctagcc ttcgagaagt ccatggcaag tctatacct cttaacaaca atttgccttc     1200
tcaccttggt aatgccatcg gtcgctaccc tgaagacact tacaatggca acggaaattc     1260
ccagggcaac ccgtggttcc tggctactac tgcctttaca gaactttact atcgtgccat     1320
tctcgaatgg aagaacacag gtgtgacagt gacgccaatc agcaaagact tctttgtcag     1380
atttgattcc agtgctgcac ccggcaagaa atacaacccc ggctctcaag aatttgccac     1440
gttgacccag agcatcgccg cagctgccga ccgtttatg tcgacagtac aatatcacca     1500
gaatccaaac ggatctcttt ctgaggagtt tgaccgctcc tcaggataca tgaccggtgc     1560
tcgcgatctc acctggtccc acgctgcttt tatcacagct gctcaagcaa gagctggctc     1620
accatccttc taa                                                       1633
```

<210> SEQ ID NO 2
<211> LENGTH: 2498
<212> TYPE: DNA
<213> ORGANISM: Backusella circina

<400> SEQUENCE: 2

```
atgaaacttt ttggtactct aaaggcatct tttgtcttcc ttattggatg catagtgttt       60
gctatggcag acactgtccc tactacccag gttaaactcc agtcctacac ttattctgga      120
ggtgtattgt ctggtacaat ctatgtaaga gaatgattgc ccaagtctat ttcgtttttt      180
tctcttccaa actcatatat tattttgata ggttcaaaat atagactaca ctaaggttgt      240
cactgttatc tattctgatg gttctggtaa ctggaataac aacggcaata ctatctccgc      300
ttcctactct tcctccattt ctggaacaaa ctatgaatac tggacattct cagcatcagt      360
tagtagcatc cagcaatttt acatctcagt aagtgtaaaa cacaaaaaaa gtaggaaatt      420
tcagttattt atgcattaat cgattctttc tttttttttt agtatcttgt agatggtact      480
acctattatg acaacaatgg tggctatggc gccaactatg ctggtaagct caaattcaaa      540
```

-continued

```
ttttattttc atttacttaa agatgaataa atagtcactg caaccaccac aactgcttca      600
tctactacta aaaccacttc tggtacaaca aagacatcta ctacgtcaac agccactgct      660
acttcaacag gcacatcctc ttttccttct ggtaattcta ccatcagtac ttggagcccc      720
agtcaacaca gtatcagtct ttacgctatg cttcgtaata tcaatcctcc aggaagtgct      780
gctggattca tttctgcctc cttgtctacc tctggacctg attattatta ttcctggaca      840
agagtaaata gttaaaattt aaaatacatc atgctgtttg agtgctcatt ttttgatatt      900
taggattctg cacttgttgc tcatgtcatt gtcaacgaat ataatactac atatcaagga      960
aacagcaccc ttctcggtat tttgaaggat tatgttacct attctcttaa cgctcaaact     1020
acctctactg tttgtaactg tcttggtgag ccaaaattca accctgatgg ttcgagcttc     1080
actggtgcct ggggaaggta aacaagattc atgaagagag acgaaaagat attaaccgtt     1140
tatttagacc tcaaaatgat ggtccagctg agcgtgctgt cagttttatt tattttgcag     1200
atagttatct cactcaaact agcgactcat cttatgttac tggcacactt gcacctggta     1260
agagtcaatt ttttttatga tttttgcaaa tttcaggaat cttattttgt ttcataagct     1320
atttataagg atttggatta tgttgttagc gtatggagta acggttgttt cgatctttgg     1380
taaattgtat ttactttttt ccttaattgt aatactaata tatgtttgaa tttttttttt     1440
agggaggaag taaatggtat ccatttttac acactgatgt ttatgcgcag aggtctcctt     1500
gatggagcca actttgcctc acgaaacggt gactctactc gtgcttccac ttatacctct     1560
accgctgctt ctattaagac caagattgat ggcttctggg tatcgagtgg aaactatgtt     1620
caggtcagtc aaagtgttac aagcggtgtc agcaaagctg gatatgacgc ttctacctta     1680
attgctgcaa atcaagccag tcggggtgat ggtaagttgt gtcttttttt ttttaccaaa     1740
aaataaaaaa aagaatctca attaaacaaa attgatgttt aggtttctat acacctggat     1800
ccgataaggt aacgcaatag ataaagttaa aacctctata tgactaacat aaagattaca     1860
gatgctggct acagctgttg ctattgaatc ccaattctca agcttgtact caatcaacac     1920
caacaaggct tcttatctag gaaatgctat tggcaggtga gttcctttaa cactacattt     1980
tcttctaaaa ttctgataat atcatattaa taccttatta aaagatatcc cgaagatacc     2040
tataacggca atggtaactc tcaaggcaac ccttggttct tgtaagtaaa tcattctcat     2100
aaattatata aattgcatat ctttaatttt attttttataa aaggtgcact aatgcatttg     2160
gagagctttt ctatcgcgcc atcagtgaat ggaacgctgc tggtagcgtc accgtaaaca     2220
gcgtcaatct tgccttcttc aagaaatacg attcttctac ctcctctggt acaacgtata     2280
cagttggaac aagtgcttac aataatctcg ttcagaatgt tgctcttgct gctgatgcct     2340
acttctccac cgtcaaatat catgctctta ctaatggttc catgtctgaa caatacgatc     2400
gtagctctgg tatggctaca ggtgcaagag atcttacatg gtcacacgcc gctatgatta     2460
ctgccttgaa ggcaaaatct ggaacaccag tttactaa                           2498
```

<210> SEQ ID NO 3
<211> LENGTH: 2550
<212> TYPE: DNA
<213> ORGANISM: Backusella circina

<400> SEQUENCE: 3

```
atgaagcctt tcggaccaat caagaccact cttttatta ttattagcca cttctctttg       60
aattctttag ctgatacagt tcctactacc caggtagagg tcaaaactta tacttactcg      120
ggtggagagc tgtctggtac aatctacgta agtttctcgc tctaactttg gctttcttct      180
```

-continued

```
gtatatcaaa atcttattta aatacacttc cttcatatgt ttaggtcgag aacattgatt      240
atactaaggt tgttacggtc atttatgctg atggttcaga tgactggaat aacaatggca      300
ataccattgc tgccgccttc tctgaatcaa tctctgatac taattacgaa tactggactt      360
tctccagttc tgttaacagc attaaggagt tctatgttaa ggtgaatagt ttattcaata      420
cttttaatta tgattttacc atataaagat tatacatatg cttatcattc acttattaaa      480
tagtatgatg ttgatggaaa cacctactat gacaataatg gaaatgccaa ctaccaaggt      540
attttttttt atcaaactta atatttgtca atgttaacgc taacacatga tcatatagtc      600
tctgcttctt ccactaccac aactactgct acaaagacta caaccactgc aacaaaaacg      660
actgctactg ccacatctac tgccactggt tcaacttcat tcccttctgg taactccact      720
atctcttcct ggattaaggg tcaagaagat accagtcgat ctgttatgct tggcaacatt      780
aacccacctg gaagtgccac tggtttttatc tctgcttctt tgtcaactag tggtcctgat      840
tattattatc attggacacg cgtaagtcaa ttccaatttg aacattatag aagttacctc      900
tctaatattc gaaaactaac ttttctcatt tatctatttt catcaggatg ctgctcttgt      960
tgctcacgtt attgtcaatg attataatac tactctttct ggagatagct ctactcttca     1020
agttattaag gattatgtta ctttctctgt taacagccag tctgaatcta ccgtatgcaa     1080
ctgccttggt gagcctaaat tcaatccgga tggatcaagc tacactggtg catggggcag     1140
gtaagatatt atagcattta ataaaatcat gcgcatgtta tattcattat taattttgta     1200
taacattaat cagacctcaa aacgatggtc ctgctgaacg tgccacaaca ttcattttct     1260
ttgctgacac ttatctcgca cagggtggtg actctagcta tgtgactggt acacttgccc     1320
caggtatata tagcctttta aaaaacaaat tactttaaaa agtgaatagt attactatgc     1380
taactacatt tatatattct ttactatttt gatttaaata gctatctatg ctgatctgga     1440
ttatgttgta aataactgga gcactggatg ttacgatttg tggtaaagca tctaatatga     1500
agttaatttt tgtgaagtat actcaccaaa agctgatata gggaggaagt taatggtatt     1560
catttctaca ctttgatggt tatgcgcagg ggtcttattg acggtgccag ctttgcctct     1620
cgtaatggtg actctactcg ttcaagcagc tatacttcca ctgctaaatc aattgctacc     1680
aagattgata gtttctggtc agcctccaac aactatgttg ctgtcagtca aagtgtaact     1740
tctggtgtca gtaaggctgg atatgatgct tctaccatta ttgctgctaa ccaagctagt     1800
cttggtgatg gtttctatac tcctggttca gataaggtag gctaatctta atgcaatatt     1860
ataaacgtag aaaaagaaac atgtatatta atgccaattg agtagatgct tgccacctcc     1920
gtcgctgttg agaatgcttt ctcttctctt tacaccgtta atactggaaa ggcttcttac     1980
ttaggaaatg ctattggcag gtgagtgcat ttgacacttc attttcttcg tataatttct     2040
cactaaaaaa actactacca tattaaaaga taccccgaag ataccctataa tggtaatggc     2100 aactctcaag gcaacccttg gtatttgtaa gtaaaactct tttatgctcg ataattatcc     2160
cttcctaaca catcattttt attttttaaaa aaaaggtgta ctaacgctct tggtgagtta     2220
tactaccgtg caattaagga atggaatgcc gctggatccg ttacggtcaa cagtgtcaat     2280
ctcggcttct tccaaaagat tgattcctca atttcatctg gcaccaccttt taccttaggc     2340 acttctgact acagcaccct cgttgacaat gttgcacttg ctgctgataa gttcttcgcc     2400
gttgtccagt atcatgaacg cagtaatgga tctatgcctg agcaatttgg ccgtgaggac     2460
ggtcttccta ctggtgctag agatcttaca tggtctcatg ctgccatgat ttctgctgcc     2520
```

-continued cgtgctaagg ctggtactcc tgtgtattag                                     2550

<210> SEQ ID NO 4
<211> LENGTH: 2256
<212> TYPE: DNA
<213> ORGANISM: Benjaminiella poitrasii

<400> SEQUENCE: 4
atgaagtttt ctcatctctt caggaagcca acgcttctta ttgtgacctt tttgaccgct     60
acggtttttg cagaaactgt tcctacaact tctcaagtca agcttaagag ttatacatat    120
gatggttcca ccttatccgg ccagatttat gtaagttata ttaattattc actttatatt    180
ttttttttcc cctgacctgt caaaaatata ctaattttta tttcaaattt taccagattc    240
aaaatattgc ttatacaaag gtggttactg taatctactc tgatgcgtct agcaactgga    300
acaacaatgg aaacacaatt gctgcttcat atactaatgg tatctcagga accaattatg    360
aatactggaa tttcactggt cctgtcagca gcatcaatgc attttacatc aaagtaaatt    420
actgaataat aatgttcaca agcaattata aattctcact ttaattgatt atatagtatg    480
atgttagcgg aaatacatat tatgataaca acaataatgc aaactatcaa ggtaaaatag    540
tcaagagaaa aaaaaaaaga cgcattaacc gaactcaatt tattaatgca ttcttataat    600
agttacaaag acatcaacta caacgactac ttccactgct actgctacta ctactaccaa    660
aacttccaca ccgacttcta ctggtgtccc ctccaatttc cccaccggta acagtactat    720
tagcacatgg ttgaaatcac aaattggcat cagtcgctat gctatgctcc gtaacatcaa    780
tcctgctggt tccgctgttg gtttttattgc tgcctcttta tcgactgcta accctgacta    840
ctattatgcc tggactcgtg attctgcttt gacctcatat gttattgcca acgattataa    900
ctctactttg gctggtaact caacaatcct tcaaatcatg aaagattacg ttactttctc    960
tgttaagagt caatcggttt ctactgcctg taactgcctt ggtgaaccca aattcaatcc   1020
tgatggatct agttacactg cgcgcttgggg aaggtatgta gataatacca taccttttttt   1080 ttttttttca taatgatata catgtaaaaa gtttaactaa catgatcaat atgtaaatac   1140
aaagacccca aaatgatggt cctgctgagc gtgctactac atttatatta tttgccgata   1200
gttatcttaa gcaaacaggc gatgctagct atgttactgg aacccttaag ccaggtaaag   1260
ttttttcctt tattacggca tgtatattat gttaacatat acacgtaatt tgaatagcta   1320
ttttcaagga tttggactat gttgtcaaca catggactaa tggatgcttt gatttatggg   1380
aagaggttaa cggtgttcac ttctatacct tgatggtaat gcgtaagggt ttgatcagag   1440
gagctaactt tgccacccgc aacggcgact ctacacgtgc ttctacttac accaacacag   1500
ctgcatccat caaaacaaag atggattcat tctggtcatc tggcaacaac tacattgctg   1560
ttagtcaaag tgttactggt ggtgtcagta aggctggtta cgatgttgct aacattattg   1620
ctgctaatgt tggcagtctc caagatggcg tatatactcc tggttctgat agagtatgta   1680
tcaacagtaa ctttatagta tcaacagaga caatcatatt aaccattgca ccccccttt   1740 tttttctaga ttcttgctac tgctgttgct gttgaagcta aatttgcttc tttatatggt   1800
gttaactcaa acttaccagg ctaccttggt aactccatcg tcgttatcc cgaagacaca   1860 tataacggta acggaaactc ccaaggtaac ccatggttct tggccacaaa tgcttacgca   1920
gaactttact accgtgccat cagagaatgg tatgacaatg gtggtgttac agtcaacagt   1980
gttaacttgc cgttcttcaa gaaattcgat agttccgctg cttctggtac aacctacact   2040
gtaggtacga ccgccttcaa cacgatggtt tccaatgttg cagctgcagc tgataagttt   2100

-continued

```
ttctcgactg tcaaattcca tgcttacacc aatggctcca tgagcgaaca attcggtcgt      2160
aatgatggtt tatgtacggg ggctcgtgat cttacatggt ctcacgcttc tttgatttct      2220
gctgctcttg caaaggctgg tactccttca gtctaa                                2256

<210> SEQ ID NO 5
<211> LENGTH: 1968
<212> TYPE: DNA
<213> ORGANISM: Choanephora cucurbitarum

<400> SEQUENCE: 5
atggtttctt ttaacttcct taaaaagcca gtattcattg tgattacttg cttgacagtc        60
tctgtctgtg ctcaatctgt gcctaccagt gaccctgtca aggtcaagac tttcagctac       120
gatggtaact ctttctctgg tcaaatttat gtaagtgtca atacttattt ggaaggtacg       180 gggggtttaat tgtttaattg gatttcgcag atcaaaaata ttgcttatga aaagaccgtt      240
actgtcatct actctgatgg tactggtaat tggaacaaca acaacaacaa gatcgctgct       300
gctttctctg aagccatctc tggttccaac tatgaatact ggactttctc tgcctctgtc       360
cctagcatta aacaatttta tgtcaaggta aagaaacaat agtttaaac ataccaatct        420 aatgtgcctt catagtatga tgtttctggt aaaacttatt acgacaacaa tggtagcaag       480
gactataatg gtaaaatcaa attttcacat gaattaagag tatgttacac taaaccctt        540 ttttttttaa tagttgttac ctctggtcct accaccactt ccagtggtcc ctcaaagaca       600
accaccaatg gtcccgctcc tacctccacc aacactaact tcccctccgg taacccttcc       660
atcacttcat ggatcgataa gcaaattgac atcagtcgct ctgccatgct taagaacatc       720
aaccctgccg gtaccgtcaa gggtttcatt gctgcctctc tctctacctc aaaccccgat       780
tacttctacg cctggacccg tgacgctgcc ttagttgccc atgttgttgc taacgactac       840
aaccgtacca agagcggtga tgccacttac ctcggcctcc tcaaggatta cgttaccttc       900
tctatcaaca gtcaaaacac gcctactgcc tgtaactgtc tcggtgaacc caagttcaac       960
aaggatggtt ctggttacaa cggtccctgg ggtcgtcctc aaaacgatgg tcctgctgaa      1020
cgtgctgaca ctttcgtctt gattgccgac agtatcttga cccaaaccaa ggacgtcagc      1080
tatgtcactg gtaccttgcg ccctgctatc tacactgatc ttgactatgt cgtcagaacc      1140
tggtccaacg gctgtttcga tctctgggaa gaagtcaacg gtgttcactt ctacaccttg      1200
atggtcatgc gtcgtgcctt gcttgtcggt gccaactttg cctctcgtaa cggtgacagt      1260
gctcgtgcca gtaactacaa caacgctgct aactccatca gtccaagat cgacagcttc       1320 tggtcttcca caacaacta tgttgccgtc agccaaagtg tcactggtgg tgtcagcaag       1380
gccggttacg atgtctctac cttgattgct gccaatgtcg gtagtctctc tgacggtttc      1440
tacacccctg gttctgaaag aatgcttgct actgccgttg ctatcgaaga caagtttgcc      1500
aacctctatg gtatcaaccg taacttggac agcagccttg gtaacgctat cggtcgttac      1560
cctgaagaca cctacaacgg taacggtaac tctcaaggta acccctggtt cattgctacc      1620
aacgcctatg ctgaactcta ctaccgtgcc atcaaggaat ggaacaacaa cggtggtgtg      1680
actgtcacca acgtcaacct caacttcttc aagaagttcg atggtagtgc ctctgtcggt      1740
accaagtaca ctgctggttc tgctgcctac aacaccttga tcaaaaacat tgctcttgct      1800
gctgataagt tcttcaacac cgtcaaggtc catgctgcca ccaacggttc catgtctgaa      1860
caataccacc gtgacaccgg ttccatgaca ggtgctcgtg acttgacttg gtctcatgcc      1920
```

-continued

```
agtttgatta ctgctgccct tgccaaggct ggtactcccg tagcttaa          1968
```

```
<210> SEQ ID NO 6
<211> LENGTH: 2204
<212> TYPE: DNA
<213> ORGANISM: Rhizopus stolonifer
<220> FEATURE:
<221> NAME/KEY: misc_feature
<222> LOCATION: (171)..(190)
<223> OTHER INFORMATION: Any nucleotide

<400> SEQUENCE: 6
atgaaactgt ttggtttgcc attgaagcct tcgctctttt ttgtggtctc ttatctttct     60
ttcctcgcct ctgctgctag tattcctagt agttctgaag ttcagcttga cacatacgcg    120
tatgatggtg ctaaattttc aggaaaaatt tatgtgagtt tttttttttt nnnnnnnnnn    180
nnnnnnnnnn tttttttttt tttttttttt ttcttctaaa ggaaggtatc tgatctcaaa    240
taaatttagg tcaaaaacat tgcttatgaa aagactgtca ctgtggtata cgctgatggt    300
tctgataact ggaataacaa tggaaatata atttctgcta ctttctctac cccaatctct    360
ggatctaact acgaatactg gaccttttct tcttctatta gtggtattaa agagttttac    420
attaaggtat agttcatttt ctttatatgt ataatttacc aaccttactt tttacagtat    480
gtggttagtg gtaaaaccta ttacgataac aacggcacta aaaactatca agtttctacc    540
acttcctcta ctaccactgc ttccaccaca accgctactc gtacaactac agctggaact    600
acttcgacct ctactacggc tgcacctaca agcacttcat ccggttcttt cccttcaggt    660
aactcgacgg tatcctcttg gattaaacgt caagaaaaaa taagtcgctt cgctatgctt    720
cgtaatatca accctcccgg aagcgctgct ggttttatcg ctgcttctct tagtacctct    780
ggccctgact actactactc atggactcgc gactctgcct taacttccaa cttgattgcc    840
tatgaatata acaccacttt gtctggaaac accactatcc ttaacatcct taaggattac    900
gtcaagttct ctatcagctc tcaaacaact tccactgtat gtaattgtct tggtgaaccc    960
aagttcaacc atgatggctc aagttacaca ggcgcttggg gaaggtagtt acacatattt   1020
ttttctggat gagaacacct gtttattaat attaacttag acctcaaaat gacggacctg   1080
ctgaacgtgc aaatactttt atcttgttcg ctgacagtta ccttgatcaa acaaaggatg   1140
catcttatgt cactggcact cttaaacctg gtaatttttt tgaattttat ttattgtata   1200
gatatgtgta cttatagttt cttaaagcca ttttttaagga tttggactac gttgtcaatg   1260
tatggtctaa cggttgttac gatttatggt aaaaaaaaat atgatgtttc tttataggat   1320
cttattgaca gtagaaaata gggaagaagt caacggagtt cattttttaca cattgatggt   1380 tatgcgcaag ggcttacttc ttggtgctga ctttgccaag cgtaacggtg actctacacg   1440
tgcatctact tacaccaata ctgcttctac tattgctaca aagatttcta gcttctgggt   1500
atcctctagc aactggattc aagtcagtca aagtgttact gctggcgtta gcaaaaaggg   1560
attggacgta tcaaccttat tggctgctaa tcttggaagt gttgaagacg gtttctttac   1620
cccaggttct gaaaaggtaa ttgtagttta tcatggataa gagtatggtt ttcgagctaa   1680
aatgcacatt taaatagatc cttgctaccg ctgttgctat tgaagatgct tttgcttcat   1740
tgtatcctat caactccaac ttaccttctt accttggtaa ttccatcgga agatatcctg   1800
aagacaccta caacggcaat ggaaattctc aaggcaaccc ttggttcttg gccgtcaatg   1860
gctttgctga gctttactac cgtgcctatca aggaatgggg caacaatggt agtgttactg   1920
tgagcaacat cagcttgtct tttttttaaga aatttgactc atctgctact gctggtaaga   1980
```

-continued

```
cctatactgc cggtactgca gactttaaca atctcgcaca aaacattgca cttggcgccg      2040
atcgtttctt atcaactgtc cagactcatg cctttaacaa cggatctctt gctgaagaat      2100
atgatcgtac aactggagta tctacaggtg ctagagactt gacttggtct catgcctctt      2160
tgattactgc tgcttatgca aaagctggtt cacctgctgc ttaa                       2204

<210> SEQ ID NO 7
<211> LENGTH: 2015
<212> TYPE: DNA
<213> ORGANISM: Mucor circinelloides

<400> SEQUENCE: 7
atgaagttct ctaaccttct caagaagcct ctccttttga tcgctggtat tttggccgct        60
actgttgtcg ctgagactgt acctactacc gctgcagtca aagtcaagtc cttcacatat       120
gatggatcca ccttcgctgg tcaaatctac gtacgtacta aaatttcgat ttattgaatt       180
caatgctaaa cccgcattct tcattctata caggtcaaga acattgctta cactaaaact       240
gttaccgtga tttactctga cgcttctaat aattggaata caatggtaa cacaatcgct        300 gcttcttaca gcgaaggcat ttcaggcacc aattacgaat actggacttt cagtgcccct       360
gtcagtggca tcaagcaatt ctacgtcaag gtaagtctgg gatcactcag tggtcggttg       420
caagtattga gcctataatc tattagtatg ttgtaagcgg taccacctac tatgacaaca       480
acaacagcgg aaactaccaa ggtatttaca ctttcacatg ttgcattagt attgtcatac       540
tgaaaaaaaa attccgtggc attcctttag ttaccactac taccactact actgctccta       600
cctctactac ttctggcggt tcttctacaa ccaccggcgg ctctactacc actgctacta       660
gcgtcccaac tggtgttcct tctgtttcc ctactggtaa ctcttctatt agctcttgga       720
tcgacggcca aacatctgtc agtcgttatg ccatgctccg caacatcaac cctgctggcg       780
cagtttctgg tttcattgct gcttccatgt ctacctctgg acctgattac ttttatgcct       840
ggactcgtga ttctgccctg acctctcatg ttgttgctta tgattacaac actactttgg       900
ctggtaactc taccattctc ggcctcttga agaactatgt tactttctct atcaacagtc       960
aaactacttc cactgtttgt aactgtctcg gtgagcccaa gttcaacaag gatggtagca      1020
gttacactgg tgcctggggt agacctcaaa atgatggccc tgctagtcgt gccgatactt      1080
tcattttaat tgctgacagt atcctcaagc aaaccggtga tgctacttat gttactggca      1140
ctcttgctcc tgccatctac aaggatttgg attatgttgt ctcaacttgg tccaacggtt      1200
gtttcgattt atgggaagaa gtcaatggcg ttcactttta cactttgatg gtgatgcgta      1260
gaggtttgat caagggtgct aactttgcct ctcgcaacgg tgacaacact cgtgccaaca      1320
cttacaccaa cactgccgcc tccatcaaga ccaagattga tagcttctgg aactccaatg      1380
gcaactatgt cactgtcagc caaagtgtca ctggcggtgt cagcaaggct ggttatgatg      1440
cctctgtgtt gattgctgcc aacttgggta gtgttcaaga tggtttctac actcctggtt      1500
ctgacaagat gcttgctact gctgttgcca ttgagagcaa gtttgcttcc ctctattcta      1560
tcaaccaaaa cttaaacggt taccttggta atgctatcgg ccgctatcct gaagatactt      1620
acaatggtaa tggtaactct caaggcaacc cttggttcat ctgtaccaat gcctttgctg      1680
agctctacta ccgtgctatc aaggaatggt ttaacaatgg tggtgttact gtcactagta      1740
tcagtttgaa cttcttcaag aaatttgatt cctctgctgc cgttggtacc aaatacactg      1800
ttggtacctc tgctttcaac agcttggtcc aaaatgttgc tgttgctgct gatgccttct      1860
```

```
tctccaccgt caagttccat gctgctacta acggctccat gagcgagcaa tatggtcgta   1920
gtgatggttt gatgaccggt gctcgtgatt tgacttggtc tcacgcttca ttgatttctg   1980
cttcttacgc aaaggctggt tcccctgctg cttaa                              2015

<210> SEQ ID NO 8
<211> LENGTH: 2398
<212> TYPE: DNA
<213> ORGANISM: Dichotomocladium elegans

<400> SEQUENCE: 8
atgaaactta acagtgtttg gaaagcattc agtattttgc ttatggccac catggctttt     60
gctgccaccg ttcctaaaac gcaagtgaag cttgaggcgt acacatactc ggattccata    120
ttctctggta gaattttcgt aagaatctat atctcctcaa atcgtttgta tgcataaagg    180
ctcatatatt gtgaataggt gcaaaacatc gactacacca agattgtaac cgtttactgg    240
tctgatgcat cgaataaatg ggactccagc aaatattata ctgaagctgc ttacacccat    300
tcgatccctg gaactaatta cgaatactgg gatttctcag ccaccattgg tccttcagga    360
atcaagcagt tctacatttc ggtaaccatt tattgaggag aatcggtaaa tccacgcacc    420
tcttttactc atcgtgttcg gatgactttc agtatcaagt ccggggtgtc acttattatg    480
ataacaacgg cggctatggt gtcaattacg gtgagcaaaa cactgtcagc tagtagctct    540
tcatgcccta cttacaaatg cgttgtagac gtcatctcgt cacccccgac cacgtccgat    600
gccactacca ttcctactac taccactagt gctattcctt cttccactac cactattccc    660
gccagtactg gggttccttc tggaaactcc actatcaccg tttgggctga ttcgcagcat    720
aagatcagct ggaaagcaat gctcgccaat attaatccac ccggttctgc tactggtttt    780
attgccgcct cgctttcgac ttctggtcca gactactact atgcctggac tcgtgatgct    840
gcgatggttg cgcacgttat tgtcaacgct tacaacacaa ccaaagcagg tgatgcaact    900
actcttggcg ttctgaagga ctttgttacc ttccagatta aggctatggc taccagcacc    960
gtctgcaact gtctcggtga acctaaattc aaccctgtaa gttaccagat agtacagcag   1020
aaagaaaata ccgtctttac catcggtcgt aggatggctc cagctatact ggtccttggg   1080
ggagaccaca aaatgatgga cccgctgagc gtgctactac tttcattcta tttgcggaca   1140
gctatctttc ccagaccgga gacgccgctt atgtcactac cttgaaaaga ggtaagcatc   1200
ctggaagctt caagtgtgca gtgattaacc tgtaaattat gcttcttcca cttcattagc   1260
tatctttacc gatcttgact atgtggtgac cacctggcag ataattgtt ttgatctctg    1320 ggaagaagtg aacggacttc acatgtatac gtaagttgtt attcctcttt ttctcgtatg   1380
cacacgcata cccgcgcccg gagtattagc agaaaaaagc ttaagctact aatggaactc   1440
ttatttcagt ttggcggtaa tgcgccgaag tctggttgat ggagcaagct ttgccgcccg   1500
caatggtgac aatacacgcg ccagtaccta taccaatact gccaaatcca tcgagaccaa   1560
gcttgcaagc ttttacaact cgagtagcaa ctatgtcgtt gtcaccaaga acttcgcagg   1620
tggtgtaaac aaggctggtt tagataccctc cacattgatc gccgcgaaca ctgccggttt   1680
gggtgatggt aagcgggaag catgatgatt aatctgaccc ttagagaggg agaaaataga   1740
tagctctctt ttcaatatgt gattctgact gccagccaac ctctccccaa ggtttcttca   1800
cccccggttc accggagatt ctagctaccg ccgccgcaat cgagagtca ttcgctgatc     1860 tatacggcat caacaaacaa attcccaact ggttaggcac tgcaattggc cgatacccgg   1920
aagacactta caatggcaac ggcaactcac agggtaaccc ggtaagtatc cctccaacct   1980
```

-continued

```
ttgtctctct cttcgttgtg ggacctataa tgcgatgctt atctatttaa cctagtggtt    2040
catctgtact gctaccttcg ccgaactcta ttatcgcgcc attctggaat ggcaacacgc    2100
tggctccgtc acagtgaaca acgtgaactt gccattcttc aaaaaattcg atagctccac    2160
ttcctctggc accacctaca ctgtcggcac tagtagcttt gattcactta tctcaaaagt    2220
agcctatgct gcggataact tcttttctac gatcaaatat cacgccgcta cgaatggttc    2280
catgagcgag cagttcaatc gtgataccgg ttttatgact ggcgctagag acttgacctg    2340
gtctcacgcg gcattcatca ccgctgctaa agccaaggct ggcactcctg tatactag      2398
```

```
<210> SEQ ID NO 9
<211> LENGTH: 2311
<212> TYPE: DNA
<213> ORGANISM: Fennellomyces sp.

<400> SEQUENCE: 9
```

```
atgagaccaa gtcttgtttg gaaaagcctg cttatggttg tgcttaccgc agccatgggc     60
acatatgctc aaactgttcc atctgtgcct atcaagttgg aaagttacac ttactcggat    120
aacgtattcg ccggtcgaat ctttgtaagt agttcgataa tttctgtttg ttaaagagaa    180
aaaaaaactc acccctttt tcgtcacgt agattcgaaa catcgcttat acaaaagtgg      240
tcaaggtttt ctggtctgat gaatctggca attggaacgg taacggaaac tatgttgatg    300
cctcgtattc ggggtctatt ccggtacca actatgaata ctgggaattt caacaacca      360 tcggatccgc cggtattagc caaagctatt tgagagtaaa gagtttgtcc tttttaagtg    420
tttcgcaagt ggggaagaga gactaaacag aatattttct tttagtatg atgtttcagg     480 ttctacgtac tatgataaca atggaaatgc aaactatggt aacgtattaa ctagaagcgg    540
tcaaatttga aatcactcaa agccttcttt tacgtgtttc agatatcgag gaagactcca    600
cacctacgcc caccaccacc actaccagta ctacgacaat aaccactacc actaccagtg    660
gaacttcaac tcctacttct gtccccactg aagttcctgc tggcaatacc actgtcactg    720
actgggtgaa tgatcaattg gaaattagtt ggccatcgct tttaaagaat gtcaatcctt    780
ccggcgcagt aaccggtttc atcgctgctt cgctttccac aaatgatccc gattattct     840 actgttggac gcgtgatgcc gctttggtcg cacgagtgat ggtttacatg tacaacacaa    900
ccgaagctgg tgacaccagt ttgagaagca agctgcaaga ttatgttaca ttccagatca    960
actccatgaa gactgcaaca gtatgcaact gcttgggtga acccaaattc aataaggtta   1020
gtagtttttt tttaaatga tgatacactt ttgacaaaa agaattagga tggttcgggt     1080
tactcgggag catggggtcg cccacaaaat gatggcccgg ctgatcgtgc tatcacgttg   1140
atcctgtttg cggacagttt cattgctcaa ggcggtgatg tctcgtacat taccaacaca   1200
ttgaagccag gtaagtaatc gggtatcacc gtaatccggt ctccaattac taatgtatgc   1260
cacagctatc tacaccaatc tcgactatgt tgttaacacc tggagcaatg tttgctttga   1320
tctatgggaa gaagtcaatg gtgtccatat ctatacgtag gttttttcgg gggagaggga   1380
aacgttaatg tgaaactttt ttttgaagt actcattgaa aatgcttatt tagactttcg    1440
gtcatgcgta agggtttgct tgaaggtgcc gactttgctt ctcgaaacgg cgattccacg   1500
cgtgccaaca cttatagaag caccgcttct tccatcaaga cccgtcttga atctttctgg   1560
tcatcgagca ataattacat cactgttact caatcatact ctggtggtgt gaacaaggcc   1620
ggtttggatg tatccacctt acttgcagcc aacggagcaa gcatgaatga tggttagttt   1680
ttgcttaaaa aaattgactt tgatatttac caaaagaata ctgcgtaggc ttctatactc   1740
```

-continued

```
ctggctctga caagatgttg gcaaccgctg ttgctattga aaattcgttt gccggtattt    1800
acgctgttaa ccagaatcga cctgattgga aaggtactgc tattggtcga tatcccgaag    1860
atacttatga tggccatggc aattcccaag gcaaccctgt aagtcatata ttccttatca    1920
caagaatgaa ttctaactta gaaaatagtg gttcattgcc acagctgcgt atgctgaaat    1980
gtactaccgt gccatcttgg aatggcaaca gcaaccgtct atcactgtga actcgatcaa    2040
cctgagcttt ttcaaaaagt ttgactcgtc cgccgctgtt ggtactgtgt acaagcccgg    2100
tacccaagct ttcaacaaca tggtttccaa tgttgcgttc gctgctgatg agttcttttc    2160
tactatgaat ttccattccg ccaccaacgg atccatgagc gaacaataca accgcaatac    2220
tggtattatg caaggtgctc gtgatcttac ttggtcccat gctgccttca tcaccgctgc    2280
caaagctaag cttggcacgc cagtattcta g                                   2311
```

```
<210> SEQ ID NO 10
<211> LENGTH: 1985
<212> TYPE: DNA
<213> ORGANISM: Gilbertella persicaria

<400> SEQUENCE: 10
```

```
atggttttct ccaagctttt taagaagcct atccttctca ttgtcactta cttgactgtt     60
actgttgtag ctgaaactgt tcctacttca gctcaagttc aagttaagtc cttcaactat    120
gatggctcta ctctttcagg tcaaatttat gtaagtaatt gagaggaagc gaatagtcat    180
tctgaatttg ctttaggttc aaaacattgc ttacgaaaag actgttactg tcgtttactc    240
tgatggctct gataactgga ataacaatgg taacaccatt gctgccagct attcttcttc    300
tatttcaggt agcaattacg aatactggac tttctcttct tctgttccta gcatcaagca    360
attctatatc aaggtataaa aaaaaagga aacatgtatg acaaattagc tttactaaca    420
tcatcatctg tattcagtat gtcgttgctg gcaagactta ctatgataac aatggtacaa    480
agaactatca aggtatgtaa ttcacatgtt gcatgaaata tcagttacac taacacaaag    540
gctttaattg tatcaattta gtgagtgcaa gcacccctac taccactact accactactt    600
cttctggagc caccaagact actactacca ttggccctac ttctacaagt actgtcttcc    660
cctctggcaa ctctaccatt tcttcttggc tcaagggtca aattgaaacc agtcgttttg    720
ccatgctccg taacatcaac cctgctggta ctgtcaaggg tttcattgct gcttcttgt    780 ctactgctaa ccctgactat ttctatgcct ggacccgtga tgctgcttta gtcggccatg    840
ttattgccaa tgactacaac cgtaccttag ctggtaacag cacttacctt ggtcttttga    900
aggactatgt tactttctct gtcaactctc aatctacttc tactatctgt aactgtctcg    960
gtgaacccaa gttaacaag gatggttctg ctacagcgg tgcatggggc cgtcctcaaa    1020
atgatggccc tgctgaacgt gctgatacat tcatcttgat tgctgacagt atcttgaaac    1080
aaactggtga tgctacctat gtaactggta ccttgcgtcc tgctatctac aaggatttgg    1140
actacgttgt caatgtttgg tctaacggtt gtttcgattt gtgggaagaa gttaatggtg    1200
ttcactttta cactttgatg gtcatgcgtc gttctttgat tttgggtgcc aactttgctt    1260
ctcgtaacgg tgattctact cgtgccagta cttacaccaa cactgccaac tctatcaaga    1320
ccaagattga cacctttctgg tcttcttcca acaactatgt tgctgtcagt caaagcgtca    1380
ctggtggtgt caacaaggct ggttatgatg ttgctaactt gattgctgct aatgttggta    1440
gtctcgatga cggtttctac actcctggtt ccgaaagaat tctcgctact gctgttgctg    1500
```

```
ttgaaagtaa atttgcttct atttacggtg ttaaccaaaa cttgcccagc tggctcggta       1560
actctatcgg tagataccct gaagacactt acaatggtaa cggtaactct caaggtaacc       1620
cttggttcat tgccactaat acttatgctg agctctacta ccgtgctatc aaggaatgga       1680
ccaacaacgg tggtgtcacc gtcactaatg ttaacttcaa cttcttcaag aagtttgata       1740
gcagtgcttc tgttggtacc aagtacactg ttggtacctc tgcctttaac accttgactc       1800
aaaatgttgc tcttgctgct gacaatttct tctctactgt taaggttcat gctgccacca       1860
atggttctat gtctgaacaa ttcggtcgtg atagcggtgt catgactggt gctcgcgatt       1920
tgacttggtc tcacgccagt ttgattactg ctgctcttgc caagacaggt gctcctgtag       1980
cttaa                                                                    1985

<210> SEQ ID NO 11
<211> LENGTH: 2018
<212> TYPE: DNA
<213> ORGANISM: Mucor circinelloides

<400> SEQUENCE: 11
atgaagttct caaatcttct caagaagcct ctccttctga tcgctggtat cttggctgtc         60
actgtagtcg ctgaaactgt ccctactact gaagcagtca aagtcaagtc ctttacctat        120
gatggatcta ccttggctgg tcaaatctat gtaagtgcta gaatcagtac caatcccttc        180
aataaacaca atgctaaata catgctctca acgaatagat caagaacatt gcttacacca        240
agacggttac tgtaatctac tctgatgcct ctgataattg aacaacaat ggtaacacga        300 tcgctgcttc ttacagtgca gccatcgcag gcaccaacta tgaatactgg actttcagtg        360
ctcctgtaag cggcatcaag caattctacg tcaaggtaag tttgggattc ctgtatgctg        420
ggtgctcaga tattaagcct ctgatccgta ttagtatgtt gtcagcggta ctacctacta        480
tgacaacaac aacagcggaa actaccaagg tatattgatt ttcacatgct ggcatttgca        540
ctgtcatact aaacgagctg aatcctctag tttcagtcac caccactacc actactgctc        600
ctaccactac cacttctggc ggttcatcca ctaccactgg cggctccact actactgcta        660
ctagcgtccc cactggtgtt ccttctggtt ccctacagg taactctacc attagctctt        720
ggatcgatgg tcaaacctct gtcagccgtt atgccatgct ccgcaacatc aaccctgctg        780
gtgccgtcac tggtttcatt gctgcctcta tgtctacttc tggtcctgac tactttttatg        840 cctggacgcg tgattctgcc ttgacctctc atgtcgttgc ctacgactac aataccactt        900
tggccggtaa ctctaccatt ctcggtctct gaagaacta tgttaccttc tctctcaaca        960
gccaaactac ctccactgtc tgtaactgtc tcggtgagcc caagttcaac aaagatggca       1020
gcggttacag cggcgcctgg ggtagacctc aaaatgacgg acctgccagc cgtgccgaca       1080
ctttcatctt gattgccgac agtatcctca agcaaaccgg cgatgctacc tatgttactg       1140
gtaccctcgc tcctgccatc tacaaggatt tggattacgt tgtctctact tggtccaacg       1200
gctgtttcga tttgtgggag gaggtcaacg gtgttcactt ttacactttg atggtgatgc       1260
gcagaggttt ggttaagggt gctaactttg cttctcgcaa tggtgacagc acacgtgcca       1320
ccacttacac caacacagct gcttccatca agaccaagat tgcagccttc tggaactcca       1380
acggtcaata tgtctctgtc agccaaagcg tcactggtgg cgtcagcaag gctggttatg       1440
atgcctctgt cttgattgct tccaacttgg gtagtcttca agatggtttc tatactcctg       1500
gctctgacaa gatgcttgct actgctgttg ccattgagag caagtttgct tctctctact       1560
ctatcaacca aaacttgaac ggttaccttg gtaatgctat cggtcgctac cctgaagaca       1620
```

-continued

```
cctacaacgg caacggtaac tctcaaggta acccttggtt catctgtacc aacgcctttg    1680
ccgagctcta ctaccgcgct atcaaggaat ggttcaacaa tggcggtgtc actgtcacta    1740
gcatcagttt gaacttcttc aagaagtttg attcctctgc tgctgttggc accaagtaca    1800
ctgtcggcac ctcttctttc aacagcttgg ttcaaaatgt tgctgtcgct gctgatgcct    1860
tcttctctac tatcaagttc catgctgcca ccaacggttc catgagcgag caatacggcc    1920
gcactgatgg cttgatgact ggtgctcgtg atttgacttg gtctcacgct tcattgatct    1980
ctgcttctta tgcaaaggct ggttctcctg ctgcctaa                            2018
```

<210> SEQ ID NO 12
<211> LENGTH: 2946
<212> TYPE: DNA
<213> ORGANISM: Circinella umbellata

<400> SEQUENCE: 12

```
atgatgccga atcatatttg gaagtgtctg tttctagcca tgaccacagt tttcatgact      60
gtactggtac aaggtgctcc tacttcagaa attgaattgg actcttatac ctacaccggt     120
ggagtatttt ctggtcggtt atatgtatgt ggtatctatt tgtacataat taaaagaaaa     180
attcaagaga atacagtttt gttaatgttg gtaattccca atatatacag gttaaaaata     240
ttgcgtacac caaggaagtg aatgtctatt ggtctgatgc ttctgaagac tgggccaata     300
atggtaatta tgtggcagct acgtattctg aagccatttc gggtacaaat tacgaatatt     360
gggaattctc tgccaaaatt ggatcttctg gtattagtga aagttacata aaggtaaatt     420
actataaatt gtttgaaact ccaaaataca aaataaaaaa tccggcatag ttattaatta     480
ttctttattt ttttcaaata aattcagtac actgtgtctg ctccacttta ttatgataat     540
aatgggggta aaaattatgg tatggtcaaa acattttaca cagtaataac gcctttcttg     600
catcatcgaa cttttaaagt atatgcttat ttttttttcg tcattttaca atagctatta     660
ctgagacaac tacacccaca ataactgcaa ccccgacatc aacaacggcg acaacgacca     720
tttcttcaac aactactacg gctacttcca ttcctacctc tgttccttcc actgttcctg     780
agggaaatgt tactgtcaca gaatgggtca ataagcaact aaaaatcagc tggtccgatc     840
ttctgcaaaa tgtaggcgta taataactaa aaatacctta tattatattc tatgcatact     900
atctgtaaaa aaaaccttaa aaattattga aaacctgttt ctcattattt atattacttc     960
tatcttatat ataggttaac ccttcaggta cagttactgg ttttattgct gcaagtttaa    1020
gtaccagcaa ccctgattac ttttactgtt ggacaagaga tgctgccatg gttgcacgtg    1080
ttatgactta tatgtataat actactgaag ctggcgactc aagtcttgaa agtgcattaa    1140
aagattatat tacgttccaa atcaattcaa tgaagactgc cactgcatgt aactgcttag    1200
gtgagcccaa gtttaatact gtaagttacg tattagagta agaaataaaa cccctcgat     1260 tgatcactag acatgttatc tgtatcacgt atcattacaa tgctaatttt ttatttattg    1320
acaaatgtgg tactgtagga tggaagtggt tatagtggcc cttggggtag gcctcaaaat    1380
gatgggcctg gtaagtttaa actatttttt ctattttatt ttactttata agatttttaa    1440
aaatatgttg atcttatgat gatcttatgc cttaacaaaa atgttttttc atatttatac    1500
atatagctga acgtgccact acaatgattt tgtttgctga tagttatctc gctcaagggg    1560
gtgatacttc ctacgttaca aatacattaa aacctggtaa atcattataa taatattttg    1620
tatactataa caaacacaga tagatgtaaa aaaaggcttt ctgtttctca tgtatattaa    1680
```

-continued

```
caaaaacaat ttacctttt ttttgttat taaaacgatt atatagctat ctataccaat    1740
cttgactatg ttgttggtac ctggtcaaat aattgtttcg atttatggga agaagttaat    1800
ggtgttcata tttgtaagca atatcatgat atttttctaa aaagaacaat acacacacat    1860
acacacacac acacacacac acacacacac acacatatat atatatatat atatatatta    1920
actgctatca acatttttac ttcataaaaa ctaaaataac aataataata ataatagtta    1980
ctctggctgt tatgcgcaag tcattacttg atggtgctga ttttgctgca cgtaatggcg    2040
atacatctcg tgtcagtggt tatcaaagca cagcttcatc tatcaagact aagttagaat    2100
cattctggtc gtccagtaac aattatatca ctgtaactca atcctattct ggaggtgttc    2160
aaaaggccgg attagatgtt tctactttaa ttgctgccaa ccaaggaagt atgggtgatg    2220
gtaagttttt atttttattt tactataata aagtagtttg taatataaaa tacgtaaaaa    2280
agaaaagacg gatttttta tatgaaatat aactattgct ctgtaggatt ctatactcct    2340
ggctctgata aaatgctggc tactgccgtc gctattgaaa actcatttgc aaatatttat    2400
actatcaata aaaacaaacc ttcttggctt ggtactgcta tcgggcgtta tcctgaagac    2460
acatataatg gtaacggcaa tggtcaaggc aacccggtaa gtttatatat aacccattta    2520
ctaaaagaag gtttcatttt atatatgtat ctaatatatt atatggtcac tactattatt    2580
tagtggttta tcgcaacagc aacctatgcc gaattatact accgagctat tttggaatgg    2640
caacaacaag agtctgttac tgtaaactct gtcaactttg atttctttag caagtttgat    2700
tcatcggcta aggttggcac tgtttataca ccaggtacag atacctttaa caccatggtt    2760
tcaaacgtag cttttgccgc tgatgaattc ctttcaacaa tggaacatta tgctgctaca    2820
aacgggtcca tgtctgaaca atttaatcga gagactggct ctctcaccgg agcccgtgat    2880
ttgacatggt cccatgccgc atttatcaca gctggtaaag ctaaattagg tattccatca    2940
ttctga                                                            2946
```

<210> SEQ ID NO 13
<211> LENGTH: 2054
<212> TYPE: DNA
<213> ORGANISM: Mucor cordense

<400> SEQUENCE: 13

```
atgaagtttt ccaagctctt tacgaagcca actctcttca tagttagcat catcatttct     60
gttgcttcct ctgaaactgt ccctactact gccaatgtcc ttgtcaaatc ttacacttgg    120
gacggtgcca ctttatctgg tcaaatttac gtaagtatat tatgtaatgg cgtgttatag    180
caaaaattga cactgcttgt ctatagatta aaaatcttgc ctatgccaag gttgtctctg    240
tcatttactc tgatgctaat gataactgga ataacaatgg taacaaagta gctgcctcct    300
actctgctgg aattgatgga acaaactacg aatactggac cttttctggc gctgttagcg    360
gtatcaagca attttatgtc aaagtaagta tagatcttct atattcaaat tgaatatata    420
aactaactgt ataatgtagt atgatgttag cggtactagt tactatgata acaatggtac    480
caagaactac caaggtaaaa attagataat gaagtaatcg tatacagatc cttacatgtc    540
gtcttcatag ttaccaagac ctctacaacc accactgctg ctactaccac taccactgcc    600
actactacta ctggtggtac tggtaccact actacaacta ccgctactgc cactgctaca    660
tctactgatt ccctacagg taacagcact atcaccactt ggctcaaatc tcaagaagac    720
atcagtcgtg gtgctatgct ccgcaacatc aaccctcctg gtgccgctac aggtttcatc    780
gccgcctcat tatccacttc cggacctgac tactactatg cctggactcg tgattccgcc    840
```

-continued

```
ttaacctccc acgtcattgc tcacgactac aacactacat tagccggtaa caccaccatt      900
ctcaacatcc tcaaggacta cgtcactttc tctgtcaaga gtcaatctgt ttccaccgtc      960
tgtaactgtc tcggtgaacc caagttcaac cctgacggct cttcttacac cggcgcttgg     1020
ggtcgtccac aaaacgacgg tcctgctgaa cgtgcttcca cattcatcct ctttggtgac     1080
agttacctca agcaaactgg cgatgctact tacgtcacgg gcacattggc tcctgctatc     1140
tacaaggatt tggactatgt cgtgaatact tggtcaaatg gttgctttga tttatgggaa     1200
gaagtcaatg gtgttcactt ttacaccttg atgagcatgc gtagaggttt gcttgatggt     1260
gctaatttcg ctaagcgtaa tggagatact acacgtgcca ctacttacac aaataccgct     1320
gcttctattg ctacaaagat cgataccttc tgggtctctt ctggtaacta tgttcaagtc     1380
agtcaaagtg tgactggtgg tgtaagcaag gctggttatg attgtgctaa tattctcgct     1440
gccaacatgg ccgccaacca cgatggtttc tatactcctg gttcaagcaa ggtaaatata     1500
catgactcac tatctcttta tgaaagtata ctaaacgttt catatagatt cttgctactg     1560
ctgttgctat tgaatccaag tttgcttcct tatacagcat taactctggt ttggctagct     1620
ggctcggtac agctattggt cgttatcctg aagacactta caacggtaat ggtaactctc     1680
aaggtaaccc ttggttcatc tgtaccaacg cctttgctga actctactac cgcgctatca     1740
aggaatggac tcaagctggt tccgtcactg ttgacagcac tagtcttaac ttctttaaga     1800
aattcgatag ctctgctgct gcaggcacga aatataccgt tggtacttct gctttcacta     1860
atttggttca aaatattgct aatggtgctg ataagttttt gtctacttcc aagttccatg     1920
ccgctaccaa tggttccatg tctgaacaat ataaccgtga ttctggtttg atgacgggtg     1980
ctcgtgattt gacttggtct catgcttctt tgatctctgc ttctagagct aaggctggct     2040
ctccttctct ttaa                                                        2054
```

<210> SEQ ID NO 14
<211> LENGTH: 2709
<212> TYPE: DNA
<213> ORGANISM: Phascolomyces articulosus

<400> SEQUENCE: 14

```
atgggtgtat tagcagacgt ccctacctct gccaatattg aactggatta ttatacttat       60
aaggataaag tattctctgg tagaatttat gtatgaattt taaaatagag taaaatgaaa      120
gaaaaaaaag atagaagaat gggaatatat aataattaaa ggttataata tatatttttat      180 taaataggtt aaaaacattg catatgagaa aacagtagct gtctattggt ccgatgcttc      240
tggtgattgg aataataacg gaaataatgt tgcagcttcg tactctgaat ctatttcagg      300
tactgactat gaatattggg atttctcaac cacaattgga tctggtggta tcaagcaaag      360
ttacttgaag gtacacttga ttgttatcat cctgttattt ttcaaattat aaatatatat      420
actaaaagta cacatactca atagtatact gtatctggta atacttacta tgataataat      480
ggaagcaata actatggtac gtctcaattt aaaaaccata taaacaagta tatttctgta      540
ttcgtattca ggaacgtatg aagctgacat ataagttttt gattatagat attaccgaga      600
ccactgctac tactactact accacaacaa caacaaccac tactggctcc accgcaacaa      660
catcaacaac ttctggtcct accagtacta ccagtaccac acccggccct acacctacca      720
atgttcctga tggcaatgtc actgttcag agtgggttaa cactcaattt gccatcagct      780
ggcctaccct cttgaaaaat gtatctatca aaaaaatata atccttctcc aaaatactca      840
```

-continued

```
catgttcatt acttatatat cgttttcttt ttaatactaa aggtcaaccc atctggtaca      900
gtgaaaggtt ttatagctgc aagtttaagt accaacaatc ccgattactt ttactcctgg      960
actcgtgaca gtgccttagt ggctcataca atgacatatc tttataatac atcggaagcc     1020
ggtgactcta ctatcgaaag tgcattgaag gattatgtta cattctctat caacgctatg     1080
aatgctgcta ctgtttgtaa ttgtttaggt gaaccgaagt tcaatactgt aagtataagg     1140
ggaaaaaaga gacgatactt taaaaatgat agacttatca ttggatgaaa cttttttttt     1200
aacaaatagg atggaagtgg ttatactgga gcatgggggaa ggtaggtttt ttatttacat    1260
gctggctcca gtgcttaaat gatatgdatta tttgggagtg aaaaataaat gttgtgagca    1320
accttgctaa acttgtttct attattatta gaccacaaaa tgatggccct gcttcaagag     1380
caacaaccat gattttgttt gctgatagtt ccttgctca aggaggtgat gtttcctatg      1440
tcatcaacac actgaagcca ggtatatact attatatgtc ccaactacat ttattgaaat     1500
ataaagtact aatcttaaca aatattatta tttatcttgc ccaatgatat ttagccatct     1560
ataaagatct tgactatgtt gttagtacct ggtccaatac ttgttatgat ttatgggaag     1620
aagtcaacgg tgttcatatc tgtaagtagt agtatatctc ttaaataatg catcattctg     1680
aatatacata tttatcttca attttttttt taaatagata cattatccgt tatgcgcaga     1740
gcactgattg atggagctaa ctttgctcaa cgtaatggtg atacttctcg cgtgagcggt     1800
tatactagta ctgcaaccac aatcaagaca cgtctcgaat ccttctggtc agatagcaat     1860
aattatatta ctgtcactca atcctattca ggtggtgttc aaaaggctgg attggatgtc     1920
tctactttga ttgcagccaa tatcggaagc gtgggtgatg gtatatttca tctattacta     1980
ctttatttcc atattattgc gttatcggat cgatcttctc tgtcatttta taacgtaata     2040
tttattaata tctcttttct aatatttata ataaggtttc tatactcctg gttcggataa     2100
agtcttggct actgctgttg ctattgaaaa atcatttgcc aatctttaca ccatcaacca     2160
aaacaagcct tcatggcttg gtaatgctat tggtcgttat cccgaagata cttatgatgg     2220
ttatggtaat tccaagggta atcccgtaag tatttttttt tatctcttcc gtttatactt     2280
ttaatgcaga taatgatgat atcatcacta tgtccggtcg aatagtaatc catttgttgt     2340
atatagtggt ttattgctac tgcaacttat gccgaattat actatcgtgc cattttggaa     2400
tggcaacaac aagcttctgt tactgtcaac tctatcaatc ttggcttctt tagcaagttt     2460
gattcctctg ctagtgtggg tacagtctat acacctggta cagatagctt tgccaacatg     2520
gtatccaatg tcgcctttgc tgccgacgaa ttcttgtcca ccattgacta tcatgccatg     2580
aacaatggat ccatgcatga acaatacaat agagatactg gtatctctca aggtgctcgt     2640
gatttgactt ggagtcatgc tgctttcatt acagctgcca aagccaaatt aggtgcccca     2700
gcattttaa                                                            2709
```

```
<210> SEQ ID NO 15
<211> LENGTH: 2033
<212> TYPE: DNA
<213> ORGANISM: Rhizopus microsporus

<400> SEQUENCE: 15
atgaagttaa tgaactcgtc gatgaagacc tgtgtcttct ttattctctc ctactttct        60 ttgttggtct cttctgctgc agtccctact agtgctgctg tacaggttga atcttacaaa      120
tatgatggca ctaccttctc tggtcgtatc tttgtaaggc taattgatct catttaaaga     180
aaaagagaga aactgatctc gtcaattagg ttaaaaacat cgcctactca aaggtagtca     240
```

-continued

```
ctgtcattta ttctgatggc tctgataact ggaacaacaa caataacaag atttctgctg      300
cttactctga agctatctct ggttcaaatt acgaatactg gacattctct gccaagttga      360
gtggtatcaa gcaattctac gtcaaggtaa ttcttttttt ttctctctat ttattgtgta      420
tactaacgcg accttttgata gtatgaagta agtggctcta cctactatga caacaacggt      480
acgaagaatt atcaaggtaa gcatatgctt aagcaatagc atttctttac tgacctatca      540
aatagtccaa gcaacaagcg ctacctctac tactgctact gctactacta ctacatccac      600
cagcactact accactagca ctggcccaac aagcactgcc tccgtctctt tccccactgg      660
taactctact atctcatctt ggattaagaa ccaagaagaa attagccgtt ttgccatgct      720
tcgtaacatc aatcctcccg gaagtgccac aggatttatt gccgcttctt tatctaccgc      780
tggaccagac tactactatt cttggacccg tgattctgca ttgacagcca atgtgatcgc      840
atatgaatac aacaccacct tcgctggtaa caccacccct ttgaaatacc tcaaggacta      900
cgtcacattc tctgtcaagt cccaatccgt ttctactgtc tgtaactgcc ttggtgaacc      960
caaattcaac gctgatggct ctagctacac tggtccatgg ggaaggcccc aaaacgatgg     1020
acctgctgag cgtgctgtta cttttatgct gattgctgac agctacctta ctcaaacaaa     1080
ggacgcttcc tatgttaccg gtaccttaaa gccagctatc tttaaggatt tggattatgt     1140
tgttagcgta tggtcaaatg gatgttatga cttgtgggaa gaggttaatg gtgttcattt     1200
ctacactttg atggttatgc gcaagggttt gattcttggt gctgattttg ctgctcgtaa     1260
tggtgactct tctcgtgctt ctacctacaa gaacactgct tccacaatgg aatctaagat     1320
atccagtttc tggagtgact ccaacaacta tgttcaagtc agtcaaagcg ttactgctgg     1380
tgtcagcaag aagggtttgg atgtttctac tctgctggct gcaaacattg gtagtcttcc     1440
agatggtttt ttcactcctg gttctgaaaa ggtatttgca aaaagtcgct caatatttca     1500
tagattgtaa acgtgatttt atctagatcc ttgctactgc tgtcgctctt gaaaatgcct     1560
ttgcttcatt gtatcccatc aactctaacc ttccctcata cctcggtaac tctattggaa     1620
gatatcctga agacacatac aacggtaatg gtaactctca aggtaaccca tggttcttag     1680
ctgtcaatgc ctacgctgag ctctactacc gtgccatcaa ggaatggatc agcaatggta     1740
aggttactgt gagcaacatc agcttgccct tctttaagaa attcgactcc tctgctactt     1800
ctggaaagac ttacactgct ggcacttctg actttaacaa ccttgctcaa aacattgcct     1860
tgggtgctga tcgcttcttg tccactgtca agttccatgc ctataacaat ggctctttgt     1920
ctgaggagta tgatcgctct actggtatgt ccactggtgc cagagatttg acttggtccc     1980
atgcctcttt gatcactgct gcttatgcaa aggctggctc tcctgctgct taa            2033
```

```
<210> SEQ ID NO 16
<211> LENGTH: 1469
<212> TYPE: DNA
<213> ORGANISM: Spinellus fusiger

<400> SEQUENCE: 16
```

```
atgaagtcac cttatagcat gaaaaccgtt ttggcattgt tgtctcttac cccgctttttc      60 acgtcagatg ttgttgctgt gccttctggt aactccacca tcactgcctg gggaagcaag     120
caggacggca ttagtttctc caccatgctt ggtaacatca accctcctgg atctagcaag     180
ggattcattg ctgcctctct ctctactgct ggtcccaatt actactactc atggacccgt     240
gactctgctt tggtagctcg tgccatcacc tacaaataca gcacttctta ccagaacgac     300
```

-continued

```
cccaagattc tcggtctctt gaaagactat gttacctacc aggtgaacga acaaacagaa    360
agcaccgtct gcaactgtct cggtgagccc aagttcaacc ccgatggttc tagcttcagt    420
ggtccatggg gaagacccca gaatgatggt cctgctgaac gtgcctccac catgattctg    480
tttgccaaga gttactatgc tcagaccaat gatgttggct atgtcagcaa tacactgaag    540
cctgccattt acaaggactt ggattacatt gtgaatgtgt ggggtaacaa ctgctttgat    600
ctctgggaag aagtcaatgg tgtccacttc tataccttga tgatgatgcg ccatggtctt    660
gtccagggct ctatctttgc taacactctc ggtgattcta ccagagccaa cacctacaag    720
acagctgccc agaacatcaa gaacagaatt gatactttct gggaatctgg aagcaactac    780
attgtcgtca ctcagaacca gagtgcaggt gttaacaagc cctctggatt ggatgttgct    840
gttttgcttg ctgccaacca aggtggtctg ggagatggtg tctatactcc tggctctgac    900
aaggtaaatg attatctgct ggtctttta gacacaccaa actcatccat tttatatgat    960
aggttcttgc tactgctgtt gctcttgaga aatctttgc cagcttatac cctatcaaca    1020
agaaccttcc ttcttactac ggtactgcca ttggaagata ccccgaagac acctacaatg    1080
gcaatggcaa ctctgaggcc aacccatggt tcattgccac caccacttat gctgagttgt    1140
actaccgtgc tatcagtgaa tggaccaatg gctcaggtgt cactgtaaac agcatcaaca    1200
aggagttctt cagcaagttt gatgccagtg ccaccaacgg aaaggtctac acacctggat    1260
ccgatagctt caacagcctg gtcaacaacg ttgccattgc tgctgataac ttcctttcta    1320
ctgtgagata ccaccaaacc agcaatggct ctttatctga acagttcaac cgctacactg    1380
gattcatgac aggtgcccgt gatcttacct ggtcccatgc tgccatggtc actgctcttg    1440
ctgccaaggc cggtactcct tccccttaa                                       1469
```

<210> SEQ ID NO 17
<211> LENGTH: 2402
<212> TYPE: DNA
<213> ORGANISM: Syncephalastrum racemosum

<400> SEQUENCE: 17

```
atgcagctaa acctttactg gaaaagtctg gccgtgctcg ccctgattca gatggtcatg     60
gcggccactg tgccaaccac tcaggttcag ctagactact acacgtactc caacaatgta    120
ctgtcgggcc gcatctatgt aagccgagat agaccaggaa acgccgctga aagagtgctc    180
attacatata tatctttct tgcaggtgca aaatattgca tactcaaagg tggtcaaagt    240
gatttactca gacgcgtctg gaaactggaa caacaacggc aatactatct ccgcaagcta    300
tgtcgagagt atctctggta ccaactatga gtattgggat ttctcggcca ccattggcac    360
ggctggtatc aagcaattct atcttcgcgt gagtttgtca cctgccttgt ctcttattat    420
taagccatta ggctcgagtg acattaatgc tgtatttcat gtgcatatta gtatgacgta    480
tcaggtagca cttactatga caacaatggt ggggataata acaactacag tacgtattat    540
cggacagcga gagtcactta gccacttatg taacatatta cacatataga cgtcgtcgcg    600
acgacttcaa caacctcgtc atccacaacc acgactacgg ctacaacgac aaccgccaca    660
aagactacta gcaccacaag tgccacagct acgcccacgt catctgcgac ttttcctagc    720
ggcaattcaa cgatcaccac ttgggcaaaa tctcaaaagg atattagctg gaagacactg    780
ctcaccagcc tgaatccctc cggcactgcc aaaggcttca ttgctgcatc gctttccaca    840
tcgaacccag actattatta tgcttggacc cgcgactcgg ccctggttgc caggttggtc    900
gactccattt attgcacttg ggcaagcacc cttcttacgc gacgaattga tggttagaac    960
```

```
catggtcaac atgtacaaca ccacggaagc tggaagtgcg tcggttctag gccttttgca      1020
agactatgtc accttccaaa ttaatgccat gagcacttct acggtatgca actgccttgg      1080
tgagcccaag ttcaacccgg atggctcgag ttacaccggt gcctggggcc ggtaattgca      1140
aaatcacgac ggtttgcgtt tcgtaatggt tgatttctgt gtttgtagtc cccagaacga      1200
tggccccgct gaacgtgcca gtaccttcat tctgtttgcc gatagttata tcgctcaagg      1260
tggccagctc tcatatgtga caggaactct cgctcctgct atctacaagg atctcaacta      1320
tgtcgtgagc acctggtcaa ataactgctt tgatctttgg tatgatattg gtcgatattg      1380
catatttccg tcacgtattt ctaactcgtt ctaatatagg gaggaagtca atggccgaca      1440
tatgttcacg taaggaagga tatgcgctaa cgttcctttc tcagatttga tctcatttct      1500
tgtagccttg ctgtcatgcg ccgtgctctc ttggatggtg tcaacttcgc ttcgcgcatc      1560
ggcgatacga cttactcgag cacgtggtcc agtaccgcat cgtctatcca gtcaactttg      1620
tccggctact atttgtcgag cggcaattac attactacgg tgcagaactt ccagtcaggc      1680
gtcagcaaag ccggttatga cgtctcgact ttgattgctg ctaatgtggc cggtatgggc      1740
gatggcttct ttacgcctgg ctcggacgag gtgaaccatc aaaccgcgta aacttcgtag      1800
tagaagactg accgtggtgt aggtactcgc cactgctgtg gctatcgaga acaaattctc      1860
cagcttgtac ggcgtcaacg cgaacaaagc ttcttatctc ggcactgcca tcggacgcta      1920
cccagaggat acctataatg gctatggtaa cggccaagga aacccggtaa gtattactgc      1980 actttttcgtt tgtactcaaa catgcagaac cgcgatctaa atggcaggtc cgtatgtagt      2040
ggtttattgc aacggcggca tatgctgagc tgtactatcg tgccattttg gagtggcaga      2100
ccaagtcctc catcgtagtc aactccaaaa acctcggttt cttctccaag tttgattcat      2160
ccgctgcagt gggtactacc tatacgcctg gcaccacagc ttacagcaac atggtgcaaa      2220
atgttgcctt ggctgccgac cggttcttgt cgaccgtaca gctccacgcc gctaccaatg      2280
ggtccatgag cgaacagttc aatcgtgata caggcgttat gcagggtgca cgggatttga      2340
cttggtctca ctctgctttc attaccgctg cgcgcgccaa gcttggttcg cccgtctact      2400
ag                                                                     2402
```

```
<210> SEQ ID NO 18
<211> LENGTH: 1827
<212> TYPE: DNA
<213> ORGANISM: Syncephalastrum racemosum

<400> SEQUENCE: 18
atgcgcgcta caacagctat tctgtctctc tttaccactg cgtccatggc gctggccgcc       60
aacagcactg tcccggatgg caactcaacc acgaccgccc gggtcaagaa gcaagaagcc      120
atctcttgga cagatctcaa gaccaatgtc aaccctgaag gtgcggccaa gggctttatt      180
gctgcgtctc tttccacatc ggagccagat tattactatg cttggacgcg tgattctgct      240
cttgttgcgc ggtatgctca acgtgacatt tacaatgcct aatactgaca taataatatt      300
cagcgtcatg gtcaacaagt acaacacgac cgatgcgggt gacgccaacc tgctaggtct      360
tttgcaagac tatgtgtcgt ttcagatcaa tgccatgggt gaaagcactg tctgcaactg      420
cttgggtgag cccaagttta acccggtaag aagacaaaaa acataagaca gaaaagaaca      480
atcggctgat tctgggacct tgttacacac aggatggctc tagctacact ggagcctggg      540
gccggtgcgt atttgattag atgctcctgt accacgttaa tgttaatatt tgcccacata      600
```

-continued

```
tagccctcag aacgatggcc ccgcggagcg tgcttcgact tttatcttgc ttgctgatag      660
catgattgct caaaagtcag cgaatggttc ttatgtctcg dataccttag ccoctgccat      720 ttacaaggac ttggcctatg ttgcctccac ctgggagaat gcttgctacg atctttggta      780
aggctattcc aatgcaaatt atgtctgcta gcttcatttc taacgaaccg gttctttaat      840
cttttaggga agaagtcaat ggcaagcaca tgtacacgta agtactatat attctttgaa      900
tgattattag taaagtatat atatgactaa tgatgctttg tctttgtatc gctagcctgt      960
ccgtgatgcg ccgcgctctt ctagatggtg ctgattttgc tagccgccag ggtcagacgg     1020
cgaatgtgac ctcgtggaag tcaaccgccg acaagatcaa gtcttcgctc gagggtttct     1080
tctcatccga taatggttac attgaggtga cccaagatat gcagggcggt gtccaaaaga     1140
agggcctcga tgtgtcgacc ttgatcgcag ccaatattgg cagcatgggc gacggtaata     1200
tcttcttatg cgagctatat gcctgcgctc aacaacatta ttaggcttct acaccccggg     1260
ctcagacgag gtgctagcca ctgccgtggc tgtcgaggct gcgttcgctg acctctacaa     1320
gatcaatcag aacacgaact ccaccggcct tggtaccgcc atcggccggt accccgaaga     1380
cacttacaat ggtgtcggca acagccaagg caaccccgta agtcactatc atctttgttg     1440
attatctatt ttaacttcta ttagtggttc attgcaacca acacgtttgc tgaactctac     1500
tatcgcgcta ttcttgagtg gcagaacaag ggtacaatca cggtcaactc ggtcaacgcg     1560
gccttcttct ccaagtttga ttcctcggct aaggctggca ctacatacaa gtcaggcagc     1620
actgaatttg acagcttgat caataaggtg gctttggctg ccgatgcctt cttgaacaca     1680
gtccagacgt atgctgcaag caacggctcg atgagtgagc aatacaaccg tgacaccggt     1740
gcgctgacgg gtgctcgcga ccttacttgg tcacacgcca gcttgatcac tgctgcaaac     1800
gccaagctcg gtactcctta taactag                                         1827
```

<210> SEQ ID NO 19
<211> LENGTH: 1796
<212> TYPE: DNA
<213> ORGANISM: Thermomucor sp.

<400> SEQUENCE: 19

```
atgaagcttg gccgtatcgg attcagtatc ctgtcagttg cctccgtctt ttctcaagct       60
gttgttactg ctgctgctgc tgcttcggta ccctccggaa acgcgaccat cacgtcgtgg      120
atccaagagc aactggccat tagctggaac accatgctga cgagcgtcaa tccggttggc      180
gccgtgaccg gcttcattgc cgcgtcgtta tcgaccgcga acccggacta ctactactgc      240
tggacgcgcg acgctgcgct ggtggcacgc gtcatgacgt tcatgtacaa caccacccaa      300
gccggcgaca gtggcctttt gggaatcctg caagactatg tgtcgttcca gatccatgcc      360
atgggtgaat ccacggtttg caactgcctt ggtgagccca aatttaatcc ggtaaatgcg      420
cggccaatcc cccaaacttt ctatacgtat atatattggt tcaagctgaa cgatggttta      480
ggatggttcg agttacactg cgcgcatggg ccggccccag aacgatggac ctgccgagcg      540
ggcgtcgacg tttatcaaaa ttgcagatag ttaccttacc caaaccggtg acgtttcgta      600
cgtcacgaat acgctgaaac caggtgcgta tatatatata tatatatatg tatatatata      660
tagaacagga tacaacaaaa ggtagtagac gaagaactca acttttttc ggacaaagcg      720 atctatgagg atctggacta tatcgtgaat gtttggcaaa atacgtgctt tgatctgtgg      780
gaagaagtct atggcatgca tatgtacacg taagttgtat tctctctatt atgtccattc      840
ctgtggatct tcgtacttat gatgtatgtc catgtaaaga ttggccgtga tgcgccgcgg      900
```

```
gttactggac ggcgcggatt tcgcgacgcg caacggcgac accgacaaag ccagcaccta      960
caccagcacg gcaacgtcca tccagacccg gctcgcgacg ttctggtcgg atagcaatgg     1020
ctacattact gtgacgcaag attaccaaag tggggttagc aaagccggac ttgacgtctc     1080
gactctgatt gctgcgaatg tggccggcat gaacgatggg ttctttacgc cgggctcgga     1140
tgaggttcgt gttatacata cttgtacacc aaggaggatg cctattgaca aaaaaagcgc     1200
ggttgttcta gatacttgct acggctgtca aggtggaagc tgcgtttgca aacctttacg     1260
gtatcaacat caacaaggcc agttatcttg gtaatgcaat tggtcggtat cctgaagaca     1320
cgtataacgg caacggcaac tcggaaggca acccggtaag ctatcccatt tttgtccccc     1380
gatttctaag tttgcaactt tctctaacca atgttgcttg gtgttaaaag tggttcattg     1440
ccacagcggc gttcgcggag ctttactacc gggcgatcat ggagtggcaa ttgcgcggca     1500
gcagcatcac ggtgaactcg gtcaaccagg gcttcttcac caagtttgat ccgtcggcta     1560
cggctggcac gacgtatacg ccaggcacgg acgcgtttaa ctcgctgatt gacaatgtgg     1620
cgctggcagc cgatcagttc ttctcgacca tccacctgca ccgtgcgacg aacggctcca     1680
tgagtgagca gtataaccgc gatacggggt tcatgcaagg cgcgcgggat ctgacttggt     1740
cccatgcggc gtttatcacg gccgccaagg cgaagcaggg caccccgtca ttctag        1796
```

```
<210> SEQ ID NO 20
<211> LENGTH: 2883
<212> TYPE: DNA
<213> ORGANISM: Zychaea mexicana

<400> SEQUENCE: 20
atgagaccag ttcatctttg gaaaagcctg cttttagctg cggctactgc agtcacgggt      60
acaatagctg ttgatgtacc ttcggtgcct attcagttgg agtcctatac ttattccgaa     120
aatgtattcg ctggtcgaat tttcgtaagt tatggaagcc ataataataa agtggcagga     180
tctatgatgc acaataacta aactctctga ttactcgtta actccctttg tattttgata     240
tctaggttca aaacattgcg tacaccaaag aagtcaacgt gttctggtcc gatgcttctg     300
atgactggaa cgacaatggc aactctgtgg cagctagtta ttccgaatcc atcgcagaca     360
ccaactatga gtactgggaa ttttcaacca cgattggatc tgccggtatc agccaaagtt     420
atttgagagt aagtcccaat cgccatttta tatatattgt gcacgtcagc aatagagctc     480
tgcagtaaag atataacttc agataacctt gacatctatg tctgaacaat ttcgggtttt     540
agtatgacgt atctggatca atctattatg acaataacga cagccagaac tacggtaagc     600
agagtatgag ctacatcttt gaagccttca taatgaagca gctgcacata tactgcctcc     660
taattgggtt gcacgtacaa cgggaaggat tattgctaac tttatatgtt acgtttgtac     720
cagatatcac cgagacatcg acccctacca caaccactgc tgctcccact tctaccacta     780
gcactcctac tactactacg gatggtggat cgacaactac taccactgcg acatctgttc     840
ctacgtctac tggtgttcca gagggcaatg ccaccatcag cgaatgggca agcgctcaat     900
tggatatcag ctggccaaac cttatgatga atgtaagtca acaatactct gtatagtgca     960
gcatacatta caagccattc aattaatcga attttcttac attctctttt tttgttccca    1020
ggtaaaccca tcaggtgcag tgactggctc tatcgttgcc tctttgtcga ctagtaaccc    1080
agattatttt tacatttgga cgcgagatgc tgcaatggtt gcacgcgtga tggtatacat    1140
gtacaacaca accgaagctg gtgacacaaa tctgttaaat gccttgaccg actatgttac    1200
```

-continued

```
gttctccatc agctccatga atgtggatac cgtctgcgac tgtttgggcg agcccaaatt      1260
caatgtggta agtagagaaa ttttataaaa acagggctaa gtgatactga agagcaagga      1320
taaaaaagtg aggacaaaaa gagtagcaat actagtgtta ataatatacg attcattata      1380
ggatggaagc ggttacaccg gtgcgtgggg aaggtacagt aattatggaa ctagaggaca      1440
gaaaaggctg tattttttgt attatgtgat atgcactgaa aggttggatg aatctttgt       1500 ttgcaacaat gtactcacat tcatttatgc attagacccc aaaatgatgg acctgcagag      1560
cgtgcttcaa ccatgatttt gatcgcagac agctatatcg ctcagggcgg tgatgtttcc      1620
tatgttactg acacgctgaa gccaggtatg taaattttct atactttact caccatcagc      1680
aacacggagt tttcctgtca tagataacaa acgatcattg acacattatg gtctgtgatc      1740 tttttttatag ccatttacac cgatcttgat tatgttgttg atacttggtc taacgtttgc     1800
ttcgatcttt gggaagaagt gaatggcatt catatgtgta agctatttgt gataatcatt      1860
tttatatgat gtaaaaggaa agtctcttgg ctcactagta tgatgaaaca tagacacctt      1920
gtcggtgatg cgcaaggctc ttctcgatgg cgccaatttt gctacccgca atggcgacac      1980
ctcgcgtgtc agcggttatg aaagcaccgc ttcatccatc aagaccagac tcgaatcatt      2040
ctggtcctct agcaacaact acatcaccgt tacccaatcg ttctcgggag gtgtttcaaa      2100
ggccggcttg gatgtctcta cattgattgc tgccaacctt gcaagcatga acgatggtaa      2160
gtgattactt cacatgaaaa aggtgtatat ttttactcac atatgtctgt cccttgatgg      2220
ttgtaattta ggtttctata ctcctggctc tgatgaaatc ttggccacgg ctgtcgctat      2280
tgaaaactct tttataagtg agtatacgct caatcaaaac agaccatcgt ggctcagcac      2340
agctattggc cgatatcctg aagattctta tgatggctat ggtaactcgc aaggcaatcc      2400
agtaagtaaa aagagtagtt cctttacgta acgctactac tcgtagtgat gatgtgcaca      2460
agagcagcaa atccaattca gctgtagttc gattactgac aatgcaatta tgtcctctag      2520
tggttcattg ccactgccac atatgctgag ctctactacc gtgccatttt ggagtggcaa      2580
caacaagcat ccatcagtgt caactctgtc aacctgggct tctttagcaa gtttgattcc      2640
gatgcttctg tcggcactgt gtacacaccg ggcactgaag attttgccaa catggtctcc      2700
aacgtagcct tcgctgctga cgaattcttg gctaccattg agaaccattc tgccgttaat      2760
ggatccctct ctgagcaata taacagagat actggtatta tgcaaggcgc cagagatctc      2820
acctggtccc atgccgcatt tattactgct gcgaaggcaa agcagggtgc accaatacac      2880
tga                                                                    2883
```

<210> SEQ ID NO 21
<211> LENGTH: 1407
<212> TYPE: DNA
<213> ORGANISM: Artificial Sequence
<220> FEATURE:
<223> OTHER INFORMATION: Sequence is synthesized

<400> SEQUENCE: 21

```
atgccttctt ggaaaaccct gttcctcctc ctgggcccta tcgccaccgc tgccgctgct        60
cccgttgaca agcagtctct gcctaccggc aacagcacca ttagctcttg ggtcagcaag       120
caggaggaca tcagcttcag cgagatgctc cgaaacgtca accctgaggg caccgccaag       180
ggcttcgttg ccgcgtcgct cagcaccgct ggccccgact acttctacac ctggacccga       240
gacgccgctc tcgtttcccg agttattgct tacaagtaca acaccaccaa cgctggcgac       300
tctaagatcc acggcgttct ggacgactac gttaacttcc agattaacac ccagtctgag       360
```

-continued

```
tctacccctt gcaactgcct gggcgagcct aagttcaacc ctgacggcag ctctttcacc        420
ggcccttggg gccgccccca gaacgacggc cccgctgagc gagcctccag tttcatgctg        480
attgccgact ctttcctcag ccagaccaag aacgcctctt acttcaccaa caccctcaag        540
cctgccattt acaaggacct cgactacgtc gttgacacct ggtctaaccc ttgcttcgac        600
ctgtgggagg aggttaacgg catccacttc tacaccctca tggttatgcg acgatctctc        660
ctcgacggcg ctaacttcgc cacccgaaac ggcgacaact ccaaggcctc aacctactcc        720
ggcgtcgccg ccaagattca ggctcgactg aactctttct gggacgccgg caagaactac        780
attaccgtta cccaggacta caagaacggc gttgagaagc ctagcggcct cgacgttagc        840
accctcattg ctgctaacgt cgctggcatg ggcgacggct tctacacccc cggcagcgag        900
cgcatcctcg ctaccgctct ggctttcgag aagagcatgg caagtctgta ccctctgaac        960
aacaacctgc ctagccacct gggcaacgcc attggccgat accccgagga cacctacaac       1020
ggcaacggca actcccaggg caaccttggg ttcctcgcta ccaccgcttt caccgagctg       1080
tactaccgcg ccattctgga gtggaagaac accggcgtta ccgtcacccc tatttctaag       1140
gacttcttcg tccgattcga cagcagcgct gctcctggca agaagtacaa ccccggctcc       1200
caggagttcg ctaccctgac ccagtctatt gctgccgccg ctgaccgatt catgtccacc       1260
gtccagtacc accagaaccc taacggctct ctgtctgagg agttcgaccg atctagcggc       1320
tacatgaccg gcgcccgaga cctgacctgg agtcacgctg ctttcattac cgctgctcag       1380
gcccgagctg gctctccttc tttctaa                                           1407
```

<210> SEQ ID NO 22
<211> LENGTH: 1818
<212> TYPE: DNA
<213> ORGANISM: Artificial Sequence
<220> FEATURE:
<223> OTHER INFORMATION: Sequence is synthesized

<400> SEQUENCE: 22

```
atgaagctgt tcggcaccct gaaggcttct ttcgtttttcc tgattggctg cattgttttc         60
gctatggccg acaccgtccc taccacccag gttaagctgc agtcttacac ctactctggc        120
ggcgtcctgt ctggcaccat ctacgtccag aacattgact acaccaaggt tgttaccgtt        180
atatattccg acggctctgg caactggaac aacaacggca acaccattag cgcttcttac        240
agcagctcca tttctggcac caactacgag tactggacct ctctgccag cgtcagctct         300 attcagcagt ctacatctc ttacctcgtt gacggcacca cctactacga caacaacggc        360
ggctacggcg ctaactacgc cgttaccgcc accaccacca ccgcttcttc caccaccaag        420
accacctccg gcaccaccaa gacctccacc accagcaccg ctaccgccac cagcaccggc        480
acctcttcct tccctagcgg caactctacc attagcacct ggagcccttc ccagcacagc        540
attagcctgt acgccatgct gcgaaacatt aaccctcccg gctctgctgc tggcttcatc        600
tctgctagtc tgtctacctc cggcccccac tactactact cttggacccg agacagcgcc        660
ctcgttgctc acgtcatcgt taacgagtac aacaccacct accagggcaa ctccaccctg        720
ctgggcatcc tcaaggacta cgtcacctac agcctgaacg cccagaccac ctctaccgtt        780
tgcaactgcc tgggcgagcc taagttcaac cccgacggct cctccttcac cggcgcttgg        840
ggccgccctc agaacgacgg ccccgctgag cgagctgttt ctttcatata tttcgctgac        900
tcttacctga cccagaccct ctgacagctct tacgtcaccg gcaccctcgc ccccgctata        960
```

-continued

```
tacaaggacc tcgactacgt tgtttccgtt tggtctaacg gctgcttcga cctgtgggag      1020
gaagttaacg gcattcactt ctacaccctc atgttcatgc gacgaggcct gctcgacggc      1080
gctaacttcg caagccgaaa cggcgactct acccgagcga gcacctacac ctctaccgct      1140
gctagtatca agaccaagat tgacggcttc tgggtcagca gcggcaacta cgtccaggtt      1200
tcccagtctg ttacctctgg cgtctctaag gctggctacg acgcttccac cctgattgcc      1260
gctaaccagg cctctcgggg cgacggcttc tacacccccg gctccgacaa gatgctcgct      1320
accgccgttg ctattgagtc tcagttcagc agcctgtact ctattaacac caacaaggct      1380
tcttacctgg gcaacgccat tggccgatac cccgaggaca cctacaacgg caacggcaac      1440
tcccagggca accettggtt cctgtgcacc aacgctttcg gcgagctgtt ctaccgcgcc      1500
attagcgagt ggaacgccgc tggctccgtt accgttaaca gcgttaacct cgctttcttc      1560
aagaagtacg actctagcac cagcagcggc accacctaca ccgttggcac cagcgcttac      1620
aacaacctgg ttcagaacgt tgccctcgct gccgacgctt acttctctac cgtcaagtac      1680
cacgccctga ccaacggctc catgtctgag cagtacgacc gatctagcgg catggctacc      1740
ggcgcaagag acctgacctg gtctcacgcc gccatgatta ccgccctgaa ggccaagtcc      1800
ggcacccccg tttactaa                                                    1818
```

```
<210> SEQ ID NO 23
<211> LENGTH: 1809
<212> TYPE: DNA
<213> ORGANISM: Artificial Sequence
<220> FEATURE:
<223> OTHER INFORMATION: Sequence is synthesized

<400> SEQUENCE: 23
```

```
atgaagcctt tcggccctat caagaccacc ctgttcatta ttatctctca cttcagcctg        60
aactccctcg ctgacaccgt tcctaccacc caggttgagg tcaagaccta cacctactct       120
ggcggcgagc tgtctggcac catatacgta gagaacatag actacaccaa ggttgttacc       180
gtcatctacg ctgacggctc tgacgactgg aacaacaacg gcaacaccat tgctgccgct       240
ttcagcgagt ccatctctga caccaactac gagtactgga ccttctctag ctctgttaac       300
tctattaaag agttctacgt caagtacgac gttgacggca acacctacta cgacaacaac       360
ggcaacgcta actaccaggt ttctgctagt agcaccacca ccaccaccgc caccaagacc       420
accaccaccg ctaccaagac caccgccacc gctaccagca ccgccaccgg cagcacctct       480
ttccctagcg gcaacagcac catcagctct tggattaagg ccaggaaga cacctcccgg       540 tccgtcatgc tcggcaacat taaccctcct ggctctgcta ccggcttcat tagcgccagc       600
ctgtctacct ctggccccga ctactactac cactggaccc gagacgctgc cctcgttgct       660
cacgttattg ttaacgacta caacaccacc ctgtctggcg actctagcac cctgcaggtc       720
atcaaggact acgttacctt cagcgtcaac tcccagtccg agtctaccgt ttgcaactgc       780
ctgggcgagc ctaagttcaa ccccgacggc tcctcttaca ccggcgcttg gggccgcccc       840
cagaacgacg ccccgctga gcgagctacc accttcattt tcttcgccga cacctacctc       900
gcccagggcg cgacagctc ttacgttacc ggcaccctcg ccccgctat atatgctgac        960 ctggactacg ttgttaacaa ctggtctacc ggctgctacg acctgtggga agaggttaac      1020
ggcattcact tctacaccct catggttatg cgccgaggcc tcatagatgg cgcttccttc      1080
gcttcccgaa acggcgacag cacccgaagc tcctcttaca cctccaccgc caagtctatt      1140
gctaccaaga ttgactcttt ctggtctgct tctaacaact acgttgctgt ttcccagagc      1200
```

-continued

```
gttacctctg gcgtctccaa ggctggctac gacgcctcta ctattattgc tgctaaccag     1260
gcgtcgctgg gcgacggctt ctacacccc ggctccgaca agatgctcgc tacctccgtt      1320
gccgttgaga acgctttcag cagcctgtac accgttaaca ccggcaaggc ttcttacctg     1380
ggcaacgcca ttggccgata ccctgaggac acctacaacg gcaacggcaa ctctcagggc     1440
aacccttggt atctgtgcac caacgccctg ggcgagctgt actaccgcgc catcaaagag     1500
tggaacgctg cgggaagcgt taccgtcaac tccgttaacc tgggcttctt ccagaagatt     1560
gactccagca ttagcagcgg caccaccttc accctgggca cctccgacta cagcaccctc     1620
gttgacaacg tcgccctcgc cgctgacaag ttcttcgccg tcgtccagta ccacgagcga     1680
tctaacggct ccatgcctga gcagttcggc cgagaggacg gcctgcctac cggcgcgaga     1740
gacctgacct ggtctcacgc cgccatgatt agcgctgccc gagctaaggc tggcacccc      1800 gtttactaa                                                             1809

<210> SEQ ID NO 24
<211> LENGTH: 1806
<212> TYPE: DNA
<213> ORGANISM: Artificial Sequence
<220> FEATURE:
<223> OTHER INFORMATION: Sequence is synthesized

<400> SEQUENCE: 24
atgaagttct ctcacctgtt ccgaaagcct accctcctca ttgttacctt cctgaccgcc       60
accgttttcg ccgagaccgt ccctaccacc tcccaggtta agctcaagtc ttacacctac      120
gacggctcta ccctgtctgg ccagatttac atccagaaca ttgcttacac caaggttgtt      180
accgtcattt actctgacgc cagctctaac tggaacaaca acggcaacac cattgctgcc      240
tcttacacca acggcattag cggcaccaac tacgagtact ggaacttcac cggccccgtc      300
agctctatta acgccttcta cattaagtac gacgtttctg gcaacaccta ctacgacaac      360
aacaacaacg ctaactacca ggttaccaag acctccacca ccaccaccac cagcaccgcc      420
accgctacca ccaccaccaa gacctctacc cctacctcca ccggcgttcc ttctaacttc      480
cctaccggca actctaccat cagcacctgg ctcaagtccc agattggcat ctctcgatac      540
gccatgctgc gaaacattaa ccccgctggc tctgccgttg gcttcattgc tgctagcctc      600
agcaccgcta accccgacta ctactacgct tggacccgag acagcgccct gacctcttac      660
gtcatcgcta acgactacaa ctctaccctc gctggcaaca gcaccatcct gcagattatg      720
aaggactacg ttaccttcag cgtcaagtct cagtccgttt ctaccgcttg caactgcctg      780
ggcgagccta agttcaacccc cgacggcagc tcttacaccg gcgcttgggg ccgcccccag      840
aacgacggcc ccgccgagcg agctaccacc ttcatcctgt cgctgactc ttacctgaag      900 cagaccggcg acgcttctta cgttaccggc accctgaagc ccgctatttt caaggacctc      960
gactacgttg ttaacacctg gaccaacggc tgcttcgacc tgtgggagga ggttaacggc      1020
gtccacttct acaccctcat ggtcatgcga aagggcctga tccgaggcgc caacttcgct      1080
acccgaaacg gcgacagcac ccgagctagc acctacacca caccgctgc tagcatcaag      1140 accaagatgg actctttctg gagctctggc aacaactaca ttgctgtctc ccagtctgtt      1200
accggcggcg tctccaaggc tggctacgac gttgctaaca ttattgccgc taacgttggc      1260
agcctgcagg acgcgttta caccccggc tccgaccgca ttctcgccac cgccgttgcc       1320
gttgaggcta agttcgccag cctgtacggc gttaactcta acctcccgg ctacctgggc       1380
```

-continued

```
aactctattg gccgatacc ctgaggacacc tacaacggca acggcaactc ccagggcaac    1440
ccttggttcc tcgccaccaa cgcttacgcc gagctgtact accgcgccat cgcgagtgg     1500 tacgacaacg gcggcgtcac cgttaactct gttaacctcc ctttcttcaa gaagttcgac   1560
agcagcgctg ctagcggcac cacctacacc gttggcacca ccgctttcaa caccatggtt   1620
tctaacgttg ctgctgccgc tgacaagttc ttcagcaccg tcaagttcca cgcttacacc   1680
aacggctcca tgtctgagca gttcggccga aacgacggcc tgtgcaccgg cgcaagagac   1740
ctgacctggt ctcacgctag cctgattagc gctgccctcg ccaaggctgg caccccctagc  1800 gtctaa                                                              1806
```

<210> SEQ ID NO 25
<211> LENGTH: 1797
<212> TYPE: DNA
<213> ORGANISM: Artificial Sequence
<220> FEATURE:
<223> OTHER INFORMATION: Sequence is synthesized

<400> SEQUENCE: 25

```
atgggtttctt tcaacttcct gaagaagcct gttttcattg ttatcacctg cctcaccgtc    60
agcgtttgcg cccagtctgt tcctaccagc gaccccgtta aggttaagac cttctcttac   120
gacggcaact ctttctctgg ccagatttac atcaagaaca ttgcttacga gaagaccgtt   180
accgttattt actccgacgg caccggcaac tggaacaaca caacaacaa gattgccgct    240 gctttcagcg aggccatctc cggctctaac tacgagtact ggaccttcag cgctagcgtt   300
cctagcatca agcagttcta cgtcaagtac gacgtttccg gcaagaccta ctacgacaac   360
aacggctcta aggactacaa cgtcgttacc agcggcccta ccaccaccag ctctggccct   420
agcaagacca ccaccaacgg ccccgctcct accagcacca acaccaactt ccctagcggc   480
aaccctagca ttacctcttg gattgacaag cagattgaca tctcccgatc tgccatgctg   540
aagaacatta accccgctgg caccgttaag ggcttcattg ccgccagcct cagcacctct   600
aaccccgact acttctacgc ttggacccga gacgccgctc tcgttgccca cgttgttgct   660
aacgactaca accgaaccaa gtctggcgac gccacctacc tgggcctcct gaaggactac   720
gtcaccttct ctattaactc ccagaacacc cctaccgctt gcaactgcct gggcgagcct   780
aagttcaaca aggacggctc cggctacaac ggcccttggg gccgccctca gaacgacggc   840
cccgccgagc gagctgacac cttcgtcctc attgccgact ccattctgac ccagaccaag   900
gacgtctctt acgttaccgg caccctgcgc ccgctatt acaccgacct cgactacgtt    960
gtccgaacct ggtctaacgg ctgcttcgac ctgtgggagg aggttaacgg cgtccacttc  1020
tacaccctca tggttatgcg acgagctctc ctcgttggcg ctaacttcgc tagccgaaac  1080
ggcgactctg cccgagcttc taactacaac aacgctgcta actccattaa gtctaagatt  1140
gactctttct ggtcctctaa caacaactac gttgctgttt cccagtctgt taccggcggc  1200
gtttccaagg ctggctacga cgtcagcacc ctcatcgctg ctaacgttgg cagcctgtct  1260
gacggcttct acacccctgg ctctgagcgc atgctcgcca ccgccgtcgc tattgaggac  1320
aagttcgcta acctgtacgg cattaaccga aacctgacac agcctgggc caacgccatt   1380 ggccgatacc ccgaggacac ctacaacggc aacggcaact cccagggcaa ccccttggtc  1440
atcgccacca acgcttacgc tgagctgtac taccgagcta ttaaggagtg gaacaacaac  1500
ggcggcgtca ccgtcaccaa cgttaacctg aacttcttca agaagttcga cggcagcgct  1560
agcgttggca ccaagtacac cgctggctct gctgcttaca acaccctgac ccagaacatc  1620
```

-continued

```
gccctcgccg ctgacaagtt cttcaacacc gtcaaggtcc acgctgccac caacggctcc   1680
atgtctgagc agtaccaccg agacaccggc agcatgaccg gcgcaaggga cctgacctgg   1740
tctcacgcta gcctgattac cgccgccctc gccaaggctg gcacccccgt cgcctaa       1797

<210> SEQ ID NO 26
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 26
atgaagctgt tcggcctgcc cctcaagcct agcctgttct tcgtcgtctc ttacctgtct    60
ttcctcgctt ctgctgccag catccctagc agcagcgagg tccagctcga cacctacgct   120
tacgacggcg ccaagttctc tggcaagatt tacgtcaaga acattgctta cgagaagacc   180
gttaccgttg tttacgctga cggctctgac aactggaaca caacggcaa cattattagc     240 gctaccttca gcacccctat ttccggctct aactacgagt actggacctt cagctctagc   300
attagcggca ttaaggagtt ctacatcaag tacgtcgttt ccggcaagac ctactacgac   360
aacaacggca ccaagaacta ccaggtttcc accaccagct ctaccaccac cgctagcacc   420
accaccgcta cccgaaccac caccgctggc accaccagca cctctaccac cgctgccct    480 acctctacct ccagcggctc cttccctagc ggcaactcta ccgttagctc ttggattaag   540
cgacaggaga agatctcccg attcgccatg ctgcgaaaca ttaaccccc tggcagcgct     600 gctggcttca ttgctgctag cctgtctacc tctggcccg actactacta ctcttggacc     660
cgcgacagcg ccctgacctc taacctgatt gcttacgagt acaacaccac cctgtctggc    720
aacaccacca ttctgaacat cctgaaggac tacgttaagt tctccatcag ctcccagacc   780
accagcaccg tttgcaactg cctgggcgag cctaagttca accacgacgg cagctcttac   840
accggcgctt ggggccgccc ccagaacgac ggccccgctg agcgagctaa caccttcatc   900
ctgttcgccg actcttacct cgaccagacc aaggacgctt cttacgtcac cggcaccctg   960
aagcccgcta ttttcaagga cctcgactac gttgttaacg tttggtctaa cggctgctac   1020
gacctgtggg aggaggttaa cggcgttcac ttctacaccc tcatggtcat gcgaaagggc   1080
ctcctgctgg gcgctgactt cgctaagcga aacggcgact ctacccgagc tagcacctac   1140
accaacaccg ctagcaccat tgctaccaag atctcctctt tctgggttag cagctctaac   1200
tggatccagg tttctcagtc tgttaccgcc ggcgtttcca agaagggcct cgacgtcagc   1260
accctcctcg ctgccaacct gggctccgtt gaggacggct tcttcacccc cggctccgag   1320
aagattctgg ccaccgccgt tgccattgag gacgctttcg ctagcctgta ccctattaac   1380
tctaacctgc cttcttacct gggcaactcc attggccgat accccgagga cacctacaac   1440
ggcaacggca actcccaggg caaccCttgg ttcctcgccg ttaacggctt cgccgagctg   1500
tactaccgag ctatcaagga gtgggttaac aacggctccg ttaccgtctc taacatctcc   1560
ctgtccttct tcaagaagtt cgacagcagc gccaccgccg gcaagaccta caccgccggc   1620
accgctgact tcaacaacct cgcccagaac attgctctgg gcgctgaccg attcctgtcc   1680
accgtccaga cccacgcttt caacaacggc tccctcgccg aggagtacga ccgaaccacc   1740
ggcgtcagca ccgcgcccg agacctgacc tggtctcacg ctagcctcat taccgctgct   1800
tacgccaagg ctggcagccc tgccgcctaa                                     1830
```

<210> SEQ ID NO 27
<211> LENGTH: 1827
<212> TYPE: DNA
<213> ORGANISM: Artificial Sequence
<220> FEATURE:
<223> OTHER INFORMATION: Sequence is synthesized

<400> SEQUENCE: 27

```
atgaagttct ctaacctcct gaagaagccc ctcctgctca ttgctggcat tctcgctgcc       60
accgtcgttg ccgagaccgt ccctaccacc gctgctgtta aggttaagtc tttcacctac      120
gacggcagca ccttcgctgg ccagatttac gtcaagaaca tcgcttacac caagaccgtt      180
accgttattt actctgacgc ctctaacaac tggaacaaca acggcaacac cattgccgcc      240
tcttacagcg agggcatctc tggcaccaac tacgagtact ggaccttcag cgcccctgtt      300
tccggcatca agcagttcta cgtcaagtac gttgtcagcg gcaccaccta ctacgacaac      360
aacaactctg gcaactacca ggttaccacc accaccacca ccaccgcccc taccagcacc      420
acctccggcg gctctagcac caccaccggc ggctccacca ccaccgccac ctctgtccct      480
accggcgtcc ctagcggctt ccctaccggc aacagctcta ttagctcttg gattgacggc      540
cagacctccg tttctcgata cgccatgctg cgaaacatta accccgctgg cgctgtttcc      600
ggcttcattg ctgctagcat gtctacctct ggccccgact acttctacgc ttggacccga      660
gacagcgccc tgacctctca cgtcgttgct tacgactaca acaccaccct cgctggcaac      720
tctaccatcc tgggcctcct gaagaactac gttaccttct ctattaactc tcagaccacc      780
agcaccgttt gcaactgcct gggcgagcct aagttcaaca aggacggcag ctcctacacc      840
ggcgcttggg ccgaccccca gaacgacggc cctgctagcc gagctgacac cttcatcctc      900
attgccgact ctattctgaa gcagaccggc gacgctacct acgttaccgg cacccctcgcc      960 cccgctattt acaaggacct cgactacgtt gtcagcacct ggtctaacgg ctgcttcgac     1020
ctgtgggagg aggttaacgg cgttcacttc tacaccctca tggtcatgcg acgaggcctg     1080
attaagggcg ctaacttcgc ttcccgaaac ggcgacaaca cccgagctaa cacctacacc     1140
aacaccgccg ctagcatcaa gaccaagatt gactctttct ggaactctaa cggcaactac     1200
gttaccgttt cccagtctgt taccggcggc gtctccaagg ctggctacga cgctagcgtc     1260
ctgattgctg ctaacctggg ctctgtccag gacggcttct acacccctgg ctccgacaag     1320
atgctcgcta ccgctgttgc cattgagtct aagttcgcca gcctgtactc cattaaccag     1380
aacctgaacg gctacctggg caacgccatt ggccgatacc ccgaggacac ctacaacggc     1440
aacggcaact cccagggcaa ccccttggtt catttgcacca acgctttcgc cgagctgtac     1500
taccgcgcca ttaaggagtg gttcaacaac ggcggcgtta ccgttacctc catcagcctg     1560
aacttcttca agaagttcga cagctctgct gccgttggca ccaagtacac cgttggcacc     1620
tccgccttca acagcctcgt ccagaacgtc gccgtcgctg ccgacgcttt cttcagcacc     1680
gtcaagttcc acgccgctac caacggctcc atgagcgagc agtacggccg atctgacggc     1740
ctcatgaccg gcgccagaga cctgacctgg tctcacgcta gcctgattag cgcttcttac     1800
gccaaggctg gcagccccgc cgcctaa                                        1827
```

<210> SEQ ID NO 28
<211> LENGTH: 1809
<212> TYPE: DNA
<213> ORGANISM: Artificial Sequence
<220> FEATURE:
<223> OTHER INFORMATION: Sequence is synthesized -continued

```
<400> SEQUENCE: 28
atgaagctga actccgtttg gaaggctttc agcattctgc tcatggctac tatggctttc      60
gctgctaccg tccccaagac ccaggttaag ttagaggctt acacctactc tgactctatt     120
ttctctggcc gaattttcgt ccagaacatc gactacacca agattgttac cgtttactgg     180
tctgacgcct ctaacaagtg ggacagctct aagtactaca ccgaggccgc ttacacccac     240
agcatccccg gcaccaacta cgagtactgg gacttcagcg ctaccattgg ccctagcggc     300
atcaagcagt tctacatctc ttaccaggtc cgaggcgtca cctactacga caacaacggc     360
ggctacggcg tcaactacga cgtcatctcc agccctccta ccacctctga cgccaccacc     420
attcctacca ccaccacctc cgctattcct agctctacca ccaccatccc tgccagcacc     480
ggcgtcccta cgggcaactc caccattacc gtttgggctg actcccagca caagatttct     540
tggaaggcta tgctcgctaa cattaaccct cccggcagcg ccaccggctt cattgctgcc     600
tccctgtcta cctccggccc tgactactac tacgcttgga cccgagacgc cgcaatggtt     660
gctcacgtta tcgttaacgc ttacaacacc accaaggctg gcgacgctac caccctgggc     720
gttctgaagg acttcgttac cttccagatc aaggctatgg ctacctctac cgtttgcaac     780
tgcctgggcg agcctaagtt caaccccgac ggctcctctt acaccggccc ttggggccgc     840
ccccagaacg acgccctgc tgagcgcgct accaccttca tcctgttcgc cgactcttac     900
ctgtctcaga ccggcgacgc tgcttacgtc accaccctga agcgagccat tttcaccgac     960
ctcgactacg ttgttaccac ctggcaggac aactgcttcg acctgtggga ggaggttaac    1020
ggcctgcaca tgtacaccct cgctgttatg cgacgatctc tcgttgacgg cgcctctttc    1080
gccgctcgaa acggcgacaa cacccgagcc tctacctaca ccaacaccgc caagtctatt    1140
gagaccaagc tcgcctcttt ctacaacagc tcctctaact acgtcgttgt taccaagaac    1200
ttcgctggcg cgttaacaa ggctggcctg gacacctcca ccctgattgc tgccaacacc    1260
gctggcctgg gcgacggctt cttcacccc ggcagccccg agatcctcgc taccgccgct    1320
gccattgaga gtctttcgc cgacctgtac ggcattaaca agcagattcc taactggctg    1380
ggcaccgcta ttggccgata ccccgaggac acctacaacg gcaacggcaa ctctcagggc    1440
aacccttggt tcatttgcac cgccaccttc gccgagctgt actaccgagc tattctggag    1500
tggcagcacg ccggcagcgt taccgtcaac aacgttaacc tgcctttctt caagaagttc    1560
gactctagca cctccagcgg caccacctac accgttggca ccagctcctt cgacagcctg    1620
attagcaagg ttgcttacgc cgctgacaac ttcttctcta ccattaagta ccacgctgcc    1680
accaacggca gcatgtctga gcagttcaac cgagacaccg gcttcatgac cggcgccagg    1740
gacctgacct ggtcgcacgc tgccttcatt accgccgcta aggctaaggc tggcacccc    1800 gtttactaa                                                           1809
```

```
<210> SEQ ID NO 29
<211> LENGTH: 1821
<212> TYPE: DNA
<213> ORGANISM: Artificial Sequence
<220> FEATURE:
<223> OTHER INFORMATION: Sequence is synthesized

<400> SEQUENCE: 29
atgcgcccta gctcgtttg gaagtctctc ctgatggttg tcctgaccgc tgcaatgggc      60
acctacgccc agaccgtccc tagcgttcct attaagttag aatcttacac ctactctgac     120
```

-continued

```
aacgttttcg ctggccgaat tttcatccga aacattgctt acaccaaggt tgtcaaggtt      180
ttctggtctg acgagtccgg caactggaac ggcaacggca actacgttga cgcctcttac      240
tctggctcca tctccggcac caactacgag tactgggagt tcagcaccac cattggctct      300
gccggcatct cccagtctta cctgcgatac gacgtcagcg gctctaccta ctacgacaac      360
aacggcaacg ctaactacga cattgaggag gacagcaccc ctacccctac caccaccacc      420
acctctacca ccaccatcac caccaccacc acctccggca cctctacccc tacctctgtt      480
cctaccgagg tccctgccgg caacaccacc gtcaccgact gggttaacga ccagttagaa      540
atttcttggc ctagcctcct caagaacgtc aaccctagcg cgctgttac cggcttcatt       600 gctgcatctc tgtctaccaa cgaccccgac tacttctact gctggacccg agacgccgcc      660
ctcgttgccc gcgtcatggt ttacatgtac aacaccaccg aggctggcga cacctccctg      720
cgatctaagt tacaggacta cgttaccttc cagattaact ccatgaaaac cgccaccgtt      780
tgcaactgcc tgggcgagcc taagttcaac aaggacggct ccggctacag cggcgcttgg      840
ggccgccctc agaacgacgg ccccgctgac cgagctatta ccctgattct gttcgctgac      900
tctttcatcg cccagggcgg cgatgtttct tacatcacca acaccctgaa gcctgctatt      960
tacaccaacc tggactacgt tgttaacacc tggtctaacg tttgcttcga cctgtgggag     1020
gaggttaacg gcgtccacat ttacaccctg tctgttatgc gaaagggcct cctggaaggc     1080
gctgacttcg cttctcgaaa cggcgacagc acccgcgcca acacctaccg atctaccgcg     1140
tcctccatca gacccgact ggagtccttc tggagcagct ctaacaacta cattaccgtc      1200
acccagtctt actctggcgg cgttaacaag gctggcctgg acgtcagcac cctcctcgcc     1260
gctaacggcg ccagcatgaa cgacggcttc tacacccccg gctctgacaa gatgctcgct     1320
accgccgttg ccattgagaa ctccttcgcc ggcatttacg ccgttaacca gaaccgcccc     1380
gactggaagg gcaccgctat tggccgatac cctgaggaca cctacgacgg ccacggcaac     1440
tcccagggca acccttggtt cattgctacc gccgcttacg ctgagatgta ctaccgagct     1500
atactggaat ggcagcagca gccttccatt accgttaact ctattaacct cagcttcttc     1560
aagaagttcg actctagcgc tgctgttggc accgtttaca gcccggcac ccaggctttc      1620 aacaacatgg tttctaacgt tgctttcgct gccgacgagt tcttcagcac catgaacttc     1680
cacagcgcta ccaacggctc tatgagcgag cagtacaacc gaaacaccgg cattatgcag     1740
ggcgcaagag acctgacctg gagccacgct gctttcatta ccgctgctaa ggccaagctg     1800
ggcacccccg ttttctaata a                                               1821
```

```
<210> SEQ ID NO 30
<211> LENGTH: 1809
<212> TYPE: DNA
<213> ORGANISM: Artificial Sequence
<220> FEATURE:
<223> OTHER INFORMATION: Sequence is synthesized

<400> SEQUENCE: 30
```

```
atggttttca gcaagctgtt caagaagcct attctcctga ttgttaccta cctgaccgtt      60
accgtcgtcg ccgagaccgt tcctacctct gctcaggtcc aggttaagtc tttcaactac      120
gacggcagca ccctgtccgg ccagatttac gtccagaaca ttgcttacga aaagaccgtt      180
accgttgttt actctgacgg ctccgacaac tggaacaaca acggcaacac cattgctgcc      240
tcttacagct ctagcattag cggctctaac tacgagtact ggaccttcag ctctagcgtc      300
cccagcatta agcagttcta catcaagtac gttgtcgctg gcaagaccta ctacgacaac      360
```

-continued

```
aacggcacca agaactacca ggtttccgct tccacccta ccaccaccac caccaccacc      420
tcctctggcg ccaccaagac caccaccacc atcggcccta ccagcaccag caccgttttc      480
cctagcggca acagcaccat cagctcttgg ctgaagggcc agattgagac ctcccgattc      540
gccatgctgc gaaacattaa ccccgctggc accgtcaagg gcttcatcgc cgcctcgctg      600
tctaccgcta accccgacta cttctacgct tggacccgag acgctgctct cgtcggccac      660
gtcattgcta acgactacaa ccgaaccctc gctggcaaca gcacctacct gggcctcctg      720
aaggactacg tcaccttctc tgttaactcc cagtctacct ccaccatttg caactgcctg      780
ggcgagccta agttcaacaa ggacggctct ggctactctg gcgcttgggg ccgccctcag      840
aacgacggcc ccgccgagcg agctgacacc ttcatcctca ttgccgactc catcctgaag      900
cagaccggcg acgccaccta cgttaccggc accctgcgcc ctgctattta caaggacctc      960
gactacgtcg ttaacgtttg gtctaacggc tgcttcgacc tgtgggagga ggttaacggc     1020
gtccacttct acaccctcat ggttatgcga cgatctctga tcctgggcgc taacttcgct     1080
tctcgaaacg gcgacagcac ccgagcgtcc acctacacca acaccgctaa ctctattaag     1140
accaagattg acaccttctg gtcttcctct aacaactacg ttgctgtttc ccagtctgtt     1200
accggcggcg ttaacaaggc tggctacgac gttgctaacc tcatcgccgc taacgttggc     1260
agcctcgacg acggcttcta cacccccggc agcgagcgaa tactcgccac cgctgttgct     1320
gttgagtcta agttcgcttc gatttacggc gtcaaccaga acctgccttc ttggctgggc     1380
aactccattg gccgataccc cgaggacacc tacaacggca acggcaactc tcagggcaac     1440
ccttggttca ttgctaccaa cacctacgcc gagctgtact accgcgctat taaggagtgg     1500
accaacaacg gcggcgttac cgtcaccaac gttaacttca acttcttcaa gaagttcgac     1560
agctccgctt ctgttggcac caagtacacc gttggcacca gcgcttcaa caccctgacc     1620 cagaacgttg ccctcgctgc cgacaacttc ttctctaccg tcaaggttca cgctgccacc     1680
aacggctcca tgtctgagca gttcggccga gactccggcg tcatgaccgg cgcccgcgac     1740
ctgacctgga gtcacgcatc actgattacc gccgccctcg ccaagaccgg cgccctgtt     1800 gcctaataa                                                            1809
```

```
<210> SEQ ID NO 31
<211> LENGTH: 1833
<212> TYPE: DNA
<213> ORGANISM: Artificial Sequence
<220> FEATURE:
<223> OTHER INFORMATION: Sequence is synthesized

<400> SEQUENCE: 31
```

```
atgaagttct ctaacctcct gaagaagccc ctgctcctga ttgccggcat tctcgctgtt       60
accgtcgttg ccgagaccgt ccctaccacc gaggctgtta aggtcaagtc tttcacctac      120
gacggcagca ccctcgctgg ccagatttac atcaagaaca tcgcttacac caagaccgtt      180
accgttattt actccgacgc ctccgacaac tggaacaaca acggcaacac cattgctgct      240
tcttactccg ctgctattgc tggcaccaac tacgagtact ggaccttcag cgcccccgtg      300
tccggcatta agcagttcta cgtcaagtac gttgtttctg gcaccaccta ctacgacaac      360
aacaactctg gcaactacca ggtttccgtt accaccacca ccaccaccgc ccctaccacc      420
accacctctg gcggctctag caccaccacc ggcggcagca ccaccaccgc cacctccgtc      480
cctaccggcg tccctagcgg cttccctacc ggcaacagca ccattagctc ttggattgac      540
```

-continued

```
ggccagacct ctgtttcccg atacgccatg ctgcgaaaca ttaaccctgc tggcgctgtt      600
accggcttca ttgccgcatc catgtctacc tctggccccg actacttcta cgcttggacc      660
cgagacagcg ccctgacctc tcacgtcgtt gcttacgact acaacaccac cctcgccggc      720
aacagcacca tcctgggcct cctgaagaac tacgttacct tcagcctgaa ctctcagacc      780
acctctaccg tttgcaactg cctgggcgag cctaagttca caaggacgg ctctggctac      840 tccggcgctt ggggccgccc ccagaacgac ggccccgcta gtcgagctga caccttcatc      900
ctcatcgctg acagcattct gaagcagacc ggcgacgcca cctacgtcac cggcaccctc      960
gcccccgcta tttacaagga cctcgactac gttgtctcta cctggtctaa cggctgcttc     1020
gacctgtggg aggaggttaa cggcgttcac ttctacaccc tcatggttat gcgacgaggc     1080
ctcgtcaagg gcgctaactt cgcatcccga aacggcgact ctacccgagc taccacctac     1140
accaacaccg ccgcgagcat taagaccaag attgactcct tctggaactc taacggccag     1200
tacgtcagcg tttcccagtc tgttaccggc ggcgtttcca aggctggcta cgacgccagc     1260
gtcctgattg cttctaacct gggctctctc caggacggct tctacacccc tggcagcgac     1320
aagatgctcg ccaccgctgt cgccattgag tccaagttcg ccagcctgta ctccattaac     1380
cagaacctga acggctacct gggcaacgct attggccgat accccgagga cacctacaac     1440
ggcaacggca actcccaggg caacccttgg ttcatttgca ccaacgcttt cgccgagctg     1500
tactaccgag ctattaagga gtggttcaac aacggcggcg ttaccgttac ctccattagc     1560
ctgaacttct tcaagaagtt cgacagctct gccgccgttg gcaccaagta caccgttggc     1620
accagctctt tcaacagcct cgtccagaac gttgctgttg ctgccgacgc tttcttcagc     1680
accatcaagt tccacgccgc taccaacggc tccatgagcg agcagtacgg ccgaaccgac     1740
ggcctcatga ccggcgctag agacctgacc tggagtcacg catctctgat cagcgcctct     1800
tacgctaagg ctggctctcc cgctgcctaa taa                                 1833
```

```
<210> SEQ ID NO 32
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 32
```

```
atgatgccta accacatttg gaagtgcctg ttcctcgcca tgaccaccgt tttcatgacc       60
gtcctcgtcc agggcgctcc cacctctgag attgaactag actcttacac ctacaccggc      120 ggcgtttttct ccggccgact gtacgtcaag aacatcgctt acaccaagga ggttaacgtt     180
tactggtctg acgccagcga ggactgggct aacaacggca actacgttgc cgctacctac      240
tctgaggcta tctccggcac caactacgag tactgggagt tcagcgctaa gattggctct      300
agcggcatca gcgagtctta catcaagtac accgtttccg gctctaccta ctacgacaac      360
aacggcggca agaactacgc catcaccgag accaccaccc ctaccattac cgccacccct      420
acctctacca ccgctaccac caccattagc tctaccacca ccaccgccac ctccatccct      480
acctctgttc ctagcaccgt ccccgagggc aacgttaccg tcaccgagtg ggttaacaag      540
cagctcaaaa tatcttggtc cgacctcttg caaaacgtta acccttctgg caccgttacc      600
ggcttcattg ctgcctcact cagcacctcc aaccccgact acttctactg ctggaccccg       660
gacgccgcaa tggttgcccg cgttatgacc tacatgtaca acaccaccga ggctggcgac      720
agcagcctgg agagcgccct gaaggactac attaccttcc agattaactc tatgaaaacc      780
```

-continued

```
gctaccgctt gcaactgcct gggcgagcct aagttcaaca ccgacggctc cggctactcc    840
ggcccttggg gccgccccca gaacgacggc cctgctgagc gcgctaccac catgattctg    900
ttcgctgact cttacctcgc ccagggcggc gacacctctt acgttaccaa caccctgaag    960
cctgctattt acaccaacct ggactacgtt gttggcacct ggtctaacaa ctgcttcgac   1020
ctgtgggagg aggttaacgg cgttcacatt ttcacccctcg ccgtcatgcg aaagtctctc   1080
ctcgacggcg ctgacttcgc tgcccgaaac ggcgacacct cccgcgttag cggctaccag   1140
agcaccgctt ctagcattaa gaccaagctg gagtctttct ggtctagctc caacaactac   1200
attaccgtca cccagtctta ctctggcggc gtccagaagg ccggcctgga cgtcagcacc   1260
ctgattgctg ctaaccaggg ctcgatgggc gacggcttct acacccctgg ctctgacaag   1320
atgctcgcca ccgctgttgc tattgagaac tctttcgcta acatttacac cattaacaag   1380
aacaagcctt cttggctggg caccgctatt ggccgatacc ccgaggacac ctacaacggc   1440
aacggcaacg gccagggcaa cccttggttc atcgctaccg ccacctacgc cgagctgtac   1500
taccgagcta ttttggaatg gcagcagcag gagtctgtta ccgttaacag cgtcaacttc   1560
gacttcttct ctaagttcga cagcagcgcc aaggttggca ccgtttacac ccctggcacc   1620
gacaccttca acactatggt ttctaacgtt gctttcgctg ccgacgagtt cctcagcact   1680
atggagcact acgctgccac caacggctct atgtctgagc agttcaaccg agagaccggc   1740
agcctgaccg gcgcccgaga cctgacctgg tcgcacgctg ctttcattac cgctggcaag   1800
gccaagctgg gcattcctag cttctaataa                                    1830
```

```
<210> SEQ ID NO 33
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 33
```

```
atgaagttca gcaagctgtt caccaagcct accctgttca tcgtttctat tattatcagc     60
gttgcttcta gcgagaccgt ccctaccacc gctaacgtcc tcgttaagtc ttacacctgg    120
gacggcgcta ccctgtctgg ccagatttac attaagaacc tcgcttacgc caaggttgtt    180
agcgttattt actctgacgc taacgacaac tggaacaaca acggcaacaa ggttgccgct    240
tcttactctg ctggcattga cggcaccaac tacgagtact ggaccttcag cggcgccgtt    300
tccggcatca agcagttcta cgtcaagtac gacgtcagcg gcacctctta ctacgacaac    360
aacggcacca agaactacca ggttaccaag acctctacca ccaccaccgc cgctaccacc    420
accaccaccg ctaccaccac caccggcggc accggcacca ccaccaccac caccgccacc    480
gccaccgcta ccagcaccga cttccctacc ggcaacagca ccattaccac ctggctgaag    540
tcccaggagg acatctcccg aggcgccatg ctccgaaaca ttaaccccccc tggcgctgct    600 accggcttca ttgctgccag cctgtctacc tccggccccg actactacta cgcttggacc    660
cgagactccg ccctgacctc tcacgtcatc gctcacgact acaacaccac cctcgctggc    720
aacaccacca tcctgaacat cctgaaggac tacgttacct tctccgtcaa gtcccagtcc    780
gtttctaccg tttgcaactg cctgggcgag cctaagttca accccgacgg cagctcttac    840
accggcgctt gggggccgccc ccagaacgac ggccctgccg agcgagcctc caccttcatc    900
ctgttcggcg actcttacct gaagcagacc ggcgacgcta cctacgttac cggcaccctc    960
```

-continued

```
gctcctgcca tttacaagga cctcgactac gttgttaaca cctggtctaa cggctgcttc      1020
gacctgtggg aggaggttaa cggcgttcac ttctacaccc tcatgtctat gcgacgaggc      1080
ctcctcgacg gcgccaactt cgccaagcga aacggcgaca ccacccgagc taccacctac      1140
accaacaccg ccgcttccat tgctaccaag attgacacct tctgggttag ctctggcaac      1200
tacgtccagg tttcccagtc tgttaccggc ggcgtcagca aggctggcta cgactgcgct      1260
aacattctcg ctgctaacat ggctgctaac cacgacggct tctacacccc tggcagctct      1320
aagattctcg ctaccgccgt tgccattgag tctaagttcg ccagcctgta ctctattaac      1380
tctggcctcg cttcttggct gggcaccgcc attggccgat accccgagga cacctacaac      1440
ggcaacggca actctcaggg caacccttgg ttcatttgca ccaacgcttt cgctgagctg      1500
tactaccgag ccatcaagga gtggacccag gctggctccg ttaccgttga cagcacctct      1560
ctgaacttct tcaagaagtt cgacagctct gctgccgccg gcaccaagta caccgttggc      1620
acctctgctt tcaccaacct cgtccagaac attgctaacg cgctgacaa gttcctgtct       1680 acctccaagt tccacgccgc taccaacggc tccatgtctg agcagtacaa ccgagacagc      1740
ggcctcatga ccggcgcccg agacctgacc tggtcgcacg cctcactgat tagcgcctcc      1800
cgagctaagg ctggctctcc tagcctctaa      1830
```

```
<210> SEQ ID NO 34
<211> LENGTH: 1845
<212> TYPE: DNA
<213> ORGANISM: Artificial Sequence
<220> FEATURE:
<223> OTHER INFORMATION: Sequence is synthesized

<400> SEQUENCE: 34
```

```
atgaagccta ttcacctgtg gcactacctg ttcctcgcca tgaccgctgc cttcatgggc       60
gtcctcgctg acgtccctac ctccgccaac attgaactcg actactacac ctacaaggac      120
aaggttttct ccggccgaat ttacgtcaag aacatcgctt acgaaaaaac cgttgctgtt      180
tactggtctg acgctagtgg cgactggaac aacaacggca acaacgttgc cgcttcttac      240
tctgagtcca tctccggcac cgactacgag tactgggact tcagcaccac cattggctct      300
ggcggcatca agcagtctta cctcaagtac accgttagcg gcaacaccta ctacgacaac      360
aacggctcta caactacga cattaccgag accaccgcta ccaccaccac caccaccacc      420
accaccacca ccaccggctc taccgccacc acctctacca cctctggccc taccagcacc      480
acctctacca cccccggccc tacccctacc aacgttcccg acggcaacgt taccgtcacc      540
gagtgggtta acacccagtt cgctatttct tggcctaccc tcctgaagaa cgtcaaccct      600
agcggcaccg tcaagggctt cattgctgca tcactcagca ccaacaaccc tgactacttc      660
tactcttgga cccgagacag cgctctcgtt gctcacacca tgacctacct gtacaacacc      720
tctgaggctg cgacagcac cattgagtct gccctgaagg actacgttac cttcagcatt       780
aacgctatga acgctgctac cgtttgcaac tgcctgggcg agcctaagtt caacaccgac      840
ggctccggct acaccggcgc ttggggccgc ccccagaacg acggccccgc aagtcgagct      900
accaccatga ttctgttcgc cgactccttc ctcgcccagg cgggcgatgt ttcttacgtt      960
attaacaccc tcaagcctgc tatttacaag gacctggact acgtcgttag cacctggtct     1020
aacacctgct acgacctgtg gggaggaggtt aacggcgttc acatttacac cctgtctgtt      1080
atgcgccgcg ccctgattga cggcgctaac ttcgcccagc gaaacggcga cacctcccgc      1140
gtcagcggct acaccagcac cgccaccacc atcaagaccc gactggagtc tttctggagc      1200
```

-continued

```
gactctaaca actacattac cgttacccag tcttactccg gcggcgtcca gaaggccggc      1260
ctggacgtca gcaccctgat tgctgccaac attggcagcg ttggcgacgg cttctacacc      1320
cccggctctg acaaggtcct cgccaccgcc gtcgccatcg agaagtcctt cgctaacctg      1380
tacaccatta accagaacaa gccttcttgg ctgggcaacg ccattggccg ataccccgag      1440
gacacctacg acggctacgg caactccaag ggcaacccct ggttcattgc taccgctacc      1500
tacgctgagc tgtactaccg agctatccta gagtggcagc agcaggcttc cgttaccgtt      1560
aactctatta acctgggctt cttctccaag ttcgacagct ctgcctctgt tggcaccgtt      1620
tacacccccg gcaccgactc tttcgccaac atggtttcta acgttgcttt cgctgctgac      1680
gagttcctgt ctaccatcga ctaccacgcc atgaacaacg ctctatgca cgagcagtac      1740 aaccgagaca ccggcatctc ccagggcgca cgcgacctga cctggtcaca cgctgctttc      1800
attaccgctg ccaaggctaa gctgggcgct cccgctttct aataa                      1845
```

<210> SEQ ID NO 35
<211> LENGTH: 1818
<212> TYPE: DNA
<213> ORGANISM: Artificial Sequence
<220> FEATURE:
<223> OTHER INFORMATION: Sequence is synthesized

<400> SEQUENCE: 35

```
atgaagctca tgaactctag catgaagacc tgcgttttct tcatcctgtc ttacttcagc        60
ctcctcgtca gcagcgctgc cgttcctacc tctgctgctg ttcaggttga gtcctacaag       120
tacgacggca ccaccttcag cggccgaatt ttcgtcaaga acattgctta ctccaaggtt       180
gttaccgtca tatatagcga cggctctgac aactggaaca acaacaacaa caagatcagc       240
gctgcttaca gcgaggctat tagcggctcc aactacgagt actggacctt ctctgctaag       300
ctgtccggca ttaagcagtt ctacgtcaag tacgaggttt ctggctctac ctactacgac       360
aacaacggca ccaagaacta ccaggtccag gctacctctg ccaccagcac caccgccacc       420
gccaccacca ccacctctac cagcaccacc accaccagca ccggccctac cagcaccgca       480
agtgtttctt tccctaccgg caactccacc attagctctt ggattaagaa ccaagaagaa       540
atttcccgat tcgccatgct gcgaaacatt aaccccccccg gctccgccac cggcttcatt      600
gctgcctctc tgagcaccgc gggacccgac tactactact cttggacccg agacagcgcc       660
ctgaccgcta acgttattgc ttacgagtac aacaccacct tcgctggcaa caccaccctc       720
ctgaagtacc tgaaggacta cgttaccttc tccgtcaagt ctcagtctgt tagcaccgtt       780
tgcaactgcc tgggcgagcc taagttcaac gccgacggca gctcttacac cggcccttgg       840
ggccgacccc agaacgacgg ccccgccgaa cgggccgtca ccttcatgct cattgctgac       900
tcttacctga cccagaccaa ggacgcttct tacgtcaccg gcaccctgaa gcccgccatt       960
ttcaaggacc tcgactacgt tgtttccgtt tggtctaacg gctgctacga cctgtgggaa      1020
gaagttaacg gcgttcactt ctacacccctg atggttatgc gaaagggcct catcctgggc     1080
gctgacttcg ctgctcgaaa cggcgactct agccgagcct ctacctacaa gaacaccgcg      1140
agcaccatgg agtccaagat ctctagcttc tggtccgact ctaacaacta cgtccaggtt      1200
tcccagtctg ttaccgctgg cgtctccaag aagggcctcg acgttagcac cctcctcgcc     1260
gctaacattg ctccctgcc cgacggcttc ttcacccccg gcagcgagaa gattctggct      1320
accgccgttg ccctagaaaa cgctttcgca tctctgtacc ctattaactc taacctgcct     1380
```

```
tcttacctgg gcaactccat tggccgatac cccgaggaca cctacaacgg caacggcaac      1440
tcccagggca acccttggtt cctcgccgtt aacgcttacg ctgagctgta ctaccgagct      1500
attaaagagt ggatctctaa cggcaaggtt accgtctcta acatcagcct cccttctt      1560 aagaagttcg acagctccgc cacctctggc aagacctaca ccgctggcac cagcgacttc      1620
aacaacctcg ctcagaacat tgccctgggc gctgaccgat tcctgtctac cgttaagttc      1680
cacgcttaca acaacggcag cctgtctgaa gagtacgacc gatctaccgg catgtctacc      1740
ggcgcacgcg acctgacctg gtctcacgcc tcgctcatca ccgccgctta cgccaaggct      1800
ggcagccccg ctgcctaa                                                    1818
```

<210> SEQ ID NO 36
<211> LENGTH: 1413
<212> TYPE: DNA
<213> ORGANISM: Artificial Sequence
<220> FEATURE:
<223> OTHER INFORMATION: Sequence is synthesized

<400> SEQUENCE: 36

```
atgaagtctc cttacagcat gaaaaccgtc ctcgctctcc tgtccctgac ccctctgttc       60
accagcgacg ttgttgccgt tcctagcggc aactccacca tcaccgcttg gggctccaag      120
caggacggca tctctttcag caccatgctg ggcaacatca accctcccgg cagctctaag      180
ggcttcattg ctgcctcgct gtctaccgct ggccctaact actactactc ttggacccga      240
gacagcgctc tcgtcgcccg cgccattacc tacaagtact ccacctctta ccagaacgac      300
cccaagattc tgggcctcct gaaggactac gttacctacc aggttaacga gcagaccgag      360
tctaccgttt gcaactgcct cggcgagcct aagttcaacc ccgacggctc tagcttcagc      420
ggcccttggg gccgccctca gaacgacggc cctgctgagc gcgcttccac catgattctg      480
ttcgccaagt cttactacgc ccagaccaac gacgttggct acgtttctaa caccctgaag      540
cccgctattt acaaggacct ggactacatc gttaacgttt ggggcaacaa ctgcttcgac      600
ctgtgggagg aggttaacgg cgtccacttc tacaccctca tgatgatgcg acacggcctc      660
gtccagggca gcattttcgc taacaccctc ggcgacagca cccgagctaa cacctacaag      720
accgccgctc agaacattaa gaaccgaatt gacaccttct gggagtctgg ctctaactac      780
attgttgtta cccagaacca gtctgctggc gttaacaagc cttccggcct cgacgttgcc      840
gtcctgctgg ctgccaacca gggcggcctg ggcgacggcg tttacacccc cggctctgac      900
aaggtcctcg ccaccgccgt cgctctggag aagtctttcg caagcctgta ccccattaac      960
aagaacctgc cttcttacta cggcaccgcc attggccgat accccgagga cacctacaac     1020
ggcaacggca acagcgaggc taacccttgg ttcattgcca ccaccaccta cgctgagctg     1080
tactaccgag ctatttccga gtggaccaac ggctccggcg tcaccgtcaa ctctattaac     1140
aaggagttct tctctaagtt cgacgcctct gccaccaacg gcaaggttta caccccccggc     1200 agcgactctt tcaactccct ggtcaacaac gttgctattg ctgctgacaa cttcctcagc     1260
accgtccgat accaccagac ctccaacggc agcctgtctg agcagttcaa ccgatacacc     1320
ggcttcatga ccggcgcacg ggacctgacc tggtcccacg ccgctatggt taccgctctc     1380
gccgctaagg ctggcacccc tagcccttaa taa                                 1413
```

<210> SEQ ID NO 37
<211> LENGTH: 1830
<212> TYPE: DNA
<213> ORGANISM: Artificial Sequence

```
<220> FEATURE:
<223> OTHER INFORMATION: Sequence is synthesized

<400> SEQUENCE: 37
atgcagctga acctgtactg gaagagcctc gccgtcctcg ctctgattca gatggttatg      60
gctgctaccg tccctaccac ccaggtccag ctcgactact acacctactc taacaacgtc     120
ctgtctggcc gaatctacgt tcagaacatt gcttacagca aggttgttaa ggttatctat     180
agcgacgcct ccggcaactg gaacaacaac ggcaacacca tctccgcttc ttacgtcgag     240
tctatttccg gcaccaacta cgagtactgg gacttcagcg ccaccattgg caccgctggc     300
atcaagcagt ctacctgcg atacgacgtt tccggctcca cctactacga caacaacggc     360
ggcgacaaca acaactacaa cgttgttgct accacctcta ccacctctag ctctaccacc     420
accaccaccg ctaccaccac caccgccacc aagaccacca gcaccaccct gccaccgct     480 acccctacct ctagcgccac cttccctagc ggcaactcta ccattaccac ctgggccaag     540
tctcagaagg acatttcttg gaagaccctc ctgaccagcc tgaaccctag cggcaccgcc     600
aagggcttca ttgctgcgag tctgtctacc tctaaccctg actactacta cgcttggacc     660
cgagacagcg ctctcgttgc ccgaaccatg gttaacatgt acaacaccac cgaggctggc     720
tctgcttcag tcctgggcct cctgcaggac tacgttacct tccagattaa cgccatgagc     780
accagcaccg tttgcaactg cctgggcgag cctaagttca accccgacgg cagctcttac     840
accggcgctt ggggccgccc ccagaacgac ggccccgctg aacgtgcaag caccttcatc     900
ctgttcgctg actcttacat tgcccaggc ggccagctgt cttacgtcac cggcaccctc     960
gctcccgcca tctacaagga cctgaactac gtcgtttcta cctggtctaa caactgcttc    1020
gacctgtggg aagaggttaa cggccgacac atgttcaccc tcgccgtcat gcgacgcgcc    1080
ctcctggacg gcgttaactt cgcctcccga attggcgaca ccacctactc tagcacctgg    1140
agctctaccg cttctagcat ccagtctacc ctgtctggct actacctgtc ttccggcaac    1200
tacattacca ccgttcagaa cttccagtct ggcgtttcca aggctggcta cgacgtcagc    1260
accctcatcg ctgctaacgt tgcgggcatg ggcgacggct tcttcacccc cggctctgac    1320
gaggttctcg ctaccgccgt tgctattgag aacaagttct ctagcctgta cggcgtcaac    1380
gctaacaagg cttcttacct cggcaccgcc attggccgat accccgagga cacctacaac    1440
ggctacggca acggccaggg caaccttgg ttcattgcta ccgctgctta cgccgagctg    1500
tactaccgag ctattctgga gtggcagacc aagagcagca tcgttgttaa ctccaagaac    1560
ctcggcttct tctccaagtt cgactcttct gccgccgttg gcaccaccta caccccggc    1620 accaccgctt actctaacat ggtccagaac gtcgccctcg ctgctgaccg attcctcagc    1680
accgtccagc tgcacgctgc caccaacggc tccatgtctg agcagttcaa ccgagacacc    1740
ggcgttatgc agggagcccg tgacctgacc tggtctcaca gcgctttcat taccgctgcc    1800
cgagctaagc tgggcagccc cgtttactaa                                    1830

<210> SEQ ID NO 38
<211> LENGTH: 1404
<212> TYPE: DNA
<213> ORGANISM: Artificial Sequence
<220> FEATURE:
<223> OTHER INFORMATION: Sequence is synthesized

<400> SEQUENCE: 38
atgcgagcta ccaccgctat tctgtctctg ttcaccaccg cctctatggc tctggctgcc      60
```

```
aactctaccg tccctgacgg caactccacc accaccgctt gggtcaagaa gcaagaagcc      120
atctcttgga ccgacctgaa gaccaacgtc aaccctgagg gcgctgctaa gggcttcatt      180
gctgcctctc tgtctaccag cgagcctgac tactactacg cttggacccg agactctgcc      240
ctcgttgctc gcgttatggt taacaagtac aacaccaccg acgctgggga cgccaacctc      300
ctcggcctcc tgcaggacta cgtttctttc cagatcaacg caatgggcga gtctaccgtt      360
tgcaactgcc tgggcgagcc taagttcaac cccgacggca gctcttacac cggcgcttgg      420
ggccgccccc agaacgacgg ccccgccgag cgagcttcta ccttcattct cctcgccgac      480
agcatgattg cccagaagtc tgctaacggc tcttacgtca gcgacaccct ggctcccgct      540
atctacaagg acctggctta cgttgcaagc acctgggaga acgcttgcta cgacctgtgg      600
gaagaggtta acggcaagca catgtacacc ctcagcgtca tgcgacgagc cctcctggac      660
ggcgccgact cgcttctcg gcagggccag accgccaacg ttacctcttg gaagtctacc      720
gctgacaaga ttaagtctag cctggagggc ttcttcagct ccgacaacgg ctacattgag      780
gttacccagg acatgcaggg cggcgtccag aagaagggcc tggacgtttc caccctcatc      840
gctgctaaca ttggcagcat gggcgacggc ttctacaccc ccggcagcga cgaggttctc      900
gccaccgctg ttgccgttga ggctgccttc gctgacctgt acaagattaa ccagaacacc      960
aactccaccg gcctcggcac cgccatcggc cgatacccccg aggacaccta caacggcgtt     1020
ggcaactccc agggcaaccc ttggttcatt gctaccaaca ccttcgctga gctgtactac     1080
cgcgccatcc tggagtggca gaacaagggc accattaccg ttaactccgt taacgctgct     1140
ttcttcagca gtttgactc tagcgctaag gccggtacaa cctacaagtc tggctctacc     1200
gagtttgata gcctcattaa caaggttgct ctggctgctg acgctttcct gaacaccgtc     1260
cagacctacg ctgcttctaa cggctctatg tctgagcagt acaaccgaga caccggcgcc     1320
ctgaccggcg cccgagacct gacctggtct cacgcaagtc tcattaccgc cgctaacgcc     1380
aagctcggca ccccttacaa ctaa                                           1404
```

```
<210> SEQ ID NO 39
<211> LENGTH: 1419
<212> TYPE: DNA
<213> ORGANISM: Artificial Sequence
<220> FEATURE:
<223> OTHER INFORMATION: Sequence is synthesized

<400> SEQUENCE: 39
```

```
atgaagctcg gccgaattgg cttctctatt ctgtctgttg cctccgtttt ctctcaggcc       60
gtcgttaccg ctgccgctgc cgcctctgtc cctagcggca acgccaccat tacctcttgg      120
attcaggagc agctcgctat ttcttggaac accatgctga ccagcgttaa ccccgttggc      180
gccgtcaccg gcttcatcgc tgcgagtctg tctaccgcta accccgacta ctactactgc      240
tggacccgag acgctgctct cgtcgcgaga gttatgacct tcatgtacaa caccacccag      300
gctggcgaca gcggcctcct gggcatcctc caggactacg tttccttcca gatccacgca      360
atgggcgagt ctaccgtttg caactgcctg ggcgagccca gttcaacccc gacggcagc      420 tcttacaccg gcgcttgggg ccgccctcag aacgacggcc ctgctgagcg agcctctacc      480
ttcatcaaga ttgctgactc ttacctgacc cagaccggcg atgtatccta cgttaccaac      540
accctcaagc ccgctattta cgaggacctg gactacattg ttaacgtttg gcagaacacc      600
tgcttcgacc tgtgggagga ggtttacgga atgcacatgt acaccctggc tgttatgcga      660
cgaggcctcc tcgacggcgc cgacttcgct acccgaaacg gcgacaccga caaggcctct      720
```

-continued

```
acctacacca gcaccgccac cagcatccag acccgactgg ccaccttctg gtctgactcc        780
aacggctaca ttaccgttac ccaggactac cagtccggcg tcagcaaggc tggcctggac        840
gttagcaccc tgattgctgc taacgttgcc ggcatgaacg acggcttctt cacccctggc        900
tctgacgaga ttctcgctac cgccgtcaag gttgaggctg ctttcgctaa cctgtacggc        960
attaacatta caaggcctc ttacctgggc aacgccattg ccgatacccc cgaggacacc       1020
tacaacggca acggcaactc tgagggcaac ccttggttca ttgccaccgc tgctttcgct       1080
gagctgtact accgcgccat tatggagtgg cagctccgag gcagctctat taccgtcaac       1140
tctgttaacc agggcttctt caccaagttc gaccctagcg ccaccgccgg caccacctac       1200 accccccggca ccgacgcttt caactccctc attgacaacg ttgccctcgc tgctgaccag       1260
ttcttcagca ccatccacct ccaccgcgcc accaacggct ctatgtctga gcagtacaac       1320
cgagacaccg gcttcatgca gggcgctcgg gacctgacct ggtcccacgc cgctttcatc       1380
accgccgcta aggctaagca gggcacccct agcttctaa                            1419
```

<210> SEQ ID NO 40
<211> LENGTH: 1842
<212> TYPE: DNA
<213> ORGANISM: Artificial Sequence
<220> FEATURE:
<223> OTHER INFORMATION: Sequence is synthesized

<400> SEQUENCE: 40

```
atgcgccccg ttcacctgtg gaagagcctg ctcctcgccg ctgctaccgc tgttaccggc         60
accatcgccg ttgatgttcc ttctgttcct atccagctag agtcttacac ctactctgag        120
aacgttttcg ccggccgaat tttcgtccag aacattgctt acaccaagga ggttaacgtt        180
ttctggtctg acgcttccga cgactggaac gacaacggca actccgttgc tgcttcttac        240
tccgagtcta ttgctgacac caactacgag tactgggagt tcagcaccac cattggctct        300
gccggcatct cccagtctta cctgcgatac gatgtgtctg ctctatttta ctacgacaac        360
aacgactccc agaactacga cattaccgag accagcaccc ctaccaccac caccgctgcc        420
cctacctcta ccacctctac ccctaccacc accaccgacg gcggcagcac caccaccacc        480
accgccacct ccgtccctac ctctaccggc gtccctgagg gcaacgctac cattagcgag        540
tgggcatctg cccagctgga catctcttgg cctaacctca tgatgaacgt taaccctagc        600
ggcgctgtta ccggctccat tgttgcctca ctgtctacct ctaaccctga ctacttctac        660
atttggaccc gagacgctgc gatggttgcc cgcgttatgg tttacatgta caacaccacc        720
gaggctggcg acaccaacct gctcaacgcc ctgaccgact acgttacctt ctctatttcc        780
agcatgaacg ttgacaccgt ttgcgactgc ctgggcgagc ctaagttcaa cgttgacggc        840
tctggctaca ccggcgcttg gggccgcccc cagaacgacg ccccgccga gcgcgcctct         900 accatgatcc tgattgctga ctcttacatc gcccagggcg gcgatgtatc ttacgtcacc        960 gacacccctca agcctgctat ttacaccgac ctggactacg tcgttgacac ctggtctaac       1020
gtttgcttcg acctgtggga ggaggttaac ggcattcaca tgtacaccct cagcgtcatg       1080
cgaaaggccc tcctggacgg cgccaacttc gctacccgaa acggcgacac ctcccgcgtt       1140
agcggctacg agagcaccgc ttcatccatc aagacccgac tggagtcttt ctggtctagc       1200
tctaacaact acattaccgt cacccagtcc ttcagcggcg gcgtttccaa ggccggcctg       1260
gacgtcagca ccctgattgc tgccaacctc gcttccatga cgacggcttt ctacacccc        1320
```

```
ggctctgacg agattctcgc taccgccgtt gctattgaga actctttcat ctccgagtac     1380
accctcaacc agaaccgccc ttcttggctg tccaccgcca ttggccgata ccctgaggac     1440
tcttacgacg gctacggcaa ctcccagggc aacccttggt tcatcgctac cgctacctac     1500
gctgagctgt actaccgagc tatcctagag tggcagcagc aggcttcaat tagcgttaac     1560
agcgttaacc tgggcttctt cagcaagttc gactctgacg cttctgttgg caccgtttac     1620
acccccggca ccgaggactt cgccaacatg gtttctaacg tcgctttcgc tgctgacgag     1680
ttcctcgcca ccattgagaa ccacagcgcc gtcaacggca gcctcagcga gcagtacaac     1740
cgagacaccg gcattatgca gggcgcaaga gacctgacct ggtcacacgc tgccttcatt     1800
accgctgcca aggccaagca gggcgctcct attcactaat aa                        1842
```

<210> SEQ ID NO 41
<211> LENGTH: 19
<212> TYPE: PRT
<213> ORGANISM: Saksenaea vasiformis

<400> SEQUENCE: 41

```
Met Pro Ser Trp Lys Thr Leu Phe Leu Leu Leu Gly Pro Ile Ala Thr
1               5                   10                  15

Ala Ala Ala
```

<210> SEQ ID NO 42
<211> LENGTH: 23
<212> TYPE: PRT
<213> ORGANISM: Backusella circina

<400> SEQUENCE: 42

```
Met Lys Leu Phe Gly Thr Leu Lys Ala Ser Phe Val Phe Leu Ile Gly
1               5                   10                  15

Cys Ile Val Phe Ala Met Ala
            20
```

<210> SEQ ID NO 43
<211> LENGTH: 24
<212> TYPE: PRT
<213> ORGANISM: Backusella circina

<400> SEQUENCE: 43

```
Met Lys Pro Phe Gly Pro Ile Lys Thr Thr Leu Phe Ile Ile Ile Ser
1               5                   10                  15

His Phe Ser Leu Asn Ser Leu Ala
            20
```

<210> SEQ ID NO 44
<211> LENGTH: 24
<212> TYPE: PRT
<213> ORGANISM: Benjaminiella poitrasii

<400> SEQUENCE: 44

```
Met Lys Phe Ser His Leu Phe Arg Lys Pro Thr Leu Leu Ile Val Thr
1               5                   10                  15

Phe Leu Thr Ala Thr Val Phe Ala
            20
```

<210> SEQ ID NO 45
<211> LENGTH: 24
<212> TYPE: PRT
<213> ORGANISM: Choanephora cucurbitarum -continued

```
<400> SEQUENCE: 45

Met Val Ser Phe Asn Phe Leu Lys Lys Pro Val Phe Ile Val Ile Thr
1               5                   10                  15

Cys Leu Thr Val Ser Val Cys Ala
            20

<210> SEQ ID NO 46
<211> LENGTH: 25
<212> TYPE: PRT
<213> ORGANISM: Rhizopus stolonifer

<400> SEQUENCE: 46

Met Lys Leu Phe Gly Leu Pro Leu Lys Pro Ser Leu Phe Phe Val Val
1               5                   10                  15

Ser Tyr Leu Ser Phe Leu Ala Ser Ala
            20                  25

<210> SEQ ID NO 47
<211> LENGTH: 24
<212> TYPE: PRT
<213> ORGANISM: Mucor circinelloides

<400> SEQUENCE: 47

Met Lys Phe Ser Asn Leu Leu Lys Lys Pro Leu Leu Leu Ile Ala Gly
1               5                   10                  15

Ile Leu Ala Ala Thr Val Val Ala
            20

<210> SEQ ID NO 48
<211> LENGTH: 21
<212> TYPE: PRT
<213> ORGANISM: Dichotomocladium elegans

<400> SEQUENCE: 48

Met Lys Leu Asn Ser Val Trp Lys Ala Phe Ser Ile Leu Leu Met Ala
1               5                   10                  15

Thr Met Ala Phe Ala
            20

<210> SEQ ID NO 49
<211> LENGTH: 23
<212> TYPE: PRT
<213> ORGANISM: Fennellomyces sp.

<400> SEQUENCE: 49

Met Arg Pro Ser Leu Val Trp Lys Ser Leu Leu Met Val Val Leu Thr
1               5                   10                  15

Ala Ala Met Gly Thr Tyr Ala
            20

<210> SEQ ID NO 50
<211> LENGTH: 24
<212> TYPE: PRT
<213> ORGANISM: Gilbertella persicaria

<400> SEQUENCE: 50

Met Val Phe Ser Lys Leu Phe Lys Lys Pro Ile Leu Leu Ile Val Thr
1               5                   10                  15

Tyr Leu Thr Val Thr Val Val Ala
            20
```

-continued

```
<210> SEQ ID NO 51
<211> LENGTH: 24
<212> TYPE: PRT
<213> ORGANISM: Mucor circinelloides

<400> SEQUENCE: 51

Met Lys Phe Ser Asn Leu Leu Lys Lys Pro Leu Leu Leu Ile Ala Gly
1               5                   10                  15

Ile Leu Ala Val Thr Val Val Ala
            20

<210> SEQ ID NO 52
<211> LENGTH: 25
<212> TYPE: PRT
<213> ORGANISM: Circinella umbellata

<400> SEQUENCE: 52

Met Met Pro Asn His Ile Trp Lys Cys Leu Phe Leu Ala Met Thr Thr
1               5                   10                  15

Val Phe Met Thr Val Leu Val Gln Gly
            20                  25

<210> SEQ ID NO 53
<211> LENGTH: 24
<212> TYPE: PRT
<213> ORGANISM: Mucor cordense

<400> SEQUENCE: 53

Met Lys Phe Ser Lys Leu Phe Thr Lys Pro Thr Leu Phe Ile Val Ser
1               5                   10                  15

Ile Ile Ile Ser Val Ala Ser Ser
            20

<210> SEQ ID NO 54
<211> LENGTH: 23
<212> TYPE: PRT
<213> ORGANISM: Phascolomyces articulosus

<400> SEQUENCE: 54

Met Lys Pro Ile His Leu Trp His Tyr Leu Phe Leu Ala Met Thr Ala
1               5                   10                  15

Ala Phe Met Gly Val Leu Ala
            20

<210> SEQ ID NO 55
<211> LENGTH: 27
<212> TYPE: PRT
<213> ORGANISM: Rhizopus microsporus

<400> SEQUENCE: 55

Met Lys Leu Met Asn Ser Ser Met Lys Thr Cys Val Phe Phe Ile Leu
1               5                   10                  15

Ser Tyr Phe Ser Leu Leu Val Ser Ser Ala Ala
            20                  25

<210> SEQ ID NO 56
<211> LENGTH: 26
<212> TYPE: PRT
<213> ORGANISM: Spinellus fusiger

<400> SEQUENCE: 56

Met Lys Ser Pro Tyr Ser Met Lys Thr Val Leu Ala Leu Leu Ser Leu
1               5                   10                  15
```

```
Thr Pro Leu Phe Thr Ser Asp Val Val Ala
        20                  25

<210> SEQ ID NO 57
<211> LENGTH: 21
<212> TYPE: PRT
<213> ORGANISM: Syncephalastrum racemosum

<400> SEQUENCE: 57

Met Gln Leu Asn Leu Tyr Trp Lys Ser Leu Ala Val Leu Ala Leu Ile
1               5                   10                  15

Gln Met Val Met Ala
        20

<210> SEQ ID NO 58
<211> LENGTH: 19
<212> TYPE: PRT
<213> ORGANISM: Syncephalastrum racemosum

<400> SEQUENCE: 58

Met Arg Ala Thr Thr Ala Ile Leu Ser Leu Phe Thr Thr Ala Ser Met
1               5                   10                  15

Ala Leu Ala

<210> SEQ ID NO 59
<211> LENGTH: 20
<212> TYPE: PRT
<213> ORGANISM: Thermomucor sp.

<400> SEQUENCE: 59

Met Lys Leu Gly Arg Ile Gly Phe Ser Ile Leu Ser Val Ala Ser Val
1               5                   10                  15

Phe Ser Gln Ala
        20

<210> SEQ ID NO 60
<211> LENGTH: 23
<212> TYPE: PRT
<213> ORGANISM: Zychaea mexicana

<400> SEQUENCE: 60

Met Arg Pro Val His Leu Trp Lys Ser Leu Leu Leu Ala Ala Ala Thr
1               5                   10                  15

Ala Val Thr Gly Thr Ile Ala
        20

<210> SEQ ID NO 61
<211> LENGTH: 449
<212> TYPE: PRT
<213> ORGANISM: Saksenaea vasiformis

<400> SEQUENCE: 61

Ala Pro Val Asp Lys Gln Ser Leu Pro Thr Gly Asn Ser Thr Ile Ser
1               5                   10                  15

Ser Trp Val Ser Lys Gln Glu Asp Ile Ser Phe Ser Glu Met Leu Arg
            20                  25                  30

Asn Val Asn Pro Glu Gly Thr Ala Lys Gly Phe Val Ala Ala Ser Leu
        35                  40                  45

Ser Thr Ala Gly Pro Asp Tyr Phe Tyr Thr Trp Thr Arg Asp Ala Ala
    50                  55                  60
```

```
Leu Val Ser Arg Val Ile Ala Tyr Lys Tyr Asn Thr Thr Asn Ala Gly
65              70                  75                  80

Asp Ser Lys Ile His Gly Val Leu Asp Asp Tyr Val Asn Phe Gln Ile
                85                  90                  95

Asn Thr Gln Ser Glu Ser Thr Pro Cys Asn Cys Leu Gly Glu Pro Lys
            100                 105                 110

Phe Asn Pro Asp Gly Ser Ser Phe Thr Gly Pro Trp Gly Arg Pro Gln
            115                 120                 125

Asn Asp Gly Pro Ala Glu Arg Ala Ser Ser Phe Met Leu Ile Ala Asp
            130                 135                 140

Ser Phe Leu Ser Gln Thr Lys Asn Ala Ser Tyr Phe Thr Asn Thr Leu
145                 150                 155                 160

Lys Pro Ala Ile Tyr Lys Asp Leu Asp Tyr Val Val Asp Thr Trp Ser
                165                 170                 175

Asn Pro Cys Phe Asp Leu Trp Glu Glu Val Asn Gly Ile His Phe Tyr
            180                 185                 190

Thr Leu Met Val Met Arg Arg Ser Leu Leu Asp Gly Ala Asn Phe Ala
            195                 200                 205

Thr Arg Asn Gly Asp Asn Ser Lys Ala Ser Thr Tyr Ser Gly Val Ala
            210                 215                 220

Ala Lys Ile Gln Ala Arg Leu Asn Ser Phe Trp Asp Ala Gly Lys Asn
225                 230                 235                 240

Tyr Ile Thr Val Thr Gln Asp Tyr Lys Asn Gly Val Glu Lys Pro Ser
                245                 250                 255

Gly Leu Asp Val Ser Thr Leu Ile Ala Ala Asn Val Ala Gly Met Gly
            260                 265                 270

Asp Gly Phe Tyr Thr Pro Gly Ser Glu Arg Ile Leu Ala Thr Ala Leu
            275                 280                 285

Ala Phe Glu Lys Ser Met Ala Ser Leu Tyr Pro Leu Asn Asn Asn Leu
            290                 295                 300

Pro Ser His Leu Gly Asn Ala Ile Gly Arg Tyr Pro Glu Asp Thr Tyr
305                 310                 315                 320

Asn Gly Asn Gly Asn Ser Gln Gly Asn Pro Trp Phe Leu Ala Thr Thr
                325                 330                 335

Ala Phe Thr Glu Leu Tyr Tyr Arg Ala Ile Leu Glu Trp Lys Asn Thr
            340                 345                 350

Gly Val Thr Val Thr Pro Ile Ser Lys Asp Phe Phe Val Arg Phe Asp
            355                 360                 365

Ser Ser Ala Ala Pro Gly Lys Lys Tyr Asn Pro Gly Ser Gln Glu Phe
            370                 375                 380

Ala Thr Leu Thr Gln Ser Ile Ala Ala Ala Asp Arg Phe Met Ser
385                 390                 395                 400

Thr Val Gln Tyr His Gln Asn Pro Asn Gly Ser Leu Ser Glu Glu Phe
                405                 410                 415

Asp Arg Ser Ser Gly Tyr Met Thr Gly Ala Arg Asp Leu Thr Trp Ser
            420                 425                 430

His Ala Ala Phe Ile Thr Ala Ala Gln Ala Arg Ala Gly Ser Pro Ser
            435                 440                 445

Phe
```

<210> SEQ ID NO 62
<211> LENGTH: 582
<212> TYPE: PRT
<213> ORGANISM: Backusella circina -continued

<400> SEQUENCE: 62

```
Asp Thr Val Pro Thr Thr Gln Val Lys Leu Gln Ser Tyr Thr Tyr Ser
1               5                   10                  15

Gly Gly Val Leu Ser Gly Thr Ile Tyr Val Gln Asn Ile Asp Tyr Thr
            20                  25                  30

Lys Val Val Thr Val Ile Tyr Ser Asp Gly Ser Gly Asn Trp Asn Asn
        35                  40                  45

Asn Gly Asn Thr Ile Ser Ala Ser Tyr Ser Ser Ile Ser Gly Thr
        50                  55                  60

Asn Tyr Glu Tyr Trp Thr Phe Ser Ala Ser Val Ser Ser Ile Gln Gln
65                  70                  75                  80

Phe Tyr Ile Ser Tyr Leu Val Asp Gly Thr Thr Tyr Tyr Asp Asn Asn
                85                  90                  95

Gly Gly Tyr Gly Ala Asn Tyr Ala Val Thr Ala Thr Thr Thr Ala
            100                 105                 110

Ser Ser Thr Thr Lys Thr Thr Ser Gly Thr Thr Lys Thr Ser Thr Thr
        115                 120                 125

Ser Thr Ala Thr Ala Thr Ser Thr Gly Thr Ser Ser Phe Pro Ser Gly
        130                 135                 140

Asn Ser Thr Ile Ser Thr Trp Ser Pro Ser Gln His Ser Ile Ser Leu
145                 150                 155                 160

Tyr Ala Met Leu Arg Asn Ile Asn Pro Pro Gly Ser Ala Ala Gly Phe
                165                 170                 175

Ile Ser Ala Ser Leu Ser Thr Ser Gly Pro Asp Tyr Tyr Tyr Ser Trp
            180                 185                 190

Thr Arg Asp Ser Ala Leu Val Ala His Val Ile Val Asn Glu Tyr Asn
        195                 200                 205

Thr Thr Tyr Gln Gly Asn Ser Thr Leu Leu Gly Ile Leu Lys Asp Tyr
        210                 215                 220

Val Thr Tyr Ser Leu Asn Ala Gln Thr Thr Ser Thr Val Cys Asn Cys
225                 230                 235                 240

Leu Gly Glu Pro Lys Phe Asn Pro Asp Gly Ser Ser Phe Thr Gly Ala
                245                 250                 255

Trp Gly Arg Pro Gln Asn Asp Gly Pro Ala Glu Arg Ala Val Ser Phe
            260                 265                 270

Ile Tyr Phe Ala Asp Ser Tyr Leu Thr Gln Thr Ser Asp Ser Ser Tyr
            275                 280                 285

Val Thr Gly Thr Leu Ala Pro Ala Ile Tyr Lys Asp Leu Asp Tyr Val
        290                 295                 300

Val Ser Val Trp Ser Asn Gly Cys Phe Asp Leu Trp Glu Glu Val Asn
305                 310                 315                 320

Gly Ile His Phe Tyr Thr Leu Met Phe Met Arg Arg Gly Leu Leu Asp
                325                 330                 335

Gly Ala Asn Phe Ala Ser Arg Asn Gly Asp Ser Thr Arg Ala Ser Thr
            340                 345                 350

Tyr Thr Ser Thr Ala Ala Ser Ile Lys Thr Lys Ile Asp Gly Phe Trp
            355                 360                 365

Val Ser Ser Gly Asn Tyr Val Gln Val Ser Gln Ser Val Thr Ser Gly
        370                 375                 380

Val Ser Lys Ala Gly Tyr Asp Ala Ser Thr Leu Ile Ala Ala Asn Gln
385                 390                 395                 400

Ala Ser Arg Gly Asp Gly Phe Tyr Thr Pro Gly Ser Asp Lys Met Leu
```

-continued

```
                    405              410              415

Ala Thr Ala Val Ala Ile Glu Ser Gln Phe Ser Ser Leu Tyr Ser Ile
                420              425              430

Asn Thr Asn Lys Ala Ser Tyr Leu Gly Asn Ala Ile Gly Arg Tyr Pro
            435              440              445

Glu Asp Thr Tyr Asn Gly Asn Gly Asn Ser Gln Gly Asn Pro Trp Phe
        450              455              460

Leu Cys Thr Asn Ala Phe Gly Glu Leu Phe Tyr Arg Ala Ile Ser Glu
465              470              475              480

Trp Asn Ala Ala Gly Ser Val Thr Val Asn Ser Val Asn Leu Ala Phe
                485              490              495

Phe Lys Lys Tyr Asp Ser Ser Thr Ser Ser Gly Thr Thr Tyr Thr Val
                500              505              510

Gly Thr Ser Ala Tyr Asn Asn Leu Val Gln Asn Val Ala Leu Ala Ala
            515              520              525

Asp Ala Tyr Phe Ser Thr Val Lys Tyr His Ala Leu Thr Asn Gly Ser
        530              535              540

Met Ser Glu Gln Tyr Asp Arg Ser Ser Gly Met Ala Thr Gly Ala Arg
545              550              555              560

Asp Leu Thr Trp Ser His Ala Ala Met Ile Thr Ala Leu Lys Ala Lys
                565              570              575

Ser Gly Thr Pro Val Tyr
            580

<210> SEQ ID NO 63
<211> LENGTH: 578
<212> TYPE: PRT
<213> ORGANISM: Backusella circina

<400> SEQUENCE: 63

Asp Thr Val Pro Thr Thr Gln Val Glu Val Lys Thr Tyr Thr Tyr Ser
1               5               10               15

Gly Gly Glu Leu Ser Gly Thr Ile Tyr Val Glu Asn Ile Asp Tyr Thr
                20              25               30

Lys Val Val Thr Val Ile Tyr Ala Asp Gly Ser Asp Asp Trp Asn Asn
            35              40               45

Asn Gly Asn Thr Ile Ala Ala Ala Phe Ser Glu Ser Ile Ser Asp Thr
        50              55               60

Asn Tyr Glu Tyr Trp Thr Phe Ser Ser Ser Val Asn Ser Ile Lys Glu
65              70              75               80

Phe Tyr Val Lys Tyr Asp Val Asp Gly Asn Thr Tyr Tyr Asp Asn Asn
                85              90               95

Gly Asn Ala Asn Tyr Gln Val Ser Ala Ser Ser Thr Thr Thr Thr Thr
            100             105              110

Ala Thr Lys Thr Thr Thr Thr Ala Thr Lys Thr Thr Ala Thr Ala Thr
            115             120              125

Ser Thr Ala Thr Gly Ser Thr Ser Phe Pro Ser Gly Asn Ser Thr Ile
        130             135              140

Ser Ser Trp Ile Lys Gly Gln Glu Asp Thr Ser Arg Ser Val Met Leu
145             150             155              160

Gly Asn Ile Asn Pro Pro Gly Ser Ala Thr Gly Phe Ile Ser Ala Ser
                165             170              175

Leu Ser Thr Ser Gly Pro Asp Tyr Tyr Tyr His Trp Thr Arg Asp Ala
            180             185              190
```

-continued

```
Ala Leu Val Ala His Val Ile Val Asn Asp Tyr Asn Thr Thr Leu Ser
        195                 200                 205

Gly Asp Ser Ser Thr Leu Gln Val Ile Lys Asp Tyr Val Thr Phe Ser
        210                 215                 220

Val Asn Ser Gln Ser Glu Ser Thr Val Cys Asn Cys Leu Gly Glu Pro
225                 230                 235                 240

Lys Phe Asn Pro Asp Gly Ser Ser Tyr Thr Gly Ala Trp Gly Arg Pro
                245                 250                 255

Gln Asn Asp Gly Pro Ala Glu Arg Ala Thr Thr Phe Ile Phe Phe Ala
                260                 265                 270

Asp Thr Tyr Leu Ala Gln Gly Gly Asp Ser Ser Tyr Val Thr Gly Thr
                275                 280                 285

Leu Ala Pro Ala Ile Tyr Ala Asp Leu Asp Tyr Val Val Asn Asn Trp
        290                 295                 300

Ser Thr Gly Cys Tyr Asp Leu Trp Glu Glu Val Asn Gly Ile His Phe
305                 310                 315                 320

Tyr Thr Leu Met Val Met Arg Arg Gly Leu Ile Asp Gly Ala Ser Phe
                325                 330                 335

Ala Ser Arg Asn Gly Asp Ser Thr Arg Ser Ser Ser Tyr Thr Ser Thr
                340                 345                 350

Ala Lys Ser Ile Ala Thr Lys Ile Asp Ser Phe Trp Ser Ala Ser Asn
        355                 360                 365

Asn Tyr Val Ala Val Ser Gln Ser Val Thr Ser Gly Val Ser Lys Ala
        370                 375                 380

Gly Tyr Asp Ala Ser Thr Ile Ile Ala Ala Asn Gln Ala Ser Leu Gly
385                 390                 395                 400

Asp Gly Phe Tyr Thr Pro Gly Ser Asp Lys Met Leu Ala Thr Ser Val
                405                 410                 415

Ala Val Glu Asn Ala Phe Ser Ser Leu Tyr Thr Val Asn Thr Gly Lys
                420                 425                 430

Ala Ser Tyr Leu Gly Asn Ala Ile Gly Arg Tyr Pro Glu Asp Thr Tyr
        435                 440                 445

Asn Gly Asn Gly Asn Ser Gln Gly Asn Pro Trp Tyr Leu Cys Thr Asn
        450                 455                 460

Ala Leu Gly Glu Leu Tyr Tyr Arg Ala Ile Lys Glu Trp Asn Ala Ala
465                 470                 475                 480

Gly Ser Val Thr Val Asn Ser Val Asn Leu Gly Phe Phe Gln Lys Ile
                485                 490                 495

Asp Ser Ser Ile Ser Ser Gly Thr Thr Phe Thr Leu Gly Thr Ser Asp
                500                 505                 510

Tyr Ser Thr Leu Val Asp Asn Val Ala Leu Ala Ala Asp Lys Phe Phe
        515                 520                 525

Ala Val Val Gln Tyr His Glu Arg Ser Asn Gly Ser Met Pro Glu Gln
        530                 535                 540

Phe Gly Arg Glu Asp Gly Leu Pro Thr Gly Ala Arg Asp Leu Thr Trp
545                 550                 555                 560

Ser His Ala Ala Met Ile Ser Ala Ala Arg Ala Lys Ala Gly Thr Pro
                565                 570                 575

Val Tyr
```

<210> SEQ ID NO 64
<211> LENGTH: 577
<212> TYPE: PRT
<213> ORGANISM: Benjaminiella poitrasii -continued

```
<400> SEQUENCE: 64

Glu Thr Val Pro Thr Thr Ser Gln Val Lys Leu Lys Ser Tyr Thr Tyr
1               5                   10                  15

Asp Gly Ser Thr Leu Ser Gly Gln Ile Tyr Ile Gln Asn Ile Ala Tyr
            20                  25                  30

Thr Lys Val Val Thr Val Ile Tyr Ser Asp Ala Ser Ser Asn Trp Asn
        35                  40                  45

Asn Asn Gly Asn Thr Ile Ala Ala Ser Tyr Thr Asn Gly Ile Ser Gly
        50                  55                  60

Thr Asn Tyr Glu Tyr Trp Asn Phe Thr Gly Pro Val Ser Ser Ile Asn
65                  70                  75                  80

Ala Phe Tyr Ile Lys Tyr Asp Val Ser Gly Asn Thr Tyr Tyr Asp Asn
                85                  90                  95

Asn Asn Asn Ala Asn Tyr Gln Val Thr Lys Thr Ser Thr Thr Thr Thr
            100                 105                 110

Thr Ser Thr Ala Thr Ala Thr Thr Thr Lys Thr Ser Thr Pro Thr
        115                 120                 125

Ser Thr Gly Val Pro Ser Asn Phe Pro Thr Gly Asn Ser Thr Ile Ser
    130                 135                 140

Thr Trp Leu Lys Ser Gln Ile Gly Ile Ser Arg Tyr Ala Met Leu Arg
145                 150                 155                 160

Asn Ile Asn Pro Ala Gly Ser Ala Val Gly Phe Ile Ala Ala Ser Leu
                165                 170                 175

Ser Thr Ala Asn Pro Asp Tyr Tyr Tyr Ala Trp Thr Arg Asp Ser Ala
            180                 185                 190

Leu Thr Ser Tyr Val Ile Ala Asn Asp Tyr Asn Ser Thr Leu Ala Gly
            195                 200                 205

Asn Ser Thr Ile Leu Gln Ile Met Lys Asp Tyr Val Thr Phe Ser Val
    210                 215                 220

Lys Ser Gln Ser Val Ser Thr Ala Cys Asn Cys Leu Gly Glu Pro Lys
225                 230                 235                 240

Phe Asn Pro Asp Gly Ser Ser Tyr Thr Gly Ala Trp Gly Arg Pro Gln
                245                 250                 255

Asn Asp Gly Pro Ala Glu Arg Ala Thr Thr Phe Ile Leu Phe Ala Asp
            260                 265                 270

Ser Tyr Leu Lys Gln Thr Gly Asp Ala Ser Tyr Val Thr Gly Thr Leu
            275                 280                 285

Lys Pro Ala Ile Phe Lys Asp Leu Asp Tyr Val Val Asn Thr Trp Thr
    290                 295                 300

Asn Gly Cys Phe Asp Leu Trp Glu Glu Val Asn Gly Val His Phe Tyr
305                 310                 315                 320

Thr Leu Met Val Met Arg Lys Gly Leu Ile Arg Gly Ala Asn Phe Ala
                325                 330                 335

Thr Arg Asn Gly Asp Ser Thr Arg Ala Ser Thr Tyr Thr Asn Thr Ala
            340                 345                 350

Ala Ser Ile Lys Thr Lys Met Asp Ser Phe Trp Ser Ser Gly Asn Asn
            355                 360                 365

Tyr Ile Ala Val Ser Gln Ser Val Thr Gly Gly Val Ser Lys Ala Gly
    370                 375                 380

Tyr Asp Val Ala Asn Ile Ile Ala Ala Asn Val Gly Ser Leu Gln Asp
385                 390                 395                 400

Gly Val Tyr Thr Pro Gly Ser Asp Arg Ile Leu Ala Thr Ala Val Ala
```

-continued

```
                          405              410              415

Val Glu Ala Lys Phe Ala Ser Leu Tyr Gly Val Asn Ser Asn Leu Pro
                420              425              430

Gly Tyr Leu Gly Asn Ser Ile Gly Arg Tyr Pro Glu Asp Thr Tyr Asn
            435              440              445

Gly Asn Gly Asn Ser Gln Gly Asn Pro Trp Phe Leu Ala Thr Asn Ala
        450              455              460

Tyr Ala Glu Leu Tyr Tyr Arg Ala Ile Arg Glu Trp Tyr Asp Asn Gly
465              470              475              480

Gly Val Thr Val Asn Ser Val Asn Leu Pro Phe Phe Lys Lys Phe Asp
                485              490              495

Ser Ser Ala Ala Ser Gly Thr Thr Tyr Thr Val Gly Thr Thr Ala Phe
                500              505              510

Asn Thr Met Val Ser Asn Val Ala Ala Ala Ala Asp Lys Phe Phe Ser
            515              520              525

Thr Val Lys Phe His Ala Tyr Thr Asn Gly Ser Met Ser Glu Gln Phe
        530              535              540

Gly Arg Asn Asp Gly Leu Cys Thr Gly Ala Arg Asp Leu Thr Trp Ser
545              550              555              560

His Ala Ser Leu Ile Ser Ala Ala Leu Ala Lys Ala Gly Thr Pro Ser
                565              570              575

Val

<210> SEQ ID NO 65
<211> LENGTH: 574
<212> TYPE: PRT
<213> ORGANISM: Choanephora cucurbitarum

<400> SEQUENCE: 65

Gln Ser Val Pro Thr Ser Asp Pro Val Lys Val Lys Thr Phe Ser Tyr
1               5               10              15

Asp Gly Asn Ser Phe Ser Gly Gln Ile Tyr Ile Lys Asn Ile Ala Tyr
                20              25              30

Glu Lys Thr Val Thr Val Ile Tyr Ser Asp Gly Thr Gly Asn Trp Asn
            35              40              45

Asn Asn Asn Asn Lys Ile Ala Ala Ala Phe Ser Glu Ala Ile Ser Gly
        50              55              60

Ser Asn Tyr Glu Tyr Trp Thr Phe Ser Ala Ser Val Pro Ser Ile Lys
65              70              75              80

Gln Phe Tyr Val Lys Tyr Asp Val Ser Gly Lys Thr Tyr Tyr Asp Asn
                85              90              95

Asn Gly Ser Lys Asp Tyr Asn Val Val Thr Ser Gly Pro Thr Thr Thr
            100             105             110

Ser Ser Gly Pro Ser Lys Thr Thr Thr Asn Gly Pro Ala Pro Thr Ser
        115             120             125

Thr Asn Thr Asn Phe Pro Ser Gly Asn Pro Ser Ile Thr Ser Trp Ile
    130             135             140

Asp Lys Gln Ile Asp Ile Ser Arg Ser Ala Met Leu Lys Asn Ile Asn
145             150             155             160

Pro Ala Gly Thr Val Lys Gly Phe Ile Ala Ala Ser Leu Ser Thr Ser
                165             170             175

Asn Pro Asp Tyr Phe Tyr Ala Trp Thr Arg Asp Ala Ala Leu Val Ala
            180             185             190

His Val Val Ala Asn Asp Tyr Asn Arg Thr Lys Ser Gly Asp Ala Thr
```

-continued

```
            195               200               205
Tyr Leu Gly Leu Leu Lys Asp Tyr Val Thr Phe Ser Ile Asn Ser Gln
    210               215               220

Asn Thr Pro Thr Ala Cys Asn Cys Leu Gly Glu Pro Lys Phe Asn Lys
225               230               235               240

Asp Gly Ser Gly Tyr Asn Gly Pro Trp Gly Arg Pro Gln Asn Asp Gly
                245               250               255

Pro Ala Glu Arg Ala Asp Thr Phe Val Leu Ile Ala Asp Ser Ile Leu
                260               265               270

Thr Gln Thr Lys Asp Val Ser Tyr Val Thr Gly Thr Leu Arg Pro Ala
                275               280               285

Ile Tyr Thr Asp Leu Asp Tyr Val Val Arg Thr Trp Ser Asn Gly Cys
    290               295               300

Phe Asp Leu Trp Glu Glu Val Asn Gly Val His Phe Tyr Thr Leu Met
305               310               315               320

Val Met Arg Arg Ala Leu Leu Val Gly Ala Asn Phe Ala Ser Arg Asn
                325               330               335

Gly Asp Ser Ala Arg Ala Ser Asn Tyr Asn Asn Ala Ala Asn Ser Ile
                340               345               350

Lys Ser Lys Ile Asp Ser Phe Trp Ser Ser Asn Asn Asn Tyr Val Ala
                355               360               365

Val Ser Gln Ser Val Thr Gly Gly Val Ser Lys Ala Gly Tyr Asp Val
    370               375               380

Ser Thr Leu Ile Ala Ala Asn Val Gly Ser Leu Ser Asp Gly Phe Tyr
385               390               395               400

Thr Pro Gly Ser Glu Arg Met Leu Ala Thr Ala Val Ala Ile Glu Asp
                405               410               415

Lys Phe Ala Asn Leu Tyr Gly Ile Asn Arg Asn Leu Asp Ser Ser Leu
                420               425               430

Gly Asn Ala Ile Gly Arg Tyr Pro Glu Asp Thr Tyr Asn Gly Asn Gly
                435               440               445

Asn Ser Gln Gly Asn Pro Trp Phe Ile Ala Thr Asn Ala Tyr Ala Glu
    450               455               460

Leu Tyr Tyr Arg Ala Ile Lys Glu Trp Asn Asn Asn Gly Gly Val Thr
465               470               475               480

Val Thr Asn Val Asn Leu Asn Phe Phe Lys Lys Phe Asp Gly Ser Ala
                485               490               495

Ser Val Gly Thr Lys Tyr Thr Ala Gly Ser Ala Ala Tyr Asn Thr Leu
                500               505               510

Thr Gln Asn Ile Ala Leu Ala Ala Asp Lys Phe Phe Asn Thr Val Lys
                515               520               525

Val His Ala Ala Thr Asn Gly Ser Met Ser Glu Gln Tyr His Arg Asp
    530               535               540

Thr Gly Ser Met Thr Gly Ala Arg Asp Leu Thr Trp Ser His Ala Ser
545               550               555               560

Leu Ile Thr Ala Ala Leu Ala Lys Ala Gly Thr Pro Val Ala
                565               570
```

<210> SEQ ID NO 66
<211> LENGTH: 584
<212> TYPE: PRT
<213> ORGANISM: Rhizopus stolonifer

<400> SEQUENCE: 66

-continued

```
Ala Ser Ile Pro Ser Ser Ser Glu Val Gln Leu Asp Thr Tyr Ala Tyr
1               5                   10                  15

Asp Gly Ala Lys Phe Ser Gly Lys Ile Tyr Val Lys Asn Ile Ala Tyr
            20                  25                  30

Glu Lys Thr Val Thr Val Val Tyr Ala Asp Gly Ser Asp Asn Trp Asn
        35                  40                  45

Asn Asn Gly Asn Ile Ile Ser Ala Thr Phe Ser Thr Pro Ile Ser Gly
    50                  55                  60

Ser Asn Tyr Glu Tyr Trp Thr Phe Ser Ser Ser Ile Ser Gly Ile Lys
65                  70                  75                  80

Glu Phe Tyr Ile Lys Tyr Val Val Ser Gly Lys Thr Tyr Tyr Asp Asn
                85                  90                  95

Asn Gly Thr Lys Asn Tyr Gln Val Ser Thr Thr Ser Ser Thr Thr Thr
            100                 105                 110

Ala Ser Thr Thr Thr Ala Thr Arg Thr Thr Thr Ala Gly Thr Thr Ser
            115                 120                 125

Thr Ser Thr Thr Ala Ala Pro Thr Ser Thr Ser Ser Gly Ser Phe Pro
    130                 135                 140

Ser Gly Asn Ser Thr Val Ser Ser Trp Ile Lys Arg Gln Glu Lys Ile
145                 150                 155                 160

Ser Arg Phe Ala Met Leu Arg Asn Ile Asn Pro Pro Gly Ser Ala Ala
                165                 170                 175

Gly Phe Ile Ala Ala Ser Leu Ser Thr Ser Gly Pro Asp Tyr Tyr Tyr
                180                 185                 190

Ser Trp Thr Arg Asp Ser Ala Leu Thr Ser Asn Leu Ile Ala Tyr Glu
            195                 200                 205

Tyr Asn Thr Thr Leu Ser Gly Asn Thr Thr Ile Leu Asn Ile Leu Lys
    210                 215                 220

Asp Tyr Val Lys Phe Ser Ile Ser Ser Gln Thr Thr Ser Thr Val Cys
225                 230                 235                 240

Asn Cys Leu Gly Glu Pro Lys Phe Asn His Asp Gly Ser Ser Tyr Thr
                245                 250                 255

Gly Ala Trp Gly Arg Pro Gln Asn Asp Gly Pro Ala Glu Arg Ala Asn
            260                 265                 270

Thr Phe Ile Leu Phe Ala Asp Ser Tyr Leu Asp Gln Thr Lys Asp Ala
            275                 280                 285

Ser Tyr Val Thr Gly Thr Leu Lys Pro Ala Ile Phe Lys Asp Leu Asp
    290                 295                 300

Tyr Val Val Asn Val Trp Ser Asn Gly Cys Tyr Asp Leu Trp Glu Glu
305                 310                 315                 320

Val Asn Gly Val His Phe Tyr Thr Leu Met Val Met Arg Lys Gly Leu
                325                 330                 335

Leu Leu Gly Ala Asp Phe Ala Lys Arg Asn Gly Asp Ser Thr Arg Ala
                340                 345                 350

Ser Thr Tyr Thr Asn Thr Ala Ser Thr Ile Ala Thr Lys Ile Ser Ser
            355                 360                 365

Phe Trp Val Ser Ser Ser Asn Trp Ile Gln Val Ser Gln Ser Val Thr
    370                 375                 380

Ala Gly Val Ser Lys Lys Gly Leu Asp Val Ser Thr Leu Leu Ala Ala
385                 390                 395                 400

Asn Leu Gly Ser Val Glu Asp Gly Phe Phe Thr Pro Gly Ser Glu Lys
                405                 410                 415

Ile Leu Ala Thr Ala Val Ala Ile Glu Asp Ala Phe Ala Ser Leu Tyr
```

```
                      420              425              430
Pro Ile Asn Ser Asn Leu Pro Ser Tyr Leu Gly Asn Ser Ile Gly Arg
            435              440              445

Tyr Pro Glu Asp Thr Tyr Asn Gly Asn Gly Asn Ser Gln Gly Asn Pro
    450              455              460

Trp Phe Leu Ala Val Asn Gly Phe Ala Glu Leu Tyr Tyr Arg Ala Ile
465              470              475              480

Lys Glu Trp Val Asn Asn Gly Ser Val Thr Val Ser Asn Ile Ser Leu
            485              490              495

Ser Phe Phe Lys Lys Phe Asp Ser Ser Ala Thr Ala Gly Lys Thr Tyr
            500              505              510

Thr Ala Gly Thr Ala Asp Phe Asn Asn Leu Ala Gln Asn Ile Ala Leu
            515              520              525

Gly Ala Asp Arg Phe Leu Ser Thr Val Gln Thr His Ala Phe Asn Asn
            530              535              540

Gly Ser Leu Ala Glu Glu Tyr Asp Arg Thr Thr Gly Val Ser Thr Gly
545              550              555              560

Ala Arg Asp Leu Thr Trp Ser His Ala Ser Leu Ile Thr Ala Ala Tyr
                565              570              575

Ala Lys Ala Gly Ser Pro Ala Ala
                580

<210> SEQ ID NO 67
<211> LENGTH: 584
<212> TYPE: PRT
<213> ORGANISM: Mucor circinelloides

<400> SEQUENCE: 67

Glu Thr Val Pro Thr Thr Ala Ala Val Lys Val Lys Ser Phe Thr Tyr
1               5                10               15

Asp Gly Ser Thr Phe Ala Gly Gln Ile Tyr Val Lys Asn Ile Ala Tyr
            20               25               30

Thr Lys Thr Val Thr Val Ile Tyr Ser Asp Ala Ser Asn Asn Trp Asn
            35               40               45

Asn Asn Gly Asn Thr Ile Ala Ala Ser Tyr Ser Glu Gly Ile Ser Gly
    50               55               60

Thr Asn Tyr Glu Tyr Trp Thr Phe Ser Ala Pro Val Ser Gly Ile Lys
65               70               75               80

Gln Phe Tyr Val Lys Tyr Val Val Ser Gly Thr Thr Tyr Tyr Asp Asn
                85               90               95

Asn Asn Ser Gly Asn Tyr Gln Val Thr Thr Thr Thr Thr Thr Thr Ala
            100              105              110

Pro Thr Ser Thr Thr Ser Gly Gly Ser Ser Thr Thr Thr Gly Gly Ser
            115              120              125

Thr Thr Thr Ala Thr Ser Val Pro Thr Gly Val Pro Ser Gly Phe Pro
    130              135              140

Thr Gly Asn Ser Ser Ile Ser Ser Trp Ile Asp Gly Gln Thr Ser Val
145              150              155              160

Ser Arg Tyr Ala Met Leu Arg Asn Ile Asn Pro Ala Gly Ala Val Ser
                165              170              175

Gly Phe Ile Ala Ala Ser Met Ser Thr Ser Gly Pro Asp Tyr Phe Tyr
            180              185              190

Ala Trp Thr Arg Asp Ser Ala Leu Thr Ser His Val Val Ala Tyr Asp
            195              200              205
```

```
Tyr Asn Thr Thr Leu Ala Gly Asn Ser Thr Ile Leu Gly Leu Leu Lys
    210                 215                 220

Asn Tyr Val Thr Phe Ser Ile Asn Ser Gln Thr Thr Ser Thr Val Cys
225                 230                 235                 240

Asn Cys Leu Gly Glu Pro Lys Phe Asn Lys Asp Gly Ser Ser Tyr Thr
            245                 250                 255

Gly Ala Trp Gly Arg Pro Gln Asn Asp Gly Pro Ala Ser Arg Ala Asp
            260                 265                 270

Thr Phe Ile Leu Ile Ala Asp Ser Ile Leu Lys Gln Thr Gly Asp Ala
        275                 280                 285

Thr Tyr Val Thr Gly Thr Leu Ala Pro Ala Ile Tyr Lys Asp Leu Asp
    290                 295                 300

Tyr Val Val Ser Thr Trp Ser Asn Gly Cys Phe Asp Leu Trp Glu Glu
305                 310                 315                 320

Val Asn Gly Val His Phe Tyr Thr Leu Met Val Met Arg Arg Gly Leu
            325                 330                 335

Ile Lys Gly Ala Asn Phe Ala Ser Arg Asn Gly Asp Asn Thr Arg Ala
            340                 345                 350

Asn Thr Tyr Thr Asn Thr Ala Ala Ser Ile Lys Thr Lys Ile Asp Ser
        355                 360                 365

Phe Trp Asn Ser Asn Gly Asn Tyr Val Thr Val Ser Gln Ser Val Thr
    370                 375                 380

Gly Gly Val Ser Lys Ala Gly Tyr Asp Ala Ser Val Leu Ile Ala Ala
385                 390                 395                 400

Asn Leu Gly Ser Val Gln Asp Gly Phe Tyr Thr Pro Gly Ser Asp Lys
            405                 410                 415

Met Leu Ala Thr Ala Val Ala Ile Glu Ser Lys Phe Ala Ser Leu Tyr
            420                 425                 430

Ser Ile Asn Gln Asn Leu Asn Gly Tyr Leu Gly Asn Ala Ile Gly Arg
        435                 440                 445

Tyr Pro Glu Asp Thr Tyr Asn Gly Asn Gly Asn Ser Gln Gly Asn Pro
    450                 455                 460

Trp Phe Ile Cys Thr Asn Ala Phe Ala Glu Leu Tyr Tyr Arg Ala Ile
465                 470                 475                 480

Lys Glu Trp Phe Asn Asn Gly Gly Val Thr Val Thr Ser Ile Ser Leu
            485                 490                 495

Asn Phe Phe Lys Lys Phe Asp Ser Ser Ala Ala Val Gly Thr Lys Tyr
            500                 505                 510

Thr Val Gly Thr Ser Ala Phe Asn Ser Leu Val Gln Asn Val Ala Val
        515                 520                 525

Ala Ala Asp Ala Phe Phe Ser Thr Val Lys Phe His Ala Ala Thr Asn
    530                 535                 540

Gly Ser Met Ser Glu Gln Tyr Gly Arg Ser Asp Gly Leu Met Thr Gly
545                 550                 555                 560

Ala Arg Asp Leu Thr Trp Ser His Ala Ser Leu Ile Ser Ala Ser Tyr
            565                 570                 575

Ala Lys Ala Gly Ser Pro Ala Ala
            580
```

<210> SEQ ID NO 68
<211> LENGTH: 581
<212> TYPE: PRT
<213> ORGANISM: Dichotomocladium elegans
<400> SEQUENCE: 68

-continued

```
Ala Thr Val Pro Lys Thr Gln Val Lys Leu Glu Ala Tyr Thr Tyr Ser
1               5                   10                  15

Asp Ser Ile Phe Ser Gly Arg Ile Phe Val Gln Asn Ile Asp Tyr Thr
            20                  25                  30

Lys Ile Val Thr Val Tyr Trp Ser Asp Ala Ser Asn Lys Trp Asp Ser
        35                  40                  45

Ser Lys Tyr Tyr Thr Glu Ala Ala Tyr Thr His Ser Ile Pro Gly Thr
    50                  55                  60

Asn Tyr Glu Tyr Trp Asp Phe Ser Ala Thr Ile Gly Pro Ser Gly Ile
65                  70                  75                  80

Lys Gln Phe Tyr Ile Ser Tyr Gln Val Arg Gly Val Thr Tyr Tyr Asp
                85                  90                  95

Asn Asn Gly Gly Tyr Gly Val Asn Tyr Asp Val Ile Ser Ser Pro Pro
            100                 105                 110

Thr Thr Ser Asp Ala Thr Thr Ile Pro Thr Thr Thr Ser Ala Ile
            115                 120                 125

Pro Ser Ser Thr Thr Thr Ile Pro Ala Ser Thr Gly Val Pro Ser Gly
    130                 135                 140

Asn Ser Thr Ile Thr Val Trp Ala Asp Ser Gln His Lys Ile Ser Trp
145                 150                 155                 160

Lys Ala Met Leu Ala Asn Ile Asn Pro Pro Gly Ser Ala Thr Gly Phe
            165                 170                 175

Ile Ala Ala Ser Leu Ser Thr Ser Gly Pro Asp Tyr Tyr Tyr Ala Trp
            180                 185                 190

Thr Arg Asp Ala Ala Met Val Ala His Val Ile Val Asn Ala Tyr Asn
        195                 200                 205

Thr Thr Lys Ala Gly Asp Ala Thr Thr Leu Gly Val Leu Lys Asp Phe
    210                 215                 220

Val Thr Phe Gln Ile Lys Ala Met Ala Thr Ser Thr Val Cys Asn Cys
225                 230                 235                 240

Leu Gly Glu Pro Lys Phe Asn Pro Asp Gly Ser Ser Tyr Thr Gly Pro
            245                 250                 255

Trp Gly Arg Pro Gln Asn Asp Gly Pro Ala Glu Arg Ala Thr Thr Phe
            260                 265                 270

Ile Leu Phe Ala Asp Ser Tyr Leu Ser Gln Thr Gly Asp Ala Ala Tyr
            275                 280                 285

Val Thr Thr Leu Lys Arg Ala Ile Phe Thr Asp Leu Asp Tyr Val Val
    290                 295                 300

Thr Thr Trp Gln Asp Asn Cys Phe Asp Leu Trp Glu Glu Val Asn Gly
305                 310                 315                 320

Leu His Met Tyr Thr Leu Ala Val Met Arg Arg Ser Leu Val Asp Gly
            325                 330                 335

Ala Ser Phe Ala Ala Arg Asn Gly Asp Asn Thr Arg Ala Ser Thr Tyr
            340                 345                 350

Thr Asn Thr Ala Lys Ser Ile Glu Thr Lys Leu Ala Ser Phe Tyr Asn
            355                 360                 365

Ser Ser Ser Asn Tyr Val Val Val Thr Lys Asn Phe Ala Gly Gly Val
    370                 375                 380

Asn Lys Ala Gly Leu Asp Thr Ser Thr Leu Ile Ala Ala Asn Thr Ala
385                 390                 395                 400

Gly Leu Gly Asp Gly Phe Phe Thr Pro Gly Ser Pro Glu Ile Leu Ala
            405                 410                 415
```

-continued

```
Thr Ala Ala Ala Ile Glu Lys Ser Phe Ala Asp Leu Tyr Gly Ile Asn
            420                 425                 430

Lys Gln Ile Pro Asn Trp Leu Gly Thr Ala Ile Gly Arg Tyr Pro Glu
            435                 440                 445

Asp Thr Tyr Asn Gly Asn Gly Asn Ser Gln Gly Asn Pro Trp Phe Ile
            450                 455                 460

Cys Thr Ala Thr Phe Ala Glu Leu Tyr Tyr Arg Ala Ile Leu Glu Trp
465                 470                 475                 480

Gln His Ala Gly Ser Val Thr Val Asn Asn Val Asn Leu Pro Phe Phe
                485                 490                 495

Lys Lys Phe Asp Ser Ser Thr Ser Ser Gly Thr Thr Tyr Thr Val Gly
            500                 505                 510

Thr Ser Ser Phe Asp Ser Leu Ile Ser Lys Val Ala Tyr Ala Ala Asp
            515                 520                 525

Asn Phe Phe Ser Thr Ile Lys Tyr His Ala Ala Thr Asn Gly Ser Met
            530                 535                 540

Ser Glu Gln Phe Asn Arg Asp Thr Gly Phe Met Thr Gly Ala Arg Asp
545                 550                 555                 560

Leu Thr Trp Ser His Ala Ala Phe Ile Thr Ala Ala Lys Ala Lys Ala
                565                 570                 575

Gly Thr Pro Val Tyr
            580

<210> SEQ ID NO 69
<211> LENGTH: 582
<212> TYPE: PRT
<213> ORGANISM: Fennellomyces sp.

<400> SEQUENCE: 69

Gln Thr Val Pro Ser Val Pro Ile Lys Leu Glu Ser Tyr Thr Tyr Ser
1               5                   10                  15

Asp Asn Val Phe Ala Gly Arg Ile Phe Ile Arg Asn Ile Ala Tyr Thr
            20                  25                  30

Lys Val Val Lys Val Phe Trp Ser Asp Glu Ser Gly Asn Trp Asn Gly
            35                  40                  45

Asn Gly Asn Tyr Val Asp Ala Ser Tyr Ser Gly Ser Ile Ser Gly Thr
            50                  55                  60

Asn Tyr Glu Tyr Trp Glu Phe Ser Thr Thr Ile Gly Ser Ala Gly Ile
65                  70                  75                  80

Ser Gln Ser Tyr Leu Arg Tyr Asp Val Ser Gly Ser Thr Tyr Tyr Asp
                85                  90                  95

Asn Asn Gly Asn Ala Asn Tyr Asp Ile Glu Glu Asp Ser Thr Pro Thr
            100                 105                 110

Pro Thr Thr Thr Thr Thr Ser Thr Thr Thr Ile Thr Thr Thr Thr Thr
            115                 120                 125

Ser Gly Thr Ser Thr Pro Thr Ser Val Pro Thr Glu Val Pro Ala Gly
            130                 135                 140

Asn Thr Thr Val Thr Asp Trp Val Asn Asp Gln Leu Glu Ile Ser Trp
145                 150                 155                 160

Pro Ser Leu Leu Lys Asn Val Asn Pro Ser Gly Ala Val Thr Gly Phe
                165                 170                 175

Ile Ala Ala Ser Leu Ser Thr Asn Asp Pro Asp Tyr Phe Tyr Cys Trp
            180                 185                 190

Thr Arg Asp Ala Ala Leu Val Ala Arg Val Met Val Tyr Met Tyr Asn
            195                 200                 205
```

-continued

```
Thr Thr Glu Ala Gly Asp Thr Ser Leu Arg Ser Lys Leu Gln Asp Tyr
    210             215             220

Val Thr Phe Gln Ile Asn Ser Met Lys Thr Ala Thr Val Cys Asn Cys
225             230             235             240

Leu Gly Glu Pro Lys Phe Asn Lys Asp Gly Ser Gly Tyr Ser Gly Ala
            245             250             255

Trp Gly Arg Pro Gln Asn Asp Gly Pro Ala Asp Arg Ala Ile Thr Leu
            260             265             270

Ile Leu Phe Ala Asp Ser Phe Ile Ala Gln Gly Gly Asp Val Ser Tyr
            275             280             285

Ile Thr Asn Thr Leu Lys Pro Ala Ile Tyr Thr Asn Leu Asp Tyr Val
    290             295             300

Val Asn Thr Trp Ser Asn Val Cys Phe Asp Leu Trp Glu Glu Val Asn
305             310             315             320

Gly Val His Ile Tyr Thr Leu Ser Val Met Arg Lys Gly Leu Leu Glu
            325             330             335

Gly Ala Asp Phe Ala Ser Arg Asn Gly Asp Ser Thr Arg Ala Asn Thr
            340             345             350

Tyr Arg Ser Thr Ala Ser Ser Ile Lys Thr Arg Leu Glu Ser Phe Trp
            355             360             365

Ser Ser Ser Asn Asn Tyr Ile Thr Val Thr Gln Ser Tyr Ser Gly Gly
    370             375             380

Val Asn Lys Ala Gly Leu Asp Val Ser Thr Leu Leu Ala Ala Asn Gly
385             390             395             400

Ala Ser Met Asn Asp Gly Phe Tyr Thr Pro Gly Ser Asp Lys Met Leu
            405             410             415

Ala Thr Ala Val Ala Ile Glu Asn Ser Phe Ala Gly Ile Tyr Ala Val
            420             425             430

Asn Gln Asn Arg Pro Asp Trp Lys Gly Thr Ala Ile Gly Arg Tyr Pro
            435             440             445

Glu Asp Thr Tyr Asp Gly His Gly Asn Ser Gln Gly Asn Pro Trp Phe
    450             455             460

Ile Ala Thr Ala Ala Tyr Ala Glu Met Tyr Tyr Arg Ala Ile Leu Glu
465             470             475             480

Trp Gln Gln Gln Pro Ser Ile Thr Val Asn Ser Ile Asn Leu Ser Phe
            485             490             495

Phe Lys Lys Phe Asp Ser Ser Ala Ala Val Gly Thr Val Tyr Lys Pro
            500             505             510

Gly Thr Gln Ala Phe Asn Asn Met Val Ser Asn Val Ala Phe Ala Ala
    515             520             525

Asp Glu Phe Phe Ser Thr Met Asn Phe His Ser Ala Thr Asn Gly Ser
    530             535             540

Met Ser Glu Gln Tyr Asn Arg Asn Thr Gly Ile Met Gln Gly Ala Arg
545             550             555             560

Asp Leu Thr Trp Ser His Ala Ala Phe Ile Thr Ala Ala Lys Ala Lys
            565             570             575

Leu Gly Thr Pro Val Phe
            580
```

```
<210> SEQ ID NO 70
<211> LENGTH: 577
<212> TYPE: PRT
<213> ORGANISM: Gilbertella persicaria
```

```
<400> SEQUENCE: 70

Glu Thr Val Pro Thr Ser Ala Gln Val Gln Val Lys Ser Phe Asn Tyr
1               5                   10                  15

Asp Gly Ser Thr Leu Ser Gly Gln Ile Tyr Val Gln Asn Ile Ala Tyr
            20                  25                  30

Glu Lys Thr Val Thr Val Val Tyr Ser Asp Gly Ser Asp Asn Trp Asn
        35                  40                  45

Asn Asn Gly Asn Thr Ile Ala Ala Ser Tyr Ser Ser Ser Ile Ser Gly
    50                  55                  60

Ser Asn Tyr Glu Tyr Trp Thr Phe Ser Ser Ser Val Pro Ser Ile Lys
65                  70                  75                  80

Gln Phe Tyr Ile Lys Tyr Val Val Ala Gly Lys Thr Tyr Tyr Asp Asn
                85                  90                  95

Asn Gly Thr Lys Asn Tyr Gln Val Ser Ala Ser Thr Pro Thr Thr Thr
            100                 105                 110

Thr Thr Thr Thr Ser Ser Gly Ala Thr Lys Thr Thr Thr Thr Ile Gly
            115                 120                 125

Pro Thr Ser Thr Ser Thr Val Phe Pro Ser Gly Asn Ser Thr Ile Ser
    130                 135                 140

Ser Trp Leu Lys Gly Gln Ile Glu Thr Ser Arg Phe Ala Met Leu Arg
145                 150                 155                 160

Asn Ile Asn Pro Ala Gly Thr Val Lys Gly Phe Ile Ala Ala Ser Leu
                165                 170                 175

Ser Thr Ala Asn Pro Asp Tyr Phe Tyr Ala Trp Thr Arg Asp Ala Ala
            180                 185                 190

Leu Val Gly His Val Ile Ala Asn Asp Tyr Asn Arg Thr Leu Ala Gly
            195                 200                 205

Asn Ser Thr Tyr Leu Gly Leu Leu Lys Asp Tyr Val Thr Phe Ser Val
    210                 215                 220

Asn Ser Gln Ser Thr Ser Thr Ile Cys Asn Cys Leu Gly Glu Pro Lys
225                 230                 235                 240

Phe Asn Lys Asp Gly Ser Gly Tyr Ser Gly Ala Trp Gly Arg Pro Gln
                245                 250                 255

Asn Asp Gly Pro Ala Glu Arg Ala Asp Thr Phe Ile Leu Ile Ala Asp
            260                 265                 270

Ser Ile Leu Lys Gln Thr Gly Asp Ala Thr Tyr Val Thr Gly Thr Leu
            275                 280                 285

Arg Pro Ala Ile Tyr Lys Asp Leu Asp Tyr Val Val Asn Val Trp Ser
    290                 295                 300

Asn Gly Cys Phe Asp Leu Trp Glu Glu Val Asn Gly Val His Phe Tyr
305                 310                 315                 320

Thr Leu Met Val Met Arg Arg Ser Leu Ile Leu Gly Ala Asn Phe Ala
                325                 330                 335

Ser Arg Asn Gly Asp Ser Thr Arg Ala Ser Thr Tyr Thr Asn Thr Ala
            340                 345                 350

Asn Ser Ile Lys Thr Lys Ile Asp Thr Phe Trp Ser Ser Ser Asn Asn
            355                 360                 365

Tyr Val Ala Val Ser Gln Ser Val Thr Gly Gly Val Asn Lys Ala Gly
    370                 375                 380

Tyr Asp Val Ala Asn Leu Ile Ala Ala Asn Val Gly Ser Leu Asp Asp
385                 390                 395                 400

Gly Phe Tyr Thr Pro Gly Ser Glu Arg Ile Leu Ala Thr Ala Val Ala
                405                 410                 415
```

-continued

```
Val Glu Ser Lys Phe Ala Ser Ile Tyr Gly Val Asn Gln Asn Leu Pro
            420             425             430

Ser Trp Leu Gly Asn Ser Ile Gly Arg Tyr Pro Glu Asp Thr Tyr Asn
            435             440             445

Gly Asn Gly Asn Ser Gln Gly Asn Pro Trp Phe Ile Ala Thr Asn Thr
            450             455             460

Tyr Ala Glu Leu Tyr Tyr Arg Ala Ile Lys Glu Trp Thr Asn Asn Gly
465             470             475             480

Gly Val Thr Val Thr Asn Val Asn Phe Asn Phe Phe Lys Lys Phe Asp
            485             490             495

Ser Ser Ala Ser Val Gly Thr Lys Tyr Thr Val Gly Thr Ser Ala Phe
            500             505             510

Asn Thr Leu Thr Gln Asn Val Ala Leu Ala Ala Asp Asn Phe Phe Ser
            515             520             525

Thr Val Lys Val His Ala Ala Thr Asn Gly Ser Met Ser Glu Gln Phe
            530             535             540

Gly Arg Asp Ser Gly Val Met Thr Gly Ala Arg Asp Leu Thr Trp Ser
545             550             555             560

His Ala Ser Leu Ile Thr Ala Ala Leu Ala Lys Thr Gly Ala Pro Val
            565             570             575

Ala

<210> SEQ ID NO 71
<211> LENGTH: 585
<212> TYPE: PRT
<213> ORGANISM: Mucor circinelloides

<400> SEQUENCE: 71

Glu Thr Val Pro Thr Thr Glu Ala Val Lys Val Lys Ser Phe Thr Tyr
1               5               10              15

Asp Gly Ser Thr Leu Ala Gly Gln Ile Tyr Ile Lys Asn Ile Ala Tyr
            20              25              30

Thr Lys Thr Val Thr Val Ile Tyr Ser Asp Ala Ser Asp Asn Trp Asn
            35              40              45

Asn Asn Gly Asn Thr Ile Ala Ala Ser Tyr Ser Ala Ala Ile Ala Gly
            50              55              60

Thr Asn Tyr Glu Tyr Trp Thr Phe Ser Ala Pro Val Ser Gly Ile Lys
65              70              75              80

Gln Phe Tyr Val Lys Tyr Val Val Ser Gly Thr Thr Tyr Tyr Asp Asn
            85              90              95

Asn Asn Ser Gly Asn Tyr Gln Val Ser Val Thr Thr Thr Thr Thr
            100             105             110

Ala Pro Thr Thr Thr Thr Ser Gly Gly Ser Ser Thr Thr Gly Gly
            115             120             125

Ser Thr Thr Thr Ala Thr Ser Val Pro Thr Gly Val Pro Ser Gly Phe
            130             135             140

Pro Thr Gly Asn Ser Thr Ile Ser Ser Trp Ile Asp Gly Gln Thr Ser
145             150             155             160

Val Ser Arg Tyr Ala Met Leu Arg Asn Ile Asn Pro Ala Gly Ala Val
            165             170             175

Thr Gly Phe Ile Ala Ala Ser Met Ser Thr Ser Gly Pro Asp Tyr Phe
            180             185             190

Tyr Ala Trp Thr Arg Asp Ser Ala Leu Thr Ser His Val Val Ala Tyr
            195             200             205
```

-continued

```
Asp Tyr Asn Thr Thr Leu Ala Gly Asn Ser Thr Ile Leu Gly Leu Leu
    210             215             220

Lys Asn Tyr Val Thr Phe Ser Leu Asn Ser Gln Thr Thr Ser Thr Val
225             230             235             240

Cys Asn Cys Leu Gly Glu Pro Lys Phe Asn Lys Asp Gly Ser Gly Tyr
            245             250             255

Ser Gly Ala Trp Gly Arg Pro Gln Asn Asp Gly Pro Ala Ser Arg Ala
            260             265             270

Asp Thr Phe Ile Leu Ile Ala Asp Ser Ile Leu Lys Gln Thr Gly Asp
            275             280             285

Ala Thr Tyr Val Thr Gly Thr Leu Ala Pro Ala Ile Tyr Lys Asp Leu
    290             295             300

Asp Tyr Val Val Ser Thr Trp Ser Asn Gly Cys Phe Asp Leu Trp Glu
305             310             315             320

Glu Val Asn Gly Val His Phe Tyr Thr Leu Met Val Met Arg Arg Gly
            325             330             335

Leu Val Lys Gly Ala Asn Phe Ala Ser Arg Asn Gly Asp Ser Thr Arg
            340             345             350

Ala Thr Thr Tyr Thr Asn Thr Ala Ala Ser Ile Lys Thr Lys Ile Asp
            355             360             365

Ser Phe Trp Asn Ser Asn Gly Gln Tyr Val Ser Val Ser Gln Ser Val
    370             375             380

Thr Gly Gly Val Ser Lys Ala Gly Tyr Asp Ala Ser Val Leu Ile Ala
385             390             395             400

Ser Asn Leu Gly Ser Leu Gln Asp Gly Phe Tyr Thr Pro Gly Ser Asp
            405             410             415

Lys Met Leu Ala Thr Ala Val Ala Ile Glu Ser Lys Phe Ala Ser Leu
            420             425             430

Tyr Ser Ile Asn Gln Asn Leu Asn Gly Tyr Leu Gly Asn Ala Ile Gly
            435             440             445

Arg Tyr Pro Glu Asp Thr Tyr Asn Gly Asn Gly Asn Ser Gln Gly Asn
    450             455             460

Pro Trp Phe Ile Cys Thr Asn Ala Phe Ala Glu Leu Tyr Tyr Arg Ala
465             470             475             480

Ile Lys Glu Trp Phe Asn Asn Gly Gly Val Thr Val Thr Ser Ile Ser
            485             490             495

Leu Asn Phe Phe Lys Lys Phe Asp Ser Ser Ala Ala Val Gly Thr Lys
            500             505             510

Tyr Thr Val Gly Thr Ser Ser Phe Asn Ser Leu Val Gln Asn Val Ala
            515             520             525

Val Ala Ala Asp Ala Phe Phe Ser Thr Ile Lys Phe His Ala Ala Thr
    530             535             540

Asn Gly Ser Met Ser Glu Gln Tyr Gly Arg Thr Asp Gly Leu Met Thr
545             550             555             560

Gly Ala Arg Asp Leu Thr Trp Ser His Ala Ser Leu Ile Ser Ala Ser
            565             570             575

Tyr Ala Lys Ala Gly Ser Pro Ala Ala
            580             585
```

<210> SEQ ID NO 72
<211> LENGTH: 583
<212> TYPE: PRT
<213> ORGANISM: Circinella umbellata -continued

```
<400> SEQUENCE: 72

Ala Pro Thr Ser Glu Ile Glu Leu Asp Ser Tyr Thr Tyr Thr Gly Gly
1               5                   10                  15

Val Phe Ser Gly Arg Leu Tyr Val Lys Asn Ile Ala Tyr Thr Lys Glu
                20                  25                  30

Val Asn Val Tyr Trp Ser Asp Ala Ser Glu Asp Trp Ala Asn Asn Gly
            35                  40                  45

Asn Tyr Val Ala Ala Thr Tyr Ser Glu Ala Ile Ser Gly Thr Asn Tyr
        50                  55                  60

Glu Tyr Trp Glu Phe Ser Ala Lys Ile Gly Ser Ser Gly Ile Ser Glu
65                  70                  75                  80

Ser Tyr Ile Lys Tyr Thr Val Ser Gly Ser Thr Tyr Tyr Asp Asn Asn
                85                  90                  95

Gly Gly Lys Asn Tyr Ala Ile Thr Glu Thr Thr Thr Pro Thr Ile Thr
            100                 105                 110

Ala Thr Pro Thr Ser Thr Thr Ala Thr Thr Thr Ile Ser Ser Thr Thr
        115                 120                 125

Thr Thr Ala Thr Ser Ile Pro Thr Ser Val Pro Ser Thr Val Pro Glu
    130                 135                 140

Gly Asn Val Thr Val Thr Glu Trp Val Asn Lys Gln Leu Lys Ile Ser
145                 150                 155                 160

Trp Ser Asp Leu Leu Gln Asn Val Asn Pro Ser Gly Thr Val Thr Gly
                165                 170                 175

Phe Ile Ala Ala Ser Leu Ser Thr Ser Asn Pro Asp Tyr Phe Tyr Cys
            180                 185                 190

Trp Thr Arg Asp Ala Ala Met Val Ala Arg Val Met Thr Tyr Met Tyr
        195                 200                 205

Asn Thr Thr Glu Ala Gly Asp Ser Ser Leu Glu Ser Ala Leu Lys Asp
    210                 215                 220

Tyr Ile Thr Phe Gln Ile Asn Ser Met Lys Thr Ala Thr Ala Cys Asn
225                 230                 235                 240

Cys Leu Gly Glu Pro Lys Phe Asn Thr Asp Gly Ser Gly Tyr Ser Gly
                245                 250                 255

Pro Trp Gly Arg Pro Gln Asn Asp Gly Pro Ala Glu Arg Ala Thr Thr
            260                 265                 270

Met Ile Leu Phe Ala Asp Ser Tyr Leu Ala Gln Gly Gly Asp Thr Ser
        275                 280                 285

Tyr Val Thr Asn Thr Leu Lys Pro Ala Ile Tyr Thr Asn Leu Asp Tyr
    290                 295                 300

Val Val Gly Thr Trp Ser Asn Asn Cys Phe Asp Leu Trp Glu Glu Val
305                 310                 315                 320

Asn Gly Val His Ile Phe Thr Leu Ala Val Met Arg Lys Ser Leu Leu
                325                 330                 335

Asp Gly Ala Asp Phe Ala Ala Arg Asn Gly Asp Thr Ser Arg Val Ser
            340                 345                 350

Gly Tyr Gln Ser Thr Ala Ser Ser Ile Lys Thr Lys Leu Glu Ser Phe
        355                 360                 365

Trp Ser Ser Ser Asn Asn Tyr Ile Thr Val Thr Gln Ser Tyr Ser Gly
    370                 375                 380

Gly Val Gln Lys Ala Gly Leu Asp Val Ser Thr Leu Ile Ala Ala Asn
385                 390                 395                 400

Gln Gly Ser Met Gly Asp Gly Phe Tyr Thr Pro Gly Ser Asp Lys Met
                405                 410                 415
```

-continued

```
Leu Ala Thr Ala Val Ala Ile Glu Asn Ser Phe Ala Asn Ile Tyr Thr
            420                 425                 430

Ile Asn Lys Asn Lys Pro Ser Trp Leu Gly Thr Ala Ile Gly Arg Tyr
            435                 440                 445

Pro Glu Asp Thr Tyr Asn Gly Asn Gly Asn Gly Gln Gly Asn Pro Trp
            450                 455                 460

Phe Ile Ala Thr Ala Thr Tyr Ala Glu Leu Tyr Tyr Arg Ala Ile Leu
465                 470                 475                 480

Glu Trp Gln Gln Gln Glu Ser Val Thr Val Asn Ser Val Asn Phe Asp
                485                 490                 495

Phe Phe Ser Lys Phe Asp Ser Ser Ala Lys Val Gly Thr Val Tyr Thr
            500                 505                 510

Pro Gly Thr Asp Thr Phe Asn Thr Met Val Ser Asn Val Ala Phe Ala
            515                 520                 525

Ala Asp Glu Phe Leu Ser Thr Met Glu His Tyr Ala Ala Thr Asn Gly
            530                 535                 540

Ser Met Ser Glu Gln Phe Asn Arg Glu Thr Gly Ser Leu Thr Gly Ala
545                 550                 555                 560

Arg Asp Leu Thr Trp Ser His Ala Ala Phe Ile Thr Ala Gly Lys Ala
                565                 570                 575

Lys Leu Gly Ile Pro Ser Phe
                580

<210> SEQ ID NO 73
<211> LENGTH: 585
<212> TYPE: PRT
<213> ORGANISM: Mucor cordense

<400> SEQUENCE: 73

Glu Thr Val Pro Thr Thr Ala Asn Val Leu Val Lys Ser Tyr Thr Trp
1               5                   10                  15

Asp Gly Ala Thr Leu Ser Gly Gln Ile Tyr Ile Lys Asn Leu Ala Tyr
            20                  25                  30

Ala Lys Val Val Ser Val Ile Tyr Ser Asp Ala Asn Asp Asn Trp Asn
            35                  40                  45

Asn Asn Gly Asn Lys Val Ala Ala Ser Tyr Ser Ala Gly Ile Asp Gly
            50                  55                  60

Thr Asn Tyr Glu Tyr Trp Thr Phe Ser Gly Ala Val Ser Gly Ile Lys
65                  70                  75                  80

Gln Phe Tyr Val Lys Tyr Asp Val Ser Gly Thr Ser Tyr Tyr Asp Asn
                85                  90                  95

Asn Gly Thr Lys Asn Tyr Gln Val Thr Lys Thr Ser Thr Thr Thr Thr
            100                 105                 110

Ala Ala Thr Thr Thr Thr Thr Ala Thr Thr Thr Thr Gly Gly Thr Gly
            115                 120                 125

Thr Thr Thr Thr Thr Thr Ala Thr Ala Thr Ala Thr Ser Thr Asp Phe
            130                 135                 140

Pro Thr Gly Asn Ser Thr Ile Thr Thr Trp Leu Lys Ser Gln Glu Asp
145                 150                 155                 160

Ile Ser Arg Gly Ala Met Leu Arg Asn Ile Asn Pro Pro Gly Ala Ala
                165                 170                 175

Thr Gly Phe Ile Ala Ala Ser Leu Ser Thr Ser Gly Pro Asp Tyr Tyr
                180                 185                 190

Tyr Ala Trp Thr Arg Asp Ser Ala Leu Thr Ser His Val Ile Ala His
```

-continued

```
              195                 200                 205

Asp Tyr Asn Thr Thr Leu Ala Gly Asn Thr Thr Ile Leu Asn Ile Leu
    210                 215                 220

Lys Asp Tyr Val Thr Phe Ser Val Lys Ser Gln Ser Val Ser Thr Val
225                 230                 235                 240

Cys Asn Cys Leu Gly Glu Pro Lys Phe Asn Pro Asp Gly Ser Ser Tyr
                245                 250                 255

Thr Gly Ala Trp Gly Arg Pro Gln Asn Asp Gly Pro Ala Glu Arg Ala
                260                 265                 270

Ser Thr Phe Ile Leu Phe Gly Asp Ser Tyr Leu Lys Gln Thr Gly Asp
                275                 280                 285

Ala Thr Tyr Val Thr Gly Thr Leu Ala Pro Ala Ile Tyr Lys Asp Leu
    290                 295                 300

Asp Tyr Val Val Asn Thr Trp Ser Asn Gly Cys Phe Asp Leu Trp Glu
305                 310                 315                 320

Glu Val Asn Gly Val His Phe Tyr Thr Leu Met Ser Met Arg Arg Gly
                325                 330                 335

Leu Leu Asp Gly Ala Asn Phe Ala Lys Arg Asn Gly Asp Thr Thr Arg
                340                 345                 350

Ala Thr Thr Tyr Thr Asn Thr Ala Ala Ser Ile Ala Thr Lys Ile Asp
                355                 360                 365

Thr Phe Trp Val Ser Ser Gly Asn Tyr Val Gln Val Ser Gln Ser Val
    370                 375                 380

Thr Gly Gly Val Ser Lys Ala Gly Tyr Asp Cys Ala Asn Ile Leu Ala
385                 390                 395                 400

Ala Asn Met Ala Ala Asn His Asp Gly Phe Tyr Thr Pro Gly Ser Ser
                405                 410                 415

Lys Ile Leu Ala Thr Ala Val Ala Ile Glu Ser Lys Phe Ala Ser Leu
                420                 425                 430

Tyr Ser Ile Asn Ser Gly Leu Ala Ser Trp Leu Gly Thr Ala Ile Gly
                435                 440                 445

Arg Tyr Pro Glu Asp Thr Tyr Asn Gly Asn Gly Asn Ser Gln Gly Asn
    450                 455                 460

Pro Trp Phe Ile Cys Thr Asn Ala Phe Ala Glu Leu Tyr Tyr Arg Ala
465                 470                 475                 480

Ile Lys Glu Trp Thr Gln Ala Gly Ser Val Thr Val Asp Ser Thr Ser
                485                 490                 495

Leu Asn Phe Phe Lys Lys Phe Asp Ser Ser Ala Ala Ala Gly Thr Lys
                500                 505                 510

Tyr Thr Val Gly Thr Ser Ala Phe Thr Asn Leu Val Gln Asn Ile Ala
                515                 520                 525

Asn Gly Ala Asp Lys Phe Leu Ser Thr Ser Lys Phe His Ala Ala Thr
    530                 535                 540

Asn Gly Ser Met Ser Glu Gln Tyr Asn Arg Asp Ser Gly Leu Met Thr
545                 550                 555                 560

Gly Ala Arg Asp Leu Thr Trp Ser His Ala Ser Leu Ile Ser Ala Ser
                565                 570                 575

Arg Ala Lys Ala Gly Ser Pro Ser Leu
                580                 585
```

```
<210> SEQ ID NO 74
<211> LENGTH: 590
<212> TYPE: PRT
<213> ORGANISM: Phascolomyces articulosus
```

-continued

<400> SEQUENCE: 74

Asp Val Pro Thr Ser Ala Asn Ile Glu Leu Asp Tyr Tyr Thr Tyr Lys
1               5                   10                  15

Asp Lys Val Phe Ser Gly Arg Ile Tyr Val Lys Asn Ile Ala Tyr Glu
            20                  25                  30

Lys Thr Val Ala Val Tyr Trp Ser Asp Ala Ser Gly Asp Trp Asn Asn
        35                  40                  45

Asn Gly Asn Asn Val Ala Ala Ser Tyr Ser Glu Ser Ile Ser Gly Thr
    50                  55                  60

Asp Tyr Glu Tyr Trp Asp Phe Ser Thr Thr Ile Gly Ser Gly Gly Ile
65                  70                  75                  80

Lys Gln Ser Tyr Leu Lys Tyr Thr Val Ser Gly Asn Thr Tyr Tyr Asp
            85                  90                  95

Asn Asn Gly Ser Asn Asn Tyr Asp Ile Thr Glu Thr Thr Ala Thr Thr
            100                 105                 110

Thr Thr Thr Thr Thr Thr Thr Thr Thr Thr Gly Ser Thr Ala Thr Thr
        115                 120                 125

Ser Thr Thr Ser Gly Pro Thr Ser Thr Thr Ser Thr Thr Pro Gly Pro
    130                 135                 140

Thr Pro Thr Asn Val Pro Asp Gly Asn Val Thr Val Thr Glu Trp Val
145                 150                 155                 160

Asn Thr Gln Phe Ala Ile Ser Trp Pro Thr Leu Leu Lys Asn Val Asn
            165                 170                 175

Pro Ser Gly Thr Val Lys Gly Phe Ile Ala Ala Ser Leu Ser Thr Asn
            180                 185                 190

Asn Pro Asp Tyr Phe Tyr Ser Trp Thr Arg Asp Ser Ala Leu Val Ala
            195                 200                 205

His Thr Met Thr Tyr Leu Tyr Asn Thr Ser Glu Ala Gly Asp Ser Thr
        210                 215                 220

Ile Glu Ser Ala Leu Lys Asp Tyr Val Thr Phe Ser Ile Asn Ala Met
225                 230                 235                 240

Asn Ala Ala Thr Val Cys Asn Cys Leu Gly Glu Pro Lys Phe Asn Thr
            245                 250                 255

Asp Gly Ser Gly Tyr Thr Gly Ala Trp Gly Arg Pro Gln Asn Asp Gly
            260                 265                 270

Pro Ala Ser Arg Ala Thr Thr Met Ile Leu Phe Ala Asp Ser Phe Leu
            275                 280                 285

Ala Gln Gly Gly Asp Val Ser Tyr Val Ile Asn Thr Leu Lys Pro Ala
    290                 295                 300

Ile Tyr Lys Asp Leu Asp Tyr Val Val Ser Thr Trp Ser Asn Thr Cys
305                 310                 315                 320

Tyr Asp Leu Trp Glu Glu Val Asn Gly Val His Ile Tyr Thr Leu Ser
            325                 330                 335

Val Met Arg Arg Ala Leu Ile Asp Gly Ala Asn Phe Ala Gln Arg Asn
            340                 345                 350

Gly Asp Thr Ser Arg Val Ser Gly Tyr Thr Ser Thr Ala Thr Thr Ile
            355                 360                 365

Lys Thr Arg Leu Glu Ser Phe Trp Ser Asp Ser Asn Asn Tyr Ile Thr
        370                 375                 380

Val Thr Gln Ser Tyr Ser Gly Gly Val Gln Lys Ala Gly Leu Asp Val
385                 390                 395                 400

Ser Thr Leu Ile Ala Ala Asn Ile Gly Ser Val Gly Asp Gly Phe Tyr

-continued

```
                    405                 410                 415

Thr Pro Gly Ser Asp Lys Val Leu Ala Thr Ala Val Ala Ile Glu Lys
            420                 425                 430

Ser Phe Ala Asn Leu Tyr Thr Ile Asn Gln Asn Lys Pro Ser Trp Leu
            435                 440                 445

Gly Asn Ala Ile Gly Arg Tyr Pro Glu Asp Thr Tyr Asp Gly Tyr Gly
            450                 455                 460

Asn Ser Lys Gly Asn Pro Trp Phe Ile Ala Thr Ala Thr Tyr Ala Glu
465                 470                 475                 480

Leu Tyr Tyr Arg Ala Ile Leu Glu Trp Gln Gln Gln Ala Ser Val Thr
                    485                 490                 495

Val Asn Ser Ile Asn Leu Gly Phe Phe Ser Lys Phe Asp Ser Ser Ala
            500                 505                 510

Ser Val Gly Thr Val Tyr Thr Pro Gly Thr Asp Ser Phe Ala Asn Met
            515                 520                 525

Val Ser Asn Val Ala Phe Ala Ala Asp Glu Phe Leu Ser Thr Ile Asp
            530                 535                 540

Tyr His Ala Met Asn Asn Gly Ser Met His Glu Gln Tyr Asn Arg Asp
545                 550                 555                 560

Thr Gly Ile Ser Gln Gly Ala Arg Asp Leu Thr Trp Ser His Ala Ala
                    565                 570                 575

Phe Ile Thr Ala Ala Lys Ala Lys Leu Gly Ala Pro Ala Phe
                    580                 585                 590

<210> SEQ ID NO 75
<211> LENGTH: 578
<212> TYPE: PRT
<213> ORGANISM: Rhizopus microsporus

<400> SEQUENCE: 75

Val Pro Thr Ser Ala Ala Val Gln Val Glu Ser Tyr Lys Tyr Asp Gly
1                   5                   10                  15

Thr Thr Phe Ser Gly Arg Ile Phe Val Lys Asn Ile Ala Tyr Ser Lys
            20                  25                  30

Val Val Thr Val Ile Tyr Ser Asp Gly Ser Asp Asn Trp Asn Asn Asn
            35                  40                  45

Asn Asn Lys Ile Ser Ala Ala Tyr Ser Glu Ala Ile Ser Gly Ser Asn
            50                  55                  60

Tyr Glu Tyr Trp Thr Phe Ser Ala Lys Leu Ser Gly Ile Lys Gln Phe
65                  70                  75                  80

Tyr Val Lys Tyr Glu Val Ser Gly Ser Thr Tyr Tyr Asp Asn Asn Gly
                    85                  90                  95

Thr Lys Asn Tyr Gln Val Gln Ala Thr Ser Ala Thr Ser Thr Thr Ala
            100                 105                 110

Thr Ala Thr Thr Thr Thr Ser Thr Ser Thr Thr Thr Ser Thr Gly
            115                 120                 125

Pro Thr Ser Thr Ala Ser Val Ser Phe Pro Thr Gly Asn Ser Thr Ile
            130                 135                 140

Ser Ser Trp Ile Lys Asn Gln Glu Glu Ile Ser Arg Phe Ala Met Leu
145                 150                 155                 160

Arg Asn Ile Asn Pro Pro Gly Ser Ala Thr Gly Phe Ile Ala Ala Ser
                    165                 170                 175

Leu Ser Thr Ala Gly Pro Asp Tyr Tyr Tyr Ser Trp Thr Arg Asp Ser
            180                 185                 190
```

-continued

```
Ala Leu Thr Ala Asn Val Ile Ala Tyr Glu Tyr Asn Thr Thr Phe Ala
        195                 200                 205

Gly Asn Thr Thr Leu Leu Lys Tyr Leu Lys Asp Tyr Val Thr Phe Ser
        210                 215                 220

Val Lys Ser Gln Ser Val Ser Thr Val Cys Asn Cys Leu Gly Glu Pro
225                 230                 235                 240

Lys Phe Asn Ala Asp Gly Ser Ser Tyr Thr Gly Pro Trp Gly Arg Pro
                245                 250                 255

Gln Asn Asp Gly Pro Ala Glu Arg Ala Val Thr Phe Met Leu Ile Ala
                260                 265                 270

Asp Ser Tyr Leu Thr Gln Thr Lys Asp Ala Ser Tyr Val Thr Gly Thr
        275                 280                 285

Leu Lys Pro Ala Ile Phe Lys Asp Leu Asp Tyr Val Val Ser Val Trp
        290                 295                 300

Ser Asn Gly Cys Tyr Asp Leu Trp Glu Glu Val Asn Gly Val His Phe
305                 310                 315                 320

Tyr Thr Leu Met Val Met Arg Lys Gly Leu Ile Leu Gly Ala Asp Phe
                325                 330                 335

Ala Ala Arg Asn Gly Asp Ser Ser Arg Ala Ser Thr Tyr Lys Asn Thr
                340                 345                 350

Ala Ser Thr Met Glu Ser Lys Ile Ser Ser Phe Trp Ser Asp Ser Asn
        355                 360                 365

Asn Tyr Val Gln Val Ser Gln Ser Val Thr Ala Gly Val Ser Lys Lys
        370                 375                 380

Gly Leu Asp Val Ser Thr Leu Leu Ala Ala Asn Ile Gly Ser Leu Pro
385                 390                 395                 400

Asp Gly Phe Phe Thr Pro Gly Ser Glu Lys Ile Leu Ala Thr Ala Val
                405                 410                 415

Ala Leu Glu Asn Ala Phe Ala Ser Leu Tyr Pro Ile Asn Ser Asn Leu
                420                 425                 430

Pro Ser Tyr Leu Gly Asn Ser Ile Gly Arg Tyr Pro Glu Asp Thr Tyr
        435                 440                 445

Asn Gly Asn Gly Asn Ser Gln Gly Asn Pro Trp Phe Leu Ala Val Asn
        450                 455                 460

Ala Tyr Ala Glu Leu Tyr Tyr Arg Ala Ile Lys Glu Trp Ile Ser Asn
465                 470                 475                 480

Gly Lys Val Thr Val Ser Asn Ile Ser Leu Pro Phe Phe Lys Lys Phe
                485                 490                 495

Asp Ser Ser Ala Thr Ser Gly Lys Thr Tyr Thr Ala Gly Thr Ser Asp
                500                 505                 510

Phe Asn Asn Leu Ala Gln Asn Ile Ala Leu Gly Ala Asp Arg Phe Leu
        515                 520                 525

Ser Thr Val Lys Phe His Ala Tyr Asn Asn Gly Ser Leu Ser Glu Glu
        530                 535                 540

Tyr Asp Arg Ser Thr Gly Met Ser Thr Gly Ala Arg Asp Leu Thr Trp
545                 550                 555                 560

Ser His Ala Ser Leu Ile Thr Ala Ala Tyr Ala Lys Ala Gly Ser Pro
                565                 570                 575

Ala Ala
```

```
<210> SEQ ID NO 76
<211> LENGTH: 443
<212> TYPE: PRT
<213> ORGANISM: Spinellus fusiger
```

<400> SEQUENCE: 76

```
Val Pro Ser Gly Asn Ser Thr Ile Thr Ala Trp Gly Ser Lys Gln Asp
1               5                   10                  15

Gly Ile Ser Phe Ser Thr Met Leu Gly Asn Ile Asn Pro Pro Gly Ser
            20                  25                  30

Ser Lys Gly Phe Ile Ala Ala Ser Leu Ser Thr Ala Gly Pro Asn Tyr
        35                  40                  45

Tyr Tyr Ser Trp Thr Arg Asp Ser Ala Leu Val Ala Arg Ala Ile Thr
    50                  55                  60

Tyr Lys Tyr Ser Thr Ser Tyr Gln Asn Asp Pro Lys Ile Leu Gly Leu
65                  70                  75                  80

Leu Lys Asp Tyr Val Thr Tyr Gln Val Asn Glu Gln Thr Glu Ser Thr
            85                  90                  95

Val Cys Asn Cys Leu Gly Glu Pro Lys Phe Asn Pro Asp Gly Ser Ser
            100                 105                 110

Phe Ser Gly Pro Trp Gly Arg Pro Gln Asn Asp Gly Pro Ala Glu Arg
            115                 120                 125

Ala Ser Thr Met Ile Leu Phe Ala Lys Ser Tyr Tyr Ala Gln Thr Asn
        130                 135                 140

Asp Val Gly Tyr Val Ser Asn Thr Leu Lys Pro Ala Ile Tyr Lys Asp
145                 150                 155                 160

Leu Asp Tyr Ile Val Asn Val Trp Gly Asn Asn Cys Phe Asp Leu Trp
                165                 170                 175

Glu Glu Val Asn Gly Val His Phe Tyr Thr Leu Met Met Met Arg His
                180                 185                 190

Gly Leu Val Gln Gly Ser Ile Phe Ala Asn Thr Leu Gly Asp Ser Thr
            195                 200                 205

Arg Ala Asn Thr Tyr Lys Thr Ala Ala Gln Asn Ile Lys Asn Arg Ile
        210                 215                 220

Asp Thr Phe Trp Glu Ser Gly Ser Asn Tyr Ile Val Val Thr Gln Asn
225                 230                 235                 240

Gln Ser Ala Gly Val Asn Lys Pro Ser Gly Leu Asp Val Ala Val Leu
            245                 250                 255

Leu Ala Ala Asn Gln Gly Gly Leu Gly Asp Gly Val Tyr Thr Pro Gly
            260                 265                 270

Ser Asp Lys Val Leu Ala Thr Ala Val Ala Leu Glu Lys Ser Phe Ala
        275                 280                 285

Ser Leu Tyr Pro Ile Asn Lys Asn Leu Pro Ser Tyr Tyr Gly Thr Ala
    290                 295                 300

Ile Gly Arg Tyr Pro Glu Asp Thr Tyr Asn Gly Asn Gly Asn Ser Glu
305                 310                 315                 320

Ala Asn Pro Trp Phe Ile Ala Thr Thr Thr Tyr Ala Glu Leu Tyr Tyr
            325                 330                 335

Arg Ala Ile Ser Glu Trp Thr Asn Gly Ser Gly Val Thr Val Asn Ser
        340                 345                 350

Ile Asn Lys Glu Phe Phe Ser Lys Phe Asp Ala Ser Ala Thr Asn Gly
        355                 360                 365

Lys Val Tyr Thr Pro Gly Ser Asp Ser Phe Asn Ser Leu Val Asn Asn
    370                 375                 380

Val Ala Ile Ala Ala Asp Asn Phe Leu Ser Thr Val Arg Tyr His Gln
385                 390                 395                 400

Thr Ser Asn Gly Ser Leu Ser Glu Gln Phe Asn Arg Tyr Thr Gly Phe
```

-continued

```
                    405                 410                 415
Met Thr Gly Ala Arg Asp Leu Thr Trp Ser His Ala Ala Met Val Thr
                420                 425                 430

Ala Leu Ala Ala Lys Ala Gly Thr Pro Ser Pro
        435                 440

<210> SEQ ID NO 77
<211> LENGTH: 588
<212> TYPE: PRT
<213> ORGANISM: Syncephalastrum racemosum

<400> SEQUENCE: 77

Ala Thr Val Pro Thr Thr Gln Val Gln Leu Asp Tyr Tyr Thr Tyr Ser
1               5                   10                  15

Asn Asn Val Leu Ser Gly Arg Ile Tyr Val Gln Asn Ile Ala Tyr Ser
            20                  25                  30

Lys Val Val Lys Val Ile Tyr Ser Asp Ala Ser Gly Asn Trp Asn Asn
        35                  40                  45

Asn Gly Asn Thr Ile Ser Ala Ser Tyr Val Glu Ser Ile Ser Gly Thr
    50                  55                  60

Asn Tyr Glu Tyr Trp Asp Phe Ser Ala Thr Ile Gly Thr Ala Gly Ile
65                  70                  75                  80

Lys Gln Phe Tyr Leu Arg Tyr Asp Val Ser Gly Ser Thr Tyr Tyr Asp
                85                  90                  95

Asn Asn Gly Gly Asp Asn Asn Asn Tyr Asn Val Val Ala Thr Thr Ser
            100                 105                 110

Thr Thr Ser Ser Ser Thr Thr Thr Thr Thr Ala Thr Thr Thr Thr Ala
            115                 120                 125

Thr Lys Thr Thr Ser Thr Thr Ser Ala Thr Ala Thr Pro Thr Ser Ser
        130                 135                 140

Ala Thr Phe Pro Ser Gly Asn Ser Thr Ile Thr Thr Trp Ala Lys Ser
145                 150                 155                 160

Gln Lys Asp Ile Ser Trp Lys Thr Leu Leu Thr Ser Leu Asn Pro Ser
                165                 170                 175

Gly Thr Ala Lys Gly Phe Ile Ala Ala Ser Leu Ser Thr Ser Asn Pro
            180                 185                 190

Asp Tyr Tyr Tyr Ala Trp Thr Arg Asp Ser Ala Leu Val Ala Arg Thr
            195                 200                 205

Met Val Asn Met Tyr Asn Thr Thr Glu Ala Gly Ser Ala Ser Val Leu
        210                 215                 220

Gly Leu Leu Gln Asp Tyr Val Thr Phe Gln Ile Asn Ala Met Ser Thr
225                 230                 235                 240

Ser Thr Val Cys Asn Cys Leu Gly Glu Pro Lys Phe Asn Pro Asp Gly
                245                 250                 255

Ser Ser Tyr Thr Gly Ala Trp Gly Arg Pro Gln Asn Asp Gly Pro Ala
            260                 265                 270

Glu Arg Ala Ser Thr Phe Ile Leu Phe Ala Asp Ser Tyr Ile Ala Gln
            275                 280                 285

Gly Gly Gln Leu Ser Tyr Val Thr Gly Thr Leu Ala Pro Ala Ile Tyr
    290                 295                 300

Lys Asp Leu Asn Tyr Val Val Ser Thr Trp Ser Asn Asn Cys Phe Asp
305                 310                 315                 320

Leu Trp Glu Glu Val Asn Gly Arg His Met Phe Thr Leu Ala Val Met
                325                 330                 335
```

-continued

```
Arg Arg Ala Leu Leu Asp Gly Val Asn Phe Ala Ser Arg Ile Gly Asp
            340                 345                 350

Thr Thr Tyr Ser Ser Thr Trp Ser Ser Thr Ala Ser Ser Ile Gln Ser
            355                 360                 365

Thr Leu Ser Gly Tyr Tyr Leu Ser Ser Gly Asn Tyr Ile Thr Thr Val
        370                 375                 380

Gln Asn Phe Gln Ser Gly Val Ser Lys Ala Gly Tyr Asp Val Ser Thr
385                 390                 395                 400

Leu Ile Ala Ala Asn Val Ala Gly Met Gly Asp Gly Phe Phe Thr Pro
                405                 410                 415

Gly Ser Asp Glu Val Leu Ala Thr Ala Val Ala Ile Glu Asn Lys Phe
            420                 425                 430

Ser Ser Leu Tyr Gly Val Asn Ala Asn Lys Ala Ser Tyr Leu Gly Thr
            435                 440                 445

Ala Ile Gly Arg Tyr Pro Glu Asp Thr Tyr Asn Gly Tyr Gly Asn Gly
        450                 455                 460

Gln Gly Asn Pro Trp Phe Ile Ala Thr Ala Ala Tyr Ala Glu Leu Tyr
465                 470                 475                 480

Tyr Arg Ala Ile Leu Glu Trp Gln Thr Lys Ser Ser Ile Val Val Asn
                485                 490                 495

Ser Lys Asn Leu Gly Phe Phe Ser Lys Phe Asp Ser Ser Ala Ala Val
            500                 505                 510

Gly Thr Thr Tyr Thr Pro Gly Thr Thr Ala Tyr Ser Asn Met Val Gln
            515                 520                 525

Asn Val Ala Leu Ala Ala Asp Arg Phe Leu Ser Thr Val Gln Leu His
            530                 535                 540

Ala Ala Thr Asn Gly Ser Met Ser Glu Gln Phe Asn Arg Asp Thr Gly
545                 550                 555                 560

Val Met Gln Gly Ala Arg Asp Leu Thr Trp Ser His Ser Ala Phe Ile
                565                 570                 575

Thr Ala Ala Arg Ala Lys Leu Gly Ser Pro Val Tyr
            580                 585
```

```
<210> SEQ ID NO 78
<211> LENGTH: 448
<212> TYPE: PRT
<213> ORGANISM: Syncephalastrum racemosum

<400> SEQUENCE: 78

Ala Asn Ser Thr Val Pro Asp Gly Asn Ser Thr Thr Thr Ala Trp Val
1               5                   10                  15

Lys Lys Gln Glu Ala Ile Ser Trp Thr Asp Leu Lys Thr Asn Val Asn
            20                  25                  30

Pro Glu Gly Ala Ala Lys Gly Phe Ile Ala Ala Ser Leu Ser Thr Ser
            35                  40                  45

Glu Pro Asp Tyr Tyr Tyr Ala Trp Thr Arg Asp Ser Ala Leu Val Ala
        50                  55                  60

Arg Val Met Val Asn Lys Tyr Asn Thr Thr Asp Ala Gly Asp Ala Asn
65                  70                  75                  80

Leu Leu Gly Leu Leu Gln Asp Tyr Val Ser Phe Gln Ile Asn Ala Met
                85                  90                  95

Gly Glu Ser Thr Val Cys Asn Cys Leu Gly Glu Pro Lys Phe Asn Pro
            100                 105                 110

Asp Gly Ser Ser Tyr Thr Gly Ala Trp Gly Arg Pro Gln Asn Asp Gly
            115                 120                 125
```

-continued

```
Pro Ala Glu Arg Ala Ser Thr Phe Ile Leu Leu Ala Asp Ser Met Ile
    130                 135                 140

Ala Gln Lys Ser Ala Asn Gly Ser Tyr Val Ser Asp Thr Leu Ala Pro
145                 150                 155                 160

Ala Ile Tyr Lys Asp Leu Ala Tyr Val Ala Ser Thr Trp Glu Asn Ala
            165                 170                 175

Cys Tyr Asp Leu Trp Glu Glu Val Asn Gly Lys His Met Tyr Thr Leu
            180                 185                 190

Ser Val Met Arg Arg Ala Leu Leu Asp Gly Ala Asp Phe Ala Ser Arg
            195                 200                 205

Gln Gly Gln Thr Ala Asn Val Thr Ser Trp Lys Ser Thr Ala Asp Lys
    210                 215                 220

Ile Lys Ser Ser Leu Glu Gly Phe Phe Ser Ser Asp Asn Gly Tyr Ile
225                 230                 235                 240

Glu Val Thr Gln Asp Met Gln Gly Gly Val Gln Lys Lys Gly Leu Asp
                245                 250                 255

Val Ser Thr Leu Ile Ala Ala Asn Ile Gly Ser Met Gly Asp Gly Phe
            260                 265                 270

Tyr Thr Pro Gly Ser Asp Glu Val Leu Ala Thr Ala Val Ala Val Glu
            275                 280                 285

Ala Ala Phe Ala Asp Leu Tyr Lys Ile Asn Gln Asn Thr Asn Ser Thr
    290                 295                 300

Gly Leu Gly Thr Ala Ile Gly Arg Tyr Pro Glu Asp Thr Tyr Asn Gly
305                 310                 315                 320

Val Gly Asn Ser Gln Gly Asn Pro Trp Phe Ile Ala Thr Asn Thr Phe
                325                 330                 335

Ala Glu Leu Tyr Tyr Arg Ala Ile Leu Glu Trp Gln Asn Lys Gly Thr
            340                 345                 350

Ile Thr Val Asn Ser Val Asn Ala Ala Phe Phe Ser Lys Phe Asp Ser
            355                 360                 365

Ser Ala Lys Ala Gly Thr Thr Tyr Lys Ser Gly Ser Thr Glu Phe Asp
    370                 375                 380

Ser Leu Ile Asn Lys Val Ala Leu Ala Ala Asp Ala Phe Leu Asn Thr
385                 390                 395                 400

Val Gln Thr Tyr Ala Ala Ser Asn Gly Ser Met Ser Glu Gln Tyr Asn
                405                 410                 415

Arg Asp Thr Gly Ala Leu Thr Gly Ala Arg Asp Leu Thr Trp Ser His
            420                 425                 430

Ala Ser Leu Ile Thr Ala Ala Asn Ala Lys Leu Gly Thr Pro Tyr Asn
    435                 440                 445
```

```
<210> SEQ ID NO 79
<211> LENGTH: 452
<212> TYPE: PRT
<213> ORGANISM: Thermomucor sp.

<400> SEQUENCE: 79
```

```
Val Val Thr Ala Ala Ala Ala Ala Ser Val Pro Ser Gly Asn Ala Thr
1               5                   10                  15

Ile Thr Ser Trp Ile Gln Glu Gln Leu Ala Ile Ser Trp Asn Thr Met
            20                  25                  30

Leu Thr Ser Val Asn Pro Val Gly Ala Val Thr Gly Phe Ile Ala Ala
        35                  40                  45

Ser Leu Ser Thr Ala Asn Pro Asp Tyr Tyr Tyr Cys Trp Thr Arg Asp
```

-continued

```
        50              55              60

Ala Ala Leu Val Ala Arg Val Met Thr Phe Met Tyr Asn Thr Thr Gln
65              70              75              80

Ala Gly Asp Ser Gly Leu Leu Gly Ile Leu Gln Asp Tyr Val Ser Phe
                85              90              95

Gln Ile His Ala Met Gly Glu Ser Thr Val Cys Asn Cys Leu Gly Glu
            100             105             110

Pro Lys Phe Asn Pro Asp Gly Ser Ser Tyr Thr Gly Ala Trp Gly Arg
        115             120             125

Pro Gln Asn Asp Gly Pro Ala Glu Arg Ala Ser Thr Phe Ile Lys Ile
        130             135             140

Ala Asp Ser Tyr Leu Thr Gln Thr Gly Asp Val Ser Tyr Val Thr Asn
145             150             155             160

Thr Leu Lys Pro Ala Ile Tyr Glu Asp Leu Asp Tyr Ile Val Asn Val
            165             170             175

Trp Gln Asn Thr Cys Phe Asp Leu Trp Glu Glu Val Tyr Gly Met His
            180             185             190

Met Tyr Thr Leu Ala Val Met Arg Arg Gly Leu Leu Asp Gly Ala Asp
            195             200             205

Phe Ala Thr Arg Asn Gly Asp Thr Asp Lys Ala Ser Thr Tyr Thr Ser
        210             215             220

Thr Ala Thr Ser Ile Gln Thr Arg Leu Ala Thr Phe Trp Ser Asp Ser
225             230             235             240

Asn Gly Tyr Ile Thr Val Thr Gln Asp Tyr Gln Ser Gly Val Ser Lys
            245             250             255

Ala Gly Leu Asp Val Ser Thr Leu Ile Ala Ala Asn Val Ala Gly Met
            260             265             270

Asn Asp Gly Phe Phe Thr Pro Gly Ser Asp Glu Ile Leu Ala Thr Ala
            275             280             285

Val Lys Val Glu Ala Ala Phe Ala Asn Leu Tyr Gly Ile Asn Ile Asn
        290             295             300

Lys Ala Ser Tyr Leu Gly Asn Ala Ile Gly Arg Tyr Pro Glu Asp Thr
305             310             315             320

Tyr Asn Gly Asn Gly Asn Ser Glu Gly Asn Pro Trp Phe Ile Ala Thr
            325             330             335

Ala Ala Phe Ala Glu Leu Tyr Tyr Arg Ala Ile Met Glu Trp Gln Leu
            340             345             350

Arg Gly Ser Ser Ile Thr Val Asn Ser Val Asn Gln Gly Phe Phe Thr
            355             360             365

Lys Phe Asp Pro Ser Ala Thr Ala Gly Thr Thr Tyr Thr Pro Gly Thr
        370             375             380

Asp Ala Phe Asn Ser Leu Ile Asp Asn Val Ala Leu Ala Ala Asp Gln
385             390             395             400

Phe Phe Ser Thr Ile His Leu His Arg Ala Thr Asn Gly Ser Met Ser
            405             410             415

Glu Gln Tyr Asn Arg Asp Thr Gly Phe Met Gln Gly Ala Arg Asp Leu
            420             425             430

Thr Trp Ser His Ala Ala Phe Ile Thr Ala Ala Lys Ala Lys Gln Gly
            435             440             445

Thr Pro Ser Phe
    450
```

<210> SEQ ID NO 80

```
<211> LENGTH: 589
<212> TYPE: PRT
<213> ORGANISM: Zychaea mexicana

<400> SEQUENCE: 80

Val Asp Val Pro Ser Val Pro Ile Gln Leu Glu Ser Tyr Thr Tyr Ser
1               5                   10                  15

Glu Asn Val Phe Ala Gly Arg Ile Phe Val Gln Asn Ile Ala Tyr Thr
                20                  25                  30

Lys Glu Val Asn Val Phe Trp Ser Asp Ala Ser Asp Asp Trp Asn Asp
            35                  40                  45

Asn Gly Asn Ser Val Ala Ala Ser Tyr Ser Glu Ser Ile Ala Asp Thr
        50                  55                  60

Asn Tyr Glu Tyr Trp Glu Phe Ser Thr Thr Ile Gly Ser Ala Gly Ile
65                  70                  75                  80

Ser Gln Ser Tyr Leu Arg Tyr Asp Val Ser Gly Ser Ile Tyr Tyr Asp
                85                  90                  95

Asn Asn Asp Ser Gln Asn Tyr Asp Ile Thr Glu Thr Ser Thr Pro Thr
                100                 105                 110

Thr Thr Thr Ala Ala Pro Thr Ser Thr Thr Ser Thr Pro Thr Thr Thr
            115                 120                 125

Thr Asp Gly Gly Ser Thr Thr Thr Thr Thr Ala Thr Ser Val Pro Thr
        130                 135                 140

Ser Thr Gly Val Pro Glu Gly Asn Ala Thr Ile Ser Glu Trp Ala Ser
145                 150                 155                 160

Ala Gln Leu Asp Ile Ser Trp Pro Asn Leu Met Met Asn Val Asn Pro
                165                 170                 175

Ser Gly Ala Val Thr Gly Ser Ile Val Ala Ser Leu Ser Thr Ser Asn
                180                 185                 190

Pro Asp Tyr Phe Tyr Ile Trp Thr Arg Asp Ala Ala Met Val Ala Arg
                195                 200                 205

Val Met Val Tyr Met Tyr Asn Thr Thr Glu Ala Gly Asp Thr Asn Leu
            210                 215                 220

Leu Asn Ala Leu Thr Asp Tyr Val Thr Phe Ser Ile Ser Ser Met Asn
225                 230                 235                 240

Val Asp Thr Val Cys Asp Cys Leu Gly Glu Pro Lys Phe Asn Val Asp
                245                 250                 255

Gly Ser Gly Tyr Thr Gly Ala Trp Gly Arg Pro Gln Asn Asp Gly Pro
                260                 265                 270

Ala Glu Arg Ala Ser Thr Met Ile Leu Ile Ala Asp Ser Tyr Ile Ala
            275                 280                 285

Gln Gly Gly Asp Val Ser Tyr Val Thr Asp Thr Leu Lys Pro Ala Ile
        290                 295                 300

Tyr Thr Asp Leu Asp Tyr Val Val Asp Thr Trp Ser Asn Val Cys Phe
305                 310                 315                 320

Asp Leu Trp Glu Glu Val Asn Gly Ile His Met Tyr Thr Leu Ser Val
                325                 330                 335

Met Arg Lys Ala Leu Leu Asp Gly Ala Asn Phe Ala Thr Arg Asn Gly
            340                 345                 350

Asp Thr Ser Arg Val Ser Gly Tyr Glu Ser Thr Ala Ser Ser Ile Lys
            355                 360                 365

Thr Arg Leu Glu Ser Phe Trp Ser Ser Ser Asn Asn Tyr Ile Thr Val
        370                 375                 380

Thr Gln Ser Phe Ser Gly Gly Val Ser Lys Ala Gly Leu Asp Val Ser
```

-continued

```
385            390            395            400

Thr Leu Ile Ala Ala Asn Leu Ala Ser Met Asn Asp Gly Phe Tyr Thr
            405            410            415

Pro Gly Ser Asp Glu Ile Leu Ala Thr Ala Val Ala Ile Glu Asn Ser
            420            425            430

Phe Ile Ser Glu Tyr Thr Leu Asn Gln Asn Arg Pro Ser Trp Leu Ser
            435            440            445

Thr Ala Ile Gly Arg Tyr Pro Glu Asp Ser Tyr Asp Gly Tyr Gly Asn
            450            455            460

Ser Gln Gly Asn Pro Trp Phe Ile Ala Thr Ala Thr Tyr Ala Glu Leu
465            470            475            480

Tyr Tyr Arg Ala Ile Leu Glu Trp Gln Gln Gln Ala Ser Ile Ser Val
            485            490            495

Asn Ser Val Asn Leu Gly Phe Phe Ser Lys Phe Asp Ser Asp Ala Ser
            500            505            510

Val Gly Thr Val Tyr Thr Pro Gly Thr Glu Asp Phe Ala Asn Met Val
            515            520            525

Ser Asn Val Ala Phe Ala Ala Asp Glu Phe Leu Ala Thr Ile Glu Asn
            530            535            540

His Ser Ala Val Asn Gly Ser Leu Ser Glu Gln Tyr Asn Arg Asp Thr
545            550            555            560

Gly Ile Met Gln Gly Ala Arg Asp Leu Thr Trp Ser His Ala Ala Phe
            565            570            575

Ile Thr Ala Ala Lys Ala Lys Gln Gly Ala Pro Ile His
            580            585
```

```
<210> SEQ ID NO 81
<211> LENGTH: 432
<212> TYPE: PRT
<213> ORGANISM: Saksenaea vasiformis

<400> SEQUENCE: 81

Trp Val Ser Lys Gln Glu Asp Ile Ser Phe Ser Glu Met Leu Arg Asn
1               5               10              15

Val Asn Pro Glu Gly Thr Ala Lys Gly Phe Val Ala Ala Ser Leu Ser
            20              25              30

Thr Ala Gly Pro Asp Tyr Phe Tyr Thr Trp Thr Arg Asp Ala Ala Leu
            35              40              45

Val Ser Arg Val Ile Ala Tyr Lys Tyr Asn Thr Thr Asn Ala Gly Asp
            50              55              60

Ser Lys Ile His Gly Val Leu Asp Asp Tyr Val Asn Phe Gln Ile Asn
65              70              75              80

Thr Gln Ser Glu Ser Thr Pro Cys Asn Cys Leu Gly Glu Pro Lys Phe
            85              90              95

Asn Pro Asp Gly Ser Ser Phe Thr Gly Pro Trp Gly Arg Pro Gln Asn
            100             105             110

Asp Gly Pro Ala Glu Arg Ala Ser Ser Phe Met Leu Ile Ala Asp Ser
            115             120             125

Phe Leu Ser Gln Thr Lys Asn Ala Ser Tyr Phe Thr Asn Thr Leu Lys
            130             135             140

Pro Ala Ile Tyr Lys Asp Leu Asp Tyr Val Val Asp Thr Trp Ser Asn
145             150             155             160

Pro Cys Phe Asp Leu Trp Glu Glu Val Asn Gly Ile His Phe Tyr Thr
            165             170             175
```

-continued

```
Leu Met Val Met Arg Arg Ser Leu Leu Asp Gly Ala Asn Phe Ala Thr
            180                 185                 190

Arg Asn Gly Asp Asn Ser Lys Ala Ser Thr Tyr Ser Gly Val Ala Ala
            195                 200                 205

Lys Ile Gln Ala Arg Leu Asn Ser Phe Trp Asp Ala Gly Lys Asn Tyr
    210                 215                 220

Ile Thr Val Thr Gln Asp Tyr Lys Asn Gly Val Glu Lys Pro Ser Gly
225                 230                 235                 240

Leu Asp Val Ser Thr Leu Ile Ala Ala Asn Val Ala Gly Met Gly Asp
                245                 250                 255

Gly Phe Tyr Thr Pro Gly Ser Glu Arg Ile Leu Ala Thr Ala Leu Ala
            260                 265                 270

Phe Glu Lys Ser Met Ala Ser Leu Tyr Pro Leu Asn Asn Asn Leu Pro
            275                 280                 285

Ser His Leu Gly Asn Ala Ile Gly Arg Tyr Pro Glu Asp Thr Tyr Asn
    290                 295                 300

Gly Asn Gly Asn Ser Gln Gly Asn Pro Trp Phe Leu Ala Thr Thr Ala
305                 310                 315                 320

Phe Thr Glu Leu Tyr Tyr Arg Ala Ile Leu Glu Trp Lys Asn Thr Gly
                325                 330                 335

Val Thr Val Thr Pro Ile Ser Lys Asp Phe Phe Val Arg Phe Asp Ser
            340                 345                 350

Ser Ala Ala Pro Gly Lys Lys Tyr Asn Pro Gly Ser Gln Glu Phe Ala
            355                 360                 365

Thr Leu Thr Gln Ser Ile Ala Ala Ala Ala Asp Arg Phe Met Ser Thr
    370                 375                 380

Val Gln Tyr His Gln Asn Pro Asn Gly Ser Leu Ser Glu Glu Phe Asp
385                 390                 395                 400

Arg Ser Ser Gly Tyr Met Thr Gly Ala Arg Asp Leu Thr Trp Ser His
                405                 410                 415

Ala Ala Phe Ile Thr Ala Ala Gln Ala Arg Ala Gly Ser Pro Ser Phe
            420                 425                 430
```

<210> SEQ ID NO 82
<211> LENGTH: 432
<212> TYPE: PRT
<213> ORGANISM: Backusella circina

<400> SEQUENCE: 82

```
Trp Ser Pro Ser Gln His Ser Ile Ser Leu Tyr Ala Met Leu Arg Asn
1               5                   10                  15

Ile Asn Pro Pro Gly Ser Ala Ala Gly Phe Ile Ser Ala Ser Leu Ser
            20                  25                  30

Thr Ser Gly Pro Asp Tyr Tyr Tyr Ser Trp Thr Arg Asp Ser Ala Leu
            35                  40                  45

Val Ala His Val Ile Val Asn Glu Tyr Asn Thr Thr Tyr Gln Gly Asn
    50                  55                  60

Ser Thr Leu Leu Gly Ile Leu Lys Asp Tyr Val Thr Tyr Ser Leu Asn
65                  70                  75                  80

Ala Gln Thr Thr Ser Thr Val Cys Asn Cys Leu Gly Glu Pro Lys Phe
                85                  90                  95

Asn Pro Asp Gly Ser Ser Phe Thr Gly Ala Trp Gly Arg Pro Gln Asn
            100                 105                 110

Asp Gly Pro Ala Glu Arg Ala Val Ser Phe Ile Tyr Phe Ala Asp Ser
            115                 120                 125
```

-continued

```
Tyr Leu Thr Gln Thr Ser Asp Ser Ser Tyr Val Thr Gly Thr Leu Ala
    130                 135                 140

Pro Ala Ile Tyr Lys Asp Leu Asp Tyr Val Val Ser Val Trp Ser Asn
145                 150                 155                 160

Gly Cys Phe Asp Leu Trp Glu Glu Val Asn Gly Ile His Phe Tyr Thr
                165                 170                 175

Leu Met Phe Met Arg Arg Gly Leu Leu Asp Gly Ala Asn Phe Ala Ser
                180                 185                 190

Arg Asn Gly Asp Ser Thr Arg Ala Ser Thr Tyr Thr Ser Thr Ala Ala
                195                 200                 205

Ser Ile Lys Thr Lys Ile Asp Gly Phe Trp Val Ser Ser Gly Asn Tyr
    210                 215                 220

Val Gln Val Ser Gln Ser Val Thr Ser Gly Val Ser Lys Ala Gly Tyr
225                 230                 235                 240

Asp Ala Ser Thr Leu Ile Ala Ala Asn Gln Ala Ser Arg Gly Asp Gly
                245                 250                 255

Phe Tyr Thr Pro Gly Ser Asp Lys Met Leu Ala Thr Ala Val Ala Ile
                260                 265                 270

Glu Ser Gln Phe Ser Ser Leu Tyr Ser Ile Asn Thr Asn Lys Ala Ser
                275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Phe Leu Cys Thr Asn Ala Phe
305                 310                 315                 320

Gly Glu Leu Phe Tyr Arg Ala Ile Ser Glu Trp Asn Ala Ala Gly Ser
                325                 330                 335

Val Thr Val Asn Ser Val Asn Leu Ala Phe Phe Lys Lys Tyr Asp Ser
                340                 345                 350

Ser Thr Ser Ser Gly Thr Thr Tyr Thr Val Gly Thr Ser Ala Tyr Asn
                355                 360                 365

Asn Leu Val Gln Asn Val Ala Leu Ala Ala Asp Ala Tyr Phe Ser Thr
    370                 375                 380

Val Lys Tyr His Ala Leu Thr Asn Gly Ser Met Ser Glu Gln Tyr Asp
385                 390                 395                 400

Arg Ser Ser Gly Met Ala Thr Gly Ala Arg Asp Leu Thr Trp Ser His
                405                 410                 415

Ala Ala Met Ile Thr Ala Leu Lys Ala Lys Ser Gly Thr Pro Val Tyr
                420                 425                 430
```

```
<210> SEQ ID NO 83
<211> LENGTH: 432
<212> TYPE: PRT
<213> ORGANISM: Backusella circina

<400> SEQUENCE: 83
```

```
Trp Ile Lys Gly Gln Glu Asp Thr Ser Arg Ser Val Met Leu Gly Asn
1                   5                   10                  15

Ile Asn Pro Pro Gly Ser Ala Thr Gly Phe Ile Ser Ala Ser Leu Ser
                20                  25                  30

Thr Ser Gly Pro Asp Tyr Tyr His Trp Thr Arg Asp Ala Ala Leu
            35                  40                  45

Val Ala His Val Ile Val Asn Asp Tyr Asn Thr Thr Leu Ser Gly Asp
    50                  55                  60

Ser Ser Thr Leu Gln Val Ile Lys Asp Tyr Val Thr Phe Ser Val Asn
```

-continued

```
65                  70                  75                  80

Ser Gln Ser Glu Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
                100                 105                 110

Asp Gly Pro Ala Glu Arg Ala Thr Thr Phe Ile Phe Phe Ala Asp Thr
                115                 120                 125

Tyr Leu Ala Gln Gly Gly Asp Ser Ser Tyr Val Thr Gly Thr Leu Ala
            130                 135                 140

Pro Ala Ile Tyr Ala Asp Leu Asp Tyr Val Val Asn Asn Trp Ser Thr
145                 150                 155                 160

Gly Cys Tyr Asp Leu Trp Glu Glu Val Asn Gly Ile His Phe Tyr Thr
                165                 170                 175

Leu Met Val Met Arg Arg Gly Leu Ile Asp Gly Ala Ser Phe Ala Ser
                180                 185                 190

Arg Asn Gly Asp Ser Thr Arg Ser Ser Ser Tyr Thr Ser Thr Ala Lys
                195                 200                 205

Ser Ile Ala Thr Lys Ile Asp Ser Phe Trp Ser Ala Ser Asn Asn Tyr
        210                 215                 220

Val Ala Val Ser Gln Ser Val Thr Ser Gly Val Ser Lys Ala Gly Tyr
225                 230                 235                 240

Asp Ala Ser Thr Ile Ile Ala Ala Asn Gln Ala Ser Leu Gly Asp Gly
                245                 250                 255

Phe Tyr Thr Pro Gly Ser Asp Lys Met Leu Ala Thr Ser Val Ala Val
                260                 265                 270

Glu Asn Ala Phe Ser Ser Leu Tyr Thr Val Asn Thr Gly Lys Ala Ser
        275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Tyr Leu Cys Thr Asn Ala Leu
305                 310                 315                 320

Gly Glu Leu Tyr Tyr Arg Ala Ile Lys Glu Trp Asn Ala Ala Gly Ser
                325                 330                 335

Val Thr Val Asn Ser Val Asn Leu Gly Phe Phe Gln Lys Ile Asp Ser
                340                 345                 350

Ser Ile Ser Ser Gly Thr Thr Phe Thr Leu Gly Thr Ser Asp Tyr Ser
        355                 360                 365

Thr Leu Val Asp Asn Val Ala Leu Ala Ala Asp Lys Phe Phe Ala Val
    370                 375                 380

Val Gln Tyr His Glu Arg Ser Asn Gly Ser Met Pro Glu Gln Phe Gly
385                 390                 395                 400

Arg Glu Asp Gly Leu Pro Thr Gly Ala Arg Asp Leu Thr Trp Ser His
                405                 410                 415

Ala Ala Met Ile Ser Ala Ala Arg Ala Lys Ala Gly Thr Pro Val Tyr
                420                 425                 430
```

<210> SEQ ID NO 84
<211> LENGTH: 432
<212> TYPE: PRT
<213> ORGANISM: Benjaminiella poitrasii

<400> SEQUENCE: 84

```
Trp Leu Lys Ser Gln Ile Gly Ile Ser Arg Tyr Ala Met Leu Arg Asn
1               5                   10                  15
```

-continued

```
Ile Asn Pro Ala Gly Ser Ala Val Gly Phe Ile Ala Ala Ser Leu Ser
            20              25                  30

Thr Ala Asn Pro Asp Tyr Tyr Tyr Ala Trp Thr Arg Asp Ser Ala Leu
            35              40              45

Thr Ser Tyr Val Ile Ala Asn Asp Tyr Asn Ser Thr Leu Ala Gly Asn
        50              55              60

Ser Thr Ile Leu Gln Ile Met Lys Asp Tyr Val Thr Phe Ser Val Lys
65              70              75              80

Ser Gln Ser Val Ser Thr Ala Cys Asn Cys Leu Gly Glu Pro Lys Phe
                85              90              95

Asn Pro Asp Gly Ser Ser Tyr Thr Gly Ala Trp Gly Arg Pro Gln Asn
            100             105             110

Asp Gly Pro Ala Glu Arg Ala Thr Thr Phe Ile Leu Phe Ala Asp Ser
            115             120             125

Tyr Leu Lys Gln Thr Gly Asp Ala Ser Tyr Val Thr Gly Thr Leu Lys
        130             135             140

Pro Ala Ile Phe Lys Asp Leu Asp Tyr Val Val Asn Thr Trp Thr Asn
145             150             155             160

Gly Cys Phe Asp Leu Trp Glu Glu Val Asn Gly Val His Phe Tyr Thr
                165             170             175

Leu Met Val Met Arg Lys Gly Leu Ile Arg Gly Ala Asn Phe Ala Thr
            180             185             190

Arg Asn Gly Asp Ser Thr Arg Ala Ser Thr Tyr Thr Asn Thr Ala Ala
        195             200             205

Ser Ile Lys Thr Lys Met Asp Ser Phe Trp Ser Ser Gly Asn Asn Tyr
    210             215             220

Ile Ala Val Ser Gln Ser Val Thr Gly Gly Val Ser Lys Ala Gly Tyr
225             230             235             240

Asp Val Ala Asn Ile Ile Ala Ala Asn Val Gly Ser Leu Gln Asp Gly
            245             250             255

Val Tyr Thr Pro Gly Ser Asp Arg Ile Leu Ala Thr Ala Val Ala Val
            260             265             270

Glu Ala Lys Phe Ala Ser Leu Tyr Gly Val Asn Ser Asn Leu Pro Gly
            275             280             285

Tyr Leu Gly Asn Ser Ile Gly Arg Tyr Pro Glu Asp Thr Tyr Asn Gly
        290             295             300

Asn Gly Asn Ser Gln Gly Asn Pro Trp Phe Leu Ala Thr Asn Ala Tyr
305             310             315             320

Ala Glu Leu Tyr Tyr Arg Ala Ile Arg Glu Trp Tyr Asp Asn Gly Gly
            325             330             335

Val Thr Val Asn Ser Val Asn Leu Pro Phe Phe Lys Lys Phe Asp Ser
        340             345             350

Ser Ala Ala Ser Gly Thr Thr Tyr Thr Val Gly Thr Thr Ala Phe Asn
        355             360             365

Thr Met Val Ser Asn Val Ala Ala Ala Asp Lys Phe Phe Ser Thr
    370             375             380

Val Lys Phe His Ala Tyr Thr Asn Gly Ser Met Ser Glu Gln Phe Gly
385             390             395             400

Arg Asn Asp Gly Leu Cys Thr Gly Ala Arg Asp Leu Thr Trp Ser His
                405             410             415

Ala Ser Leu Ile Ser Ala Ala Leu Ala Lys Ala Gly Thr Pro Ser Val
            420             425             430
```

```
<210> SEQ ID NO 85
<211> LENGTH: 432
<212> TYPE: PRT
<213> ORGANISM: Choanephora cucurbitarum

<400> SEQUENCE: 85

Trp Ile Asp Lys Gln Ile Asp Ile Ser Arg Ser Ala Met Leu Lys Asn
1               5                   10                  15

Ile Asn Pro Ala Gly Thr Val Lys Gly Phe Ile Ala Ala Ser Leu Ser
            20                  25                  30

Thr Ser Asn Pro Asp Tyr Phe Tyr Ala Trp Thr Arg Asp Ala Ala Leu
            35                  40                  45

Val Ala His Val Val Ala Asn Asp Tyr Asn Arg Thr Lys Ser Gly Asp
        50                  55                  60

Ala Thr Tyr Leu Gly Leu Leu Lys Asp Tyr Val Thr Phe Ser Ile Asn
65                  70                  75                  80

Ser Gln Asn Thr Pro Thr Ala Cys Asn Cys Leu Gly Glu Pro Lys Phe
                85                  90                  95

Asn Lys Asp Gly Ser Gly Tyr Asn Gly Pro Trp Gly Arg Pro Gln Asn
            100                 105                 110

Asp Gly Pro Ala Glu Arg Ala Asp Thr Phe Val Leu Ile Ala Asp Ser
            115                 120                 125

Ile Leu Thr Gln Thr Lys Asp Val Ser Tyr Val Thr Gly Thr Leu Arg
        130                 135                 140

Pro Ala Ile Tyr Thr Asp Leu Asp Tyr Val Val Arg Thr Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Ala Leu Leu Val Gly Ala Asn Phe Ala Ser
            180                 185                 190

Arg Asn Gly Asp Ser Ala Arg Ala Ser Asn Tyr Asn Asn Ala Ala Asn
            195                 200                 205

Ser Ile Lys Ser Lys Ile Asp Ser Phe Trp Ser Ser Asn Asn Asn Tyr
        210                 215                 220

Val Ala Val Ser Gln Ser Val Thr Gly Gly Val Ser Lys Ala Gly Tyr
225                 230                 235                 240

Asp Val Ser Thr Leu Ile Ala Ala Asn Val Gly Ser Leu Ser Asp Gly
            245                 250                 255

Phe Tyr Thr Pro Gly Ser Glu Arg Met Leu Ala Thr Ala Val Ala Ile
            260                 265                 270

Glu Asp Lys Phe Ala Asn Leu Tyr Gly Ile Asn Arg Asn Leu Asp Ser
        275                 280                 285

Ser Leu Gly Asn Ala Ile Gly Arg Tyr Pro Glu Asp Thr Tyr Asn Gly
        290                 295                 300

Asn Gly Asn Ser Gln Gly Asn Pro Trp Phe Ile Ala Thr Asn Ala Tyr
305                 310                 315                 320

Ala Glu Leu Tyr Tyr Arg Ala Ile Lys Glu Trp Asn Asn Asn Gly Gly
                325                 330                 335

Val Thr Val Thr Asn Val Asn Leu Asn Phe Phe Lys Lys Phe Asp Gly
            340                 345                 350

Ser Ala Ser Val Gly Thr Lys Tyr Thr Ala Gly Ser Ala Ala Tyr Asn
        355                 360                 365

Thr Leu Thr Gln Asn Ile Ala Leu Ala Ala Asp Lys Phe Phe Asn Thr
    370                 375                 380
```

-continued

Val Lys Val His Ala Ala Thr Asn Gly Ser Met Ser Glu Gln Tyr His
385                 390                 395                 400

Arg Asp Thr Gly Ser Met Thr Gly Ala Arg Asp Leu Thr Trp Ser His
                405                 410                 415

Ala Ser Leu Ile Thr Ala Ala Leu Ala Lys Ala Gly Thr Pro Val Ala
                420                 425                 430

<210> SEQ ID NO 86
<211> LENGTH: 432
<212> TYPE: PRT
<213> ORGANISM: Rhizopus stolonifer

<400> SEQUENCE: 86

Trp Ile Lys Arg Gln Glu Lys Ile Ser Arg Phe Ala Met Leu Arg Asn
1               5                   10                  15

Ile Asn Pro Pro Gly Ser Ala Ala Gly Phe Ile Ala Ala Ser Leu Ser
                20                  25                  30

Thr Ser Gly Pro Asp Tyr Tyr Tyr Ser Trp Thr Arg Asp Ser Ala Leu
            35                  40                  45

Thr Ser Asn Leu Ile Ala Tyr Glu Tyr Asn Thr Thr Leu Ser Gly Asn
        50                  55                  60

Thr Thr Ile Leu Asn Ile Leu Lys Asp Tyr Val Lys Phe Ser Ile Ser
65                  70                  75                  80

Ser Gln Thr Thr Ser Thr Val Cys Asn Cys Leu Gly Glu Pro Lys Phe
                85                  90                  95

Asn His Asp Gly Ser Ser Tyr Thr Gly Ala Trp Gly Arg Pro Gln Asn
            100                 105                 110

Asp Gly Pro Ala Glu Arg Ala Asn Thr Phe Ile Leu Phe Ala Asp Ser
        115                 120                 125

Tyr Leu Asp Gln Thr Lys Asp Ala Ser Tyr Val Thr Gly Thr Leu Lys
        130                 135                 140

Pro Ala Ile Phe Lys Asp Leu Asp Tyr Val Val Asn Val Trp Ser Asn
145                 150                 155                 160

Gly Cys Tyr Asp Leu Trp Glu Glu Val Asn Gly Val His Phe Tyr Thr
                165                 170                 175

Leu Met Val Met Arg Lys Gly Leu Leu Leu Gly Ala Asp Phe Ala Lys
                180                 185                 190

Arg Asn Gly Asp Ser Thr Arg Ala Ser Thr Tyr Thr Asn Thr Ala Ser
            195                 200                 205

Thr Ile Ala Thr Lys Ile Ser Ser Phe Trp Val Ser Ser Ser Asn Trp
        210                 215                 220

Ile Gln Val Ser Gln Ser Val Thr Ala Gly Val Ser Lys Lys Gly Leu
225                 230                 235                 240

Asp Val Ser Thr Leu Leu Ala Ala Asn Leu Gly Ser Val Glu Asp Gly
                245                 250                 255

Phe Phe Thr Pro Gly Ser Glu Lys Ile Leu Ala Thr Ala Val Ala Ile
                260                 265                 270

Glu Asp Ala Phe Ala Ser Leu Tyr Pro Ile Asn Ser Asn Leu Pro Ser
            275                 280                 285

Tyr Leu Gly Asn Ser Ile Gly Arg Tyr Pro Glu Asp Thr Tyr Asn Gly
        290                 295                 300

Asn Gly Asn Ser Gln Gly Asn Pro Trp Phe Leu Ala Val Asn Gly Phe
305                 310                 315                 320

Ala Glu Leu Tyr Tyr Arg Ala Ile Lys Glu Trp Val Asn Asn Gly Ser
                325                 330                 335

```
Val Thr Val Ser Asn Ile Ser Leu Ser Phe Phe Lys Lys Phe Asp Ser
        340                 345                 350

Ser Ala Thr Ala Gly Lys Thr Tyr Thr Ala Gly Thr Ala Asp Phe Asn
        355                 360                 365

Asn Leu Ala Gln Asn Ile Ala Leu Gly Ala Asp Arg Phe Leu Ser Thr
        370                 375                 380

Val Gln Thr His Ala Phe Asn Asn Gly Ser Leu Ala Glu Glu Tyr Asp
385                 390                 395                 400

Arg Thr Thr Gly Val Ser Thr Gly Ala Arg Asp Leu Thr Trp Ser His
                405                 410                 415

Ala Ser Leu Ile Thr Ala Ala Tyr Ala Lys Ala Gly Ser Pro Ala Ala
        420                 425                 430

<210> SEQ ID NO 87
<211> LENGTH: 432
<212> TYPE: PRT
<213> ORGANISM: Mucor circinelloides

<400> SEQUENCE: 87

Trp Ile Asp Gly Gln Thr Ser Val Ser Arg Tyr Ala Met Leu Arg Asn
1               5                   10                  15

Ile Asn Pro Ala Gly Ala Val Ser Gly Phe Ile Ala Ala Ser Met Ser
        20                  25                  30

Thr Ser Gly Pro Asp Tyr Phe Tyr Ala Trp Thr Arg Asp Ser Ala Leu
        35                  40                  45

Thr Ser His Val Val Ala Tyr Asp Tyr Asn Thr Thr Leu Ala Gly Asn
        50                  55                  60

Ser Thr Ile Leu Gly Leu Leu Lys Asn Tyr Val Thr Phe Ser Ile Asn
65                  70                  75                  80

Ser Gln Thr Thr Ser Thr Val Cys Asn Cys Leu Gly Glu Pro Lys Phe
                85                  90                  95

Asn Lys Asp Gly Ser Ser Tyr Thr Gly Ala Trp Gly Arg Pro Gln Asn
        100                 105                 110

Asp Gly Pro Ala Ser Arg Ala Asp Thr Phe Ile Leu Ile Ala Asp Ser
        115                 120                 125

Ile Leu Lys Gln Thr Gly Asp Ala Thr Tyr Val Thr Gly Thr Leu Ala
        130                 135                 140

Pro Ala Ile Tyr Lys Asp Leu Asp Tyr Val Val Ser Thr Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Gly Leu Ile Lys Gly Ala Asn Phe Ala Ser
                180                 185                 190

Arg Asn Gly Asp Asn Thr Arg Ala Asn Thr Tyr Thr Asn Thr Ala Ala
        195                 200                 205

Ser Ile Lys Thr Lys Ile Asp Ser Phe Trp Asn Ser Asn Gly Asn Tyr
        210                 215                 220

Val Thr Val Ser Gln Ser Val Thr Gly Gly Val Ser Lys Ala Gly Tyr
225                 230                 235                 240

Asp Ala Ser Val Leu Ile Ala Ala Asn Leu Gly Ser Val Gln Asp Gly
                245                 250                 255

Phe Tyr Thr Pro Gly Ser Asp Lys Met Leu Ala Thr Ala Val Ala Ile
                260                 265                 270

Glu Ser Lys Phe Ala Ser Leu Tyr Ser Ile Asn Gln Asn Leu Asn Gly
```

-continued

```
              275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Phe Asn Asn Gly Gly
                325                 330                 335

Val Thr Val Thr Ser Ile Ser Leu Asn Phe Phe Lys Lys Phe Asp Ser
            340                 345                 350

Ser Ala Ala Val Gly Thr Lys Tyr Thr Val Gly Thr Ser Ala Phe Asn
        355                 360                 365

Ser Leu Val Gln Asn Val Ala Val Ala Ala Asp Ala Phe Phe Ser Thr
    370                 375                 380

Val Lys Phe His Ala Ala Thr Asn Gly Ser Met Ser Glu Gln Tyr Gly
385                 390                 395                 400

Arg Ser Asp Gly Leu Met Thr Gly Ala Arg Asp Leu Thr Trp Ser His
                405                 410                 415

Ala Ser Leu Ile Ser Ala Ser Tyr Ala Lys Ala Gly Ser Pro Ala Ala
            420                 425                 430

<210> SEQ ID NO 88
<211> LENGTH: 431
<212> TYPE: PRT
<213> ORGANISM: Dichotomocladium elegans

<400> SEQUENCE: 88

Trp Ala Asp Ser Gln His Lys Ile Ser Trp Lys Ala Met Leu Ala Asn
1               5                   10                  15

Ile Asn Pro Pro Gly Ser Ala Thr Gly Phe Ile Ala Ala Ser Leu Ser
            20                  25                  30

Thr Ser Gly Pro Asp Tyr Tyr Tyr Ala Trp Thr Arg Asp Ala Ala Met
        35                  40                  45

Val Ala His Val Ile Val Asn Ala Tyr Asn Thr Thr Lys Ala Gly Asp
    50                  55                  60

Ala Thr Thr Leu Gly Val Leu Lys Asp Phe Val Thr Phe Gln Ile Lys
65                  70                  75                  80

Ala Met Ala Thr Ser Thr Val Cys Asn Cys Leu Gly Glu Pro Lys Phe
                85                  90                  95

Asn Pro Asp Gly Ser Ser Tyr Thr Gly Pro Trp Gly Arg Pro Gln Asn
            100                 105                 110

Asp Gly Pro Ala Glu Arg Ala Thr Thr Phe Ile Leu Phe Ala Asp Ser
        115                 120                 125

Tyr Leu Ser Gln Thr Gly Asp Ala Ala Tyr Val Thr Thr Leu Lys Arg
    130                 135                 140

Ala Ile Phe Thr Asp Leu Asp Tyr Val Val Thr Thr Trp Gln Asp Asn
145                 150                 155                 160

Cys Phe Asp Leu Trp Glu Glu Val Asn Gly Leu His Met Tyr Thr Leu
                165                 170                 175

Ala Val Met Arg Arg Ser Leu Val Asp Gly Ala Ser Phe Ala Ala Arg
            180                 185                 190

Asn Gly Asp Asn Thr Arg Ala Ser Thr Tyr Thr Asn Thr Ala Lys Ser
        195                 200                 205

Ile Glu Thr Lys Leu Ala Ser Phe Tyr Asn Ser Ser Ser Asn Tyr Val
    210                 215                 220
```

-continued

```
Val Val Thr Lys Asn Phe Ala Gly Gly Val Asn Lys Ala Gly Leu Asp
225                 230                 235                 240

Thr Ser Thr Leu Ile Ala Ala Asn Thr Ala Gly Leu Gly Asp Gly Phe
                245                 250                 255

Phe Thr Pro Gly Ser Pro Glu Ile Leu Ala Thr Ala Ala Ala Ile Glu
                260                 265                 270

Lys Ser Phe Ala Asp Leu Tyr Gly Ile Asn Lys Gln Ile Pro Asn Trp
                275                 280                 285

Leu Gly Thr Ala Ile Gly Arg Tyr Pro Glu Asp Thr Tyr Asn Gly Asn
                290                 295                 300

Gly Asn Ser Gln Gly Asn Pro Trp Phe Ile Cys Thr Ala Thr Phe Ala
305                 310                 315                 320

Glu Leu Tyr Tyr Arg Ala Ile Leu Glu Trp Gln His Ala Gly Ser Val
                325                 330                 335

Thr Val Asn Asn Val Asn Leu Pro Phe Phe Lys Lys Phe Asp Ser Ser
                340                 345                 350

Thr Ser Ser Gly Thr Thr Tyr Thr Val Gly Thr Ser Ser Phe Asp Ser
                355                 360                 365

Leu Ile Ser Lys Val Ala Tyr Ala Ala Asp Asn Phe Phe Ser Thr Ile
                370                 375                 380

Lys Tyr His Ala Ala Thr Asn Gly Ser Met Ser Glu Gln Phe Asn Arg
385                 390                 395                 400

Asp Thr Gly Phe Met Thr Gly Ala Arg Asp Leu Thr Trp Ser His Ala
                405                 410                 415

Ala Phe Ile Thr Ala Ala Lys Ala Lys Ala Gly Thr Pro Val Tyr
                420                 425                 430

<210> SEQ ID NO 89
<211> LENGTH: 432
<212> TYPE: PRT
<213> ORGANISM: Fennellomyces sp.

<400> SEQUENCE: 89

Trp Val Asn Asp Gln Leu Glu Ile Ser Trp Pro Ser Leu Leu Lys Asn
1               5                   10                  15

Val Asn Pro Ser Gly Ala Val Thr Gly Phe Ile Ala Ala Ser Leu Ser
                20                  25                  30

Thr Asn Asp Pro Asp Tyr Phe Tyr Cys Trp Thr Arg Asp Ala Ala Leu
                35                  40                  45

Val Ala Arg Val Met Val Tyr Met Tyr Asn Thr Thr Glu Ala Gly Asp
                50                  55                  60

Thr Ser Leu Arg Ser Lys Leu Gln Asp Tyr Val Thr Phe Gln Ile Asn
65                  70                  75                  80

Ser Met Lys Thr Ala Thr Val Cys Asn Cys Leu Gly Glu Pro Lys Phe
                85                  90                  95

Asn Lys Asp Gly Ser Gly Tyr Ser Gly Ala Trp Gly Arg Pro Gln Asn
                100                 105                 110

Asp Gly Pro Ala Asp Arg Ala Ile Thr Leu Ile Leu Phe Ala Asp Ser
                115                 120                 125

Phe Ile Ala Gln Gly Gly Asp Val Ser Tyr Ile Thr Asn Thr Leu Lys
                130                 135                 140

Pro Ala Ile Tyr Thr Asn Leu Asp Tyr Val Val Asn Thr Trp Ser Asn
145                 150                 155                 160

Val Cys Phe Asp Leu Trp Glu Glu Val Asn Gly Val His Ile Tyr Thr
                165                 170                 175
```

```
Leu Ser Val Met Arg Lys Gly Leu Leu Glu Gly Ala Asp Phe Ala Ser
            180             185             190

Arg Asn Gly Asp Ser Thr Arg Ala Asn Thr Tyr Arg Ser Thr Ala Ser
            195             200             205

Ser Ile Lys Thr Arg Leu Glu Ser Phe Trp Ser Ser Ser Asn Asn Tyr
        210             215             220

Ile Thr Val Thr Gln Ser Tyr Ser Gly Gly Val Asn Lys Ala Gly Leu
    225             230             235             240

Asp Val Ser Thr Leu Leu Ala Ala Asn Gly Ala Ser Met Asn Asp Gly
                245             250             255

Phe Tyr Thr Pro Gly Ser Asp Lys Met Leu Ala Thr Ala Val Ala Ile
            260             265             270

Glu Asn Ser Phe Ala Gly Ile Tyr Ala Val Asn Gln Asn Arg Pro Asp
            275             280             285

Trp Lys Gly Thr Ala Ile Gly Arg Tyr Pro Glu Asp Thr Tyr Asp Gly
        290             295             300

His Gly Asn Ser Gln Gly Asn Pro Trp Phe Ile Ala Thr Ala Ala Tyr
305             310             315             320

Ala Glu Met Tyr Tyr Arg Ala Ile Leu Glu Trp Gln Gln Gln Pro Ser
            325             330             335

Ile Thr Val Asn Ser Ile Asn Leu Ser Phe Phe Lys Lys Phe Asp Ser
            340             345             350

Ser Ala Ala Val Gly Thr Val Tyr Lys Pro Gly Thr Gln Ala Phe Asn
            355             360             365

Asn Met Val Ser Asn Val Ala Phe Ala Ala Asp Glu Phe Phe Ser Thr
    370             375             380

Met Asn Phe His Ser Ala Thr Asn Gly Ser Met Ser Glu Gln Tyr Asn
385             390             395             400

Arg Asn Thr Gly Ile Met Gln Gly Ala Arg Asp Leu Thr Trp Ser His
            405             410             415

Ala Ala Phe Ile Thr Ala Ala Lys Ala Lys Leu Gly Thr Pro Val Phe
            420             425             430
```

```
<210> SEQ ID NO 90
<211> LENGTH: 432
<212> TYPE: PRT
<213> ORGANISM: Gilbertella persicaria

<400> SEQUENCE: 90
```

```
Trp Leu Lys Gly Gln Ile Glu Thr Ser Arg Phe Ala Met Leu Arg Asn
1               5               10              15

Ile Asn Pro Ala Gly Thr Val Lys Gly Phe Ile Ala Ala Ser Leu Ser
            20              25              30

Thr Ala Asn Pro Asp Tyr Phe Tyr Ala Trp Thr Arg Asp Ala Ala Leu
        35              40              45

Val Gly His Val Ile Ala Asn Asp Tyr Asn Arg Thr Leu Ala Gly Asn
    50              55              60

Ser Thr Tyr Leu Gly Leu Leu Lys Asp Tyr Val Thr Phe Ser Val Asn
65              70              75              80

Ser Gln Ser Thr Ser Thr Ile Cys Asn Cys Leu Gly Glu Pro Lys Phe
            85              90              95

Asn Lys Asp Gly Ser Gly Tyr Ser Gly Ala Trp Gly Arg Pro Gln Asn
            100             105             110

Asp Gly Pro Ala Glu Arg Ala Asp Thr Phe Ile Leu Ile Ala Asp Ser
```

-continued

```
            115                 120                 125
Ile Leu Lys Gln Thr Gly Asp Ala Thr Tyr Val Thr Gly Thr Leu Arg
    130                 135                 140

Pro Ala Ile Tyr Lys Asp Leu Asp Tyr Val Val Asn Val Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Ser Leu Ile Leu Gly Ala Asn Phe Ala Ser
                180                 185                 190

Arg Asn Gly Asp Ser Thr Arg Ala Ser Thr Tyr Thr Asn Thr Ala Asn
                195                 200                 205

Ser Ile Lys Thr Lys Ile Asp Thr Phe Trp Ser Ser Ser Asn Asn Tyr
    210                 215                 220

Val Ala Val Ser Gln Ser Val Thr Gly Gly Val Asn Lys Ala Gly Tyr
225                 230                 235                 240

Asp Val Ala Asn Leu Ile Ala Ala Asn Val Gly Ser Leu Asp Asp Gly
                245                 250                 255

Phe Tyr Thr Pro Gly Ser Glu Arg Ile Leu Ala Thr Ala Val Ala Val
                260                 265                 270

Glu Ser Lys Phe Ala Ser Ile Tyr Gly Val Asn Gln Asn Leu Pro Ser
                275                 280                 285

Trp Leu Gly Asn Ser Ile Gly Arg Tyr Pro Glu Asp Thr Tyr Asn Gly
    290                 295                 300

Asn Gly Asn Ser Gln Gly Asn Pro Trp Phe Ile Ala Thr Asn Thr Tyr
305                 310                 315                 320

Ala Glu Leu Tyr Tyr Arg Ala Ile Lys Glu Trp Thr Asn Asn Gly Gly
                325                 330                 335

Val Thr Val Thr Asn Val Asn Phe Asn Phe Phe Lys Lys Phe Asp Ser
                340                 345                 350

Ser Ala Ser Val Gly Thr Lys Tyr Thr Val Gly Thr Ser Ala Phe Asn
                355                 360                 365

Thr Leu Thr Gln Asn Val Ala Leu Ala Ala Asp Asn Phe Phe Ser Thr
    370                 375                 380

Val Lys Val His Ala Ala Thr Asn Gly Ser Met Ser Glu Gln Phe Gly
385                 390                 395                 400

Arg Asp Ser Gly Val Met Thr Gly Ala Arg Asp Leu Thr Trp Ser His
                405                 410                 415

Ala Ser Leu Ile Thr Ala Ala Leu Ala Lys Thr Gly Ala Pro Val Ala
                420                 425                 430
```

<210> SEQ ID NO 91
<211> LENGTH: 432
<212> TYPE: PRT
<213> ORGANISM: Mucor circinelloides

<400> SEQUENCE: 91

```
Trp Ile Asp Gly Gln Thr Ser Val Ser Arg Tyr Ala Met Leu Arg Asn
1               5                   10                  15

Ile Asn Pro Ala Gly Ala Val Thr Gly Phe Ile Ala Ala Ser Met Ser
                20                  25                  30

Thr Ser Gly Pro Asp Tyr Phe Tyr Ala Trp Thr Arg Asp Ser Ala Leu
            35                  40                  45

Thr Ser His Val Val Ala Tyr Asp Tyr Asn Thr Thr Leu Ala Gly Asn
    50                  55                  60
```

```
Ser Thr Ile Leu Gly Leu Leu Lys Asn Tyr Val Thr Phe Ser Leu Asn
65                  70                  75                  80

Ser Gln Thr Thr Ser Thr Val Cys Asn Cys Leu Gly Glu Pro Lys Phe
                85                  90                  95

Asn Lys Asp Gly Ser Gly Tyr Ser Gly Ala Trp Gly Arg Pro Gln Asn
            100                 105                 110

Asp Gly Pro Ala Ser Arg Ala Asp Thr Phe Ile Leu Ile Ala Asp Ser
            115                 120                 125

Ile Leu Lys Gln Thr Gly Asp Ala Thr Tyr Val Thr Gly Thr Leu Ala
        130                 135                 140

Pro Ala Ile Tyr Lys Asp Leu Asp Tyr Val Val Ser Thr Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Gly Leu Val Lys Gly Ala Asn Phe Ala Ser
                180                 185                 190

Arg Asn Gly Asp Ser Thr Arg Ala Thr Thr Tyr Thr Asn Thr Ala Ala
            195                 200                 205

Ser Ile Lys Thr Lys Ile Asp Ser Phe Trp Asn Ser Asn Gly Gln Tyr
        210                 215                 220

Val Ser Val Ser Gln Ser Val Thr Gly Gly Val Ser Lys Ala Gly Tyr
225                 230                 235                 240

Asp Ala Ser Val Leu Ile Ala Ser Asn Leu Gly Ser Leu Gln Asp Gly
                245                 250                 255

Phe Tyr Thr Pro Gly Ser Asp Lys Met Leu Ala Thr Ala Val Ala Ile
            260                 265                 270

Glu Ser Lys Phe Ala Ser Leu Tyr Ser Ile Asn Gln Asn Leu Asn Gly
            275                 280                 285

Tyr Leu Gly Asn Ala Ile Gly Arg Tyr Pro Glu Asp Thr Tyr Asn Gly
        290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Phe Asn Asn Gly Gly
                325                 330                 335

Val Thr Val Thr Ser Ile Ser Leu Asn Phe Phe Lys Lys Phe Asp Ser
                340                 345                 350

Ser Ala Ala Val Gly Thr Lys Tyr Thr Val Gly Thr Ser Ser Phe Asn
            355                 360                 365

Ser Leu Val Gln Asn Val Ala Val Ala Ala Asp Ala Phe Phe Ser Thr
        370                 375                 380

Ile Lys Phe His Ala Ala Thr Asn Gly Ser Met Ser Glu Gln Tyr Gly
385                 390                 395                 400

Arg Thr Asp Gly Leu Met Thr Gly Ala Arg Asp Leu Thr Trp Ser His
                405                 410                 415

Ala Ser Leu Ile Ser Ala Ser Tyr Ala Lys Ala Gly Ser Pro Ala Ala
            420                 425                 430
```

<210> SEQ ID NO 92
<211> LENGTH: 432
<212> TYPE: PRT
<213> ORGANISM: Circinella umbellata

<400> SEQUENCE: 92

```
Trp Val Asn Lys Gln Leu Lys Ile Ser Trp Ser Asp Leu Leu Gln Asn
1                   5                   10                  15
```

-continued

```
Val Asn Pro Ser Gly Thr Val Thr Gly Phe Ile Ala Ala Ser Leu Ser
            20                  25                  30

Thr Ser Asn Pro Asp Tyr Phe Tyr Cys Trp Thr Arg Asp Ala Ala Met
        35                  40                  45

Val Ala Arg Val Met Thr Tyr Met Tyr Asn Thr Thr Glu Ala Gly Asp
    50                  55                  60

Ser Ser Leu Glu Ser Ala Leu Lys Asp Tyr Ile Thr Phe Gln Ile Asn
65                  70                  75                  80

Ser Met Lys Thr Ala Thr Ala Cys Asn Cys Leu Gly Glu Pro Lys Phe
                85                  90                  95

Asn Thr Asp Gly Ser Gly Tyr Ser Gly Pro Trp Gly Arg Pro Gln Asn
                100                 105                 110

Asp Gly Pro Ala Glu Arg Ala Thr Thr Met Ile Leu Phe Ala Asp Ser
            115                 120                 125

Tyr Leu Ala Gln Gly Gly Asp Thr Ser Tyr Val Thr Asn Thr Leu Lys
    130                 135                 140

Pro Ala Ile Tyr Thr Asn Leu Asp Tyr Val Val Gly Thr Trp Ser Asn
145                 150                 155                 160

Asn Cys Phe Asp Leu Trp Glu Glu Val Asn Gly Val His Ile Phe Thr
                165                 170                 175

Leu Ala Val Met Arg Lys Ser Leu Leu Asp Gly Ala Asp Phe Ala Ala
                180                 185                 190

Arg Asn Gly Asp Thr Ser Arg Val Ser Gly Tyr Gln Ser Thr Ala Ser
            195                 200                 205

Ser Ile Lys Thr Lys Leu Glu Ser Phe Trp Ser Ser Ser Asn Asn Tyr
    210                 215                 220

Ile Thr Val Thr Gln Ser Tyr Ser Gly Gly Val Gln Lys Ala Gly Leu
225                 230                 235                 240

Asp Val Ser Thr Leu Ile Ala Ala Asn Gln Gly Ser Met Gly Asp Gly
                245                 250                 255

Phe Tyr Thr Pro Gly Ser Asp Lys Met Leu Ala Thr Ala Val Ala Ile
                260                 265                 270

Glu Asn Ser Phe Ala Asn Ile Tyr Thr Ile Asn Lys Asn Lys Pro Ser
            275                 280                 285

Trp Leu Gly Thr Ala Ile Gly Arg Tyr Pro Glu Asp Thr Tyr Asn Gly
    290                 295                 300

Asn Gly Asn Gly Gln Gly Asn Pro Trp Phe Ile Ala Thr Ala Thr Tyr
305                 310                 315                 320

Ala Glu Leu Tyr Tyr Arg Ala Ile Leu Glu Trp Gln Gln Gln Glu Ser
                325                 330                 335

Val Thr Val Asn Ser Val Asn Phe Asp Phe Phe Ser Lys Phe Asp Ser
            340                 345                 350

Ser Ala Lys Val Gly Thr Val Tyr Thr Pro Gly Thr Asp Thr Phe Asn
        355                 360                 365

Thr Met Val Ser Asn Val Ala Phe Ala Ala Asp Glu Phe Leu Ser Thr
    370                 375                 380

Met Glu His Tyr Ala Ala Thr Asn Gly Ser Met Ser Glu Gln Phe Asn
385                 390                 395                 400

Arg Glu Thr Gly Ser Leu Thr Gly Ala Arg Asp Leu Thr Trp Ser His
                405                 410                 415

Ala Ala Phe Ile Thr Ala Gly Lys Ala Lys Leu Gly Ile Pro Ser Phe
                420                 425                 430
```

-continued

```
<210> SEQ ID NO 93
<211> LENGTH: 432
<212> TYPE: PRT
<213> ORGANISM: Mucor cordense

<400> SEQUENCE: 93

Trp Leu Lys Ser Gln Glu Asp Ile Ser Arg Gly Ala Met Leu Arg Asn
1               5                   10                  15

Ile Asn Pro Pro Gly Ala Ala Thr Gly Phe Ile Ala Ala Ser Leu Ser
            20                  25                  30

Thr Ser Gly Pro Asp Tyr Tyr Tyr Ala Trp Thr Arg Asp Ser Ala Leu
        35                  40                  45

Thr Ser His Val Ile Ala His Asp Tyr Asn Thr Thr Leu Ala Gly Asn
    50                  55                  60

Thr Thr Ile Leu Asn Ile Leu Lys Asp Tyr Val Thr Phe Ser Val Lys
65                  70                  75                  80

Ser Gln Ser Val Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Ser Thr Phe Ile Leu Phe Gly Asp Ser
            115                 120                 125

Tyr Leu Lys Gln Thr Gly Asp Ala Thr Tyr Val Thr Gly Thr Leu Ala
    130                 135                 140

Pro Ala Ile Tyr Lys Asp Leu Asp Tyr Val Val Asn Thr Trp Ser Asn
145                 150                 155                 160

Gly Cys Phe Asp Leu Trp Glu Glu Val Asn Gly Val His Phe Tyr Thr
                165                 170                 175

Leu Met Ser Met Arg Arg Gly Leu Leu Asp Gly Ala Asn Phe Ala Lys
            180                 185                 190

Arg Asn Gly Asp Thr Thr Arg Ala Thr Thr Tyr Thr Asn Thr Ala Ala
            195                 200                 205

Ser Ile Ala Thr Lys Ile Asp Thr Phe Trp Val Ser Ser Gly Asn Tyr
    210                 215                 220

Val Gln Val Ser Gln Ser Val Thr Gly Gly Val Ser Lys Ala Gly Tyr
225                 230                 235                 240

Asp Cys Ala Asn Ile Leu Ala Ala Asn Met Ala Ala Asn His Asp Gly
                245                 250                 255

Phe Tyr Thr Pro Gly Ser Ser Lys Ile Leu Ala Thr Ala Val Ala Ile
            260                 265                 270

Glu Ser Lys Phe Ala Ser Leu Tyr Ser Ile Asn Ser Gly Leu Ala Ser
    275                 280                 285

Trp Leu Gly Thr Ala Ile Gly Arg Tyr Pro Glu Asp Thr Tyr Asn Gly
    290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Thr Gln Ala Gly Ser
            325                 330                 335

Val Thr Val Asp Ser Thr Ser Leu Asn Phe Phe Lys Lys Phe Asp Ser
            340                 345                 350

Ser Ala Ala Ala Gly Thr Lys Tyr Thr Val Gly Thr Ser Ala Phe Thr
    355                 360                 365

Asn Leu Val Gln Asn Ile Ala Asn Gly Ala Asp Lys Phe Leu Ser Thr
    370                 375                 380
```

```
Ser Lys Phe His Ala Ala Thr Asn Gly Ser Met Ser Glu Gln Tyr Asn
385                 390                 395                 400

Arg Asp Ser Gly Leu Met Thr Gly Ala Arg Asp Leu Thr Trp Ser His
                405                 410                 415

Ala Ser Leu Ile Ser Ala Ser Arg Ala Lys Ala Gly Ser Pro Ser Leu
                420                 425                 430

<210> SEQ ID NO 94
<211> LENGTH: 432
<212> TYPE: PRT
<213> ORGANISM: Phascolomyces articulosus

<400> SEQUENCE: 94

Trp Val Asn Thr Gln Phe Ala Ile Ser Trp Pro Thr Leu Leu Lys Asn
1               5                   10                  15

Val Asn Pro Ser Gly Thr Val Lys Gly Phe Ile Ala Ala Ser Leu Ser
                20                  25                  30

Thr Asn Asn Pro Asp Tyr Phe Tyr Ser Trp Thr Arg Asp Ser Ala Leu
            35                  40                  45

Val Ala His Thr Met Thr Tyr Leu Tyr Asn Thr Ser Glu Ala Gly Asp
        50                  55                  60

Ser Thr Ile Glu Ser Ala Leu Lys Asp Tyr Val Thr Phe Ser Ile Asn
65                  70                  75                  80

Ala Met Asn Ala Ala Thr Val Cys Asn Cys Leu Gly Glu Pro Lys Phe
                85                  90                  95

Asn Thr Asp Gly Ser Gly Tyr Thr Gly Ala Trp Gly Arg Pro Gln Asn
            100                 105                 110

Asp Gly Pro Ala Ser Arg Ala Thr Thr Met Ile Leu Phe Ala Asp Ser
        115                 120                 125

Phe Leu Ala Gln Gly Gly Asp Val Ser Tyr Val Ile Asn Thr Leu Lys
        130                 135                 140

Pro Ala Ile Tyr Lys Asp Leu Asp Tyr Val Val Ser Thr Trp Ser Asn
145                 150                 155                 160

Thr Cys Tyr Asp Leu Trp Glu Glu Val Asn Gly Val His Ile Tyr Thr
                165                 170                 175

Leu Ser Val Met Arg Arg Ala Leu Ile Asp Gly Ala Asn Phe Ala Gln
                180                 185                 190

Arg Asn Gly Asp Thr Ser Arg Val Ser Gly Tyr Thr Ser Thr Ala Thr
            195                 200                 205

Thr Ile Lys Thr Arg Leu Glu Ser Phe Trp Ser Asp Ser Asn Asn Tyr
        210                 215                 220

Ile Thr Val Thr Gln Ser Tyr Ser Gly Gly Val Gln Lys Ala Gly Leu
225                 230                 235                 240

Asp Val Ser Thr Leu Ile Ala Ala Asn Ile Gly Ser Val Gly Asp Gly
                245                 250                 255

Phe Tyr Thr Pro Gly Ser Asp Lys Val Leu Ala Thr Ala Val Ala Ile
                260                 265                 270

Glu Lys Ser Phe Ala Asn Leu Tyr Thr Ile Asn Gln Asn Lys Pro Ser
                275                 280                 285

Trp Leu Gly Asn Ala Ile Gly Arg Tyr Pro Glu Asp Thr Tyr Asp Gly
        290                 295                 300

Tyr Gly Asn Ser Lys Gly Asn Pro Trp Phe Ile Ala Thr Ala Thr Tyr
305                 310                 315                 320

Ala Glu Leu Tyr Tyr Arg Ala Ile Leu Glu Trp Gln Gln Gln Ala Ser
```

-continued

```
                 325             330             335

Val Thr Val Asn Ser Ile Asn Leu Gly Phe Phe Ser Lys Phe Asp Ser
            340             345             350

Ser Ala Ser Val Gly Thr Val Tyr Thr Pro Gly Thr Asp Ser Phe Ala
            355             360             365

Asn Met Val Ser Asn Val Ala Phe Ala Ala Asp Glu Phe Leu Ser Thr
        370             375             380

Ile Asp Tyr His Ala Met Asn Asn Gly Ser Met His Glu Gln Tyr Asn
385             390             395             400

Arg Asp Thr Gly Ile Ser Gln Gly Ala Arg Asp Leu Thr Trp Ser His
            405             410             415

Ala Ala Phe Ile Thr Ala Ala Lys Ala Lys Leu Gly Ala Pro Ala Phe
            420             425             430

<210> SEQ ID NO 95
<211> LENGTH: 432
<212> TYPE: PRT
<213> ORGANISM: Rhizopus microsporus

<400> SEQUENCE: 95

Trp Ile Lys Asn Gln Glu Glu Ile Ser Arg Phe Ala Met Leu Arg Asn
1               5               10              15

Ile Asn Pro Pro Gly Ser Ala Thr Gly Phe Ile Ala Ala Ser Leu Ser
            20              25              30

Thr Ala Gly Pro Asp Tyr Tyr Tyr Ser Trp Thr Arg Asp Ser Ala Leu
            35              40              45

Thr Ala Asn Val Ile Ala Tyr Glu Tyr Asn Thr Thr Phe Ala Gly Asn
        50              55              60

Thr Thr Leu Leu Lys Tyr Leu Lys Asp Tyr Val Thr Phe Ser Val Lys
65              70              75              80

Ser Gln Ser Val Ser Thr Val Cys Asn Cys Leu Gly Glu Pro Lys Phe
                85              90              95

Asn Ala Asp Gly Ser Ser Tyr Thr Gly Pro Trp Gly Arg Pro Gln Asn
            100             105             110

Asp Gly Pro Ala Glu Arg Ala Val Thr Phe Met Leu Ile Ala Asp Ser
            115             120             125

Tyr Leu Thr Gln Thr Lys Asp Ala Ser Tyr Val Thr Gly Thr Leu Lys
        130             135             140

Pro Ala Ile Phe Lys Asp Leu Asp Tyr Val Val Ser Val Trp Ser Asn
145             150             155             160

Gly Cys Tyr Asp Leu Trp Glu Glu Val Asn Gly Val His Phe Tyr Thr
            165             170             175

Leu Met Val Met Arg Lys Gly Leu Ile Leu Gly Ala Asp Phe Ala Ala
            180             185             190

Arg Asn Gly Asp Ser Ser Arg Ala Ser Thr Tyr Lys Asn Thr Ala Ser
            195             200             205

Thr Met Glu Ser Lys Ile Ser Ser Phe Trp Ser Asp Ser Asn Asn Tyr
        210             215             220

Val Gln Val Ser Gln Ser Val Thr Ala Gly Val Ser Lys Lys Gly Leu
225             230             235             240

Asp Val Ser Thr Leu Leu Ala Ala Asn Ile Gly Ser Leu Pro Asp Gly
            245             250             255

Phe Phe Thr Pro Gly Ser Glu Lys Ile Leu Ala Thr Ala Val Ala Leu
            260             265             270
```

```
Glu Asn Ala Phe Ala Ser Leu Tyr Pro Ile Asn Ser Asn Leu Pro Ser
        275                 280                 285

Tyr Leu Gly Asn Ser Ile Gly Arg Tyr Pro Glu Asp Thr Tyr Asn Gly
        290                 295                 300

Asn Gly Asn Ser Gln Gly Asn Pro Trp Phe Leu Ala Val Asn Ala Tyr
305                 310                 315                 320

Ala Glu Leu Tyr Tyr Arg Ala Ile Lys Glu Trp Ile Ser Asn Gly Lys
                325                 330                 335

Val Thr Val Ser Asn Ile Ser Leu Pro Phe Phe Lys Lys Phe Asp Ser
                340                 345                 350

Ser Ala Thr Ser Gly Lys Thr Tyr Thr Ala Gly Thr Ser Asp Phe Asn
        355                 360                 365

Asn Leu Ala Gln Asn Ile Ala Leu Gly Ala Asp Arg Phe Leu Ser Thr
        370                 375                 380

Val Lys Phe His Ala Tyr Asn Asn Gly Ser Leu Ser Glu Glu Tyr Asp
385                 390                 395                 400

Arg Ser Thr Gly Met Ser Thr Gly Ala Arg Asp Leu Thr Trp Ser His
                405                 410                 415

Ala Ser Leu Ile Thr Ala Ala Tyr Ala Lys Ala Gly Ser Pro Ala Ala
                420                 425                 430
```

```
<210> SEQ ID NO 96
<211> LENGTH: 433
<212> TYPE: PRT
<213> ORGANISM: Spinellus fusiger

<400> SEQUENCE: 96
```

```
Trp Gly Ser Lys Gln Asp Gly Ile Ser Phe Ser Thr Met Leu Gly Asn
1               5                   10                  15

Ile Asn Pro Pro Gly Ser Ser Lys Gly Phe Ile Ala Ala Ser Leu Ser
            20                  25                  30

Thr Ala Gly Pro Asn Tyr Tyr Tyr Ser Trp Thr Arg Asp Ser Ala Leu
        35                  40                  45

Val Ala Arg Ala Ile Thr Tyr Lys Tyr Ser Thr Ser Tyr Gln Asn Asp
        50                  55                  60

Pro Lys Ile Leu Gly Leu Leu Lys Asp Tyr Val Thr Tyr Gln Val Asn
65                  70                  75                  80

Glu Gln Thr Glu Ser Thr Val Cys Asn Cys Leu Gly Glu Pro Lys Phe
                85                  90                  95

Asn Pro Asp Gly Ser Ser Phe Ser Gly Pro Trp Gly Arg Pro Gln Asn
            100                 105                 110

Asp Gly Pro Ala Glu Arg Ala Ser Thr Met Ile Leu Phe Ala Lys Ser
        115                 120                 125

Tyr Tyr Ala Gln Thr Asn Asp Val Gly Tyr Val Ser Asn Thr Leu Lys
        130                 135                 140

Pro Ala Ile Tyr Lys Asp Leu Asp Tyr Ile Val Asn Val Trp Gly Asn
145                 150                 155                 160

Asn Cys Phe Asp Leu Trp Glu Glu Val Asn Gly Val His Phe Tyr Thr
                165                 170                 175

Leu Met Met Met Arg His Gly Leu Val Gln Gly Ser Ile Phe Ala Asn
                180                 185                 190

Thr Leu Gly Asp Ser Thr Arg Ala Asn Thr Tyr Lys Thr Ala Ala Gln
        195                 200                 205

Asn Ile Lys Asn Arg Ile Asp Thr Phe Trp Glu Ser Gly Ser Asn Tyr
        210                 215                 220
```

-continued

```
Ile Val Val Thr Gln Asn Gln Ser Ala Gly Val Asn Lys Pro Ser Gly
225             230             235             240

Leu Asp Val Ala Val Leu Leu Ala Ala Asn Gln Gly Gly Leu Gly Asp
                245             250             255

Gly Val Tyr Thr Pro Gly Ser Asp Lys Val Leu Ala Thr Ala Val Ala
                260             265             270

Leu Glu Lys Ser Phe Ala Ser Leu Tyr Pro Ile Asn Lys Asn Leu Pro
            275             280             285

Ser Tyr Tyr Gly Thr Ala Ile Gly Arg Tyr Pro Glu Asp Thr Tyr Asn
    290             295             300

Gly Asn Gly Asn Ser Glu Ala Asn Pro Trp Phe Ile Ala Thr Thr Thr
305             310             315             320

Tyr Ala Glu Leu Tyr Tyr Arg Ala Ile Ser Glu Trp Thr Asn Gly Ser
                325             330             335

Gly Val Thr Val Asn Ser Ile Asn Lys Glu Phe Phe Ser Lys Phe Asp
                340             345             350

Ala Ser Ala Thr Asn Gly Lys Val Tyr Thr Pro Gly Ser Asp Ser Phe
            355             360             365

Asn Ser Leu Val Asn Asn Val Ala Ile Ala Ala Asp Asn Phe Leu Ser
    370             375             380

Thr Val Arg Tyr His Gln Thr Ser Asn Gly Ser Leu Ser Glu Gln Phe
385             390             395             400

Asn Arg Tyr Thr Gly Phe Met Thr Gly Ala Arg Asp Leu Thr Trp Ser
                405             410             415

His Ala Ala Met Val Thr Ala Leu Ala Ala Lys Ala Gly Thr Pro Ser
            420             425             430

Pro

<210> SEQ ID NO 97
<211> LENGTH: 432
<212> TYPE: PRT
<213> ORGANISM: Syncephalastrum racemosum

<400> SEQUENCE: 97

Trp Ala Lys Ser Gln Lys Asp Ile Ser Trp Lys Thr Leu Leu Thr Ser
1               5               10              15

Leu Asn Pro Ser Gly Thr Ala Lys Gly Phe Ile Ala Ala Ser Leu Ser
                20              25              30

Thr Ser Asn Pro Asp Tyr Tyr Tyr Ala Trp Thr Arg Asp Ser Ala Leu
            35              40              45

Val Ala Arg Thr Met Val Asn Met Tyr Asn Thr Thr Glu Ala Gly Ser
    50              55              60

Ala Ser Val Leu Gly Leu Leu Gln Asp Tyr Val Thr Phe Gln Ile Asn
65              70              75              80

Ala Met Ser Thr Ser Thr Val Cys Asn Cys Leu Gly Glu Pro Lys Phe
                85              90              95

Asn Pro Asp Gly Ser Ser Tyr Thr Gly Ala Trp Gly Arg Pro Gln Asn
                100             105             110

Asp Gly Pro Ala Glu Arg Ala Ser Thr Phe Ile Leu Phe Ala Asp Ser
            115             120             125

Tyr Ile Ala Gln Gly Gly Gln Leu Ser Tyr Val Thr Gly Thr Leu Ala
    130             135             140

Pro Ala Ile Tyr Lys Asp Leu Asn Tyr Val Val Ser Thr Trp Ser Asn
145             150             155             160
```

```
Asn Cys Phe Asp Leu Trp Glu Glu Val Asn Gly Arg His Met Phe Thr
                165             170             175

Leu Ala Val Met Arg Arg Ala Leu Leu Asp Gly Val Asn Phe Ala Ser
            180             185             190

Arg Ile Gly Asp Thr Thr Tyr Ser Ser Thr Trp Ser Ser Thr Ala Ser
            195             200             205

Ser Ile Gln Ser Thr Leu Ser Gly Tyr Tyr Leu Ser Ser Gly Asn Tyr
    210             215             220

Ile Thr Thr Val Gln Asn Phe Gln Ser Gly Val Ser Lys Ala Gly Tyr
225             230             235             240

Asp Val Ser Thr Leu Ile Ala Ala Asn Val Ala Gly Met Gly Asp Gly
            245             250             255

Phe Phe Thr Pro Gly Ser Asp Glu Val Leu Ala Thr Ala Val Ala Ile
            260             265             270

Glu Asn Lys Phe Ser Ser Leu Tyr Gly Val Asn Ala Asn Lys Ala Ser
    275             280             285

Tyr Leu Gly Thr Ala Ile Gly Arg Tyr Pro Glu Asp Thr Tyr Asn Gly
    290             295             300

Tyr Gly Asn Gly Gln Gly Asn Pro Trp Phe Ile Ala Thr Ala Ala Tyr
305             310             315             320

Ala Glu Leu Tyr Tyr Arg Ala Ile Leu Glu Trp Gln Thr Lys Ser Ser
            325             330             335

Ile Val Val Asn Ser Lys Asn Leu Gly Phe Phe Ser Lys Phe Asp Ser
            340             345             350

Ser Ala Ala Val Gly Thr Thr Tyr Thr Pro Gly Thr Thr Ala Tyr Ser
    355             360             365

Asn Met Val Gln Asn Val Ala Leu Ala Ala Asp Arg Phe Leu Ser Thr
    370             375             380

Val Gln Leu His Ala Ala Thr Asn Gly Ser Met Ser Glu Gln Phe Asn
385             390             395             400

Arg Asp Thr Gly Val Met Gln Gly Ala Arg Asp Leu Thr Trp Ser His
            405             410             415

Ser Ala Phe Ile Thr Ala Ala Arg Ala Lys Leu Gly Ser Pro Val Tyr
            420             425             430

<210> SEQ ID NO 98
<211> LENGTH: 434
<212> TYPE: PRT
<213> ORGANISM: Syncephalastrum racemosum

<400> SEQUENCE: 98

Trp Val Lys Lys Gln Glu Ala Ile Ser Trp Thr Asp Leu Lys Thr Asn
1               5               10              15

Val Asn Pro Glu Gly Ala Ala Lys Gly Phe Ile Ala Ala Ser Leu Ser
            20              25              30

Thr Ser Glu Pro Asp Tyr Tyr Tyr Ala Trp Thr Arg Asp Ser Ala Leu
        35              40              45

Val Ala Arg Val Met Val Asn Lys Tyr Asn Thr Thr Asp Ala Gly Asp
    50              55              60

Ala Asn Leu Leu Gly Leu Leu Gln Asp Tyr Val Ser Phe Gln Ile Asn
65              70              75              80

Ala Met Gly Glu Ser Thr Val Cys Asn Cys Leu Gly Glu Pro Lys Phe
            85              90              95

Asn Pro Asp Gly Ser Ser Tyr Thr Gly Ala Trp Gly Arg Pro Gln Asn
```

-continued

```
                    100                 105                 110
Asp Gly Pro Ala Glu Arg Ala Ser Thr Phe Ile Leu Leu Ala Asp Ser
            115                 120                 125
Met Ile Ala Gln Lys Ser Ala Asn Gly Ser Tyr Val Ser Asp Thr Leu
        130                 135                 140
Ala Pro Ala Ile Tyr Lys Asp Leu Ala Tyr Val Ala Ser Thr Trp Glu
145                 150                 155                 160
Asn Ala Cys Tyr Asp Leu Trp Glu Glu Val Asn Gly Lys His Met Tyr
                165                 170                 175
Thr Leu Ser Val Met Arg Arg Ala Leu Leu Asp Gly Ala Asp Phe Ala
            180                 185                 190
Ser Arg Gln Gly Gln Thr Ala Asn Val Thr Ser Trp Lys Ser Thr Ala
        195                 200                 205
Asp Lys Ile Lys Ser Ser Leu Glu Gly Phe Phe Ser Ser Asp Asn Gly
        210                 215                 220
Tyr Ile Glu Val Thr Gln Asp Met Gln Gly Gly Val Gln Lys Lys Gly
225                 230                 235                 240
Leu Asp Val Ser Thr Leu Ile Ala Ala Asn Ile Gly Ser Met Gly Asp
                245                 250                 255
Gly Phe Tyr Thr Pro Gly Ser Asp Glu Val Leu Ala Thr Ala Val Ala
            260                 265                 270
Val Glu Ala Ala Phe Ala Asp Leu Tyr Lys Ile Asn Gln Asn Thr Asn
        275                 280                 285
Ser Thr Gly Leu Gly Thr Ala Ile Gly Arg Tyr Pro Glu Asp Thr Tyr
    290                 295                 300
Asn Gly Val Gly Asn Ser Gln Gly Asn Pro Trp Phe Ile Ala Thr Asn
305                 310                 315                 320
Thr Phe Ala Glu Leu Tyr Tyr Arg Ala Ile Leu Glu Trp Gln Asn Lys
                325                 330                 335
Gly Thr Ile Thr Val Asn Ser Val Asn Ala Ala Phe Phe Ser Lys Phe
            340                 345                 350
Asp Ser Ser Ala Lys Ala Gly Thr Thr Tyr Lys Ser Gly Ser Thr Glu
        355                 360                 365
Phe Asp Ser Leu Ile Asn Lys Val Ala Leu Ala Ala Asp Ala Phe Leu
    370                 375                 380
Asn Thr Val Gln Thr Tyr Ala Ala Ser Asn Gly Ser Met Ser Glu Gln
385                 390                 395                 400
Tyr Asn Arg Asp Thr Gly Ala Leu Thr Gly Ala Arg Asp Leu Thr Trp
                405                 410                 415
Ser His Ala Ser Leu Ile Thr Ala Ala Asn Ala Lys Leu Gly Thr Pro
            420                 425                 430
Tyr Asn

<210> SEQ ID NO 99
<211> LENGTH: 433
<212> TYPE: PRT
<213> ORGANISM: Thermomucor sp.

<400> SEQUENCE: 99

Trp Ile Gln Glu Gln Leu Ala Ile Ser Trp Asn Thr Met Leu Thr Ser
1                   5                   10                  15
Val Asn Pro Val Gly Ala Val Thr Gly Phe Ile Ala Ala Ser Leu Ser
                20                  25                  30
Thr Ala Asn Pro Asp Tyr Tyr Tyr Cys Trp Thr Arg Asp Ala Ala Leu
```

-continued

```
              35                 40                 45
Val Ala Arg Val Met Thr Phe Met Tyr Asn Thr Thr Gln Ala Gly Asp
    50                 55                 60

Ser Gly Leu Leu Gly Ile Leu Gln Asp Tyr Val Ser Phe Gln Ile His
65                 70                 75                 80

Ala Met Gly Glu Ser Thr Val Cys Asn Cys Leu Gly Glu Pro Lys Phe
                85                 90                 95

Asn Pro Asp Gly Ser Ser Tyr Thr Gly Ala Trp Gly Arg Pro Gln Asn
                100                105                110

Asp Gly Pro Ala Glu Arg Ala Ser Thr Phe Ile Lys Ile Ala Asp Ser
                115                120                125

Tyr Leu Thr Gln Thr Gly Asp Val Ser Tyr Val Thr Asn Thr Leu Lys
    130                135                140

Pro Ala Ile Tyr Glu Asp Leu Asp Tyr Ile Val Asn Val Trp Gln Asn
145                150                155                160

Thr Cys Phe Asp Leu Trp Glu Glu Val Tyr Gly Met His Met Tyr Thr
                165                170                175

Leu Ala Val Met Arg Arg Gly Leu Leu Asp Gly Ala Asp Phe Ala Thr
                180                185                190

Arg Asn Gly Asp Thr Asp Lys Ala Ser Thr Tyr Thr Ser Thr Ala Thr
                195                200                205

Ser Ile Gln Thr Arg Leu Ala Thr Phe Trp Ser Asp Ser Asn Gly Tyr
    210                215                220

Ile Thr Val Thr Gln Asp Tyr Gln Ser Gly Val Ser Lys Ala Gly Leu
225                230                235                240

Asp Val Ser Thr Leu Ile Ala Ala Asn Val Ala Gly Met Asn Asp Gly
                245                250                255

Phe Phe Thr Pro Gly Ser Asp Glu Ile Leu Ala Thr Ala Val Lys Val
                260                265                270

Glu Ala Ala Phe Ala Asn Leu Tyr Gly Ile Asn Ile Asn Lys Ala Ser
                275                280                285

Tyr Leu Gly Asn Ala Ile Gly Arg Tyr Pro Glu Asp Thr Tyr Asn Gly
    290                295                300

Asn Gly Asn Ser Glu Gly Asn Pro Trp Phe Ile Ala Thr Ala Ala Phe
305                310                315                320

Ala Glu Leu Tyr Tyr Arg Ala Ile Met Glu Trp Gln Leu Arg Gly Ser
                325                330                335

Ser Ile Thr Val Asn Ser Val Asn Gln Gly Phe Phe Thr Lys Phe Asp
                340                345                350

Pro Ser Ala Thr Ala Gly Thr Thr Tyr Thr Pro Gly Thr Asp Ala Phe
                355                360                365

Asn Ser Leu Ile Asp Asn Val Ala Leu Ala Ala Asp Gln Phe Phe Ser
    370                375                380

Thr Ile His Leu His Arg Ala Thr Asn Gly Ser Met Ser Glu Gln Tyr
385                390                395                400

Asn Arg Asp Thr Gly Phe Met Gln Gly Ala Arg Asp Leu Thr Trp Ser
                405                410                415

His Ala Ala Phe Ile Thr Ala Ala Lys Ala Lys Gln Gly Thr Pro Ser
                420                425                430

Phe
```

<210> SEQ ID NO 100
<211> LENGTH: 432

```
<212> TYPE: PRT
<213> ORGANISM: Zychaea mexicana

<400> SEQUENCE: 100

Trp Ala Ser Ala Gln Leu Asp Ile Ser Trp Pro Asn Leu Met Met Asn
1               5                   10                  15

Val Asn Pro Ser Gly Ala Val Thr Gly Ser Ile Val Ala Ser Leu Ser
            20                  25                  30

Thr Ser Asn Pro Asp Tyr Phe Tyr Ile Trp Thr Arg Asp Ala Ala Met
        35                  40                  45

Val Ala Arg Val Met Val Tyr Met Tyr Asn Thr Thr Glu Ala Gly Asp
    50                  55                  60

Thr Asn Leu Leu Asn Ala Leu Thr Asp Tyr Val Thr Phe Ser Ile Ser
65                  70                  75                  80

Ser Met Asn Val Asp Thr Val Cys Asp Cys Leu Gly Glu Pro Lys Phe
                85                  90                  95

Asn Val Asp Gly Ser Gly Tyr Thr Gly Ala Trp Gly Arg Pro Gln Asn
            100                 105                 110

Asp Gly Pro Ala Glu Arg Ala Ser Thr Met Ile Leu Ile Ala Asp Ser
        115                 120                 125

Tyr Ile Ala Gln Gly Gly Asp Val Ser Tyr Val Thr Asp Thr Leu Lys
    130                 135                 140

Pro Ala Ile Tyr Thr Asp Leu Asp Tyr Val Val Asp Thr Trp Ser Asn
145                 150                 155                 160

Val Cys Phe Asp Leu Trp Glu Glu Val Asn Gly Ile His Met Tyr Thr
            165                 170                 175

Leu Ser Val Met Arg Lys Ala Leu Leu Asp Gly Ala Asn Phe Ala Thr
            180                 185                 190

Arg Asn Gly Asp Thr Ser Arg Val Ser Gly Tyr Glu Ser Thr Ala Ser
            195                 200                 205

Ser Ile Lys Thr Arg Leu Glu Ser Phe Trp Ser Ser Ser Asn Asn Tyr
    210                 215                 220

Ile Thr Val Thr Gln Ser Phe Ser Gly Gly Val Ser Lys Ala Gly Leu
225                 230                 235                 240

Asp Val Ser Thr Leu Ile Ala Ala Asn Leu Ala Ser Met Asn Asp Gly
            245                 250                 255

Phe Tyr Thr Pro Gly Ser Asp Glu Ile Leu Ala Thr Ala Val Ala Ile
            260                 265                 270

Glu Asn Ser Phe Ile Ser Glu Tyr Thr Leu Asn Gln Asn Arg Pro Ser
        275                 280                 285

Trp Leu Ser Thr Ala Ile Gly Arg Tyr Pro Glu Asp Ser Tyr Asp Gly
    290                 295                 300

Tyr Gly Asn Ser Gln Gly Asn Pro Trp Phe Ile Ala Thr Ala Thr Tyr
305                 310                 315                 320

Ala Glu Leu Tyr Tyr Arg Ala Ile Leu Glu Trp Gln Gln Ala Ser
            325                 330                 335

Ile Ser Val Asn Ser Val Asn Leu Gly Phe Phe Ser Lys Phe Asp Ser
            340                 345                 350

Asp Ala Ser Val Gly Thr Val Tyr Thr Pro Gly Thr Glu Asp Phe Ala
        355                 360                 365

Asn Met Val Ser Asn Val Ala Phe Ala Ala Asp Glu Phe Leu Ala Thr
    370                 375                 380

Ile Glu Asn His Ser Ala Val Asn Gly Ser Leu Ser Glu Gln Tyr Asn
385                 390                 395                 400
```

Arg Asp Thr Gly Ile Met Gln Gly Ala Arg Asp Leu Thr Trp Ser His
                405                 410                 415

Ala Ala Phe Ile Thr Ala Ala Lys Ala Lys Gln Gly Ala Pro Ile His
                420                 425                 430

<210> SEQ ID NO 101
<211> LENGTH: 609
<212> TYPE: PRT
<213> ORGANISM: Mucor ambiguus

<400> SEQUENCE: 101

Met Lys Phe Ser Ser Leu Leu Lys Lys Pro Leu Leu Leu Ile Ala Gly
1                   5                   10                  15

Ile Leu Ala Ala Thr Val Val Ala Glu Thr Val Pro Thr Thr Ala Glu
                20                  25                  30

Val Lys Val Lys Ser Phe Thr Tyr Asp Gly Ser Thr Phe Ala Gly Gln
            35                  40                  45

Ile Tyr Ile Lys Asn Ile Ala Tyr Thr Lys Thr Val Thr Val Ile Tyr
    50                  55                  60

Ser Asp Gly Ser Asn Asn Trp Asn Asn Asn Gly Asn Thr Ile Ala Ala
65                  70                  75                  80

Ser Tyr Ser Ala Ala Ile Ser Gly Ser Asn Tyr Glu Tyr Trp Thr Phe
                85                  90                  95

Ser Ala Pro Val Ser Ser Ile Lys Gln Phe Tyr Val Lys Tyr Val Val
            100                 105                 110

Ser Gly Thr Thr Tyr Tyr Asp Asn Asn Ser Ser Gly Asn Tyr Gln Val
            115                 120                 125

Ser Thr Thr Thr Thr Thr Thr Thr Ala Pro Thr Thr Thr Thr Ser Gly
    130                 135                 140

Gly Ser Ser Thr Thr Thr Gly Gly Ser Thr Thr Thr Ala Thr Ser Val
145                 150                 155                 160

Pro Thr Ala Val Pro Ser Gly Phe Pro Thr Gly Asn Ser Thr Ile Ser
                165                 170                 175

Ser Trp Ile Asp Gly Gln Thr Ser Val Ser Arg Tyr Ala Met Leu Arg
                180                 185                 190

Asn Ile Asn Pro Ala Gly Thr Val Thr Gly Phe Ile Ala Ala Ser Met
            195                 200                 205

Ser Thr Ser Gly Pro Asp Tyr Phe Tyr Ala Trp Thr Arg Asp Ser Ala
    210                 215                 220

Leu Thr Ser His Val Val Ala Tyr Asp Tyr Asn Thr Thr Leu Ala Gly
225                 230                 235                 240

Asn Ser Thr Ile Leu Gly Leu Leu Lys Asn Tyr Val Thr Phe Ser Leu
                245                 250                 255

Asn Ser Gln Thr Thr Ser Thr Val Cys Asn Cys Leu Gly Glu Pro Lys
                260                 265                 270

Phe Asn Lys Asp Gly Ser Ser Tyr Thr Gly Ala Trp Gly Arg Pro Gln
            275                 280                 285

Asn Asp Gly Pro Ala Ser Arg Ala Asp Thr Phe Ile Leu Ile Ala Asp
    290                 295                 300

Ser Ile Leu Lys Gln Thr Gly Asp Ala Thr Tyr Val Thr Gly Thr Leu
305                 310                 315                 320

Ala Pro Ala Ile Tyr Lys Asp Leu Asp Tyr Val Val Ser Thr Trp Ser
                325                 330                 335

Asn Gly Cys Phe Asp Leu Trp Glu Glu Val Asn Gly Val His Phe Tyr

-continued

```
                  340                 345                 350
Thr Leu Met Val Met Arg Arg Gly Leu Val Lys Gly Ala Ser Phe Ala
        355                 360                 365

Ser Arg Asn Gly Asp Ser Thr Arg Ala Asn Thr Tyr Thr Asn Thr Ala
        370                 375                 380

Ala Ser Ile Lys Thr Lys Ile Asp Ser Phe Trp Asn Ser Asn Gly Gln
385                 390                 395                 400

Tyr Val Ser Val Ser Gln Ser Val Thr Gly Gly Val Ser Lys Ala Gly
                405                 410                 415

Tyr Asp Ala Ser Val Leu Ile Ala Ser Asn Leu Gly Ser Leu Gln Asp
                420                 425                 430

Gly Phe Tyr Thr Pro Gly Ser Asp Lys Met Leu Ala Thr Ala Val Ala
            435                 440                 445

Ile Glu Ser Lys Phe Ala Ser Leu Tyr Ser Ile Asn Gln Asn Leu Asn
        450                 455                 460

Gly Tyr Leu Gly Asn Ala Ile Gly Arg Tyr Pro Glu Asp Thr Tyr Asn
465                 470                 475                 480

Gly Asn Gly Asn Ser Gln Gly Asn Pro Trp Phe Ile Cys Thr Asn Ala
                485                 490                 495

Phe Ala Glu Leu Tyr Tyr Arg Ala Ile Lys Glu Trp Phe Asn Asn Gly
                500                 505                 510

Gly Val Thr Val Thr Ser Ile Ser Leu Asn Phe Phe Lys Lys Phe Asp
            515                 520                 525

Ser Ser Ala Ala Val Gly Thr Lys Tyr Thr Val Gly Thr Ser Ala Phe
        530                 535                 540

Asn Ser Leu Val Gln Asn Val Ala Val Ala Ala Asp Ala Phe Phe Ser
545                 550                 555                 560

Thr Ile Lys Phe His Ala Ala Thr Asn Gly Ser Met Ser Glu Gln Tyr
                565                 570                 575

Gly Arg Thr Asp Gly Leu Met Thr Gly Ala Arg Asp Leu Thr Trp Ser
            580                 585                 590

His Ala Ser Leu Ile Ser Ala Ser Tyr Ala Lys Ala Gly Ser Pro Ala
        595                 600                 605

Ala

<210> SEQ ID NO 102
<211> LENGTH: 605
<212> TYPE: PRT
<213> ORGANISM: Rhizopus microsporus

<400> SEQUENCE: 102

Met Lys Leu Met Asn Pro Ser Ile Lys Ala Cys Val Phe Phe Ile Leu
1               5                   10                  15

Ser Tyr Leu Ser Leu Leu Val Ser Ser Ala Ala Val Pro Thr Ser Ala
                20                  25                  30

Ala Val Gln Val Glu Ser Tyr Lys Tyr Asp Gly Thr Thr Phe Ser Gly
            35                  40                  45

Arg Ile Phe Val Lys Asn Ile Ala Tyr Ser Lys Val Val Thr Val Ile
        50                  55                  60

Tyr Ser Asp Gly Ser Asp Asn Trp Asn Asn Asn Asn Asn Lys Ile Ser
65                  70                  75                  80

Ala Ala Tyr Ser Glu Ala Ile Ser Gly Ser Asn Tyr Glu Tyr Trp Thr
                85                  90                  95

Phe Ser Ala Lys Val Ser Gly Ile Lys Gln Phe Tyr Val Lys Tyr Glu
```

```
                100                 105                 110
Val Ser Gly Ser Thr Tyr Tyr Asp Asn Asn Gly Thr Lys Asn Tyr Gln
        115                 120                 125

Val Gln Ala Thr Ser Ala Thr Ser Thr Thr Ala Thr Ala Thr Thr Thr
    130                 135                 140

Thr Thr Thr Ser Thr Pro Ala Thr Ser Thr Gly Pro Ala Asn Asn Ala
145                 150                 155                 160

Pro Val Ser Phe Pro Thr Gly Asn Ser Thr Ile Ser Ser Trp Ile Lys
            165                 170                 175

Lys Gln Glu Glu Ile Ser Arg Phe Ala Met Leu Arg Asn Ile Asn Pro
            180                 185                 190

Pro Gly Ser Ala Thr Gly Phe Ile Ala Ala Ser Leu Ser Thr Ala Gly
        195                 200                 205

Pro Asp Tyr Tyr Tyr Ser Trp Thr Arg Asp Ser Ala Leu Thr Ala Asn
    210                 215                 220

Val Ile Ala Tyr Glu Tyr Asn Thr Thr Phe Thr Gly Asn Thr Thr Leu
225                 230                 235                 240

Leu Lys Tyr Leu Lys Asp Tyr Val Thr Phe Ser Val Lys Ser Gln Ser
            245                 250                 255

Val Ser Thr Val Cys Asn Cys Leu Gly Glu Pro Lys Phe Asn Ala Asp
        260                 265                 270

Gly Ser Ser Tyr Thr Gly Pro Trp Gly Arg Pro Gln Asn Asp Gly Pro
        275                 280                 285

Ala Glu Arg Ala Val Thr Phe Met Leu Ile Ala Asp Ser Tyr Leu Thr
    290                 295                 300

Gln Thr Lys Asp Ala Ser Tyr Val Thr Gly Thr Leu Lys Pro Ala Ile
305                 310                 315                 320

Phe Lys Asp Leu Asp Tyr Val Val Ser Val Trp Ser Asn Gly Cys Tyr
            325                 330                 335

Asp Leu Trp Glu Glu Val Asn Gly Val His Phe Tyr Thr Leu Met Val
            340                 345                 350

Met Arg Lys Gly Leu Ile Leu Gly Ala Asp Phe Ala Ala Arg Asn Gly
            355                 360                 365

Asp Ser Ser Arg Ala Ser Thr Tyr Lys Lys Thr Ala Ser Thr Met Glu
    370                 375                 380

Ser Lys Ile Ser Ser Phe Trp Ser Asp Ser Asn Asn Tyr Ile Gln Val
385                 390                 395                 400

Ser Gln Ser Val Thr Ala Gly Val Ser Lys Lys Gly Leu Asp Val Ser
            405                 410                 415

Thr Leu Leu Ala Ala Asn Ile Gly Ser Leu Pro Asp Gly Phe Phe Thr
            420                 425                 430

Pro Gly Ser Glu Lys Ile Leu Ala Thr Ala Val Ala Leu Glu Asn Ala
        435                 440                 445

Phe Ala Ser Leu Tyr Pro Ile Asn Ser Asn Leu Pro Ser Tyr Leu Gly
    450                 455                 460

Asn Ser Ile Gly Arg Tyr Pro Glu Asp Thr Tyr Asn Gly Asn Gly Asn
465                 470                 475                 480

Ser Gln Gly Asn Pro Trp Phe Leu Ala Val Asn Ala Tyr Ala Glu Leu
            485                 490                 495

Tyr Tyr Arg Ala Ile Ser Glu Trp Ile Ser Asn Gly Lys Val Thr Val
            500                 505                 510

Ser Asn Ile Ser Leu Pro Phe Phe Lys Lys Phe Asp Pro Ser Ala Thr
            515                 520                 525
```

-continued

```
Ser Gly Lys Thr Tyr Thr Ala Gly Thr Ser Asp Phe Asp Asn Leu Ala
    530             535             540

Gln Asn Ile Ala Leu Gly Ala Asp Arg Phe Leu Ser Thr Val Lys Phe
545             550             555             560

His Ala Tyr Thr Asn Gly Ser Leu Ser Glu Glu Tyr Asp Arg Ser Thr
            565             570             575

Gly Met Ser Thr Gly Ala Arg Asp Leu Thr Trp Ser His Ala Ser Leu
        580             585             590

Ile Thr Ala Ala Tyr Ala Lys Ala Gly Ser Pro Ala Ala
        595             600             605

<210> SEQ ID NO 103
<211> LENGTH: 605
<212> TYPE: PRT
<213> ORGANISM: Rhizopus azygosporus

<400> SEQUENCE: 103

Met Lys Leu Met Asn Pro Ser Met Lys Ala Cys Val Phe Phe Ile Leu
1               5               10              15

Ser Tyr Phe Ser Leu Leu Val Ser Ser Ala Ala Val Pro Thr Ser Ala
            20              25              30

Ala Val Gln Val Glu Ser Tyr Asn Tyr Asp Gly Thr Thr Phe Ser Gly
        35              40              45

Arg Ile Phe Val Lys Asn Ile Ala Tyr Ser Lys Val Val Thr Val Ile
    50              55              60

His Ser Asp Gly Ser Asp Asn Trp Asn Asn Asn Asn Lys Val Ser
65              70              75              80

Ala Ala Tyr Ser Glu Ala Ile Ser Gly Ser Asn Tyr Glu Tyr Trp Thr
            85              90              95

Phe Ser Ala Lys Leu Ser Gly Ile Lys Gln Phe Tyr Val Lys Tyr Glu
            100             105             110

Val Ser Gly Ser Thr Tyr Tyr Asp Asn Asn Gly Thr Lys Asn Tyr Gln
        115             120             125

Val Gln Ala Thr Ser Ala Thr Ser Thr Ala Thr Ala Thr Thr Thr
    130             135             140

Thr Ala Thr Gly Thr Thr Thr Thr Ser Thr Gly Pro Thr Ser Thr Ala
145             150             155             160

Ser Val Ser Phe Pro Thr Gly Asn Ser Thr Ile Ser Ser Trp Ile Lys
            165             170             175

Asn Gln Glu Glu Ile Ser Arg Phe Ala Met Leu Arg Asn Ile Asn Pro
            180             185             190

Pro Gly Ser Ala Thr Gly Phe Ile Ala Ala Ser Leu Ser Thr Ala Gly
        195             200             205

Pro Asp Tyr Tyr Tyr Ser Trp Thr Arg Asp Ser Ala Leu Thr Ala Asn
    210             215             220

Val Ile Ala Tyr Glu Tyr Asn Thr Thr Phe Thr Gly Asn Thr Thr Leu
225             230             235             240

Leu Lys Tyr Leu Lys Asp Tyr Val Thr Phe Ser Val Lys Ser Gln Ser
            245             250             255

Val Ser Thr Val Cys Asn Cys Leu Gly Glu Pro Lys Phe Asn Ala Asp
        260             265             270

Gly Ser Ser Phe Thr Gly Pro Trp Gly Arg Pro Gln Asn Asp Gly Pro
        275             280             285

Ala Glu Arg Ala Val Thr Phe Met Leu Ile Ala Asp Ser Tyr Leu Thr
```

```
            290               295               300

Gln Thr Lys Asp Ala Ser Tyr Val Thr Gly Thr Leu Lys Pro Ala Ile
305               310               315               320

Phe Lys Asp Leu Asp Tyr Val Val Ser Val Trp Ser Asn Gly Cys Tyr
                325               330               335

Asp Leu Trp Glu Glu Val Asn Gly Val His Phe Tyr Thr Leu Met Val
                340               345               350

Met Arg Lys Gly Leu Ile Leu Gly Ala Asp Phe Ala Ala Arg Asn Gly
            355               360               365

Asp Ser Ser Arg Ala Ser Thr Tyr Lys Lys Thr Ala Ser Thr Met Glu
        370               375               380

Ser Lys Ile Ser Ser Phe Trp Ser Asp Ser Asn Asn Tyr Ile Gln Val
385               390               395               400

Ser Gln Ser Val Thr Ala Gly Val Ser Lys Lys Gly Leu Asp Val Ser
                405               410               415

Thr Leu Leu Ala Ala Asn Ile Gly Ser Leu Pro Asp Gly Phe Phe Thr
                420               425               430

Pro Gly Ser Glu Lys Ile Leu Ala Thr Ala Val Ala Leu Glu Asn Ala
            435               440               445

Phe Ala Ser Leu Tyr Pro Ile Asn Ser Asn Leu Pro Ser Tyr Leu Gly
        450               455               460

Asn Ser Ile Gly Arg Tyr Pro Glu Asp Thr Tyr Asn Gly Asn Gly Asn
465               470               475               480

Ser Gln Gly Asn Pro Trp Phe Leu Ala Val Asn Ala Tyr Ala Glu Leu
                485               490               495

Tyr Tyr Arg Ala Ile Lys Glu Trp Ile Ser Asn Gly Lys Val Thr Val
            500               505               510

Ser Asn Ile Ser Leu Pro Phe Phe Lys Lys Phe Asp Ser Ser Ala Thr
            515               520               525

Ser Gly Lys Thr Tyr Thr Ala Gly Thr Ser Asp Phe Asn Asn Leu Ala
        530               535               540

Gln Asn Ile Ala Leu Gly Ala Asp Arg Phe Leu Ser Thr Val Lys Phe
545               550               555               560

His Ala Tyr Thr Asn Gly Ser Leu Ser Glu Glu Tyr Asp Arg Ser Thr
                565               570               575

Gly Met Ser Thr Gly Ala Arg Asp Leu Thr Trp Ser His Ala Ser Leu
            580               585               590

Ile Thr Ala Ala Tyr Ala Lys Ala Gly Ser Pro Ala Ala
            595               600               605
```

<210> SEQ ID NO 104
<211> LENGTH: 468
<212> TYPE: PRT
<213> ORGANISM: Saksenaea vasiformis

<400> SEQUENCE: 104

```
Met Pro Ser Trp Lys Thr Leu Phe Leu Leu Leu Gly Pro Ile Ala Thr
1               5                10                15

Ala Ala Ala Ala Pro Val Asp Lys Gln Ser Leu Pro Thr Gly Asn Ser
                20                25                30

Thr Ile Ser Ser Trp Val Ser Lys Gln Glu Asp Ile Ser Phe Ser Glu
            35                40                45

Met Leu Arg Asn Val Asn Pro Glu Gly Thr Ala Lys Gly Phe Val Ala
        50                55                60
```

```
Ala Ser Leu Ser Thr Ala Gly Pro Asp Tyr Phe Tyr Thr Trp Thr Arg
65                  70                  75                  80

Asp Ala Ala Leu Val Ser Arg Val Ile Ala Tyr Lys Tyr Asn Thr Thr
                85                  90                  95

Asn Ala Gly Asp Ser Lys Ile His Gly Val Leu Asp Asp Tyr Val Asn
            100                 105                 110

Phe Gln Ile Asn Thr Gln Ser Glu Pro Thr Pro Cys Asn Cys Leu Gly
        115                 120                 125

Glu Pro Lys Phe Asn Pro Asp Gly Ser Ser Phe Thr Gly Pro Trp Gly
    130                 135                 140

Arg Pro Gln Asn Asp Gly Pro Ala Glu Arg Ala Ser Ser Phe Met Leu
145                 150                 155                 160

Ile Ala Asp Ser Phe Leu Ser Gln Thr Lys Asn Ala Ser Tyr Phe Thr
                165                 170                 175

Asn Thr Leu Lys Pro Ala Ile Tyr Lys Asp Leu Asp Tyr Val Val Asp
            180                 185                 190

Thr Trp Ser Asn Pro Cys Phe Asp Leu Trp Glu Glu Val Asn Gly Ile
            195                 200                 205

His Phe Tyr Thr Leu Met Val Met Arg Arg Ser Leu Leu Asp Gly Ala
    210                 215                 220

Asn Phe Ala Thr Arg Asn Gly Asp Asn Ser Lys Ala Ser Thr Tyr Ser
225                 230                 235                 240

Gly Val Ala Ala Lys Ile Gln Ala Arg Leu Asn Ser Phe Trp Asp Ala
                245                 250                 255

Gly Lys Asn Tyr Ile Thr Val Thr Gln Asp Tyr Lys Asn Gly Val Glu
            260                 265                 270

Lys Pro Ser Gly Leu Asp Val Ser Thr Leu Ile Ala Ala Asn Val Ala
            275                 280                 285

Gly Met Gly Asp Gly Phe Tyr Thr Pro Gly Ser Glu Arg Ile Leu Ala
    290                 295                 300

Thr Ala Leu Ala Phe Glu Lys Ser Met Ala Ser Leu Tyr Pro Leu Asn
305                 310                 315                 320

Asn Asn Leu Pro Ser His Leu Gly Asn Ala Ile Gly Arg Tyr Pro Glu
            325                 330                 335

Asp Thr Tyr Asn Gly Asn Gly Asn Ser Gln Gly Asn Pro Trp Phe Leu
            340                 345                 350

Ala Thr Thr Ala Phe Thr Glu Leu Tyr Tyr Arg Ala Ile Leu Glu Trp
        355                 360                 365

Lys Asn Thr Gly Val Thr Val Thr Pro Ile Ser Lys Asp Phe Phe Val
    370                 375                 380

Arg Phe Asp Ser Ser Ala Ala Pro Gly Lys Lys Tyr Asn Pro Gly Ser
385                 390                 395                 400

Gln Glu Phe Ala Thr Leu Thr Gln Ser Ile Ala Ala Ala Asp Arg
                405                 410                 415

Phe Met Ser Thr Val Gln Tyr His Gln Asn Pro Asn Gly Ser Leu Ser
            420                 425                 430

Glu Glu Phe Asp Arg Ser Ser Gly Tyr Met Thr Gly Ala Arg Asp Leu
        435                 440                 445

Thr Trp Ser His Ala Ala Phe Ile Thr Ala Ala Gln Ala Arg Ala Gly
    450                 455                 460

Ser Pro Ser Phe
465
```

-continued

```
<210> SEQ ID NO 105
<211> LENGTH: 640
<212> TYPE: PRT
<213> ORGANISM: Aspergillus niger

<400> SEQUENCE: 105

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
                20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380
```

-continued

```
Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
                420                 425                 430

Gln Leu Ser Ala Arg Asp Leu Thr Trp Ser Tyr Ala Ala Leu Leu Thr
            435                 440                 445

Ala Asn Asn Arg Arg Asn Ser Val Val Pro Ala Ser Trp Gly Glu Thr
            450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
                500                 505                 510

Ser Thr Ser Lys Thr Thr Ala Thr Ala Ser Lys Thr Ser Thr Ser Thr
            515                 520                 525

Ser Ser Thr Ser Cys Thr Thr Pro Thr Ala Val Ala Val Thr Phe Asp
            530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
                580                 585                 590

Leu Pro Ala Gly Glu Ser Phe Glu Tyr Lys Phe Ile Arg Ile Glu Ser
            595                 600                 605

Asp Asp Ser Val Glu Trp Glu Ser Asp Pro Asn Arg Glu Tyr Thr Val
            610                 615                 620

Pro Gln Ala Cys Gly Thr Ser Thr Ala Thr Val Thr Asp Thr Trp Arg
625                 630                 635                 640

<210> SEQ ID NO 106
<211> LENGTH: 631
<212> TYPE: PRT
<213> ORGANISM: Aspergillus fumigatus

<400> SEQUENCE: 106

Met Pro Arg Leu Ser Tyr Ala Leu Cys Ala Leu Ser Leu Gly His Ala
1               5                   10                  15

Ala Ile Ala Ala Pro Gln Leu Ser Ala Arg Ala Thr Gly Ser Leu Asp
                20                  25                  30

Ser Trp Leu Gly Thr Glu Thr Thr Val Ala Leu Asn Gly Ile Leu Ala
            35                  40                  45

Asn Ile Gly Ala Asp Gly Ala Tyr Ala Lys Ser Ala Lys Pro Gly Ile
        50                  55                  60

Ile Ile Ala Ser Pro Ser Thr Ser Glu Pro Asp Tyr Tyr Tyr Thr Trp
65                  70                  75                  80

Thr Arg Asp Ala Ala Leu Val Thr Lys Val Leu Val Asp Leu Phe Arg
                85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Asn Pro Ser Gly Gly Leu Ala Ser
            115                 120                 125
```

-continued

```
Gly Gly Leu Ala Glu Pro Lys Tyr Asn Val Asp Met Thr Ala Phe Thr
    130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
        195                 200                 205

Asn Ser Met Ser Phe Phe Thr Val Ala Val Gln His Arg Ala Leu Val
    210                 215                 220

Glu Gly Ser Thr Phe Ala Lys Arg Val Gly Ala Ser Cys Ser Trp Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ala Asn Thr Val Leu Ala Ser Ile His Thr Phe Asp Pro Glu Ala Gly
        275                 280                 285

Cys Asp Asp Thr Thr Phe Gln Pro Cys Ser Pro Arg Ala Leu Ala Asn
    290                 295                 300

His Lys Val Tyr Thr Asp Ser Phe Arg Ser Val Tyr Ala Ile Asn Ser
305                 310                 315                 320

Gly Ile Pro Gln Gly Ala Ala Val Ser Ala Gly Arg Tyr Pro Glu Asp
                325                 330                 335

Val Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Lys Lys Ile Gly Ser Ile
        355                 360                 365

Ser Ile Thr Ser Thr Ser Leu Ala Phe Phe Lys Asp Ile Tyr Ser Ser
    370                 375                 380

Ala Ala Val Gly Thr Tyr Ala Ser Ser Thr Ser Thr Phe Thr Asp Ile
385                 390                 395                 400

Ile Asn Ala Val Lys Thr Tyr Ala Asp Gly Tyr Val Ser Ile Val Gln
                405                 410                 415

Ala His Ala Met Asn Asn Gly Ser Leu Ser Glu Gln Phe Asp Lys Ser
            420                 425                 430

Ser Gly Leu Ser Leu Ser Ala Arg Asp Leu Thr Trp Ser Tyr Ala Ala
        435                 440                 445

Phe Leu Thr Ala Asn Met Arg Arg Asn Gly Val Val Pro Ala Pro Trp
    450                 455                 460

Gly Ala Ala Ser Ala Asn Ser Val Pro Ser Ser Cys Ser Met Gly Ser
465                 470                 475                 480

Ala Thr Gly Thr Tyr Ser Thr Ala Thr Ala Thr Ser Trp Pro Ser Thr
                485                 490                 495

Leu Thr Ser Gly Ser Pro Gly Ser Thr Thr Thr Val Gly Thr Thr Thr
            500                 505                 510

Ser Thr Thr Ser Gly Thr Ala Ala Glu Thr Ala Cys Ala Thr Pro Thr
        515                 520                 525

Ala Val Ala Val Thr Phe Asn Glu Ile Ala Thr Thr Thr Tyr Gly Glu
    530                 535                 540
```

-continued

```
Asn Val Tyr Ile Val Gly Ser Ile Ser Glu Leu Gly Asn Trp Asp Thr
545                 550                 555                 560

Ser Lys Ala Val Ala Leu Ser Ala Ser Lys Tyr Thr Ser Ser Asn Asn
                565                 570                 575

Leu Trp Tyr Val Ser Val Thr Leu Pro Ala Gly Thr Thr Phe Glu Tyr
                580                 585                 590

Lys Tyr Ile Arg Lys Glu Ser Asp Gly Ser Ile Val Trp Glu Ser Asp
                595                 600                 605

Pro Asn Arg Ser Tyr Thr Val Pro Ala Ala Cys Gly Val Ser Thr Ala
        610                 615                 620

Thr Glu Asn Asp Thr Trp Gln
625                 630

<210> SEQ ID NO 107
<211> LENGTH: 567
<212> TYPE: PRT
<213> ORGANISM: Fibroporia radiculosa

<400> SEQUENCE: 107

Met Leu Phe Leu Leu Ala Ala Leu Gly Leu Ala Cys Ser Ala Ala Ala
1               5                   10                  15

Gln Ser Thr Ser Val Ser Ala Tyr Ile Ala Ser Glu Ser Pro Val Ala
                20                  25                  30

Lys Ala Gly Val Leu Ala Asn Ile Gly Thr Glu Gly Ser Leu Ser Ser
        35                  40                  45

Gly Ala Tyr Ser Gly Val Val Ile Ala Ser Pro Ser Thr Val Asn Pro
    50                  55                  60

Asp Tyr Leu Tyr Thr Trp Val Arg Asp Ser Ser Leu Thr Phe Gln Ala
65                  70                  75                  80

Leu Ile Asp Gln Tyr Val Tyr Gly Glu Asp Pro Thr Leu Arg Ser Leu
                85                  90                  95

Ile Asp Glu Phe Ile Thr Ala Glu Ser Ile Leu Gln Gln Thr Thr Asn
                100                 105                 110

Pro Ser Gly Thr Val Ser Thr Gly Gly Leu Gly Glu Pro Lys Phe Asn
        115                 120                 125

Ile Asn Glu Thr Ala Phe Thr Gly Pro Trp Gly Arg Pro Gln Arg Asp
    130                 135                 140

Gly Pro Ala Leu Arg Ser Thr Ala Ile Ile Thr Tyr Ala Thr Tyr Leu
145                 150                 155                 160

Trp Asn Ser Gly Asn Thr Ser Tyr Val Ser Asp Ser Leu Trp Pro Ile
                165                 170                 175

Ile Glu Leu Asp Leu Asn Tyr Ile Ala Thr Tyr Trp Asn Phe Ser Thr
                180                 185                 190

Phe Asp Leu Trp Glu Glu Ile Asp Ser Ser Ser Phe Trp Thr Thr Ala
        195                 200                 205

Val Gln His Arg Ala Leu Arg Gln Gly Ile Thr Phe Ala Asn Leu Ile
    210                 215                 220

Gly Gln Thr Ser Pro Val Ser Asn Tyr Glu Thr Gln Ala Gly Asp Ile
225                 230                 235                 240

Leu Cys Phe Leu Gln Thr Tyr Trp Asn Pro Thr Gly Asn Tyr Met Thr
                245                 250                 255

Ala Asn Thr Gly Gly Gly Arg Ser Gly Lys Asp Ser Asn Thr Val Leu
        260                 265                 270

Ala Ser Val His Thr Phe Asp Pro Asp Ala Gly Cys Asp Ser Thr Thr
    275                 280                 285
```

```
Phe Gln Pro Cys Ser Asp Lys Ala Leu Ser Asn Leu Lys Val Tyr Val
    290                 295                 300

Asp Ser Phe Arg Ser Leu Tyr Ala Ile Asn Asp Gly Ile Ala Ser Asp
305                 310                 315                 320

Ala Ala Val Ala Thr Gly Arg Tyr Pro Glu Asp Val Tyr Tyr Gly Gly
                325                 330                 335

Asn Pro Trp Tyr Leu Cys Thr Phe Ala Val Ala Glu Gln Leu Tyr Asp
                340                 345                 350

Ala Leu Ile Val Trp Ser Ser Gln Gly Tyr Leu Glu Ile Thr Asp Leu
            355                 360                 365

Ser Leu Ala Phe Phe Gln Gln Phe Asp Ser Asp Val Gly Thr Gly Thr
    370                 375                 380

Tyr Asp Ser Gly Ser Ser Thr Tyr Ser Thr Leu Thr Ser Ala Ile Arg
385                 390                 395                 400

Thr Phe Ala Asp Gly Phe Val Leu Thr Asn Ala Lys Tyr Thr Pro Thr
                405                 410                 415

Asn Gly Ser Leu Ser Glu Glu Tyr Thr Ser Ala Asp Gly Thr Pro Ile
                420                 425                 430

Ser Ala Tyr Asp Leu Thr Trp Ser Tyr Ala Ser Ala Leu Thr Val Phe
            435                 440                 445

Ala Ala Glu Ala Gly Thr Thr Tyr Gly Ser Trp Gly Ala Ala Gly Leu
    450                 455                 460

Thr Val Pro Ser Thr Cys Thr Ser Gly Val Ala Val Thr Phe Glu Val
465                 470                 475                 480

Asp Tyr Asp Thr Glu Tyr Gly Glu Asn Val Tyr Ile Thr Gly Ser Val
                485                 490                 495

Asn Ala Leu Glu Asn Trp Ser Ala Thr Asn Ala Leu Ile Met Ser Ala
                500                 505                 510

Ala Asp Tyr Pro Thr Trp Ser Ile Thr Val Tyr Leu Pro Pro Ser Thr
            515                 520                 525

Thr Ile Gln Tyr Lys Tyr Leu Thr Gln Tyr Asn Gly Glu Val Thr Trp
    530                 535                 540

Glu Asp Asp Pro Asn Asn Glu Ile Thr Thr Pro Ala Ser Gly Ser Met
545                 550                 555                 560

Thr Gln Val Asp Ser Trp His
                565

<210> SEQ ID NO 108
<211> LENGTH: 582
<212> TYPE: PRT
<213> ORGANISM: Fusarium verticillioides

<400> SEQUENCE: 108

Met Phe Thr Gln Ile Leu Tyr Gly Leu Thr Ala Leu Ser Ala Leu Gln
1               5                   10                  15

Gly Gln Val Thr Ala Ser Pro Gly Gly Ser Ser Leu Asp Arg Phe Ile
            20                  25                  30

Ser Lys Glu Ala Asp Ile Ser Ile Lys Gly Val Leu Ala Asn Ile Gly
        35                  40                  45

Ala Asp Gly Lys Arg Ala Gln Gly Ala Ala Pro Gly Ala Val Val Ala
    50                  55                  60

Ser Pro Ser Arg Thr Asp Pro Asp Tyr Trp Tyr Thr Trp Thr Arg Asp
65                  70                  75                  80

Ser Ala Leu Thr Tyr Lys Val Leu Val Glu Arg Phe Ile His Gly Asp
```

-continued

```
                 85                  90                  95
Lys Ser Leu Gln Arg Lys Ile Asp Glu Tyr Val Ser Ala Gln Ala Lys
            100                 105                 110
Leu Gln Gly Val Thr Asn Pro Ser Gly Gly Pro Glu Ser Gly Gly Leu
            115                 120                 125
Gly Glu Pro Lys Phe His Val Asn Leu Thr Ala Phe Thr Gly Ser Trp
        130                 135                 140
Gly Arg Pro Gln Arg Asp Gly Pro Pro Leu Arg Ala Thr Ala Leu Thr
    145                 150                 155                 160
Leu Tyr Ala Asn Trp Leu Val Ser His Gly Asp Arg Ser Lys Ala Val
                165                 170                 175
Asn Lys Val Trp Pro Val Ile Glu Lys Asp Leu Ala Tyr Thr Val Lys
                180                 185                 190
Phe Trp Asn Arg Thr Gly Tyr Asp Leu Trp Glu Glu Val Asn Gly Ser
            195                 200                 205
Ser Phe Phe Thr Leu Ser Ala Ser His Arg Ala Leu Val Glu Gly Ala
        210                 215                 220
Ala Leu Ala Lys Lys Leu Gly Lys Ser Cys Ser Asp Cys Ala Thr Asn
    225                 230                 235                 240
Ala Pro Arg Val Leu Cys Phe Met Gln Ser Phe Trp Thr Gly Ser Tyr
                245                 250                 255
Ile Asp Ser Asn Ile Asn Val Asn Asp Gly Arg Lys Gly Leu Asp Ala
            260                 265                 270
Asn Ser Ile Leu Ser Ser Ile His Thr Phe Asp Pro Ser Ser Lys Cys
            275                 280                 285
Thr Asp Ser Thr Phe Gln Pro Cys Ser Ser Arg Ala Leu Ala Asn His
        290                 295                 300
Lys Glu Val Val Asp Ser Phe Arg Ser Ile Tyr Gly Val Asn Lys Asn
    305                 310                 315                 320
Arg Gly Lys Gly Lys Ala Ala Ala Val Gly Arg Tyr Ser Glu Asp Val
                325                 330                 335
Tyr Tyr Asp Gly Asn Pro Trp Tyr Leu Ala Thr Leu Ala Ala Ala Glu
            340                 345                 350
Gln Leu Tyr Ala Ala Val Tyr Gln Trp Asn Lys Ile Gly Ser Ile Thr
            355                 360                 365
Val Asp Ser Val Ser Leu Pro Phe Phe Ser Asp Leu Val Pro Lys Val
        370                 375                 380
Ser Lys Gly Thr Tyr Arg Lys Asn Ser Lys Thr Tyr Lys Ala Ile Ile
    385                 390                 395                 400
Lys Ala Val Thr Ser Tyr Ala Asp Gly Phe Val Ala Val Gln Thr
            405                 410                 415
Tyr Thr Pro Lys Asp Gly Ser Leu Ala Glu Gln Phe Asp Lys Ser Thr
            420                 425                 430
Gly Thr Pro Lys Ser Ala Val His Leu Thr Trp Ser Tyr Ala Ser Phe
        435                 440                 445
Val Gly Ala Ala Glu Arg Arg Thr Gly Val Val Pro Pro Ala Trp Gly
    450                 455                 460
Glu Ser Asn Ala Asn Lys Val Pro Ala Val Cys Glu Ala Ala Pro Ala
465                 470                 475                 480
Cys Asp Thr Thr Ile Thr Phe Asn Val Lys Asn Val Asp Val Thr Ser
            485                 490                 495
Asp Gln Lys Val Tyr Ile Val Gly Gly Ile Thr Gln Leu Ser Asn Trp
            500                 505                 510
```

```
Ala Pro Ala Asp Gly Ile Ala Leu Glu Glu Ser Thr Ser Thr Lys Gly
        515             520             525

Leu Trp Thr Val Lys Val Lys Ile Pro Ser Asp Thr Ser Phe Glu Tyr
        530             535             540

Lys Tyr Ile Lys Lys Thr Ser Asp Gly Thr Val Thr Trp Glu Ser Asp
545             550             555             560

Pro Asn Asn Ser Ala Ala Thr Gly Ser Lys Cys Gly Ser Ser Ser Thr
                565             570             575

Ile Asn Asp Glu Trp Arg
                580
```

```
<210> SEQ ID NO 109
<211> LENGTH: 576
<212> TYPE: PRT
<213> ORGANISM: Gloeophyllum trabeum

<400> SEQUENCE: 109

Met Tyr Arg Phe Leu Val Cys Ala Leu Gly Leu Leu Gly Thr Val Leu
1               5               10              15

Ala Gln Ser Val Asp Ser Tyr Val Gly Ser Glu Gly Pro Ile Ala Lys
                20              25              30

Ala Gly Val Leu Ala Asn Ile Gly Pro Asn Gly Ser Lys Ala Ser Gly
        35              40              45

Ala Ala Ala Gly Val Val Val Ala Ser Pro Ser Lys Ser Asp Pro Asp
        50              55              60

Tyr Trp Tyr Thr Trp Thr Arg Asp Ser Ser Leu Val Phe Lys Ser Leu
65              70              75              80

Ile Asp Gln Tyr Thr Thr Gly Ile Asp Ser Thr Ser Ser Leu Arg Ser
                85              90              95

Leu Ile Asp Ser Phe Val Ile Ala Glu Ala Asn Ile Gln Gln Val Ser
                100             105             110

Asn Pro Ser Gly Thr Leu Thr Thr Gly Gly Leu Gly Glu Pro Lys Phe
        115             120             125

Asn Val Asp Glu Thr Ala Phe Thr Gly Ala Trp Gly Arg Pro Gln Arg
        130             135             140

Asp Gly Pro Ala Leu Arg Ala Thr Ala Leu Ile Thr Tyr Gly Asn Trp
145             150             155             160

Leu Leu Ser Asn Gly Asn Thr Thr Trp Val Thr Ser Thr Leu Trp Pro
                165             170             175

Ile Ile Gln Asn Asp Leu Asn Tyr Val Val Gln Tyr Trp Asn Gln Thr
                180             185             190

Thr Phe Asp Leu Trp Glu Glu Val Asn Ser Ser Ser Phe Phe Thr Thr
        195             200             205

Ala Val Gln His Arg Ala Leu Arg Glu Gly Ala Ala Phe Ala Thr Lys
        210             215             220

Ile Gly Gln Thr Ser Ser Val Ser Ser Tyr Thr Thr Gln Ala Ala Asn
225             230             235             240

Leu Leu Cys Phe Leu Gln Ser Tyr Trp Asn Pro Thr Ser Gly Tyr Ile
                245             250             255

Thr Ala Asn Thr Gly Gly Gly Arg Ser Gly Lys Asp Ala Asn Thr Leu
                260             265             270

Leu Ala Ser Ile His Thr Tyr Asp Pro Ser Ala Gly Cys Asp Ala Thr
        275             280             285

Thr Phe Gln Pro Cys Ser Asp Lys Ala Leu Ser Asn Leu Lys Val Tyr
```

-continued

```
               290                295                300

Val Asp Ser Phe Arg Ser Val Tyr Ser Ile Asn Ser Gly Ile Ala Ser
305                310                315                320

Asn Ala Ala Val Ala Thr Gly Arg Tyr Pro Glu Asp Ser Tyr Gln Gly
                 325                330                335

Gly Asn Pro Trp Tyr Leu Thr Thr Phe Ala Val Ala Glu Gln Leu Tyr
                 340                345                350

Asp Ala Leu Asn Val Trp Ala Ala Gln Gly Ser Leu Asn Val Thr Ser
                 355                360                365

Ile Ser Leu Pro Phe Phe Gln Gln Phe Ser Ser Ser Val Thr Ala Gly
                 370                375                380

Thr Tyr Ala Ser Ser Ser Thr Thr Tyr Thr Thr Leu Thr Ser Ala Ile
385                390                395                400

Lys Ser Phe Ala Asp Gly Phe Val Ala Ile Asn Ala Gln Tyr Thr Pro
                 405                410                415

Ser Asn Gly Gly Leu Ala Glu Gln Phe Ser Arg Ser Asn Gly Ala Pro
                 420                425                430

Val Ser Ala Val Asp Leu Thr Trp Ser Tyr Ala Ser Ala Leu Thr Ala
                 435                440                445

Phe Glu Ala Arg Asn Asn Thr Gln Phe Ala Gly Trp Gly Ala Val Gly
      450                455                460

Leu Thr Val Pro Thr Ser Cys Ser Ser Asn Ser Gly Gly Gly Gly Gly
465                470                475                480

Ser Thr Val Ala Val Thr Phe Asn Val Asn Ala Gln Thr Val Trp Gly
                 485                490                495

Glu Asn Ile Tyr Ile Thr Gly Ser Val Asp Ala Leu Ser Asn Trp Ser
                 500                505                510

Pro Asp Asn Ala Leu Leu Leu Ser Ser Ala Asn Tyr Pro Thr Trp Ser
                 515                520                525

Ile Thr Val Asn Leu Pro Ala Ser Thr Ala Ile Gln Tyr Lys Tyr Ile
      530                535                540

Arg Lys Asn Asn Gly Ala Val Thr Trp Glu Ser Asp Pro Asn Asn Ser
545                550                555                560

Ile Thr Thr Pro Ala Ser Gly Ser Val Thr Glu Asn Asp Thr Trp Arg
                 565                570                575

<210> SEQ ID NO 110
<211> LENGTH: 616
<212> TYPE: PRT
<213> ORGANISM: Penicillium oxalicum

<400> SEQUENCE: 110

Met Arg Leu Thr Leu Leu Ser Gly Val Ala Gly Val Leu Cys Ala Gly
1               5                  10                 15

Gln Leu Thr Ala Ala Arg Pro Asp Pro Lys Gly Gly Asn Leu Thr Pro
                 20                25                 30

Phe Ile His Lys Glu Gly Glu Arg Ser Leu Gln Gly Ile Leu Asp Asn
                 35                40                 45

Leu Gly Gly Arg Gly Lys Lys Thr Pro Gly Thr Ala Ala Gly Leu Phe
      50                55                 60

Ile Ala Ser Pro Asn Thr Glu Asn Pro Asn Tyr Tyr Tyr Thr Trp Thr
65                70                 75                 80

Arg Asp Ser Ala Leu Thr Ala Lys Cys Leu Ile Asp Leu Phe Glu Asp
                 85                90                 95
```

-continued

```
Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
            115                 120                 125

Ser Gly Thr Leu Lys Asp Gly Ser Gly Leu Gly Glu Pro Lys Phe Glu
            130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
                180                 185                 190

Ile Ala Asn Asp Leu Ala Tyr Val Gly Gln Tyr Trp Asn Asn Thr Gly
                195                 200                 205

Phe Asp Leu Trp Glu Glu Val Asp Gly Ser Ser Phe Phe Thr Ile Ala
            210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
            275                 280                 285

Ile His Thr Phe Asp Pro Glu Ala Ala Cys Asp Asp Ala Thr Phe Gln
            290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
                340                 345                 350

Trp Tyr Leu Ala Thr Leu Gly Ala Ser Glu Leu Leu Tyr Asp Ala Leu
            355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
                420                 425                 430

Ser Leu Ala Glu Gln Tyr Asp Arg Asn Thr Ala Ala Pro Leu Ser Ala
            435                 440                 445

Asn Asp Leu Thr Trp Ser Phe Ala Ser Phe Leu Thr Ala Thr Gln Arg
            450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
```

-continued

```
             515                520                525

Asn Val Phe Met Ser Gly Asn Ile Thr Ala Leu Gly Asn Trp Asp Ala
    530                535                540

Lys Lys Gly Phe Pro Leu Thr Ala Asn Leu Tyr Thr Gln Asp Gln Asn
545                550                555                560

Leu Trp Phe Ala Ser Val Glu Phe Ile Pro Ala Gly Thr Pro Phe Glu
                565                570                575

Tyr Lys Tyr Tyr Lys Val Glu Pro Asn Gly Asp Ile Thr Trp Glu Lys
                580                585                590

Gly Pro Asn Arg Val Phe Val Ala Pro Thr Gly Cys Pro Val Gln Pro
                595                600                605

His Ser Asn Asp Val Trp Gln Phe
    610                615

<210> SEQ ID NO 111
<211> LENGTH: 632
<212> TYPE: PRT
<213> ORGANISM: Trichoderma reesei

<400> SEQUENCE: 111

Met His Val Leu Ser Thr Ala Val Leu Leu Gly Ser Val Ala Val Gln
1               5                10                15

Lys Val Leu Gly Arg Pro Gly Ser Ser Gly Leu Ser Asp Val Thr Lys
                20                25                30

Arg Ser Val Asp Asp Phe Ile Ser Thr Glu Thr Pro Ile Ala Leu Asn
        35                40                45

Asn Leu Leu Cys Asn Val Gly Pro Asp Gly Cys Arg Ala Phe Gly Thr
    50                55                60

Ser Ala Gly Ala Val Ile Ala Ser Pro Ser Thr Ile Asp Pro Asp Tyr
65                70                75                80

Tyr Tyr Met Trp Thr Arg Asp Ser Ala Leu Val Phe Lys Asn Leu Ile
                85                90                95

Asp Arg Phe Thr Glu Thr Tyr Asp Ala Gly Leu Gln Arg Arg Ile Glu
                100                105                110

Gln Tyr Ile Thr Ala Gln Val Thr Leu Gln Gly Leu Ser Asn Pro Ser
        115                120                125

Gly Ser Leu Ala Asp Gly Ser Gly Leu Gly Glu Pro Lys Phe Glu Leu
    130                135                140

Thr Leu Lys Pro Phe Thr Gly Asn Trp Gly Arg Pro Gln Arg Asp Gly
145                150                155                160

Pro Ala Leu Arg Ala Ile Ala Leu Ile Gly Tyr Ser Lys Trp Leu Ile
                165                170                175

Asn Asn Asn Tyr Gln Ser Thr Val Ser Asn Val Ile Trp Pro Ile Val
                180                185                190

Arg Asn Asp Leu Asn Tyr Val Ala Gln Tyr Trp Asn Gln Thr Gly Phe
                195                200                205

Asp Leu Trp Glu Glu Val Asn Gly Ser Ser Phe Phe Thr Val Ala Asn
        210                215                220

Gln His Arg Ala Leu Val Glu Gly Ala Thr Leu Ala Ala Thr Leu Gly
225                230                235                240

Gln Ser Gly Ser Ala Tyr Ser Ser Val Ala Pro Gln Val Leu Cys Phe
                245                250                255

Leu Gln Arg Phe Trp Val Ser Ser Gly Gly Tyr Val Asp Ser Asn Ile
        260                265                270
```

```
Asn Thr Asn Glu Gly Arg Thr Gly Lys Asp Val Asn Ser Val Leu Thr
    275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
                340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
                420                 425                 430

Gly Ser Leu Ala Glu Gln Phe Asp Arg Asn Ser Gly Thr Pro Leu Ser
        435                 440                 445

Ala Leu His Leu Thr Trp Ser Tyr Ala Ser Phe Leu Thr Ala Thr Ala
    450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
                515                 520                 525

Ser Val Ala Val Thr Phe His Glu Leu Val Ser Thr Gln Phe Gly Gln
    530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
        580                 585                 590

Lys Tyr Ile Asn Val Gly Gln Asp Gly Ser Val Thr Trp Glu Ser Asp
    595                 600                 605

Pro Asn His Thr Tyr Thr Val Pro Ala Val Ala Cys Val Thr Gln Val
    610                 615                 620

Val Lys Glu Asp Thr Trp Gln Ser
625                 630
```

```
<210> SEQ ID NO 112
<211> LENGTH: 569
<212> TYPE: PRT
<213> ORGANISM: Wolfiporia cocos

<400> SEQUENCE: 112

Met Arg Leu Ser Leu Ala Ser Val Phe Ala Leu Ala Gly Gly Ala Leu
1               5                   10                  15
```

-continued

```
Ala Gln Thr Thr Ser Val Thr Ser Tyr Ile Ala Ser Glu Ser Pro Ile
            20                      25                  30

Ala Lys Ala Gly Val Leu Ala Asn Ile Gly Ala Asp Gly Ser Leu Ser
            35                      40                  45

Ser Gly Ala Tyr Ser Gly Ile Val Ile Ala Ser Pro Ser Thr Val Asn
        50                      55                  60

Pro Asn Tyr Leu Tyr Thr Trp Thr Arg Asp Ser Ser Leu Thr Phe Met
65                      70                  75                  80

Glu Leu Ile Asn Gln Tyr Ile Tyr Gly Glu Asp Asp Thr Leu Arg Thr
                85                      90                  95

Leu Ile Asp Glu Phe Val Ser Ala Glu Ala Thr Leu Gln Gln Val Thr
                100                     105                 110

Asn Pro Ser Gly Thr Val Ser Thr Gly Gly Leu Gly Glu Pro Lys Phe
            115                     120                 125

Asn Ile Asn Glu Thr Ala Phe Thr Gly Pro Trp Gly Arg Pro Gln Arg
        130                     135                 140

Asp Gly Pro Ala Leu Arg Ala Thr Ala Ile Met Ala Tyr Ala Thr Tyr
145                     150                 155                 160

Leu Tyr Glu Asn Gly Asn Thr Ser Tyr Val Thr Asp Thr Leu Trp Pro
                165                     170                 175

Ile Ile Glu Leu Asp Leu Gly Tyr Val Ala Glu Tyr Trp Asn Glu Ser
                180                     185                 190

Thr Phe Asp Leu Trp Glu Glu Ile Asp Ser Ser Ser Phe Phe Thr Thr
            195                     200                 205

Ala Val Gln His Arg Ala Leu Arg Ala Gly Val Thr Phe Ala Asn Leu
        210                     215                 220

Ile Gly Glu Thr Ser Asp Val Ser Asn Tyr Gln Glu Asn Ala Asp Asp
225                     230                 235                 240

Leu Leu Cys Phe Leu Gln Ser Tyr Trp Asn Pro Thr Gly Ser Tyr Val
            245                     250                 255

Thr Ala Asn Thr Gly Gly Gly Arg Ser Gly Lys Asp Ala Asn Thr Leu
            260                     265                 270

Leu Ala Ser Ile His Thr Phe Asp Pro Asp Ala Gly Cys Asn Ala Thr
            275                     280                 285

Thr Phe Gln Pro Cys Ser Asp Lys Ala Leu Ser Asn His Lys Val Tyr
        290                     295                 300

Val Asp Ser Phe Arg Ser Leu Tyr Ala Ile Asn Asp Asp Ile Ser Ser
305                     310                 315                 320

Asp Ala Ala Val Ala Thr Gly Arg Tyr Pro Glu Asp Val Tyr Tyr Asn
            325                     330                 335

Gly Asn Pro Trp Tyr Leu Cys Thr Leu Ala Ala Ala Glu Gln Leu Tyr
            340                     345                 350

Asp Ser Leu Ile Val Trp Lys Ala Gln Gly Tyr Ile Glu Val Thr Ser
            355                     360                 365

Leu Ser Leu Ala Phe Phe Gln Gln Phe Asp Ala Ser Val Ser Ala Gly
        370                     375                 380

Thr Tyr Asp Ser Ser Ser Asp Thr Tyr Thr Thr Leu Leu Asp Ala Val
385                     390                 395                 400

Gln Thr Tyr Ala Asp Gly Phe Val Leu Met Val Ala Gln Tyr Thr Pro
                405                     410                 415

Ala Asn Gly Ser Leu Ser Glu Gln Tyr Ala Lys Ala Asp Gly Ser Pro
            420                     425                 430
```

-continued

```
Thr Ser Ala Tyr Asp Leu Thr Trp Ser Phe Ala Ala Ala Leu Thr Ala
        435                 440                 445

Phe Ala Ala Arg Asp Gly Lys Thr Tyr Gly Ser Trp Gly Ala Ala Asp
    450                 455                 460

Leu Ser Ser Thr Cys Ser Gly Ser Thr Asp Thr Val Ala Val Thr Phe
465                 470                 475                 480

Glu Val Gln Tyr Asp Thr Gln Tyr Gly Glu Asn Leu Tyr Ile Thr Gly
                485                 490                 495

Ser Val Ser Gln Leu Glu Asp Trp Ser Ala Asp Asp Ala Leu Ile Met
            500                 505                 510

Ser Ser Ala Asp Tyr Pro Thr Trp Ser Ile Thr Val Asp Leu Pro Pro
        515                 520                 525

Ser Thr Leu Ile Gln Tyr Lys Tyr Leu Thr Lys Tyr Asn Gly Asp Val
    530                 535                 540

Thr Trp Glu Asp Asp Pro Asn Asn Glu Ile Thr Thr Pro Ala Ser Gly
545                 550                 555                 560

Ser Tyr Thr Gln Val Asp Ser Trp His
                565
```

```
<210> SEQ ID NO 113
<211> LENGTH: 8
<212> TYPE: PRT
<213> ORGANISM: Mucorales
<220> FEATURE:
<221> NAME/KEY: MISC_FEATURE
<222> LOCATION: (2)..(2)
<223> OTHER INFORMATION: N or S
<220> FEATURE:
<221> NAME/KEY: MISC_FEATURE
<222> LOCATION: (3)..(3)
<223> OTHER INFORMATION: T, S, or R
<220> FEATURE:
<221> NAME/KEY: MISC_FEATURE
<222> LOCATION: (5)..(6)
<223> OTHER INFORMATION: Any amino acid
<220> FEATURE:
<221> NAME/KEY: MISC_FEATURE
<222> LOCATION: (7)..(7)
<223> OTHER INFORMATION: G or N
<220> FEATURE:
<221> NAME/KEY: MISC_FEATURE
<222> LOCATION: (8)..(8)
<223> OTHER INFORMATION: D, N, or S

<400> SEQUENCE: 113

Tyr Xaa Xaa Thr Xaa Xaa Xaa Xaa
1               5
```

```
<210> SEQ ID NO 114
<211> LENGTH: 8
<212> TYPE: PRT
<213> ORGANISM: Mucorales
<220> FEATURE:
<221> NAME/KEY: MISC_FEATURE
<222> LOCATION: (5)..(5)
<223> OTHER INFORMATION: Any amino acid

<400> SEQUENCE: 114

Tyr Asn Thr Thr Xaa Ala Gly Asp
1               5
```

```
<210> SEQ ID NO 115
<211> LENGTH: 9
<212> TYPE: PRT
<213> ORGANISM: Mucorales
<220> FEATURE:
```

```
<221> NAME/KEY: MISC_FEATURE
<222> LOCATION: (1)..(1)
<223> OTHER INFORMATION: S or A
<220> FEATURE:
<221> NAME/KEY: MISC_FEATURE
<222> LOCATION: (2)..(2)
<223> OTHER INFORMATION: T, N, or V
<220> FEATURE:
<221> NAME/KEY: MISC_FEATURE
<222> LOCATION: (3)..(4)
<223> OTHER INFORMATION: L or I
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: A or G

<400> SEQUENCE: 115

Xaa Xaa Xaa Xaa Ala Ala Asn Xaa Xaa
1               5

<210> SEQ ID NO 116
<211> LENGTH: 9
<212> TYPE: PRT
<213> ORGANISM: Mucorales
<220> FEATURE:
<221> NAME/KEY: MISC_FEATURE
<222> LOCATION: (8)..(8)
<223> OTHER INFORMATION: Any amino acid

<400> SEQUENCE: 116

Ser Thr Leu Ile Ala Ala Asn Xaa Ala
1               5

<210> SEQ ID NO 117
<211> LENGTH: 7
<212> TYPE: PRT
<213> ORGANISM: Mucorales
<220> FEATURE:
<221> NAME/KEY: MISC_FEATURE
<222> LOCATION: (1)..(1)
<223> OTHER INFORMATION: N or D
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: Q, K, or E

<400> SEQUENCE: 117

Xaa Gly Xaa Gly Asn Xaa Xaa
1               5

<210> SEQ ID NO 118
<211> LENGTH: 7
<212> TYPE: PRT
<213> ORGANISM: Mucorales

<400> SEQUENCE: 118

Asn Gly Asn Gly Asn Ser Gln
1               5
```

```
<210> SEQ ID NO 119
<211> LENGTH: 468
<212> TYPE: PRT
<213> ORGANISM: Saksenaea oblongispora

<400> SEQUENCE: 119

Met Pro Ser Trp Lys Thr Leu Ile Phe Leu Leu Gly Pro Ile Thr Ala
1               5                   10                  15

Ala Leu Ala Ala Pro Val Asn Lys Gln Ser Phe Pro Thr Gly Asn Pro
                20                  25                  30

Asp Ile Ser Ser Trp Val Ser Lys Gln Glu Gly Ile Ser Phe Ser Glu
            35                  40                  45

Met Leu Arg Asn Val Asn Pro Pro Gly Thr Ala Lys Gly Phe Val Ala
        50                  55                  60

Ala Ser Leu Ser Thr Ala Gly Pro Asp Tyr Phe Tyr Thr Trp Thr Arg
65                  70                  75                  80

Asp Ala Ala Leu Val Ser Arg Val Ile Ala Tyr Lys Tyr Asn Thr Thr
                85                  90                  95

Asn Ala Gly Asp Asn Asn Ile His Gly Ala Leu Gln Asp Tyr Val Thr
            100                 105                 110

Phe Gln Ile Asn Thr Gln Thr Glu Ser Thr Pro Cys Asn Cys Leu Gly
        115                 120                 125

Glu Pro Lys Phe Asn Pro Asp Gly Ser Ser Phe Thr Gly Pro Trp Gly
        130                 135                 140

Arg Pro Gln Asn Asp Gly Pro Ala Glu Arg Ala Ser Ser Met Ile Leu
145                 150                 155                 160

Ile Ala Asp Ser Phe Leu Ala Gln Thr Lys Asp Thr Ala Tyr Val Thr
                165                 170                 175

Asn Thr Leu Lys Pro Ala Ile Tyr Lys Asp Leu Asp Tyr Val Val Asn
            180                 185                 190

Thr Trp Ser Asn Pro Cys Phe Asp Leu Trp Glu Glu Val Asn Gly Val
        195                 200                 205

His Phe Tyr Thr Leu Met Val Met Arg Arg Gly Leu Leu Asp Gly Ala
        210                 215                 220

Asp Phe Ala Thr Arg Asn Gly Asp Ala Ser Lys Ala Ser Ser Tyr Ser
225                 230                 235                 240

Asp Ala Ala Ser Lys Ile Lys Thr Arg Leu Asp Ser Phe Trp Val Ser
                245                 250                 255

Asp Lys Asn Tyr Ile Thr Val Thr Gln Asp Tyr Lys Glu Gly Val Lys
            260                 265                 270

Lys Asp Thr Gly Leu Asp Val Ser Thr Leu Ile Ala Ala Asn Val Ala
        275                 280                 285

Gly Lys Asp Asp Gly Phe Tyr Thr Pro Gly Ser Asp Lys Ile Leu Ala
        290                 295                 300

Thr Ala Val Ala Phe Glu Asn Ala Met Ala Lys Leu Tyr Pro Leu Asn
305                 310                 315                 320

Gln Asn Leu Asp Ser His Leu Gly Asn Ser Ile Gly Arg Tyr Pro Glu
                325                 330                 335

Asp Thr Tyr Asn Gly Asn Gly Asn Ser Gln Gly Asn Pro Trp Phe Leu
            340                 345                 350

Ala Thr Thr Ala Phe Thr Glu Leu Tyr Tyr Arg Ala Ile Leu Glu Trp
        355                 360                 365

Lys Asp Ser Gly Val Thr Val Thr Pro Val Ser Lys Asp Phe Phe Ala
        370                 375                 380
```

```
Lys Phe Asp Ser Asn Ala Val Ala Gly Lys Lys Tyr Ser Pro Asn Ser
385                 390                 395                 400

Glu Glu Phe Ala Thr Leu Thr Ala Asn Ile Ala Ala Ala Ala Asp Arg
                405                 410                 415

Phe Met Ser Thr Val Lys Tyr His Gln Asn Pro Asn Gly Ser Leu Ser
                420                 425                 430

Glu Gln Phe Asp Arg His Ser Gly Tyr Met Thr Gly Ala Arg Asp Leu
            435                 440                 445

Thr Trp Ser His Ala Ala Phe Ile Thr Ala Ala Gln Ala Arg Ala Gly
        450                 455                 460

Thr Pro Ser Phe
465
```

<210> SEQ ID NO 120
<211> LENGTH: 463
<212> TYPE: PRT
<213> ORGANISM: Apophysomyces ossiformis

<400> SEQUENCE: 120

```
Met Met Met Ser Trp Lys Ser Leu Leu Leu Leu Leu Gly Pro Ile Ala
1               5                   10                  15

Ala Ala Thr Ala Ala Ile Pro Thr Gly Asn Ser Ser Leu Asn Ala Trp
                20                  25                  30

Val Ser Ser Gln Glu Asp Ile Ser Phe Ser Val Met Leu Gly Asn Ile
            35                  40                  45

Asn Pro Pro Gly Thr Val Lys Gly Phe Val Ala Ala Ser Leu Ser Thr
        50                  55                  60

Ala Gly Pro Asp Tyr Phe Tyr Ser Trp Val Arg Asp Ser Ala Leu Val
65                  70                  75                  80

Ser Arg Val Val Thr His Lys Tyr Asn Thr Thr Glu Thr Gly Asn Ser
                85                  90                  95

Thr Val Ala Gly Phe Leu Glu Asp Tyr Val His Phe Gln Ile Asn Thr
                100                 105                 110

Gln Thr Glu Ser Thr Val Cys Asn Cys Leu Gly Glu Pro Lys Phe Asn
            115                 120                 125

Pro Asp Gly Ser Ser Tyr Thr Gly Pro Trp Gly Arg Pro Gln Asn Asp
        130                 135                 140

Gly Pro Ala Glu Arg Ala Ser Thr Met Ile Leu Ile Ala Asp Ser Phe
145                 150                 155                 160

Leu Thr Gln Thr Lys Asn Thr Ser Tyr Val Asp Asn Thr Leu Lys Pro
                165                 170                 175

Ala Ile Tyr Lys Asp Leu Asp Tyr Val Val Asn Thr Trp Ser Asn Pro
                180                 185                 190

Cys Phe Asp Leu Trp Glu Glu Val Asn Gly Ile His Phe Tyr Thr Leu
            195                 200                 205

Met Val Met Arg Arg Gly Leu Leu Asp Gly Ala Asn Phe Ala Thr Arg
        210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Asn Lys Asn Tyr Ile
                245                 250                 255

Ile Val Thr Gln Asp Tyr Gln Asn Gly Val Gln Lys Pro Ser Gly Leu
                260                 265                 270

Asp Ile Ser Thr Leu Ile Ala Ala Asn Val Ala Gly Met Asn Asp Gly
        275                 280                 285
```

```
Phe Tyr Thr Pro Gly Ser Asp Lys Met Leu Ala Thr Ala Val Ala Ile
    290             295             300

Glu Asn Ala Met Ala Asn Leu Tyr Pro Leu Asn Lys Asn Leu Pro Ser
305             310             315             320

Tyr Leu Gly Asn Ala Ile Gly Arg Tyr Pro Glu Asp Thr Tyr Asn Gly
            325             330             335

Asp Gly Asn Ser Gln Gly Asn Pro Trp Phe Leu Ala Thr Thr Ala Phe
            340             345             350

Ser Glu Leu Tyr Tyr Arg Ala Leu Leu Glu Trp Gln Glu Thr Gly Val
            355             360             365

Thr Val Thr Ser Ile Ser Lys Asp Phe Phe Ser Lys Phe Asp Pro Asn
    370             375             380

Ala Ser Ala Gly Lys Lys Tyr Ser Pro Gly Ser Asn Glu Phe Ala Ser
385             390             395             400

Leu Ala Gln Asn Ile Ala Ser Ala Ala Asp Arg Phe Leu Ser Thr Val
            405             410             415

Asn Tyr His Arg Asn Ser Asn Gly Ser Leu Ser Glu Glu Phe Asp Arg
            420             425             430

Asn Thr Gly Tyr Met Thr Gly Ala Arg Asp Leu Thr Trp Ser His Ala
            435             440             445

Ala Phe Ile Thr Ala Gly Leu Ala Arg Ala Gly Thr Pro Ser Phe
    450             455             460

<210> SEQ ID NO 121
<211> LENGTH: 462
<212> TYPE: PRT
<213> ORGANISM: Apophysomyces elegans

<400> SEQUENCE: 121

Met Met Met Ser Trp Lys Ser Leu Leu Leu Leu Gly Pro Ile Ala
1               5               10              15

Ala Ala Thr Ala Ala Ile Pro Thr Gly Asn Ser Ser Leu Asn Ala Trp
            20              25              30

Val Ser Ser Gln Glu Asp Ile Ser Phe Ser Val Met Leu Gly Asn Ile
            35              40              45

Asn Pro Pro Gly Thr Val Lys Gly Phe Val Ala Ala Ser Leu Ser Thr
    50              55              60

Ala Gly Pro Asp Tyr Phe Tyr Ser Trp Val Arg Asp Ser Ala Leu Val
65              70              75              80

Ser Arg Val Val Thr His Lys Tyr Asn Thr Thr Glu Thr Gly Asn Ser
            85              90              95

Thr Val Ala Gly Phe Leu Gln Asp Tyr Val His Phe Gln Ile Asn Thr
            100             105             110

Gln Thr Glu Ser Thr Val Cys Asn Cys Leu Gly Glu Pro Lys Phe Asn
    115             120             125

Pro Asp Gly Ser Ser Tyr Thr Gly Pro Trp Gly Arg Pro Gln Asn Asp
    130             135             140

Gly Pro Ala Glu Arg Ala Ser Thr Met Ile Leu Ile Ala Asp Ser Phe
145             150             155             160

Leu Thr Gln Thr Lys Asn Thr Ser Tyr Val Asp Asn Thr Leu Lys Pro
            165             170             175

Ala Ile Tyr Lys Asp Leu Asp Tyr Val Val Asn Thr Trp Ser Asn Pro
            180             185             190

Cys Phe Asp Leu Trp Glu Glu Val Asn Gly Ile His Phe Tyr Thr Leu
```

-continued

```
                195                    200                    205

Met Val Met Arg Arg Gly Leu Leu Asp Gly Ala Asn Phe Ala Thr Arg
    210                    215                    220

Asn Gly Asp Thr Ser Lys Ala Ser Ser Tyr Ser Ser Thr Ala Ser Gln
225                    230                    235                    240

Ile Gln Asn Lys Ile Asp Ser Phe Trp Ser Ser Ser Lys Asn Tyr Ile
                245                    250                    255

Met Val Thr Gln Asp Tyr Gln Asn Gly Ile Gln Lys Pro Ser Gly Leu
                260                    265                    270

Asp Ile Ser Thr Leu Ile Ala Ala Asn Val Ala Gly Met Asn Asp Gly
                275                    280                    285

Phe Tyr Thr Pro Gly Ser Asp Lys Met Leu Ala Thr Ala Val Ala Ile
    290                    295                    300

Glu Asn Ala Met Ala Asn Leu Tyr Pro Leu Asn Lys Asn Leu Pro Ser
305                    310                    315                    320

Tyr Leu Gly Asn Ala Ile Gly Arg Tyr Pro Glu Asp Thr Tyr Asn Gly
                325                    330                    335

Asp Gly Asn Ser Gln Gly Asn Pro Trp Phe Leu Ala Thr Thr Ala Phe
                340                    345                    350

Ser Glu Leu Tyr Tyr Arg Ala Leu Leu Glu Trp Gln Glu Thr Gly Val
                355                    360                    365

Thr Val Thr Ser Ile Ser Lys Asp Phe Phe Ser Lys Phe Asp Pro Asn
    370                    375                    380

Ala Ser Ala Gly Lys Lys Tyr Ser Pro Gly Ser Asp Glu Phe Asn Ser
385                    390                    395                    400

Leu Ala Gln Asn Ile Ala Ser Ala Ala Asp Arg Phe Leu Ser Thr Val
                405                    410                    415

Asn Tyr His Arg Asn Ser Asn Gly Ser Leu Ser Glu Glu Tyr Asp Arg
                420                    425                    430

Asn Ser Gly Tyr Met Thr Gly Ala Arg Asp Leu Thr Trp Ser His Ala
                435                    440                    445

Ala Phe Ile Thr Ala Gly Leu Ala Arg Ala Gly Thr Pro Ser
    450                    455                    460
```

```
<210> SEQ ID NO 122
<211> LENGTH: 463
<212> TYPE: PRT
<213> ORGANISM: Apophysomyces variabilis

<400> SEQUENCE: 122
```

```
Met Met Met Ser Trp Lys Ser Leu Leu Leu Leu Leu Gly Pro Ile Ala
1                5                    10                    15

Ala Ala Thr Ala Ala Ile Pro Thr Gly Asn Ser Ser Leu Asn Ala Trp
                20                    25                    30

Val Ser Ser Gln Glu Asp Ile Ser Phe Ser Val Met Leu Gly Asn Ile
                35                    40                    45

Asn Pro Pro Gly Thr Val Lys Gly Phe Val Ala Ala Ser Leu Ser Thr
    50                    55                    60

Ala Gly Pro Asp Tyr Phe Tyr Ser Trp Val Arg Asp Ser Ala Leu Val
65                    70                    75                    80

Ser Arg Val Val Thr His Lys Tyr Asn Thr Thr Glu Thr Gly Asn Ser
                85                    90                    95

Thr Val Ala Gly Phe Leu Gln Asp Tyr Val His Phe Gln Ile Asn Thr
                100                    105                    110
```

Gln Thr Glu Ser Thr Val Cys Asn Cys Leu Gly Glu Pro Lys Phe Asn
        115                 120                 125

Pro Asp Gly Ser Ser Tyr Thr Gly Pro Trp Gly Arg Pro Gln Asn Asp
        130                 135                 140

Gly Pro Ala Glu Arg Ala Ser Thr Met Ile Leu Ile Ala Asp Ser Phe
145                 150                 155                 160

Leu Ala Gln Thr Lys Asn Thr Ser Tyr Val Asp Asn Thr Leu Lys Pro
                165                 170                 175

Ala Ile Tyr Lys Asp Leu Asp Tyr Val Val Asn Thr Trp Ser Asn Pro
                180                 185                 190

Cys Phe Asp Leu Trp Glu Glu Val Asn Gly Ile His Phe Tyr Thr Leu
                195                 200                 205

Met Val Met Arg Arg Gly Leu Leu Asp Gly Ala Asn Phe Ala Thr Arg
        210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Ser Lys Asn Tyr Ile
                245                 250                 255

Met Val Thr Gln Asp Tyr Gln Asn Gly Val Gln Lys Pro Ser Gly Leu
                260                 265                 270

Asp Ile Ser Thr Leu Ile Ala Ala Asn Val Ala Gly Met Asn Asp Gly
        275                 280                 285

Phe Tyr Thr Pro Gly Ser Asp Lys Met Leu Ala Thr Ala Val Ala Ile
        290                 295                 300

Glu Asn Ala Met Ala Asn Leu Tyr Pro Leu Asn Lys Asn Leu Pro Ser
305                 310                 315                 320

Tyr Leu Gly Asn Ala Ile Gly Arg Tyr Pro Glu Asp Thr Tyr Asn Gly
                325                 330                 335

Asp Gly Asn Ser Gln Gly Asn Pro Trp Phe Leu Ala Thr Thr Ala Phe
                340                 345                 350

Ser Glu Leu Tyr Tyr Arg Ala Leu Leu Glu Trp Gln Glu Thr Gly Val
        355                 360                 365

Thr Val Thr Ser Ile Ser Lys Asp Phe Phe Ser Lys Phe Asp Pro Asn
        370                 375                 380

Ala Ser Ala Gly Lys Lys Tyr Ser Pro Gly Ser Asp Glu Phe Asn Ser
385                 390                 395                 400

Leu Ala Gln Asn Ile Ala Ser Ala Ala Asp Arg Phe Leu Ser Thr Val
                405                 410                 415

Asn Tyr His Arg Asn Ser Asn Gly Ser Leu Ser Glu Glu Tyr Asp Arg
                420                 425                 430

Asn Ser Gly Tyr Met Thr Gly Ala Arg Asp Leu Thr Trp Ser His Ala
        435                 440                 445

Ala Phe Ile Thr Ala Gly Leu Ala Arg Ala Gly Thr Pro Ser Phe
        450                 455                 460

<210> SEQ ID NO 123
<211> LENGTH: 463
<212> TYPE: PRT
<213> ORGANISM: Apophysomyces trapeziformis

<400> SEQUENCE: 123

Met Met Met Ser Trp Lys Ser Leu Leu Leu Leu Gly Pro Ile Ala
1               5                   10                  15

Ala Ala Thr Ala Ala Ile Pro Thr Gly Asn Ser Ser Leu Asn Ala Trp
        20                  25                  30

-continued

```
Val Ser Ser Gln Glu Asp Ile Ser Phe Ser Val Met Leu Gly Asn Ile
    35                  40              45

Asn Pro Pro Gly Thr Val Lys Gly Phe Val Ala Ala Ser Leu Ser Thr
    50              55              60

Ala Gly Pro Asp Tyr Phe Tyr Ser Trp Val Arg Asp Ser Ala Leu Val
65              70              75              80

Ser Arg Val Val Thr His Lys Tyr Asn Thr Thr Glu Thr Gly Asn Ser
            85              90              95

Thr Val Ala Gly Phe Leu Gln Asp Tyr Val His Phe Gln Ile Asn Thr
            100             105             110

Gln Thr Glu Ser Thr Val Cys Asn Cys Leu Gly Glu Pro Lys Phe Asn
            115             120             125

Pro Asp Gly Ser Ser Tyr Thr Gly Pro Trp Gly Arg Pro Gln Asn Asp
    130             135             140

Gly Pro Ala Glu Arg Ala Ser Thr Met Ile Leu Ile Ala Asp Ser Phe
145             150             155             160

Leu Thr Gln Thr Lys Asn Thr Ser Tyr Val Asp Asn Thr Leu Lys Pro
                165             170             175

Ala Ile Tyr Lys Asp Leu Asp Tyr Val Val Asn Thr Trp Ser Asn Pro
            180             185             190

Cys Phe Asp Leu Trp Glu Glu Val Asn Gly Ile His Phe Tyr Thr Leu
            195             200             205

Met Val Met Arg Arg Gly Leu Leu Asp Gly Ala Asn Phe Ala Thr Arg
    210             215             220

Asn Gly Asp Thr Ser Lys Ala Ser Ser Tyr Ser Ser Thr Ala Ser Gln
225             230             235             240

Ile Gln Asn Lys Ile Asp Ser Phe Trp Ser Ser Ser Lys Asn Tyr Ile
                245             250             255

Ile Val Thr Gln Asp Tyr Gln Asn Gly Val Gln Lys Pro Ser Gly Leu
            260             265             270

Asp Val Ser Thr Leu Ile Ala Ala Asn Val Ala Gly Met Asn Asp Gly
            275             280             285

Phe Tyr Thr Pro Gly Ser Asp Lys Met Leu Ala Thr Ala Val Ala Ile
    290             295             300

Glu Asn Ala Met Ala Asn Leu Tyr Pro Leu Asn Lys Asn Leu Pro Ser
305             310             315             320

Tyr Leu Gly Asn Ala Ile Gly Arg Tyr Pro Glu Asp Thr Tyr Asn Gly
            325             330             335

Asp Gly Asn Ser Gln Gly Asn Pro Trp Phe Leu Ala Thr Thr Ala Phe
            340             345             350

Ser Glu Leu Tyr Tyr Arg Ala Leu Leu Glu Trp Gln Glu Thr Gly Val
            355             360             365

Thr Val Thr Ser Ile Ser Lys Asp Phe Phe Ser Lys Phe Asp Pro Asn
    370             375             380

Ala Ser Ala Gly Lys Lys Tyr Ser Pro Gly Ser Asn Glu Tyr Ala Ser
385             390             395             400

Leu Ala Gln Asn Ile Ala Ser Ala Ala Asp Arg Phe Leu Ser Thr Val
            405             410             415

Asn Tyr His Arg Asn Pro Asn Gly Ser Leu Ser Glu Glu Tyr Asp Arg
            420             425             430

Asn Thr Gly Tyr Met Thr Gly Ala Arg Asp Leu Thr Trp Ser His Ala
            435             440             445
```

Ala Phe Ile Thr Ala Gly Leu Ala Arg Ala Gly Thr Pro Ser Phe
    450                 455                 460

<210> SEQ ID NO 124
<211> LENGTH: 1404
<212> TYPE: DNA
<213> ORGANISM: Artificial Sequence
<220> FEATURE:
<223> OTHER INFORMATION: codon modified

<400> SEQUENCE: 124
atgccttctt ggaagaccct gattttcctc ctgggcccta ttaccgccgc tctggctgct      60
cctgttaaca agcagtcttt ccctaccggc aaccccgaca tcagctcttg ggtttctaag     120
caggagggca ttagcttcag cgagatgctc cgaaacgtca accctcccgg caccgctaag     180
ggcttcgttg ctgctagcct cagcaccgcc ggccccgact acttctacac ctggaccccga     240 gacgccgctc tcgtctcccg cgtcatcgct tacaagtaca acaccaccaa cgctggcgac     300
aacaacattc acggcgctct gcaggactac gtcaccttcc agattaacac ccagaccgag     360
tccacccctt gcaactgcct gggcgagcct aagttcaacc ccgacggcag ctctttcacc     420
ggcccttggg ccgacctca gaacgacggc cctgctgagc gcgctagcag catgattctc     480
attgctgaca gcttcctcgc ccagaccaag gacaccgctt acgttaccaa caccctgaag     540
cctgccattt acaaggacct ggactacgtt gttaacacct ggtctaaccc ttgcttcgac     600
ctgtgggagg aggttaacgg cgtccacttc tacaccctca tggttatgcg acgaggcctc     660
ctcgacggcg ctgacttcgc tacccgaaac ggcgacgcc ctaaggctag ctcttactct     720
gacgctgcta gcaagatcaa gacccgactg gactctttct gggtcagcga caagaactac     780
attaccgtta cccaggacta caaggagggc gtcaagaagg acaccggcct cgacgttagc     840
accctcattg ctgccaacgt tgccggcaag gacgacggct tctacaccc cggcagcgac     900 aagattctgg ctaccgctgt tgccttcgag aacgccatgg ctaagctgta ccctctgaac     960
cagaacctcg acagccacct gggcaactct attggccgat accctgagga cacctacaac    1020
ggcaacggca actcccaggg caacccttgg ttcctcgcca ccaccgcttt caccgagctg    1080

tactaccgag ccatcttgga tggaaggac agcggcgtta ccgtcacccc cgtttccaag    1140
gacttcttcg ccaagttcga ctccaacgcc gttgccggca agaagtactc tcctaactct    1200
gaggagttcg ccaccctgac cgctaacatc gctgctgccg ctgaccgatt catgtctacc    1260
gttaagtacc accagaaccc taacggctct ctgtccgagc agttcgaccg ccacagcggc    1320

tacatgaccg cgcccgaga cctgacctgg tctcacgctg ctttcattac cgccgcccag    1380
gctcgcgctg gcacccctag cttc                                          1404

<210> SEQ ID NO 125
<211> LENGTH: 19
<212> TYPE: PRT
<213> ORGANISM: Artificial Sequence
<220> FEATURE:
<223> OTHER INFORMATION: signal peptide

<400> SEQUENCE: 125

Met Pro Ser Trp Lys Thr Leu Ile Phe Leu Leu Gly Pro Ile Thr Ala
1                 5                 10                  15

Ala Leu Ala

<210> SEQ ID NO 126
<211> LENGTH: 449

```
<212> TYPE: PRT
<213> ORGANISM: Saksenaea oblongispora

<400> SEQUENCE: 126

Ala Pro Val Asn Lys Gln Ser Phe Pro Thr Gly Asn Pro Asp Ile Ser
1               5                   10                  15

Ser Trp Val Ser Lys Gln Glu Gly Ile Ser Phe Ser Glu Met Leu Arg
                20                  25                  30

Asn Val Asn Pro Pro Gly Thr Ala Lys Gly Phe Val Ala Ala Ser Leu
            35                  40                  45

Ser Thr Ala Gly Pro Asp Tyr Phe Tyr Thr Trp Thr Arg Asp Ala Ala
        50                  55                  60

Leu Val Ser Arg Val Ile Ala Tyr Lys Tyr Asn Thr Thr Asn Ala Gly
65                  70                  75                  80

Asp Asn Asn Ile His Gly Ala Leu Gln Asp Tyr Val Thr Phe Gln Ile
                85                  90                  95

Asn Thr Gln Thr Glu Ser Thr Pro Cys Asn Cys Leu Gly Glu Pro Lys
            100                 105                 110

Phe Asn Pro Asp Gly Ser Ser Phe Thr Gly Pro Trp Gly Arg Pro Gln
            115                 120                 125

Asn Asp Gly Pro Ala Glu Arg Ala Ser Ser Met Ile Leu Ile Ala Asp
            130                 135                 140

Ser Phe Leu Ala Gln Thr Lys Asp Thr Ala Tyr Val Thr Asn Thr Leu
145                 150                 155                 160

Lys Pro Ala Ile Tyr Lys Asp Leu Asp Tyr Val Val Asn Thr Trp Ser
                165                 170                 175

Asn Pro Cys Phe Asp Leu Trp Glu Glu Val Asn Gly Val His Phe Tyr
                180                 185                 190

Thr Leu Met Val Met Arg Arg Gly Leu Leu Asp Gly Ala Asp Phe Ala
                195                 200                 205

Thr Arg Asn Gly Asp Ala Ser Lys Ala Ser Ser Tyr Ser Asp Ala Ala
            210                 215                 220

Ser Lys Ile Lys Thr Arg Leu Asp Ser Phe Trp Val Ser Asp Lys Asn
225                 230                 235                 240

Tyr Ile Thr Val Thr Gln Asp Tyr Lys Glu Gly Val Lys Lys Asp Thr
                245                 250                 255

Gly Leu Asp Val Ser Thr Leu Ile Ala Ala Asn Val Ala Gly Lys Asp
                260                 265                 270

Asp Gly Phe Tyr Thr Pro Gly Ser Asp Lys Ile Leu Ala Thr Ala Val
            275                 280                 285

Ala Phe Glu Asn Ala Met Ala Lys Leu Tyr Pro Leu Asn Gln Asn Leu
            290                 295                 300

Asp Ser His Leu Gly Asn Ser Ile Gly Arg Tyr Pro Glu Asp Thr Tyr
305                 310                 315                 320

Asn Gly Asn Gly Asn Ser Gln Gly Asn Pro Trp Phe Leu Ala Thr Thr
                325                 330                 335

Ala Phe Thr Glu Leu Tyr Tyr Arg Ala Ile Leu Glu Trp Lys Asp Ser
                340                 345                 350

Gly Val Thr Val Thr Pro Val Ser Lys Asp Phe Phe Ala Lys Phe Asp
                355                 360                 365

Ser Asn Ala Val Ala Gly Lys Lys Tyr Ser Pro Asn Ser Glu Glu Phe
        370                 375                 380

Ala Thr Leu Thr Ala Asn Ile Ala Ala Ala Ala Asp Arg Phe Met Ser
385                 390                 395                 400
```

-continued

Thr Val Lys Tyr His Gln Asn Pro Asn Gly Ser Leu Ser Glu Gln Phe
            405                 410                 415

Asp Arg His Ser Gly Tyr Met Thr Gly Ala Arg Asp Leu Thr Trp Ser
            420                 425                 430

His Ala Ala Phe Ile Thr Ala Ala Gln Ala Arg Ala Gly Thr Pro Ser
        435                 440                 445

Phe

<210> SEQ ID NO 127
<211> LENGTH: 1389
<212> TYPE: DNA
<213> ORGANISM: Artificial Sequence
<220> FEATURE:
<223> OTHER INFORMATION: codon modified

<400> SEQUENCE: 127
atgatgatgt cttggaagtc tctgctcctc ctgctgggcc ctatcgccgc tgctaccgct      60
gccatcccta ccggcaacag cagcctgaac gcttgggtta gctcccagga ggacatctct     120
ttctccgtca tgctgggcaa cattaaccct cccggcaccg tcaagggctt cgttgccgct     180
agcctgtcca ccgctggccc cgactacttc tactcttggg tccgagacag cgccctcgtt     240
tcccgcgtcg tcacccacaa gtacaacacc accgagaccg gcaactctac cgttgccggc     300
ttcttggagg actacgttca cttccagatt aacacccaga ccgagtctac cgtttgcaac     360
tgcctgggcg agcctaagtt caaccccgac ggcagctctt acaccggccc ttggggccgc     420
cctcagaacg acgccccgc tgagcgagct agcaccatga ttctgattgc cgactctttc     480
ctgacccaga ccaagaacac ctcttacgtt gacaacaccc tgaagcccgc catttacaag     540
gacctggact acgttgttaa cacctggtct aacccttgct tcgacctgtg ggaggaggtt     600
aacggcattc acttctacac cctcatggtt atgcgacgag gcctcctcga cggcgccaac     660
ttcgccaccc gaaacggcga cacctctaag gctagctctt acagcagcac cgctagccag     720
attcagaaca agattgactc cttctggagc tccaacaaga actacattat tgttacccag     780
gactaccaga acggcgtcca gaagcctagc ggcctcgaca tcagcaccct cattgctgcc     840
aacgtcgctg gcatgaacga cggcttctac acccccggct ctgacaagat gctcgccacc     900
gccgttgcta ttgagaacgc catggctaac ctgtaccccc tcaacaagaa cctgccttct     960
tacctgggca acgctattgg ccgataccct gaggacacct acaacggcga cggcaactcc    1020
cagggcaacc cttggttcct cgccaccacc gctttcagcg agctgtacta ccgagctctg    1080
ctggagtggc aggagaccgg cgttaccgtt accagcattt ctaaggactt cttcagcaag    1140 ttcgaccccta acgctagcgc tggcaagaag tactctcccg ctctaacga gttcgcttct    1200 ctggctcaga acattgctag cgctgctgac cgattcctgt ccaccgtcaa ctaccaccga    1260
aactccaacg gcagcctgtc tgaggagttc gaccgaaaca ccggctacat gaccggcgcc    1320
cgagacctga cctggtctca cgccgctttc attaccgctg cctcgctcg cgctggcacc    1380 cctagcttc                                                            1389

<210> SEQ ID NO 128
<211> LENGTH: 20
<212> TYPE: PRT
<213> ORGANISM: Artificial Sequence
<220> FEATURE:
<223> OTHER INFORMATION: signal peptide

<400> SEQUENCE: 128

```
Met Met Met Ser Trp Lys Ser Leu Leu Leu Leu Leu Gly Pro Ile Ala
1               5                   10                  15

Ala Ala Thr Ala
            20

<210> SEQ ID NO 129
<211> LENGTH: 443
<212> TYPE: PRT
<213> ORGANISM: Apophysomyces ossiformis

<400> SEQUENCE: 129

Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
            35                  40                  45

Tyr Phe Tyr Ser Trp Val Arg Asp Ser Ala Leu Val Ser Arg Val Val
        50                  55                  60

Thr His Lys Tyr Asn Thr Thr Glu Thr Gly Asn Ser Thr Val Ala Gly
65                  70                  75                  80

Phe Leu Glu Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
            115                 120                 125

Arg Ala Ser Thr Met Ile Leu Ile Ala Asp Ser Phe Leu Thr Gln Thr
        130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
                180                 185                 190

Arg Gly Leu Leu Asp Gly Ala Asn Phe Ala Thr Arg Asn Gly Asp Thr
            195                 200                 205

Ser Lys Ala Ser Ser Tyr Ser Ser Thr Ala Ser Gln Ile Gln Asn Lys
        210                 215                 220

Ile Asp Ser Phe Trp Ser Ser Asn Lys Asn Tyr Ile Ile Val Thr Gln
225                 230                 235                 240

Asp Tyr Gln Asn Gly Val Gln Lys Pro Ser Gly Leu Asp Ile Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
        290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
```

```
              340               345               350
Ile Ser Lys Asp Phe Phe Ser Lys Phe Asp Pro Asn Ala Ser Ala Gly
          355               360               365

Lys Lys Tyr Ser Pro Gly Ser Asn Glu Phe Ala Ser Leu Ala Gln Asn
      370               375               380

Ile Ala Ser Ala Ala Asp Arg Phe Leu Ser Thr Val Asn Tyr His Arg
385               390               395               400

Asn Ser Asn Gly Ser Leu Ser Glu Glu Phe Asp Arg Asn Thr Gly Tyr
              405               410               415

Met Thr Gly Ala Arg Asp Leu Thr Trp Ser His Ala Ala Phe Ile Thr
              420               425               430

Ala Gly Leu Ala Arg Ala Gly Thr Pro Ser Phe
          435               440
```

<210> SEQ ID NO 130
<211> LENGTH: 1386
<212> TYPE: DNA
<213> ORGANISM: Artificial Sequence
<220> FEATURE:
<223> OTHER INFORMATION: codon optimized

<400> SEQUENCE: 130

```
atgatgatgt cttggaagtc tctgctcctg ctcctgggcc ctattgctgc cgccaccgct     60
gccatcccta ccggcaactc tagcctcaac gcttgggtta gcagccagga ggacatttct    120
ttcagcgtca tgctgggcaa cattaaccct cccggcaccg tcaagggctt cgttgctgct    180
agcctgtcca ccgctggccc cgactacttc tactcttggg ttcgagacag cgctctcgtt    240
tctcgcgtcg ttacccacaa gtacaacacc accgagaccg gcaacagcac cgttgctggc    300
ttcctgcagg actacgttca cttccagatt aacacccaga ccgagtccac cgtttgcaac    360
tgcctgggcg agcctaagtt caaccccgac ggcagctctt acaccggccc ttggggccgc    420
cctcagaacg acgccccgc tgagcgagct agcaccatga ttctgattgc tgactccttc    480
ctgacccaga ccaagaacac ctcttacgtt gacaacaccc tgaagcccgc tatttacaag    540
gacctggact acgtcgtcaa cacctggtct aacccttgct cgacctgtg ggaggaggtt    600 aacggcattc acttctacac cctcatggtt atgcgacgag gcctcctgga cggcgccaac    660
ttcgccaccc gaaacggcga caccagcaag gctagctctt acagcagcac cgcttctcag    720
atccagaaca agattgactc tttctggtct agctctaaga actacatcat ggttacccag    780
gactaccaga acggcattca gaagcctagc ggcctcgaca ttagcaccct catcgccgct    840
aacgtcgctg gcatgaacga cggcttctac accccccggct ccgacaagat gctcgctacc    900
gccgttgcta ttgagaacgc catggctaac ctgtaccctc tgaacaagaa cctgccttct    960
tacctgggca acgccattgg ccgataccccc gaggacacct acaacggcga cggcaactct   1020
cagggcaacc cttggttcct cgccaccacc gctttcagcg agctgtacta ccgcgctctc   1080
ctggagtggc aggagaccgg cgttaccgtc accagcattt ccaaggactt cttctctaag   1140
ttcgacccta cgctagcgc tggcaagaag tactcccccg ctctgacga gttcaactcc   1200 ctcgcccaga acattgccag cgctgccgac cgattcctgt ctaccgttaa ctaccaccga   1260
aactccaacg gctctctgtc tgaggagtac gaccgaaaca gcggctacat gaccggcgcc   1320
cgagacctga cctggtccca cgccgctttc attaccgccg gcctcgcgag agctggcacc   1380
cctagc                                                             1386
```

```
<210> SEQ ID NO 131
<211> LENGTH: 20
<212> TYPE: PRT
<213> ORGANISM: Artificial Sequence
<220> FEATURE:
<223> OTHER INFORMATION: signal peptide

<400> SEQUENCE: 131

Met Met Met Ser Trp Lys Ser Leu Leu Leu Leu Leu Gly Pro Ile Ala
1               5                   10                  15

Ala Ala Thr Ala
            20

<210> SEQ ID NO 132
<211> LENGTH: 442
<212> TYPE: PRT
<213> ORGANISM: Apophysomyces elegans

<400> SEQUENCE: 132

Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
            115                 120                 125

Arg Ala Ser Thr Met Ile Leu Ile Ala Asp Ser Phe Leu Thr Gln Thr
        130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
        210                 215                 220

Ile Asp Ser Phe Trp Ser Ser Ser Lys Asn Tyr Ile Met Val Thr Gln
225                 230                 235                 240

Asp Tyr Gln Asn Gly Ile Gln Lys Pro Ser Gly Leu Asp Ile Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300
```

-continued

```
Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
            355                 360                 365

Lys Lys Tyr Ser Pro Gly Ser Asp Glu Phe Asn Ser Leu Ala Gln Asn
        370                 375                 380

Ile Ala Ser Ala Ala Asp Arg Phe Leu Ser Thr Val Asn Tyr His Arg
385                 390                 395                 400

Asn Ser Asn Gly Ser Leu Ser Glu Glu Tyr Asp Arg Asn Ser Gly Tyr
                405                 410                 415

Met Thr Gly Ala Arg Asp Leu Thr Trp Ser His Ala Ala Phe Ile Thr
                420                 425                 430

Ala Gly Leu Ala Arg Ala Gly Thr Pro Ser
            435                 440
```

```
<210> SEQ ID NO 133
<211> LENGTH: 1389
<212> TYPE: DNA
<213> ORGANISM: Artificial Sequence
<220> FEATURE:
<223> OTHER INFORMATION: codon modified

<400> SEQUENCE: 133
atgatgatgt cttggaagtc tctgctcctc ctgctgggcc ctattgccgc tgccaccgct      60
gccattccta ccggcaacag cagcctcaac gcttgggtta ctcccagga ggacatttct     120 ttcagcgtca tgctgggcaa cattaaccct cccggcaccg ttaagggctt cgttgccgct     180
agcctgtcta ccgccggccc cgactacttc tactcttggg tccgagacag cgccctcgtt     240
tcccgcgtcg tcacccacaa gtacaacacc accgagaccg gcaacagcac cgttgctggc     300
ttcctgcagg actacgtcca cttccagatt aacacccaga ccgagtccac cgtttgcaac     360
tgcctgggcg agcctaagtt caaccccgac ggcagctctt acaccggccc cttggggccga     420 cctcagaacg acgccccgc tgagcgcgct agcaccatga ttctgattgc tgactccttc     480
ctcgctcaga ccaagaacac ctcttacgtt gacaacaccc tgaagcctgc catttacaag     540
gacctggact acgtcgttaa cacctggtct aacccttgct cgacctgtg ggaggaggtt     600 aacggcattc acttctacac cctcatggtt atgcgacgag gcctcctgga cggcgccaac     660
ttcgccaccc gaaacggcga cacctccaag gctagctctt acagcagcac cgctagccag     720
atccagaaca gattgactc tttctggtct agctccaaga actacatcat ggttacccag     780
gactaccaga acggcgttca gaagcctagc ggcctcgaca ttagcaccct catcgccgct     840
aacgttgctg gcatgaacga cggcttctac accctggct ctgacaagat gctcgccacc     900
gccgttgcta ttgagaacgc tatggctaac ctgtaccctc tgaacaagaa cctgccttct     960
tacctgggca cgccattgg ccgatacccc gaggacacct acaacggcga cggcaactcc    1020
cagggcaacc cttggttcct cgctaccacc gctttcagcg agctgtacta ccgagctctg    1080
ttagagtggc aggagaccgg cgtcaccgtt accagcatct ctaaggactt cttctccaag    1140 ttcgaccccta acgctagcgc cggcaagaag tactcccccg cagcgacga gttcaactct    1200 ctcgcccaga acatcgccag cgccgctgac cgattcctgt ctaccgtcaa ctaccaccga    1260
```

-continued

```
aactctaacg gctctctgtc tgaggagtac gaccgaaact ccggctacat gaccggcgcg      1320
agagacctga cctggtctca cgctgctttc attaccgctg gcctcgcccg agctggcacc      1380
ccttctttc                                                              1389

<210> SEQ ID NO 134
<211> LENGTH: 20
<212> TYPE: PRT
<213> ORGANISM: Artificial Sequence
<220> FEATURE:
<223> OTHER INFORMATION: signal peptide

<400> SEQUENCE: 134

Met Met Met Ser Trp Lys Ser Leu Leu Leu Leu Leu Gly Pro Ile Ala
1               5                   10                  15

Ala Ala Thr Ala
            20

<210> SEQ ID NO 135
<211> LENGTH: 443
<212> TYPE: PRT
<213> ORGANISM: Apophysomyces variabilis

<400> SEQUENCE: 135

Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Ala Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
                180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
    210                 215                 220

Ile Asp Ser Phe Trp Ser Ser Ser Lys Asn Tyr Ile Met Val Thr Gln
225                 230                 235                 240

Asp Tyr Gln Asn Gly Val Gln Lys Pro Ser Gly Leu Asp Ile Ser Thr
                245                 250                 255
```

-continued

```
Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
            275                 280                 285

Ala Asn Leu Tyr Pro Leu Asn Lys Asn Leu Pro Ser Tyr Leu Gly Asn
            290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
            355                 360                 365

Lys Lys Tyr Ser Pro Gly Ser Asp Glu Phe Asn Ser Leu Ala Gln Asn
            370                 375                 380

Ile Ala Ser Ala Ala Asp Arg Phe Leu Ser Thr Val Asn Tyr His Arg
385                 390                 395                 400

Asn Ser Asn Gly Ser Leu Ser Glu Glu Tyr Asp Arg Asn Ser Gly Tyr
                405                 410                 415

Met Thr Gly Ala Arg Asp Leu Thr Trp Ser His Ala Ala Phe Ile Thr
                420                 425                 430

Ala Gly Leu Ala Arg Ala Gly Thr Pro Ser Phe
                435                 440
```

```
<210> SEQ ID NO 136
<211> LENGTH: 1389
<212> TYPE: DNA
<213> ORGANISM: Artificial Sequence
<220> FEATURE:
<223> OTHER INFORMATION: codon modified

<400> SEQUENCE: 136
atgatgatgt cttggaagtc tctgctcctc ctgctgggcc ctatcgccgc tgccaccgct      60
gccatcccta ccggcaacag cagcctcaac gcttgggtta gctctcagga ggacatctct     120
ttcagcgtca tgctgggcaa catcaaccct cccggcaccg tcaagggctt cgttgccgct     180
agcctgtcta ccgctggccc cgactacttc tactcttggg tccgagacag cgctctcgtt     240
tctcgcgttg ttacccacaa gtacaacacc accgagaccg gcaacagcac cgttgctggc     300
ttcctgcagg actacgttca cttccagatt aacacccaga ccgagtccac cgtttgcaac     360
tgcctgggcg agcctaagtt caaccccgac ggcagctctt acaccggccc ttggggccgc     420
cctcagaacg acggccccgc tgagcgcgct agcaccatga ttctgatcgc tgactccttc     480
ctgacccaga ccaagaacac ctcttacgtt gacaacaccc tgaagcccgc tatttacaag     540
gacctcgact acgtcgttaa cacctggtct aacccttgct cgacctgtg ggaggaggtt     600 aacggcattc acttctacac cctcatggtt atgcgacgag gcctcctgga cggcgccaac     660
ttcgccaccc gaaacggcga caccagcaag gctagctctt actccagcac cgcttcccag     720
attcagaaca agattgactc tttctggagc agctccaaga actacattat tgttacccag     780
gactaccaga acggcgtcca gaagcctagc ggcctcgacg tcagcaccct cattgctgcc     840
aacgtcgctg catgaacga cggcttctac acccccggca gcgacaagat gctcgccacc     900
gccgttgcca ttgagaacgc catggctaac ctgtaccctc tgaacaagaa cctgccttct     960
tacctgggca acgctattgg ccgataccc gaggacacct acaacggcga cggcaactcc    1020
```

```
cagggcaacc cttggttcct cgccaccacc gctttcagcg agctgtacta ccgagctctg   1080
cttgaatggc aggagaccgg cgtcaccgtt accagcattt ctaaggactt cttctctaag   1140 ttcgaccncta acgctagcgc cggcaagaag tactcccccg gctccaacga gtacgctagc   1200
ctcgcccaga acattgctag cgccgctgac cgattcctgt ctaccgttaa ctaccaccga   1260
aaccctaacg gctctctgtc tgaggagtac gaccgaaaca ccggctacat gaccggcgcc   1320
cgagacctga cctggtctca cgctgctttc attaccgccg gcctggccag ggctggcacc   1380
ccttctttc                                                          1389
```

<210> SEQ ID NO 137
<211> LENGTH: 20
<212> TYPE: PRT
<213> ORGANISM: Artificial Sequence
<220> FEATURE:
<223> OTHER INFORMATION: signal peptide

<400> SEQUENCE: 137

```
Met Met Met Ser Trp Lys Ser Leu Leu Leu Leu Leu Gly Pro Ile Ala
1               5                   10                  15

Ala Ala Thr Ala
            20
```

<210> SEQ ID NO 138
<211> LENGTH: 443
<212> TYPE: PRT
<213> ORGANISM: Apophysomyces trapeziformis

<400> SEQUENCE: 138

```
Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Thr Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
```

```
            210                 215                 220

Ile Asp Ser Phe Trp Ser Ser Ser Lys Asn Tyr Ile Ile Val Thr Gln
225                 230                 235                 240

Asp Tyr Gln Asn Gly Val Gln Lys Pro Ser Gly Leu Asp Val Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
            355                 360                 365

Lys Lys Tyr Ser Pro Gly Ser Asn Glu Tyr Ala Ser Leu Ala Gln Asn
    370                 375                 380

Ile Ala Ser Ala Ala Asp Arg Phe Leu Ser Thr Val Asn Tyr His Arg
385                 390                 395                 400

Asn Pro Asn Gly Ser Leu Ser Glu Glu Tyr Asp Arg Asn Thr Gly Tyr
                405                 410                 415

Met Thr Gly Ala Arg Asp Leu Thr Trp Ser His Ala Ala Phe Ile Thr
                420                 425                 430

Ala Gly Leu Ala Arg Ala Gly Thr Pro Ser Phe
                435                 440

<210> SEQ ID NO 139
<211> LENGTH: 1404
<212> TYPE: DNA
<213> ORGANISM: Artificial Sequence
<220> FEATURE:
<223> OTHER INFORMATION: Sequence is synthesized

<400> SEQUENCE: 139
atgccttctt ggaaaaccct gttcctcctc ctgggcccta tcgccaccgc tgccgctgct      60
cccgttgaca agcagtctct gcctaccggc aacagcacca ttagctcttg ggtcagcaag     120
caggaggaca tcagcttcag cgagatgctc cgaaacgtca accctgaggg caccgccaag     180
ggcttcgttg ccgcgtcgct cagcaccgct ggccccgact acttctacac ctggacccga     240
gacgccgctc tcgcctcccg agttattgct tacaagtaca acaccaccaa cgctggcgac     300
tctaagatcc acggcgttct ggacgactac gttaacttcc agattaacac ccagtctgag     360
cccacccctt gcaactgcct gggcgagcct aagttcaacc ctgacggcag ctctttcacc     420
ggcccttggg ccgcccccca gaacgacggc cccgctgagc gagcctccag tttcatgctg     480
attgccgact ctttcctcag ccagaccaag aacgcctctt acttcaccaa caccctcaag     540
cctgccattt acaaggacct cgactacgtc gttgacacct ggtctaaccc ttgcttcgac     600
ctgtgggagg aggttaacgg catccacttc tacaccctca tggttatgcg acgatctctc     660
ctcgacggcg ctaacttcgc cacccgaaac ggcgacaact ccaaggcctc aacctactcc     720
ggcgtcgccg ccaagattca ggctcgactg aactctttct gggacgccgg caagaactac     780
```

-continued

```
attaccgtta cccaggacta caagaacggc gttgagaagc ctagcggcct cgacgttagc      840
accctcattg ctgctaacgt cgctggcatg ggcgacggct tctacacccc cggcagcgag      900
cgcatcctcg ctaccgctct ggctttcgag aagagcatgg caagtctgta ccctctgaac      960
aacaacctgc ctagccacct gggcaacgcc attggccgat accccgagga cacctacaac     1020
ggcaacggca actcccaggg caacccttgg ttcctcgcta ccaccgcttt caccgagctg     1080
tactaccgcg ccattctgga gtggaagaac accggcgtta ccgtcacccc tatttctaag     1140
gacttcttcg tccgattcga cagcagcgct gctcctggca agaagtacaa ccccggctcc     1200
caggagttcg ctaccctgac ccagtctatt gctgccgccg ctgaccgatt catgtccacc     1260
gtccagtacc accagaaccc taacggctct ctgtctgagg agttcgaccg atctagcggc     1320
tacatgaccg gcgcccgaga cctgacctgg agtcacgctg ctttcattac cgctgctcag     1380
gcccgagctg gctctccttc tttc                                           1404
```

<210> SEQ ID NO 140
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 140

```
Ala Pro Val Asp Lys Gln Ser Leu Pro Thr Gly Asn Ser Thr Ile Ser
1               5                   10                  15

Ser Trp Val Ser Lys Gln Glu Asp Ile Ser Phe Ser Glu Met Leu Arg
            20                  25                  30

Asn Val Asn Pro Glu Gly Thr Ala Lys Gly Phe Val Ala Ala Ser Leu
        35                  40                  45

Ser Thr Ala Gly Pro Asp Tyr Phe Tyr Thr Trp Thr Arg Asp Ala Ala
    50                  55                  60

Leu Ala Ser Arg Val Ile Ala Tyr Lys Tyr Asn Thr Thr Asn Ala Gly
65                  70                  75                  80

Asp Ser Lys Ile His Gly Val Leu Asp Asp Tyr Val Asn Phe Gln Ile
                85                  90                  95

Asn Thr Gln Ser Glu Pro Thr Pro Cys Asn Cys Leu Gly Glu Pro Lys
            100                 105                 110

Phe Asn Pro Asp Gly Ser Ser Phe Thr Gly Pro Trp Gly Arg Pro Gln
            115                 120                 125

Asn Asp Gly Pro Ala Glu Arg Ala Ser Ser Phe Met Leu Ile Ala Asp
        130                 135                 140

Ser Phe Leu Ser Gln Thr Lys Asn Ala Ser Tyr Phe Thr Asn Thr Leu
145                 150                 155                 160

Lys Pro Ala Ile Tyr Lys Asp Leu Asp Tyr Val Val Asp Thr Trp Ser
                165                 170                 175

Asn Pro Cys Phe Asp Leu Trp Glu Glu Val Asn Gly Ile His Phe Tyr
            180                 185                 190

Thr Leu Met Val Met Arg Arg Ser Leu Leu Asp Gly Ala Asn Phe Ala
            195                 200                 205

Thr Arg Asn Gly Asp Asn Ser Lys Ala Ser Thr Tyr Ser Gly Val Ala
        210                 215                 220

Ala Lys Ile Gln Ala Arg Leu Asn Ser Phe Trp Asp Ala Gly Lys Asn
225                 230                 235                 240

Tyr Ile Thr Val Thr Gln Asp Tyr Lys Asn Gly Val Glu Lys Pro Ser
```

-continued

```
                    245              250              255

Gly Leu Asp Val Ser Thr Leu Ile Ala Ala Asn Val Ala Gly Met Gly
            260              265              270

Asp Gly Phe Tyr Thr Pro Gly Ser Glu Arg Ile Leu Ala Thr Ala Leu
            275              280              285

Ala Phe Glu Lys Ser Met Ala Ser Leu Tyr Pro Leu Asn Asn Asn Leu
            290              295              300

Pro Ser His Leu Gly Asn Ala Ile Gly Arg Tyr Pro Glu Asp Thr Tyr
305              310              315              320

Asn Gly Asn Gly Asn Ser Gln Gly Asn Pro Trp Phe Leu Ala Thr Thr
            325              330              335

Ala Phe Thr Glu Leu Tyr Tyr Arg Ala Ile Leu Glu Trp Lys Asn Thr
            340              345              350

Gly Val Thr Val Thr Pro Ile Ser Lys Asp Phe Phe Val Arg Phe Asp
            355              360              365

Ser Ser Ala Ala Pro Gly Lys Lys Tyr Asn Pro Gly Ser Gln Glu Phe
            370              375              380

Ala Thr Leu Thr Gln Ser Ile Ala Ala Ala Asp Arg Phe Met Ser
385              390              395              400

Thr Val Gln Tyr His Gln Asn Pro Asn Gly Ser Leu Ser Glu Glu Phe
            405              410              415

Asp Arg Ser Ser Gly Tyr Met Thr Gly Ala Arg Asp Leu Thr Trp Ser
            420              425              430

His Ala Ala Phe Ile Thr Ala Ala Gln Ala Arg Ala Gly Ser Pro Ser
            435              440              445

Phe
```

```
<210> SEQ ID NO 141
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 141

Ala Pro Val Asp Lys Gln Ser Leu Pro Thr Gly Asn Ser Thr Ile Ser
1               5               10              15

Ser Trp Val Ser Lys Gln Glu Asp Ile Ser Phe Ser Glu Met Leu Arg
            20              25              30

Asn Val Asn Pro Glu Gly Thr Ala Lys Gly Phe Val Ala Ala Ser Leu
            35              40              45

Ser Thr Ala Gly Pro Asp Tyr Phe Tyr Thr Trp Thr Arg Asp Ala Ala
            50              55              60

Leu Val Ser Arg Val Ile Ala Tyr Lys Tyr Asn Thr Thr Asn Ala Gly
65              70              75              80

Asp Ser Lys Ile His Gly Val Leu Asp Asp Tyr Val Asn Phe Gln Ile
            85              90              95

Asn Thr Gln Ser Glu Pro Thr Pro Cys Asn Cys Leu Gly Glu Pro Lys
            100             105             110

Phe Asn Pro Asp Gly Ser Ser Phe Thr Gly Pro Trp Gly Arg Pro Gln
            115             120             125

Asn Asp Gly Pro Ala Glu Arg Ala Ser Ser Phe Met Leu Ile Ala Asp
            130             135             140

Ser Phe Leu Ser Gln Thr Lys Asn Ala Ser Tyr Phe Thr Asn Thr Leu
145             150             155             160
```

-continued

```
Lys Pro Ala Ile Tyr Lys Asp Leu Asp Tyr Val Val Asp Thr Trp Ser
              165             170             175

Asn Pro Cys Phe Asp Leu Trp Glu Glu Val Asn Gly Ile His Phe Tyr
              180             185             190

Thr Leu Met Val Met Arg Arg Ser Leu Leu Asp Gly Ala Asn Phe Ala
              195             200             205

Thr Arg Asn Gly Asp Asn Ser Lys Ala Ser Thr Tyr Ser Gly Val Ala
        210             215             220

Ala Lys Ile Gln Ala Arg Leu Asn Ser Phe Trp Asp Ala Gly Lys Asn
225             230             235             240

Tyr Ile Thr Val Thr Gln Asp Tyr Lys Asn Gly Val Glu Lys Pro Ser
              245             250             255

Gly Leu Asp Val Ser Thr Leu Ile Ala Ala Asn Val Ala Gly Met Gly
              260             265             270

Asp Gly Phe Tyr Thr Pro Gly Ser Glu Arg Ile Leu Ala Thr Ala Leu
              275             280             285

Ala Phe Glu Lys Ser Met Ala Ser Leu Tyr Pro Leu Asn Asn Asn Leu
        290             295             300

Pro Ser His Leu Gly Asn Ala Ile Gly Arg Tyr Pro Glu Asp Thr Tyr
305             310             315             320

Asn Gly Asn Gly Asn Ser Gln Gly Asn Pro Trp Phe Leu Ala Thr Thr
              325             330             335

Ala Phe Thr Glu Leu Tyr Tyr Arg Ala Ile Leu Glu Trp Lys Asn Thr
              340             345             350

Gly Val Thr Val Thr Pro Ile Ser Lys Asp Phe Phe Val Arg Phe Asp
              355             360             365

Ser Ser Ala Ala Pro Gly Lys Lys Tyr Asn Pro Gly Ser Gln Glu Phe
        370             375             380

Ala Thr Leu Thr Gln Ser Ile Ala Ala Ala Asp Arg Phe Met Ser
385             390             395             400

Thr Val Gln Tyr His Gln Asn Pro Asn Gly Ser Leu Ser Glu Glu Phe
              405             410             415

Asp Arg Ser Ser Gly Tyr Met Thr Gly Ala Arg Asp Leu Thr Trp Ser
              420             425             430

His Ala Ala Phe Ile Thr Ala Ala Gln Ala Arg Ala Gly Ser Pro Ser
        435             440             445

Phe
```

```
<210> SEQ ID NO 142
<211> LENGTH: 468
<212> TYPE: PRT
<213> ORGANISM: Saksenaea vasiformis

<400> SEQUENCE: 142
```

```
Met Pro Ser Trp Lys Thr Leu Phe Leu Leu Leu Gly Pro Ile Ala Thr
1               5               10              15

Ala Ala Ala Ala Pro Val Asp Lys Gln Ser Leu Pro Thr Gly Asn Ser
              20              25              30

Thr Ile Ser Ser Trp Val Ser Lys Gln Glu Asp Ile Ser Phe Ser Glu
        35              40              45

Met Leu Arg Asn Val Asn Pro Glu Gly Thr Ala Lys Gly Phe Val Ala
        50              55              60

Ala Ser Leu Ser Thr Ala Gly Pro Asp Tyr Phe Tyr Thr Trp Thr Arg
65              70              75              80
```

-continued

```
Asp Ala Ala Leu Val Ser Arg Val Ile Ala Tyr Lys Tyr Asn Thr Thr
                85              90              95

Asn Ala Gly Asp Ser Lys Ile His Gly Val Leu Asp Asp Tyr Val Asn
            100             105             110

Phe Gln Ile Asn Thr Gln Ser Glu Ser Thr Pro Cys Asn Cys Leu Gly
            115             120             125

Glu Pro Lys Phe Asn Pro Asp Gly Ser Ser Phe Thr Gly Pro Trp Gly
        130             135             140

Arg Pro Gln Asn Asp Gly Pro Ala Glu Arg Ala Ser Ser Phe Met Leu
145             150             155             160

Ile Ala Asp Ser Phe Leu Ser Gln Thr Lys Asn Ala Ser Tyr Phe Thr
                165             170             175

Asn Thr Leu Lys Pro Ala Ile Tyr Lys Asp Leu Asp Tyr Val Val Asp
            180             185             190

Thr Trp Ser Asn Pro Cys Phe Asp Leu Trp Glu Glu Val Asn Gly Ile
            195             200             205

His Phe Tyr Thr Leu Met Val Met Arg Arg Ser Leu Leu Asp Gly Ala
    210             215             220

Asn Phe Ala Thr Arg Asn Gly Asp Asn Ser Lys Ala Ser Thr Tyr Ser
225             230             235             240

Gly Val Ala Ala Lys Ile Gln Ala Arg Leu Asn Ser Phe Trp Asp Ala
            245             250             255

Gly Lys Asn Tyr Ile Thr Val Thr Gln Asp Tyr Lys Asn Gly Val Glu
            260             265             270

Lys Pro Ser Gly Leu Asp Val Ser Thr Leu Ile Ala Ala Asn Val Ala
            275             280             285

Gly Met Gly Asp Gly Phe Tyr Thr Pro Gly Ser Glu Arg Ile Leu Ala
    290             295             300

Thr Ala Leu Ala Phe Glu Lys Ser Met Ala Ser Leu Tyr Pro Leu Asn
305             310             315             320

Asn Asn Leu Pro Ser His Leu Gly Asn Ala Ile Gly Arg Tyr Pro Glu
            325             330             335

Asp Thr Tyr Asn Gly Asn Gly Asn Ser Gln Gly Asn Pro Trp Phe Leu
            340             345             350

Ala Thr Thr Ala Phe Thr Glu Leu Tyr Tyr Arg Ala Ile Leu Glu Trp
        355             360             365

Lys Asn Thr Gly Val Thr Val Thr Pro Ile Ser Lys Asp Phe Phe Val
    370             375             380

Arg Phe Asp Ser Ser Ala Ala Pro Gly Lys Lys Tyr Asn Pro Gly Ser
385             390             395             400

Gln Glu Phe Ala Thr Leu Thr Gln Ser Ile Ala Ala Ala Asp Arg
            405             410             415

Phe Met Ser Thr Val Gln Tyr His Gln Asn Pro Asn Gly Ser Leu Ser
            420             425             430

Glu Glu Phe Asp Arg Ser Ser Gly Tyr Met Thr Gly Ala Arg Asp Leu
        435             440             445

Thr Trp Ser His Ala Ala Phe Ile Thr Ala Ala Gln Ala Arg Ala Gly
    450             455             460

Ser Pro Ser Phe
465
```

GLUCOAMYLASE AND METHODS OF USE THEREOF

CROSS-REFERENCE TO RELATED APPLICATIONS

This application is a continuation under 35 U.S.C. § 111(a) to International Patent Application No. PCT/US2021/027894, filed on Apr. 19, 2021, the disclosure of which is incorporated by reference herein in its entirety.

FIELD OF THE INVENTION

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

BACKGROUND

Glucoamylase (1,4-alpha-D-glucan glucohydrolase, EC 3.2.1.3) is an enzyme which catalyzes the release of D-glucose from the non-reducing ends of starch or related oligo- and poly-saccharide molecules. Glucoamylases are produced by several filamentous fungi and yeast.

The major application of glucoamylase is the saccharification of partially processed starch/dextrin to glucose, which is an essential substrate for numerous fermentation processes. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

Glucoamylase for commercial purposes has traditionally been produced employing filamentous fungi, although a diverse group of microorganisms is reported to produce glucoamylase since they secrete large quantities of the enzyme extracellularly. However, commercially used fungal glucoamylases have certain limitations such as slow catalytic activity or lack of stability that increase process costs.

There continues to be a need for new glucoamylases to improve the efficiency of saccharification and provide a high yield in fermentation products.

SUMMARY

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

1. In one aspect, a method for saccharifying a starch substrate, comprising contacting the starch substrate with a glucoamylase selected from the group consisting of:
   (a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
   (b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
   (c) a polypeptide comprising one or more sequence motifs selected from the group consisting of:
      (i) $YX_aX_bTXXX_cX_d$(SEQ ID NO: 113), wherein X is any amino acid and $X_a$ is N or S; $X_b$ is T, S, or R; $X_c$ is G or N; and $X_a$ is D, N, or S;
      (ii) YNTTXAGD (SEQ ID NO: 114), wherein X is any amino acid;
      (iii) $X_aX_bX_cX_e$AANX$X_d$ (SEQ ID NO: 115), wherein X is any amino acid and $X_a$ is S or A; $X_b$ is T, N, or V; $X_c$ is L or I; and $X_d$ is A or G;
      (iv) STLIAANXA (SEQ ID NO: 116), wherein X is any amino acid;
      (v) $X_a$GXGNX$_b$X$_c$ (SEQ ID NO: 117), wherein X is any amino acid and $X_a$ is N or D; $X_b$ is S or G; and $X_c$ is Q, K, or E; and
      (vi) NGNGNSQ (SEQ ID NO: 118);
      wherein the polypeptide has at least 70% identity to the catalytic domain of SEQ ID NO: 61.
2. In some embodiments of the method of paragraph 1, wherein the polypeptide comprises a substitution, deletion or addition at a position corresponding to position 102 of the polypeptide of SEQ ID NO: 61.
3. In some embodiments of the method of paragraph 2, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.
4. In some embodiments of the method of any one of paragraphs 1-3, the polypeptide comprises a substitution, deletion or addition at a position corresponding to position 66 of the polypeptide of SEQ ID NO: 61.
5. In some embodiments of the method of paragraph 4, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.
6. In some embodiments of the method of any one of paragraphs 1-5, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO. 101, SEQ ID NO:102, SEQ ID NO:103, SEQ ID NO:104, SEQ ID NO:119, SEQ ID NO: 120, SEQ ID NO:121, SEQ ID NO:122, SEQ ID NO:123, SEQ ID NO: 126, SEQ ID NO:129, SEQ ID NO:132, SEQ ID NO:135, SEQ ID NO: 138, SEQ ID NO:140, SEQ ID NO:141, or SEQ ID NO:142.

7. In some embodiments of the method of any one of paragraphs 1-6, wherein the starch substrate is about 15% to 65%, 15% to 60% or 15% to 35% dry solid (DS).

8. In some embodiments of the method of any one of paragraphs 1-7, wherein the starch substrate comprises liquefied starch, gelatinized starch, or granular starch.

9. In some embodiments of the method of any one of paragraphs 1-8, further comprising adding a hexokinase, a xylanase, a glucose isomerase, a xylose isomerase, a phosphatase, a phytase, a pullulanase, a beta-amylase, an alpha-amylase, a protease, a cellulase, a hemicellulase, a lipase, a cutinase, a trehalase, an isoamylase, a redox enzyme, an esterase, a transferase, a pectinase, a hydrolase, an alpha-glucosidase, a beta-glucosidase, or a combination thereof to the starch substrate.

10. In some embodiments of the method of any one of paragraphs 1-9, wherein saccharifying the starch substrate results in a high glucose syrup comprising an amount of glucose selected from the group consisting of at least 95.5% glucose, at least 95.6% glucose, at least 95.7% glucose, at least 95.8% glucose, at least 95.9% glucose, at least 96% glucose, at least 96.1% glucose, at least 96.2% glucose, at least 96.3% glucose, at least 96.4% glucose, at least 96.5% glucose and at least 97% glucose.

11. In some embodiments of the method of any one of paragraphs 1-10, further comprising fermenting the high glucose syrup to an end product.

12. In some embodiments of the method of paragraph 11, wherein saccharifying and fermenting are carried out as a simultaneous saccharification and fermentation (SSF) process.

13. In some embodiments of the method of paragraph 11 or 12, wherein the end product is an alcohol, optionally, ethanol.

14. In some embodiments of the method of paragraph 11 or 12, wherein the end product is a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene.

15. In another aspect, a process of producing a fermentation product from a starch substrate comprising the steps of:
   1) liquefying the starch substrate;
   2) saccharifying the liquefied starch substrate; and
   3) fermenting with a fermenting organism;
   wherein step 2) is carried out using at least a glucoamylase selected from the group consisting of:
      a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
      c) a polypeptide comprising one or more signature motifs selected from the group consisting of:
         (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
         (ii) YNTTXAGD (SEQ ID NO: 114), wherein X is any amino acid;
         (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
         (iv) STLIAANXA (SEQ ID NO: 116), wherein wherein X is any amino acid;
         (v) $X_aGXGNX_bX_c$ (SEQ ID NO: 117), wherein X is any amino acid and $X_a$ is N or D; $X_b$ is S or G; and $X_c$ is Q, K, or E; and
         (vi) NGNGNSQ (SEQ ID NO: 118);
         wherein the polypeptide has at least 70% identity to the catalytic domain of SEQ ID NO: 61.

16. In some embodiments of the process of paragraph 15, wherein the polypeptide comprises a substitution, deletion or addition at a position corresponding to position 102 of the polypeptide of SEQ ID NO: 61.

17. In some embodiments of the process of paragraph 16, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

18. In some embodiments of the process of any one of paragraphs 15-17, the polypeptide comprises a substitution, deletion or addition at a position corresponding to position 66 of the polypeptide of SEQ ID NO: 61.

19. In some embodiments of the process of paragraph 18, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

20. In some embodiments of the process of any one of paragraphs 15-19, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO: 96, SEQ ID NO:97, SEQ ID NO:98, SEQ ID NO:99, SEQ ID NO:100, SEQ ID NO:101, SEQ ID NO: 102, SEQ ID NO:103, SEQ ID NO:104, SEQ ID NO: 119, SEQ ID NO: 120, SEQ ID NO:121, SEQ ID NO:122, SEQ ID NO:123, SEQ ID NO: 126, SEQ ID NO:129, SEQ ID NO:132, SEQ ID NO:135, SEQ ID NO: 138, SEQ ID NO:140, SEQ ID NO:141, or SEQ ID NO:142.

21. In another aspect, a process of producing a fermentation product from a starch substrate comprising the steps of:

1) saccharifying the starch substrate at a temperature below the initial gelatinization temperature of the starch substrate; and 2) fermenting with a fermenting organism, wherein step 1) is carried out using at least a glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99/o identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;

(ii) YNTTXAGD (SEQ ID NO: 114), wherein X is any amino acid;

(iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;

(iv) STLIAANXA (SEQ ID NO: 116), wherein wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61.

22. In some embodiments of the process of paragraph 21, wherein the polypeptide comprises a substitution, deletion or addition at a position corresponding to position 102 of the polypeptide of SEQ ID NO: 61.

23. In some embodiments of the process of paragraph 22, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

24. In some embodiments of the process of any one of paragraphs 21-23, the polypeptide comprises a substitution, deletion or addition at a position corresponding to position 66 of the polypeptide of SEQ ID NO: 61.

25. In some embodiments of the process of paragraph 24, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

26. In some embodiments of the process of any one of paragraphs 21-25, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO: 96, SEQ ID NO:97, SEQ ID NO:98, SEQ ID NO:99, SEQ ID NO:100, SEQ ID NO:101, SEQ ID NO: 102, SEQ ID NO:103, SEQ ID NO:104, SEQ ID NO: 119, SEQ ID NO: 120, SEQ ID NO:121, SEQ ID NO:122, SEQ ID NO:123, SEQ ID NO: 126, SEQ ID NO:129, SEQ ID NO:132, SEQ ID NO:135, SEQ ID NO: 138, SEQ ID NO:140, SEQ ID NO:141, or SEQ ID NO:142.

27. In another aspect, a method for increasing starch digestibility in an animal which comprises adding at least one glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;

(ii) YNTTXAGD (SEQ ID NO: 114), wherein X is any amino acid;

(iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;

(iv) STLIAANXA (SEQ ID NO: 116), wherein wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61.

28. In some embodiments of the method of paragraph 27, wherein the polypeptide comprises a substitution, deletion or addition at a position corresponding to position 102 of the polypeptide of SEQ ID NO: 61.

29. In some embodiments of the method of paragraph 28, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

30. In some embodiments of the method of any one of paragraphs 27-29, the polypeptide comprises a substitution, deletion or addition at a position corresponding to position 66 of the polypeptide of SEQ ID NO: 61.

31. In some embodiments of the method of paragraph 30, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

32. In some embodiments of the method of any one of paragraphs 27-31, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO: 95, SEQ ID NO:96, SEQ ID NO: 97, SEQ ID NO:98, SEQ ID NO:99, SEQ ID NO:100, SEQ ID NO:101, SEQ ID NO:102, SEQ ID NO: 103, SEQ ID NO:104, SEQ ID NO:119, SEQ ID NO:120, SEQ ID NO:121, SEQ ID NO: 122, SEQ ID NO:123, SEQ ID NO:126, SEQ ID NO:129, SEQ ID NO: 132, SEQ ID NO:135, SEQ ID NO: 138, SEQ ID NO:140, SEQ ID NO:141, or SEQ ID NO:142.

33. In another aspect, a method of producing a fermented beverage, wherein the method comprises the step of contacting a mash and/or a worth with a glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;

(ii) YNTTXAGD (SEQ ID NO: 114), wherein X is any amino acid;

(iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;

(iv) STLIAANXA (SEQ ID NO: 116), wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61.

34. In some embodiments of the method of paragraph 33, wherein the polypeptide comprises a substitution, deletion or addition at a position corresponding to position 102 of the polypeptide of SEQ ID NO: 61.

35. In some embodiments of the method of paragraph 34, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

36. In some embodiments of the method of any one of paragraphs 33-35, the polypeptide comprises a substitution, deletion or addition at a position corresponding to position 66 of the polypeptide of SEQ ID NO: 61.

37. In some embodiments of the method of paragraph 36, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

38. In some embodiments of the method of any one of paragraphs 33-37, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

39. In another aspect, a composition comprising a starch substrate and a glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) $YX_aX_bTXXX_cX_d$ (SEQ ID NO: 113), wherein X is any amino acid and $X_a$ is N or S; $X_b$ is T, S, or R; $X_c$ is G or N, and $X_d$ is D, N, or S;

(ii) YNTTXAGD (SEQ ID NO: 114), wherein X is any amino acid;

(iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;

(iv) STLIAANXA (SEQ ID NO: 116), wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61; wherein said composition is at a temperature of about 4-40° C. and a pH of about 3-7.

40. In some embodiments of the composition of paragraph 39, wherein the polypeptide comprises a substitution, deletion or addition at a position corresponding to position 102 of the polypeptide of SEQ ID NO: 61.

41. In some embodiments of the composition of paragraph 40, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

42. In some embodiments of the composition of any one of paragraphs 39-41, the polypeptide comprises a substitution, deletion or addition at a position corresponding to position 66 of the polypeptide of SEQ ID NO: 61.

43. In some embodiments of the composition of paragraph 42, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

44. In some embodiments of the composition of any one of paragraphs 39-43, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

45. In another aspect, a recombinant host cell comprising a glucoamylase selected from the group consisting of:
   a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
   b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
   c) a polypeptide comprising one or more signature motifs selected from the group consisting of:
      (i) $YX_aX_bTXXX_cX_d$(SEQ ID NO: 113), wherein X is any amino acid and $X_a$ is N or S; $X_b$ is T, S, or R; $X_c$ is G or N; and $X_d$ is D, N, or S;
      (ii) YNTTXAGD (SEQ ID NO: 114), wherein X is any amino acid;
      (iii) $X_aX_bX_cX_c$AANXX$_d$ (SEQ ID NO: 115), wherein X is any amino acid and $X_a$ is S or A; $X_b$ is T, N, or V; $X_c$ is L or I; and $X_d$ is A or G;
      (iv) STLIAANXA (SEQ ID NO: 116), wherein wherein X is any amino acid;
      (v) $X_a$GXGNX$_b$X$_c$ (SEQ ID NO: 117), wherein X is any amino acid and $X_a$ is N or D; $X_b$ is S or G; and $X_c$ is Q, K, or E; and
      (vi) NGNGNSQ (SEQ ID NO: 118);
      wherein the polypeptide has at least 70% identity to the catalytic domain of SEQ ID NO: 61.

46. In some embodiments of the recombinant host cell of paragraph 45, wherein the polypeptide comprises a substitution, deletion or addition at a position corresponding to position 102 of the polypeptide of SEQ ID NO: 61.

47. In some embodiments of the recombinant host cell of paragraph 46, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

48. In some embodiments of the recombinant host cell of any one of paragraphs 45-47, the polypeptide comprises a substitution, deletion or addition at a position corresponding to position 66 of the polypeptide of SEQ ID NO: 61.

49. In some embodiments of the recombinant host cell of paragraph 48, wherein the polypeptide comprises a substitution selected from the group consisting of V66P, V66G, V66A, V66L, V66I, V66F, V66Y, V66W, V66S, V66T, V66C, V66M, V66N, V66Q, V66D, V66E, V66K, V66R, and V66H.

50. In some embodiments of the recombinant host cell of any one of paragraphs 45-49, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO: 80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO: 119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO: 141, or SEQ ID NO:142.

51. In some embodiments of the recombinant host cell of any one of paragraphs 45-50, which is an ethanologenic microorganism.

52. In some embodiments of the recombinant host cell of paragraph 51, which is a yeast cell.

53. In some embodiments of the recombinant host cell of any one of paragraphs 45-52, wherein said host cell is not *Saksenaea vasiformis*.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes

BRIEF DESCRIPTION OF THE DRAWINGS

FIG. 1A, FIG. 1B, FIG. 1C, FIG. 1D, FIG. 1E, FIG. 1F, FIG. 1G, FIG. 1H, FIG. 1I, FIG. 1J and FIG. 1K provide a multiple amino acid sequence alignment of the catalytic domain regions of Mucorales-clade glucoamylases and various reference fungal glucoamylases.

FIG. 3 provides an alignment of Mucorales-clade GA amino acid sequences (numbered according to SvaGa1 catalytic domain region, SEQ ID NO: 81) across region spanning residues 50 to 70, showing motif 1: $57Y\text{-}58X_a\text{-}59X_b\text{-}60T\text{-}61X\text{-}62X\text{-}63X_c\text{-}64X_d$, wherein X is any amino acid and $X_a$ is N or S; $X_b$ is T, S, or R; $X_c$ is G or N; and $X_d$ is D, N, or S.

FIG. 4 provides an alignment of Mucorales-clade GA amino acid sequences (numbered according to SvaGa1 catalytic domain region, SEQ ID NO: 81) across region spanning residues 240 to 260, showing motif 2: $244X_a\text{-}245X_b\text{-}246X_e\text{-}247X_c\text{-}248A\text{-}249A\text{-}250N\text{-}251X\text{-}252X_d$, wherein X is any amino acid and $X_a$ is S or A; $X_b$ is T, N, or V; $X_c$ is L or I; and $X_d$ is A or G.

FIG. 5 provides an alignment of Mucorales-clade GA amino acid sequences (numbered according to SvaGa1 catalytic domain region, SEQ ID NO: 81) across region spanning residues 299 to 315, showing motif 3: $304X_a\text{-}305G\text{-}306X\text{-}307G\text{-}308N\text{-}309X_b\text{-}310X_c$, wherein X is any amino acid and $X_a$ is N or D; $X_b$ is S or G; and $X_c$ is Q, K, or E.

FIG. 6A, FIG. 6B, FIG. 6C, FIG. 6D, provide[s] a multiple amino acid sequence alignment of the catalytic domain regions of additional Mucorales-clade glucoamylases and various reference fungal glucoamylases.

DETAILED DESCRIPTION

Figure 1I:
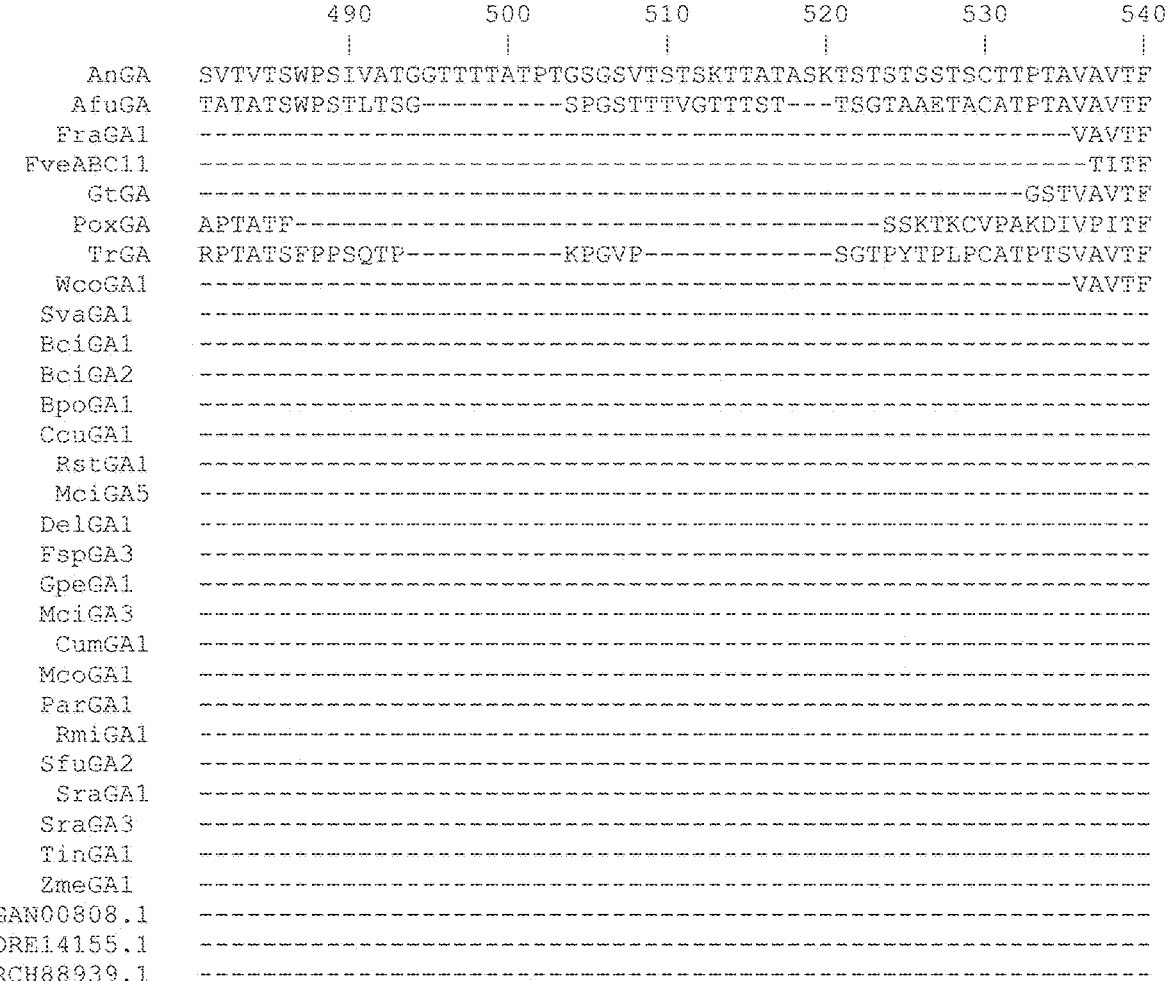

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

I. Definitions

Prior to describing the compositions and methods in detail, the following terms and abbreviations are defined.

Unless otherwise defined, all technical and scientific terms used have their ordinary meaning in the relevant scientific field. Singleton, et al., Dictionary of Microbiology and Molecular Biology, 2d Ed., John Wiley and Sons, New York (1994), and Hale & Markham, Harper Collins Dictionary of Biology, Harper Perennial, NY (1991) provide the ordinary meaning of many of the terms describing the invention.

The term "glucoamylase (1,4-alpha-D-glucan glucohydrolase, EC 3.2.1.3) activity" is defined herein as an enzyme activity, which catalyzes the release of D-glucose from the non-reducing ends of starch or related oligo- and polysaccharide molecules.

The term "amino acid sequence" is synonymous with the terms "poly peptide", "protein" and "peptide" and are used interchangeably. Where such amino acid sequences exhibit activity, they may be referred to as an "enzyme". The conventional one-letter or three-letter codes for amino acid residues are used, with amino acid sequences being presented in the standard amino-to-carboxy terminal orientation (i.e., N→C).

The term "mature polypeptide" is defined herein as a polypeptide in its final form following translation and any post-translational modifications, such as N-terminal processing, C-terminal truncation, glycosylation, phosphorylation, etc. In one aspect, the predicted mature polypeptide is SEQ ID NO: 61 based on the analysis of SignalP software version 4.0 (Nordahl Petersen et al. (2011) *Nature Methods*, 8:785-786) and SEQ ID NO: 41 is a signal peptide. In another aspect, the mature polypeptide comprises amino acid position 20-468 of SEQ ID NO:142. In another aspect, the mature polypeptide comprises amino acid position 21-468 of SEQ ID NO:142. In another aspect, the mature polypeptide comprises amino acid position 22-468 of SEQ ID NO:142. In another aspect, the mature polypeptide comprises amino acid position 23-468 of SEQ ID NO:142. In another aspect, the mature polypeptide comprises amino acid position 24-468 of SEQ ID NO:142. In another aspect, the mature polypeptide comprises amino acid position 25-468 of SEQ ID NO:142.

A "signal sequence" or "signal peptide" is a sequence of amino acids attached to the N-terminal portion of a protein, which facilitates the secretion of the protein outside the cell. The mature form of an extracellular protein lacks the signal sequence, which is cleaved off during the secretion process. In some embodiments, SEQ ID NO: 41 is a signal peptide. In other embodiments, the signal peptide comprises amino acid positions 1-20 of SEQ ID NO:142. In other embodiments, the signal peptide comprises amino acid positions 1-21 of SEQ ID NO:142. In other embodiments, the signal peptide comprises amino acid positions 1-22 of SEQ ID NO: 142. In other embodiments, the signal peptide comprises amino acid positions 1-23 of SEQ ID NO: 142. In other embodiments, the signal peptide comprises amino acid positions 1-24 of SEQ ID NO: 142.

The term "nucleic acid" encompasses DNA, RNA, heteroduplexes, and synthetic molecules capable of encoding a polypeptide. Nucleic acids may be single stranded or double stranded, and may be chemically modified. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

The term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

A "synthetic" molecule is produced by in vitro chemical or enzymatic synthesis rather than by an organism.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "expression" refers to the process by which a polypeptide is produced based on a nucleic acid sequence. The process includes both transcription and translation.

The term "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

The term "sequence motif" is a nucleotide or amino-acid sequence pattern that is widespread and has been proven or assumed to have a biological significance. In this invention, the sequence motif is an amino-acid sequence motif identified in the Mucorales-clade glucoamylases.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

"Percent sequence identity" means that a particular sequence has at least a certain percentage of amino acid residues identical to those in a specified reference sequence, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty: OFF.

The term "homologous sequence" is defined herein as a predicted protein having an E value (or expectancy score) of less than 0.001 in a tfasty search (Pearson, W. R., 1999, in Bioinformatics Methods and Protocols, S. Misener and S. A. Krawetz, ed., pp. 185-219) with the glucoamylase of SEQ ID NO: 61.

As used herein with regard to amino acid residue positions, "corresponding to" or "corresponds to" or "correspond to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms, "wild-type", "parental" or "reference" with respect to a polypeptide, refer to a naturally-occurring polypeptide that does not include a man-made substitution, insertion, or deletion at one or more amino acid positions. Similarly, the terms "wild-type", "parental" or "reference" with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

A "slurry" is an aqueous mixture containing insoluble starch granules in water.

The term "total sugar content" refers to the total soluble sugar content present in a starch composition including monosaccharides, oligosaccharides and polysaccharides.

The term "dry solids" (ds) refer to dry solids dissolved in water, dry solids dispersed in water or a combination of both. Dry solids thus include granular starch, and its hydrolysis products, including glucose.

The term "high DS" refers to aqueous starch slurry with a dry solid content greater than 38% (wt/wt).

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+(>DP3) denotes polymers with a degree of polymerization of greater than 3.

The term "contacting" refers to the placing of referenced components (including but not limited to enzymes, substrates, and fermenting organisms) in sufficiently close prox-
imity to affect an expect result, such as the enzyme acting on
the substrate or the fermenting organism fermenting a sub-
strate.

As used herein, the terms "yeast cells," "yeast strains," or
simply "yeast" refer to organisms from the Ascomycota and
Basidiomycota. Exemplary yeast is budding yeast from the
order Saccharomycetales. Particular examples of yeast are
*Saccharomyces* spp., including but not limited to *S. cerevi-
siae*. Yeast include organisms used for the production of fuel
alcohol as well as organisms used for the production of
potable alcohol, including specialty and proprietary yeast
strains used to make distinctive-tasting beers, wines, and
other fermented beverages.

An "ethanologenic microorganism" refers to a microor-
ganism with the ability to convert a sugar or other carbo-
hydrates to ethanol.

The term "biochemicals" refers to a metabolite of a
microorganism, such as citric acid, lactic acid, succinic acid,
monosodium glutamate, gluconic acid, sodium gluconate,
calcium gluconate, potassium gluconate, glucono delta-lac-
tone, sodium erythorbate, omega 3 fatty acid, butanol,
iso-butanol, an amino acid, lysine, itaconic acid, other
organic acids, 1,3-propanediol, vitamins, or isoprene or
other biomaterial.

The term "pullulanase" also called debranching enzyme
(E.C. 3.2.1.41, pullulan 6-glucanohydrolase), is capable of
hydrolyzing alpha 1-6 glucosidic linkages in an amylopectin
molecule.

Certain ranges are presented herein with numerical values
being preceded by the term "about." The term "about" is
used herein to provide literal support for the exact number
that it precedes, as well as a number that is near to or
approximately the number that the term precedes. In deter-
mining whether a number is near to or approximately a
specifically recited number, the near or approximating unre-
cited number can be a number which, in the context in which
it is presented, provides the substantial equivalent of the
specifically recited number. For example, in connection with
a numerical value, the term "about" refers to a range of
−15% to +15% of the numerical value, unless the term is
otherwise specifically defined in context.

The following abbreviations/acronyms have the following
meanings unless otherwise specified:
EC enzyme commission
CAZy carbohydrate active enzyme
w/v weight/volume
w/w weight/weight
v/v volume/volume
wt % weight percent
° C. degrees Centigrade
g or gm gram
μg microgram
mg milligram
kg kilogram
μL and μl microliter
mL and ml milliliter
mm millimeter
μm micrometer
mol mole
mmol millimole
M molar
mM millimolar
μM micromolar
nm nanometer
U unit
ppm parts per million hr and h hour
EtOH ethanol As used herein, the singular terms "a," "an," and "the"
include the plural reference unless the context clearly indi-
cates otherwise.

It is further noted that the claims may be drafted to
exclude any optional element. As such, this statement is
intended to serve as antecedent basis for use of such exclu-
sive terminology as "solely," "only" and the like in connec-
tion with the recitation of claim elements or use of a
"negative" limitation.

The term "comprising" and its cognates are used in their
inclusive sense; that is, equivalent to the term "including"
and its corresponding cognates. It is further noted that the
term "comprising," as used herein, means including, but not
limited to, the component(s) after the term "comprising."
The component(s) after the term "comprising" are required
or mandatory, but the composition comprising the compo-
nent(s) can further include other non-mandatory or optional
component(s).

It is also noted that the term "consisting essentially of," as
used herein refers to a composition wherein the component
(s) after the term is in the presence of other known compo-
nent(s) in a total amount that is less than 30% by weight of
the total composition and do not contribute to or interferes
with the actions or activities of the component(s).

It is also noted that the term "consisting of," as used
herein, means including, and limited to, the component(s)
after the term "consisting of." The component(s) after the
term "consisting of" are therefore required or mandatory,
and no other component(s) are present in the composition.

It is intended that every maximum numerical limitation
given throughout this specification includes every lower
numerical limitation, as if such lower numerical limitations
were expressly written herein. Every minimum numerical
limitation given throughout this specification will include
every higher numerical limitation, as if such higher numeri-
cal limitations were expressly written herein. Every numeri-
cal range given throughout this specification will include
every narrower numerical range that falls within such
broader numerical range, as if such narrower numerical
ranges were all expressly written herein.

Unless defined otherwise herein, all technical and scien-
tific terms used herein have the same meaning as commonly
understood by one of ordinary skill in the art to which this
invention pertains.

Other definitions of terms may appear throughout the
specification.

II. Polypeptides Having Glucoamylase Activity

In a first aspect, the present invention relates to polypep-
tides comprising an amino acid sequence having preferably
at least 70%, at least 75%, at least 80%, at least 85%, at least
90%, at least 92%, at least 93%, at least 94%, at least 95%,
at least 96%, at least 97%, at least 98%, and even at least
99%, amino acid sequence identity to the polypeptide of
SEQ ID NO: 61 or SEQ ID NO:142 and having glucoamy-
lase activity. In another aspect, provided herein are poly-
peptides comprising an amino acid sequence having prefer-
ably at least 70%, at least 75%, at least 80%, at least 85%,
at least 90%, at least 92%, at least 93%, at least 94%, at least
95%, at least 96%, at least 97%, at least 98%, and even at
least 99%, amino acid sequence identity to a polypeptide
comprising amino acid position 20-468 of SEQ ID NO:142,
amino acid position 21-468 of SEQ ID NO:142, amino acid
position 22-468 of SEQ ID NO:142, amino acid position 23-468 of SEQ ID NO:142, amino acid position 24-468 of SEQ ID NO:142, or amino acid position 25-468 of SEQ ID NO:142.

In some embodiments, the polypeptide comprises an amino acid sequence having at least 70% but less than 100% sequence identity to the polypeptide of SEQ ID NO: 61 or SEQ ID NO:142. In other embodiments, the polypeptide comprises an amino acid sequence having at least 70% but less than 100% sequence identity to the polypeptide comprising amino acid position 20-468 of SEQ ID NO:142, amino acid position 21-468 of SEQ ID NO:142, amino acid position 22-468 of SEQ ID NO:142, amino acid position 23-468 of SEQ ID NO:142, amino acid position 24-468 of SEQ ID NO:142, or amino acid position 25-468 of SEQ ID NO:142. In some embodiments, the polypeptide is non-naturally occurring (i.e. does not occur in nature and is a product of human ingenuity).

In some embodiments, the polypeptides of the present invention are homologous polypeptides comprising amino acid sequences that differ by no more than ten amino acids, no more than nine amino acids, no more than eight amino acids, no more than seven amino acids, no more than six amino acids no more than five amino acids, no more than four amino acids, no more than three amino acids, no more than two amino acids, and even no more than one amino acid from the polypeptide of SEQ ID NO: 61, the polypeptide of SEQ ID NO:142, the polypeptide comprising amino acid position 20-468 of SEQ ID NO:142, the polypeptide comprising amino acid position 21-468 of SEQ ID NO:142, the polypeptide comprising amino acid position 22-468 of SEQ ID NO:142, the polypeptide comprising amino acid position 23-468 of SEQ ID NO:142, the polypeptide comprising amino acid position 24-468 of SEQ ID NO:142, or the polypeptide comprising amino acid position 25-468 of SEQ ID NO:142.

In some embodiments, the polypeptides of the present invention are the catalytic regions comprising amino acids 18 to 449 of SEQ ID NO: 61, predicted by ClustalX Hypertext Transfer Protocol Secure://world wide web.ncbi.nlm.nih.gov/pubmed/17846036.

In some embodiments, the polypeptides of the present invention have pullulan-hydrolyzing activity.

In a second aspect, the present glucoamylases disclosed herein comprise conservative substitution(s) of one or several amino acid residues relative to the amino acid sequence of SEQ ID NO: 61, the polypeptide of SEQ ID NO:142, the polypeptide comprising amino acid position 20-468 of SEQ ID NO: 142, the polypeptide comprising amino acid position 21-468 of SEQ ID NO:142, the polypeptide comprising amino acid position 22468 of SEQ ID NO:142, the polypeptide comprising amino acid position 23468 of SEQ ID NO: 142, the polypeptide comprising amino acid position 24-468 of SEQ ID NO: 142, or the polypeptide comprising amino acid position 25-468 of SEQ ID NO: 142. Exemplary conservative amino acid substitutions are listed below. Some conservative substitutions (i.e., mutations) can be produced by genetic manipulation while others are produced by introducing synthetic amino acids into a polypeptide by other means.

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |

-continued

| For Amino Acid | Code | Replace with any of |
|---|---|---|
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the polypeptides of the present invention are the variants of the polypeptide of SEQ ID NO: 61, the polypeptide of SEQ ID NO:142, the polypeptide comprising amino acid position 20-468 of SEQ ID NO:142, the polypeptide comprising amino acid position 21-468 of SEQ ID NO: 142, the polypeptide comprising amino acid position 22-468 of SEQ ID NO:142, the polypeptide comprising amino acid position 23-468 of SEQ ID NO:142, the polypeptide comprising amino acid position 24-468 of SEQ ID NO:142, or the polypeptide comprising amino acid position 25-468 of SEQ ID NO:142, or a fragment thereof having glucoamylase activity. The variant glucoamylase comprises a deletion, substitution, insertion, or addition of one or a few amino acid residues relative to the amino acid sequence of SEQ ID NO: 61 or SEQ ID NO:142 or a homologous sequence thereof. In all cases, the expression "one or a few amino acid residues" refers to 10 or less, i.e., 1, 2, 3, 4, 5, 6, 7, 8, 9, or 10, amino acid residues. The amino acid substitutions, deletions and/or insertions of the polypeptide of SEQ ID NO: 61, the polypeptide of SEQ ID NO:142, the polypeptide comprising amino acid position 20-468 of SEQ ID NO:142, the polypeptide comprising amino acid position 21-468 of SEQ ID NO:142, the polypeptide comprising amino acid position 22-468 of SEQ ID NO:142, the polypeptide comprising amino acid position 23-468 of SEQ ID NO:142, the polypeptide comprising amino acid position 24-468 of SEQ ID NO:142, or the polypeptide comprising amino acid position 25-468 of SEQ ID NO:142 can be at most 10, at most 9, at most 8, at most 7, at most 6, at most 5, at most 4, at most 3, at most 2, and even at most 1.

In some embodiments, the variant alteration comprises or consists of a substitution at a position corresponding to position 102 of the polypeptide of SEQ ID NO: 61. In some embodiments, the amino acid at a position corresponding to position 102 of the polypeptide of SEQ ID NO: 61 is substituted with Ala, Arg, Asn, Asp, Cys, Gln, Glu, Gly, His, Leu, Ile, Lys, Met, Phe, Pro, Thr, Trp, Tyr, or Val, preferably with Pro. In some embodiments, the variant alteration comprises or consists of the substitution S102P of the polypeptide of SEQ ID NO: 61. In a further embodiment, the variant comprises or consists of the amino acid sequence of SEQ ID NO:104 or SEQ ID NO:141.

In some embodiments, the variant alteration comprises or consists of a substitution at a position corresponding to position 66 of the polypeptide of SEQ ID NO: 61. In some embodiments, the amino acid at a position corresponding to position 85 of the polypeptide of SEQ ID NO: 61 is substituted with Ala, Arg, Asn, Asp, Cys, Gln, Glu, Gly, His, Leu, Ile, Lys, Met, Phe, Pro, Ser, Thr, Trp, or Tyr. In some embodiments, the variant alteration comprises or consists of the substitution V66A of the polypeptide of SEQ ID NO: 61.

In another embodiment, the variant alteration comprises or consists of a substitution at a position corresponding to positions 66 and position 102 of the polypeptide of SEQ ID NO: 61. In some embodiments, the variant alteration comprises or consists of the substitution V66A and S102P of the polypeptide of SEQ ID NO: 61. In a further embodiment, the variant comprises or consists of the amino acid sequence of SEQ ID NO:140.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30. 10832-10837; U.S. Pat. No. 5,223,409; WO 92/06204), and region-directed mutagenesis (Derbyshire et al., 1986, Gene 46: 145; Ner et al., 1988, DNA 7: 127).

III. Production of Glucoamylase

The present glucoamylases can be produced in host cells, for example, by secretion or intracellular expression. A cultured cell material (e.g., a whole-cell broth) comprising a glucoamylase can be obtained following secretion of the glucoamylase into the cell medium. Optionally, the glucoamylase can be isolated from the host cells, or even isolated from the cell broth, depending on the desired purity of the final glucoamylase. A gene encoding a glucoamylase can be cloned and expressed according to methods well known in the art. Suitable host cells include bacterial, fungal (including yeast and filamentous fungi), and plant cells (including algae). Particularly useful host cells include *Aspergillus niger, Aspergillus oryzae, Trichoderma reesi*, or *Myceliophthora thermophila*. Other host cells include bacterial cells, e.g., *Bacillus subtilis* or *B. licheniformis*, as well as *Streptomyces*. A suitable yeast host organism can be selected from *Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism.

Additionally, the host may express one or more accessory enzymes, proteins, peptides. These may benefit liquefaction, saccharification, fermentation, SSF, and downstream processes. Furthermore, the host cell may produce ethanol and other biochemicals or biomaterials in addition to enzymes used to digest the various feedstock(s). Such host cells may be useful for fermentation or simultaneous saccharification and fermentation processes to reduce or eliminate the need to add enzymes.

A. Vectors

A DNA construct comprising a nucleic acid encoding a glucoamylase polypeptide can be constructed such that it is suitable to be expressed in a host cell. Because of the known degeneracy in the genetic code, different polynucleotides that encode an identical amino acid sequence can be designed and made with routine skill. It is also known that, depending on the desired host cells, codon optimization may be required prior to attempting expression.

A polynucleotide encoding a glucoamylase polypeptide of the present disclosure can be incorporated into a vector. Vectors can be transferred to a host cell using known transformation techniques, such as those disclosed below.

A suitable vector may be one that can be transformed into and/or replicated within a host cell. For example, a vector comprising a nucleic acid encoding a glucoamylase polypeptide of the present disclosure can be transformed and/or replicated in a bacterial host cell as a means of propagating and amplifying the vector. The vector may also be suitably transformed into an expression host, such that the encoding polynucleotide is expressed as a functional glucoamylase enzyme.

A representative useful vector is pTrex3gM (see, Published US Patent Application 20130323798) and pTTT (see, Published US Patent Application 20110020899), which can be inserted into genome of host. The vectors pTrex3gM and pTTT can both be modified with routine skill such that they comprise and express a polynucleotide encoding a glucoamylase polypeptide of the invention.

An expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the glucoamylase to a host cell organelle such as a peroxisome, or to a particular host cell compartment. For expression under the direction of control sequences, the nucleic acid sequence of the glucoamylase is operably linked to the control sequences in proper manner with respect to expression.

A polynucleotide encoding a glucoamylase polypeptide of the present invention can be operably linked to a promoter, which allows transcription in the host cell. The promoter may be any DNA sequence that shows transcriptional activity in the host cell of choice and may be derived from genes encoding proteins either homologous or heterologous to the host cell. Examples of promoters for directing the transcription of the DNA sequence encoding a glucoamylase, especially in a bacterial host, include the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xylA and xylB genes, and the like.

For transcription in a fungal host, examples of useful promoters include those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* glucoamylase, *Rhizomucor miehei* lipase, *Aspergillus oryzae* alkaline protease, *Aspergillus oryzae* triose phosphate isomerase, *Aspergillus nidulans* acetamidase and the like.

When a gene encoding a glucoamylase is expressed in a bacterial species such as an *E. coli*, a suitable promoter can be selected, for example, from a bacteriophage promoter including a T7 promoter and a phage lambda promoter. Along these lines, examples of suitable promoters for the expression in a yeast species include but are not limited to the Gal 1 and Gal 10 promoters of *Saccharomyces cerevisiae* and the *Pichia pastoris* AOX1 or AOX2 promoters. Expression in filamentous fungal host cells often involves cbh1, which is an endogenous, inducible promoter from *T. reesei*. See Liu et al. (2008) *Acta Biochim. Biophys. Sin (Shanghai)* 40(2): 158-65.

The coding sequence can be operably linked to a signal sequence. The DNA encoding the signal sequence may be a DNA sequence naturally associated with the glucoamylase gene of interest to be expressed, or may be from a different genus or species as the glucoamylase. A signal sequence and a promoter sequence comprising a DNA construct or vector can be introduced into a fungal host cell and can be derived from the same source. For example, the signal sequence may be the *Trichoderma reesei* cbh1 signal sequence, which is operably linked to a cbh1 promoter.

An expression vector may also comprise a suitable transcription terminator and, in eukaryotes, polyadenylation sequences operably linked to the DNA sequence encoding a glucoamylase. Termination and polyadenylation sequences may suitably be derived from the same sources as the promoter.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as andS, argB, niaD and xxsC, a marker giving rise to hygromycin resistance, or the selection may be accomplished by co-transformation, such as known in the art. See e.g., Published International PCT Application WO 91/17243.

B. Transformation and Culture of Host Cells

An isolated cell, either comprising a DNA construct or an expression vector, is advantageously used as a host cell in the recombinant production of a glucoamylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens. Bacillus coagulans, Bacillus lautus, Bacillus megaterium,* and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species.

Suitable host organisms among filamentous fungi include species of *Aspergillus*, e.g., *Aspergillus niger, Aspergillus oryzae. Aspergillus tubigensis. Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A glucoamylase expressed by a fungal host cell can be glycosylated, i.e., will comprise a glycosyl moiety. The glycosylation pattern can be the same or different as present in the wild-type glucoamylase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

General transformation techniques are known in the art. See, e.g., Sambrook et al. (2001), *supra*. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding a glucoamylase is stably integrated into a host cell chromosome. Transformants are then selected and purified by known techniques.

C. Expression and Fermentation

A method of producing a glucoamylase may comprise cultivating a host cell under conditions conducive to the production of the enzyme and recovering the enzyme from the cells and/or culture medium.

The medium used to cultivate the cells may be any conventional medium suitable for growing the host cell and obtaining expression of a glucoamylase polypeptide. Suitable media and media components are available from commercial suppliers or may be prepared according to published recipes (e.g., as described in catalogues of the American Type Culture Collection).

Any of the fermentation methods well known in the art can suitably used to ferment the transformed or the derivative fungal strain as described above. In some embodiments, fungal cells are grown under batch or continuous fermentation conditions.

D. Methods for Enriching and Purification

Separation and concentration techniques are known in the art and conventional methods can be used to prepare a concentrated solution or broth comprising a glucoamylase polypeptide of the invention.

After fermentation, a fermentation broth is obtained, the microbial cells and various suspended solids, including residual raw fermentation materials, are removed by conventional separation techniques in order to obtain a glucoamylase solution. Filtration, centrifugation, microfiltration, rotary vacuum drum filtration, ultrafiltration, centrifugation followed by ultra-filtration, extraction, or chromatography, or the like, are generally used.

It may at times be desirable to concentrate a solution or broth comprising a glucoamylase polypeptide to optimize recovery. Use of un-concentrated solutions or broth would typically increase incubation time in order to collect the enriched or purified enzyme precipitate.

V. Compositions

The present invention also relates to compositions comprising a polypeptide and/or a starch substrate. In some embodiments, a polypeptide comprising an amino acid sequence that is at least about 80%, at least about 85%, at least about 90%, at least about 95%, at least about 96%, at least about 97%, at least about 98%, at least about 99%, identical to that of SEQ ID NO: 61 can also be used in the enzyme composition. Preferably, the compositions are formulated to provide desirable characteristics such as low color, low odor and acceptable storage stability at a temperature of about 4-40° C. and a pH of about 3-7.

The composition may comprise a polypeptide of the present invention as the major enzymatic component. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, alpha-glucosidase, beta-glucosidase, beta-amylase, isoamylase, haloperoxidase, invertase, laccase, lipase, mannosidase, oxidase, pectinolytic enzyme, peptidoglutaminase, peroxidase, phytase, polyphenoloxidase, proteolytic enzyme, pullulanase, ribonuclease, transglutaminase, xylanase or a combination thereof, which may be added in effective amounts well known to the person skilled in the art.

The polypeptide compositions may be prepared in accordance with methods known in the art and may be in the form of a liquid or a dry composition. For instance, the compositions comprising the present glucoamylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc, for example, endogenous plant (including algal) enzymes, residual enzymes from a prior processing step, and the like. The polypeptide to be included in the composition may be stabilized in accordance with methods known in the art.

The composition may be cells expressing the polypeptide, including cells capable of producing a product from fermentation. Such cells may be provided in a liquid or in dry form along with suitable stabilizers. Such cells may further express additional polypeptides, such as those mentioned, above.

Examples are given below of preferred uses of the polypeptides or compositions of the invention. The dosage of the polypeptide composition of the invention and other conditions under which the composition is used may be determined on the basis of methods known in the art.

Above composition is suitable for use in liquefaction, saccharification, and/or fermentation process, preferably in starch conversion, especially for producing syrup and fermentation products, such as ethanol. The composition is also suitable for use in animal nutrition and fermented beverage.

V. Use

The present invention is also directed to use of a polypeptide or composition of the present invention in a liquefaction, a saccharification and/or a fermentation process. The polypeptide or composition may be used in a single process, for example, in a liquefaction process, a saccharification process, or a fermentation process. The polypeptide or composition may also be used in a combination of processes for example in a liquefaction and saccharification process, in a liquefaction and fermentation process, or in a saccharification and fermentation process, preferably in relation to starch conversion.

A. Saccharification

The liquefied starch may be saccharified into a syrup rich in lower DP (e.g., DP1+DP2) saccharides, using alpha-amylases and glucoamylases, optionally in the presence of another enzyme(s). The exact composition of the products of saccharification depends on the combination of enzymes used, as well as the type of starch processed. Advantageously, the syrup obtainable using the provided glucoamylases may contain a weight percent of DP1 of the total oligosaccharides in the saccharified starch exceeding 90%, e.g., 90%-98% or 95%-97%. The weight percent of DP2 in the saccharified starch may be as low as possible, about less than 3%, e.g., 0-3% or 0-2.8%.

Whereas liquefaction is generally run as a continuous process, saccharification is often conducted as a batch process. Saccharification conditions are dependent upon the nature of the liquefact and type of enzymes available. In some cases, a saccharification process may involve temperatures of about 60-65° C. and a pH of about 4.0-4.5, e.g., pH 4.3. Saccharification may be performed, for example, at a temperature between about 40° C., about 50° C., or about 55° C. to about 60° C. or about 65° C., necessitating cooling of the Liquefact. The pH may also be adjusted as needed. Saccharification is normally conducted in stirred tanks, which may take several hours to fill or empty. Enzymes typically are added either at a fixed ratio to dried solids, as the tanks are filled, or added as a single dose at the commencement of the filling stage. A saccharification reaction to make a syrup typically is run over about 24-72 hours, for example, 24-48 hours. A pre-saccharification can be added before saccharification in a simultaneous saccharification and fermentation (SSF), for typically 40-90 minutes at a temperature between 30-65° C., typically about 60° C.

B. Raw Starch Hydrolysis

The present invention provides a use of the glucoamylase of the invention for producing glucoses and the like from raw starch or granular starch. Generally, glucoamylase of the present invention either alone or in the presence of an alpha-amylase can be used in raw starch hydrolysis (RSH) or granular starch hydrolysis (GSH) process for producing desired sugars and fermentation products. The granular starch is solubilized by enzymatic hydrolysis below the gelatinization temperature. Such "low-temperature" systems (known also as "no-cook" or "cold-cook") have been reported to be able to process higher concentrations of dry solids than conventional systems (e.g., up to 45%).

A "raw starch hydrolysis" process (RSH) differs from conventional starch treatment processes, including sequentially or simultaneously saccharifying and fermenting granular starch at or below the gelatinization temperature of the starch substrate typically in the presence of at least an glucoamylase and/or amylase.

The glucoamylase of the invention may also be used in combination with an enzyme that hydrolyzes only alpha-(1, 6)-glucosidic bonds in molecules comprising at least four glucosyl residues. Preferably, the glucoamylase of the invention is used in combination with pullulanase or isoamylase. The use of isoamylase and pullulanase for debranching of starch, the molecular properties of the enzymes, and the potential use of the enzymes together with glucoamylase is described in G. M. A. van Beynum et al., Starch Conversion Technology, Marcel Dekker, New York, 1985, 101-142.

C. Fermentation

The soluble starch hydrolysate, particularly a glucose rich syrup, can be fermented by contacting the starch hydrolysate with a fermenting organism typically at a temperature around 32° C., such as from 30° C. to 35° C. "Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include yeast, such as *Saccharomyces cerevisiae* and bacteria, e.g., *Zymomonas mobilis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27:1049-56. Yeast that can be used for alcohol production include, but are not limited to, *Saccharomyces* spp., including *S. cerevisiae*, as well as *Kluyveromyces*, Lachancea and *Schizosaccharomyces* spp. Numerous yeast strains are commercially available, many of which have been selected or genetically engineered for desired characteristics, such as high alcohol production, rapid growth rate, and the like. The temperature and pH of the fermentation will depend upon the fermenting organism. Microorganisms that produce other metabolites, such as citric acid and lactic acid, by fermentation are also known in the art. See, e.g., Papagianni (2007) *Biotechnol. Adv.* 25:244-63; John et al. (2009) Biotechnol. Adv. 27:145-52.

The saccharification and fermentation processes may be carried out as an SSF process. An SSF process can be conducted with fungal cells that express and secrete glucoamylase continuously throughout SSF. The fungal cells expressing glucoamylase also can be the fermenting microorganism, e.g., an ethanologenic microorganism. Ethanol production thus can be carried out using a fungal cell that expresses sufficient glucoamylase so that less or no enzyme has to be added exogenously. The fungal host cell can be selected from an appropriately engineered fungal strains. Fungal host cells that express and secrete other enzymes, in addition to glucoamylase, also can be used. Such cells may express amylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzymes. Fermentation may be followed by subsequent recovery of ethanol.

26

D. Fermentation Products

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, propylene glycol, butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones.

In a preferred aspect the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred fermentation processes used include alcohol fermentation processes, which are well known in the art. Preferred fermentation processes are anaerobic fermentation processes, which are well known in the art.

E. Brewing

Processes for making beer are well known in the art. See, e.g., Wolfgang Kunze (2004) "Technology Brewing and Malting" Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer.

The brewing composition comprising a glucoamylase, in combination with an amylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

F. Animal Nutrition

The glucoamylases and the compositions described herein can be used as a feed additive for animals to increase starch digestibility. Describe herein is a method for increasing starch digestibility in an animal.

The term "animal" refers to any organism belonging to the kingdom Animalia and includes, without limitation, mammals (excluding humans), non-human animals, domestic animals, livestock, farm animals, zoo animals, breeding stock and the like. For example, there can be mentioned all non-ruminant and ruminant animals. In an embodiment, the animal is a non-ruminant, i.e., a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal is a ruminant animal including, but not limited to, cattle, young calves, goats, sheep, giraffes, bison, moose, elk, yaks, water buffalo, deer, camels, alpacas, llamas, antelope, pronghorn and nilgai.

The terms "animal feed", "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) byproducts from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

The digestibility of starch in feeds is highly variable and dependent on a number of factors including the physical structure of both the starch and feed matrix. It has been found that starch digestibility in an animal's diet can be improved by the use of at least one glucoamylase as a feed additive.

When used as, or in the preparation of, a feed, such as functional feed, the enzyme or feed additive composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

It is also possible that at least one glucoamylase (or an enzyme composition comprising at least one glucoamylase as described herein) described herein can be homogenized to produce a powder. The powder may be mixed with other components known in the art. Optionally, the feedstuff may also contain additional minerals such as, for example, calcium and/or additional vitamins. In some embodiments, the feedstuff is a corn soybean meal mix.

In an alternative preferred embodiment, an enzyme composition comprising at least one glucoamylase can be formulated to granules as described in WO2007/044968 (referred to as TPT granules) or WO1997/016076 or WO1992/012645 incorporated herein by reference. "TPT" means Thermo Protection Technology. When the feed additive composition is formulated into granules, the granules comprise a hydrated barrier salt coated over the protein core. The advantage of such salt coating is improved thermotolerance, improved storage stability and protection against other feed additives otherwise having adverse effect on the enzyme. Preferably, the salt used for the salt coating has a water activity greater than 0.25 or constant humidity greater than 60% at 20° C. In some embodiments, the salt coating comprises $Na_2SO_4$.

Alternatively, the composition is in a liquid formulation suitable for consumption preferably such liquid consumption contains one or more of the following: a buffer, salt, sorbitol and/or glycerol.

Any of the glucoamylases described herein for use as a feed additive may be used alone or in combination with at least one direct fed microbial. Categories of DFMs include *Bacillus*, Lactic Acid Bacteria and Yeasts. Further, any of the glucoamylases described herein for use as a feed additive may be used alone or in combination with at least one essential oil, for example cinnamaldehyde and/or thymol. Still further, any of the glucoamylases described herein for use as a feed additive may be used alone or in combination with at least one additional enzyme. Examples of such enzymes include, without limitation, phytases, xylanases, proteases, amylases, glucanases, or other glucoamylases.

Also disclosed is a method for improving the nutritional value of an animal feed, wherein an effective amount of any of the glucoamylases described herein can be added to animal feed.

The phrase, an "effective amount" as used herein, refers to the amount of an active agent (such as any of the glucoamylase polypeptides disclosed herein) required to confer improved performance on an animal on one or more metrics, either alone or in combination with one or more other active agents (such as, without limitation, one or more additional enzyme(s), one or more DFM(s), one or more essential oils, etc.).

The term "animal performance" as used herein may be determined by any metric such as, without limitation, the feed efficiency and/or weight gain of the animal and/or by the feed conversion ratio and/or by the digestibility of a nutrient in a feed and/or digestible energy or metabolizable energy in a feed and/or by animals' ability to avoid the negative effects of diseases or by the immune response of the subject.

Animal performance characteristics may include but are not limited to: body weight; weight gain; mass; body fat percentage; height; body fat distribution; growth; growth rate; egg size; egg weight; egg mass; egg laying rate; mineral absorption; mineral excretion, mineral retention; bone density; bone strength; feed conversion rate (FCR): average daily feed intake (ADFI); Average daily gain (ADG) retention and/or a secretion of any one or more of copper, sodium, phosphorous, nitrogen and calcium; amino acid retention or absorption; mineralization, bone mineralization carcass yield and carcass quality.

By "improved animal performance on one or more metric" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed comprising the feed additive composition described herein as compared to a feed which does not comprise said feed additive composition.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1

Identification of a Mucorales-Clade Glucoamylase Enzymes

A search for glucoamylase enzymes of the Zygomycetes phylum was performed by scanning annotated protein sequences of the Zygomycetes phylum using dbCAN (Yin et al (2012) "dbCAN: a web resource for automated carbohydrate-active enzyme annotation. *Nucleic Acids Research* 40:W4450-451) to identify all GH15 proteins based on CAZY family analysis. A number of genes were identified in the genomes of Mucorales order organisms and the sequences were further analyzed. Genes encoding the Mucorales-clade glucoamylases were identified from the sources listed on Table 1, and are assigned SEQ ID NOs shown on Table 1.

TABLE 1

Sequence source and SEQ ID NOs for *Mucorales*-clade glucoamylases evaluated in this study.

| Sample ID | SEQ ID NO | Gene sequence source *[mycocosm.jgi.doe.gov/cgi-bin/dispGeneModel?db] | Organism |
|---|---|---|---|
| SvaGA1 | 1 | *scaffold_1856: 13863-15495, protein ID: 4356 | *Saksenaea vasiformis* B4078 |
| BciGA1 | 2 | *scaffold_261: 3283-5849, protein ID: 261628 | *Backusella circina* FSU 941 |
| BciGA2 | 3 | *scaffold_67: 52720-55269, protein ID: 183741 | *Backusella circina* FSU 941 |
| BpoGA1 | 4 | *scaffold_1: 5688666-5690969, protein ID: 552608 | *Benjaminiella poitrasii* RSA 903 |
| CcuGA1 | 5 | *scaffold_32: 142308-144412, protein ID: 565216 | *Choanephora cucurbitarum* NRRL 2744 |
| RstGA1 | 6 | world wide web .ncbi.nlm.nih.gov/protein/RCI05434 | *Rhizopus stolonifer* |
| MciGA5 | 7 | world wide web ncbi.nlm.nih.gov/protein/EPB90436 | *Mucor circinelloides f. circinelloides* 1006PhL |
| DelGA1 | 8 | *scaffold_14: 156040-158505, protein ID: 307234 | *Dichotomocladium elegans* RSA 919 |
| FspGA3 | 9 | *scaffold_47: 22656-25504, protein ID: 631220 | *Fennellomyces* sp. T-0311 |
| GpeGA1 | 10 | *scaffold_27: 154515-156499, protein ID: 572732 | *Gilbertella persicaria* var. *persicaria* CBS 190.32-T |
| MciGA3 | 11 | *scaffold_04: 2553725-2555899, protein ID: 156167 | *Mucor circinelloides* CBS277.49 |
| CumGA1 | 12 | *scaffold_36: 443143-446327, protein ID: 486055 | *Circinella umbellata* NRRL 1351 |
| McoGA1 | 13 | *scaffold_20: 482726-484980, protein ID: 382429 | *Mucor cordense* RSA 1222 |
| ParGA1 | 14 | scaffold_11: 462211-464919, protein ID: 436871 1 | *Phascolomyces articulosus* |
| RmiGA1 | 15 | *scaffold_21: 172464-174631, protein ID: 230588 | *Rhizopus microsporus* var. *microsporus* ATCC 52813 |
| SfGA2 | 16 | *scaffold_162: 2818-4664, protein ID: 1870629 | *Spinellus fusiger* NRRL 22323 |
| SraGA1 | 17 | *scaffold_4: 869438-871839, protein ID: 545732 | *Syncephalastrum racemosum* NRRL 2496 |
| SraGA3 | 18 | *scaffold_9: 632087-633913, protein ID: 558396 | *Syncephalastrum racemosum* NRRL 2496 |
| TinGA1 | 19 | world wide web.ncbi.nlm.nih.gov/nuccore/JSYX01000005 | *Thermomucor indicae-seudaticae* HACC 243 |
| ZmeGA1 | 20 | *scaffold_35: 220637-223894, protein ID: 822592 | *Zychaea mexicana* RSA 1403 |

The N-terminal signal peptides were predicted by SignalP software version 4.0 (Nordahl Petersen et al. (2011) *Nature Methods*, 8:785-786). The genes encoding the various Mucorales-clade glucoamylases were codon modified for expression in *Trichoderma reesei*.

TABLE 2

Sequences of *Mucorales*-clade glucoamylases evaluated in this study. SEQ ID NOs for the nucleotide sequences of expression cassettes, predicted signal peptide and predicted mature polypeptide.

| | SEQ ID Nos | | |
|---|---|---|---|
| Sample ID | codon modified sequences used as expression cassettes | predicted signal peptide | predicted mature protein sequence |
| SvaGA1 | SEQ ID NO: 21 | SEQ ID NO: 41 | SEQ ID NO: 61 |
| BciGA1 | SEQ ID NO: 22 | SEQ ID NO: 42 | SEQ ID NO: 62 |
| BciGA2 | SEQ ID NO: 23 | SEQ ID NO: 43 | SEQ ID NO: 63 |
| BpoGA1 | SEQ ID NO: 24 | SEQ ID NO: 44 | SEQ ID NO: 64 |
| CcuGA1 | SEQ ID NO: 25 | SEQ ID NO: 45 | SEQ ID NO: 65 |
| RstGA1 | SEQ ID NO: 26 | SEQ ID NO: 46 | SEQ ID NO: 66 |
| MciGA5 | SEQ ID NO: 27 | SEQ ID NO: 47 | SEQ ID NO: 67 |
| DelGA1 | SEQ ID NO: 28 | SEQ ID NO: 48 | SEQ ID NO: 68 |
| FspGA3 | SEQ ID NO: 29 | SEQ ID NO: 49 | SEQ ID NO: 69 |
| GpeGA1 | SEQ ID NO: 30 | SEQ ID NO: 50 | SEQ ID NO: 70 |
| MciGA3 | SEQ ID NO: 31 | SEQ ID NO: 51 | SEQ ID NO: 71 |
| CumGA1 | SEQ ID NO: 32 | SEQ ID NO: 52 | SEQ ID NO: 72 |
| McoGA1 | SEQ ID NO: 33 | SEQ ID NO: 53 | SEQ ID NO: 73 |
| ParGA1 | SEQ ID NO: 34 | SEQ ID NO: 54 | SEQ ID NO: 74 |
| RmiGA1 | SEQ ID NO: 35 | SEQ ID NO: 55 | SEQ ID NO: 75 |
| SfuGA2 | SEQ ID NO: 36 | SEQ ID NO: 56 | SEQ ID NO: 76 |
| SraGA1 | SEQ ID NO: 37 | SEQ ID NO: 57 | SEQ ID NO: 77 |
| SraGA3 | SEQ ID NO: 38 | SEQ ID NO: 58 | SEQ ID NO: 78 |
| TinGA1 | SEQ ID NO: 39 | SEQ ID NO: 59 | SEQ ID NO: 79 |
| ZmeGA1 | SEQ ID NO: 40 | SEQ ID NO: 60 | SEQ ID NO: 80 |

Example 2

Expression of Mucorales-Clade Glucoamylases in *Trichoderma reesei*

The polynucleotides (codon modified sequences used as expression cassettes) encoding the Mucorales-clade glucoamylases genes (SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40) were synthesized by Generay (Generay Biotech Co., Ltd, Shanghai, China) and inserted into the pGX256 expression vector, a derivative vector from pTTT (see, Published US Patent Application 20110020899).

A polynucleotide encoding a variant of SvaGA1 glucoamylase (SEQ ID NO: 61), where a codon change introduced a mutation at amino acid position 102 of Pro in place of Ser (SvaGA1v2, S102P) was constructed. The expression cassette encoding SvaGA1v2 was inserted into the pGX256 (as described above).

All plasmids were transformed into a suitable *Trichoderma reesei* strain using protoplast transformation (Te'o et al., J. Microbiol. Methods 51:393-99, 2002). The transformants were selected and fermented by the methods described in WO 2016/138315. Supernatants from these cultures were used to confirm the protein expression by SDS-PAGE analysis.

Fungal cell cultures were grown in a defined medium as described by Lv et al (2012) in "Construction of teo vectors for gene expression in *Trichoderma reesei*". Plasmids 67:67-71. Clarified culture broth were collected after 96 hours by centrifugation. The Mucorales-clade glucoamylases were purified by methods known in the art. The column chromatography fractions containing the target protein were pooled, concentrated and equilibrated to 20 mM sodium acetate pH 5.0, 150 mM sodium chloride using an Amicon Ultra-15 device with 10 K MWCO. The purified samples were approximately 99% pure (by SDS-PAGE analysis) and were stored in 40% glycerol at −80° C. until use.

Example 3

Evaluation of SvaGA1 and SvaGA1v2 Glucoamylases in Saccharification at pH 4.5, 60° C.

The saccharification performance of SvaGA1 and the SvaGA1v2 variant were evaluated at pH 4.5 and 60° C. A sample of GC126 (a DuPont/IFF product) pre-treated corn starch liquefact (prepared at 38% ds, pH 3.3) was used as a starting substrate. The performance of the glucoamylases was tested at the dosage of 30 μg/gds. The glucoamylase *Gloeophyllum trabeum* glucoamylase (GtGA) from EXTENDA® XTRA (a Novozymes product) was included for comparison. For this evaluation, the pullulanase OPTI-MAX™ L 1000 (a DuPont product) was dosed at 10 μg/gds, and the alpha-amylase *Aspergillus kawachii* amylase (AkAA, described in WO2013169645, incorporated by reference herein) was dosed at 5 μg/gds for each incubation. The corn starch liquefact substrate and the enzymes (glucoamylase, alpha-amylase and pullulanase) were incubated at pH 4.5, 60° C. for 48 and 65 hours, respectively. All the incubations were quenched by heating at 100° C. for 15 min. Aliquots were removed and diluted 40-fold in 5 mM $H_2SO_4$ for product analysis by HPLC using an Agilent 1200 series system with a Phenomenex Rezex-RFQ Fast Fruit column (cat #OOD-0223-KO), run at 80° C. 10 μL samples were loaded on the column and separated with an isocratic gradient of 5 mM $H_2SO_4$ as the mobile phase at a flow rate of 1.0 mL/min. The oligosaccharide products were detected using a refractive index detector, and the standards were run to determine elution times of each DP(n) sugar of interest (DP3+, DP3, DP2 and DP1). The values shown in Table 3 reflect the peak area percentages of each DP(n) as a fraction of the total DP1 to DP3+. The results of DP1 generation and DP3+ hydrolysis by SvaGA1 and SvaGA1v2 glucoamylases outperformed those of the reference GtGA enzyme at pH 4.5, 60° C.

TABLE 3

Sugar composition results for glucoamylases incubated with corn starch liquefact at pH 4.5, 60° C.

| Incubation | | Percent (%) Dextrose Equivalent (DP) detected | | | |
|---|---|---|---|---|---|
| time | Sample | DP3+ | DP3 | DP2 | DP1 |
| 48 h | SvaGA1 | 0.4 | 1.2 | 2.7 | 95.7 |
| | SvaGA1v2 | 0.4 | 1.2 | 2.7 | 95.7 |
| | GGA | 0.7 | 1.5 | 3.7 | 94.0 |
| 65 h | SvaGA1 | 0.3 | 1.1 | 2.7 | 95.9 |
| | SvaGA1v2 | 0.3 | 1.0 | 2.9 | 95.8 |
| | GtGA | 0.4 | 1.3 | 2.8 | 95.4 |

Example 4

Specific Activities of Mucorales-Clade Glucoamylase Enzymes on Soluble Starch Glucoamylase specific activity was assayed based on the release of glucose from soluble starch using the coupled glucose oxidase/peroxidase (GOX/HRP) and 2,2'-Azino-bis 3-ethylbenzothiazoline-6-sulfonic acid (ABTS) method (*Anal. Biochem.* 105 (1980), 389-397). Substrate solutions were prepared by mixing 9 mL of soluble starch (1% in water, w/w) and 1 mL of 0.5 M pH 5.0 sodium acetate buffer in a 15-mL conical tube. Coupled enzyme (GOX/HRP) solution with ABTS was prepared in 50 mM sodium acetate buffer (pH 5.0), with the final concentrations of 2.74 mg/mL ABTS, 0.1 U/mL HRP, and 1 U/mL GOX. Serial dilutions of each glucoamylase sample to be evaluated and a glucose standard were prepared in purified water. Each glucoamylase sample (10 µL) was transferred into a new microtiter plate (Corning 3641) containing 90 µL of substrate solution preincubated at 50° C. for 5 min at 600 rpm. The reactions were carried out at 50° C. for 10 min with shaking (600 rpm) in a thermomixer (Eppendorf), 10 µL of reaction mixtures as well as 10 µL of serial dilutions of glucose standard were quickly transferred to new microtiter plates (Corning 3641), respectively, followed by the addition of 100 µL of ABTS/ GOX/HRP solution. Absorbance at 405 nm was immediately measured at 11 seconds intervals for 5 min using a SoftMax Pro plate reader (Molecular Device). The output was the reaction rate, Vo, for each enzyme concentration. Linear regression was used to determine the slope of the plot Vo vs. enzyme dose. The specific activity of each glucoamylase was calculated based on the glucose standard curve using Equation below:

$$\text{Specific Activity (Unit/mg)} = \text{Slope (enzyme)/slope (std)} \times 1000 \quad (1),$$

where 1 Unit=1 µmol glucose/min.

Using the method described above, specific activities of the Mucorales-clade Glucoamylases and benchmarks was determined. Results are shown in Table 4.

TABLE 4

Specific activity of *Mucorales*-clade Glucoamylases on soluble starch after 10-min incubation at pH 5.0, 50° C.

| Sample | Specific activity (U/mg) |
|---|---|
| RmiGA1 | 212.3 |
| SraGA1 | 169.5 |
| BciGA1 | 169.3 |
| SraGA3 | 144.9 |
| BciGA2 | 141.6 |
| MciGA3 | 204.1 |
| McoGA1 | 232.3 |
| DelGA1 | 191.5 |
| GpeGA1 | 233.1 |
| ParGA1 | 144.0 |
| SfuGA2 | 215.7 |
| SvaGA1 | 334.3 |
| TinGA1 | 140.4 |
| AnGA | 191.3 |

Example 5

Analysis of Homologous Mucorales-Clade Glucoamylase Sequences

Figure 2:
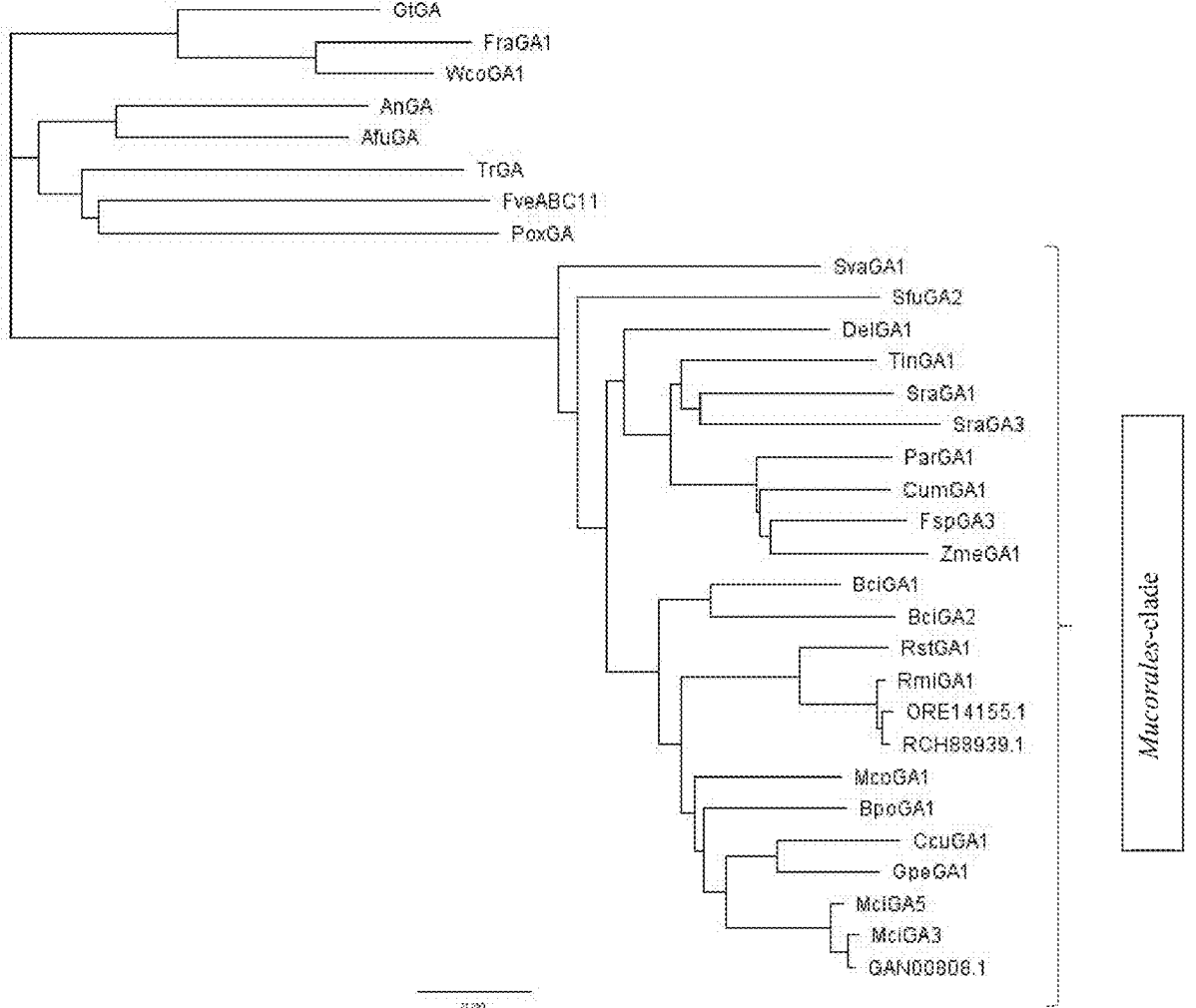
FIG. 2 provides a phylogenetic tree of Mucorales-clade glucoamylases and other fungal glucoamylases.

A multiple amino acid sequence alignment was constructed for the regions encompassing the catalytic domain of the Mucorales-clade glucoamylases:SvaGA1 SEQ ID NO:81, BciGA1 SEQ ID NO:82, BciGA2 SEQ ID NO:83, BpoGA1 SEQ ID NO:84, CcuGA1 SEQ ID NO:85, RstGA1 SEQ ID NO:86, MciGA5 SEQ ID NO: 87, DelGA1 SEQ ID NO:88, FspGA3 SEQ ID NO:89, GpeGA1 SEQ ID NO:90, MciGA3 SEQ ID NO:91, CumGA1 SEQ ID NO:92, McoGA1 SEQ ID NO:93, ParGA1 SEQ ID NO:94, RmiGA1 SEQ ID NO:95, SfuGA2 SEQ ID NO:96, SraGA1 SEQ ID NO:97, SraGA3 SEQ ID NO:98, TinGA1 SEQ ID NO:99, and ZmeGA1 SEQ ID NO:100. In the case of SvaGa1, the catalytic domain is 432 residues long and spans amino acids 18 to 449 of the predicted mature protein sequence. The above-mentioned region overlaps the previously defined catalytic domains of fungal glucoamylases, based on studies of *A. awamori* (Aleshin et al, 1994, *J. Mol. Bio.* 238:575-591) and *A. niger* (Lee and Paetzel, 2011, *Acta Cryst. F*67: 188-192) glucoamylase sequences. These sequences were aligned using MUSCLE alignment tool within Geneious 10.2 software with the default parameters. Additional homologous sequences were identified in the public domain: GAN00808.1 SEQ ID NO:101, ORE14155.1 SEQ ID NO:102, and RCH88939.1 SEQ ID NO:103, and their overlapping sequences were also included in this analysis. In addition, the catalytic domains of other glucoamylases, not members of the Mucorales order of fungi, were included in the alignment: *Aspergillus niger* glucoamylase (AnGA) SEQ ID NO:105, *Aspergillus fumigatus* glucoamylase (AfuGA) SEQ ID NO:106, *Fibroporia radiculosa* TFFH 294 glucoamylase (FraGA1) SEQ ID NO:107, *Fusarium verticillioides* glucoamylase (FveABC11) SEQ ID NO:108, *Gloeophyllum trabeum* glucoamylase (GtGA) SEQ ID NO:109, *Penicillium oxalicum* glucoamylase (PoxGA) SEQ ID NO:110, *Trichoderma reesei* glucoamylase (TrGA) SEQ ID NO: 11, and *Wolfiporia cocos* MD-104 SS10 glucoamylase (WcoGA1) SEQ ID NO:112, in order to identify regions of sequence similarities and differences. The multiple sequence alignment is shown on FIG. 1A, FIG. 1B, FIG. 1C, FIG. 1D, FIG. 1E, FIG. 1F, FIG. 1G, FIG. 1H, FIG. 1I, FIG. 1J and FIG. 1K. A phylogenetic tree was generated using Geneious 10.2 software from the alignment on FIG. 1A, FIG. 1B, FIG. 1C, FIG. 1D, FIG. 1E, FIG. 1F, FIG. 1G, FIG. 1H, FIG. 1I, FIG. 1J and FIGS. 1K and 1s shown on FIG. 2.

Figure 5:
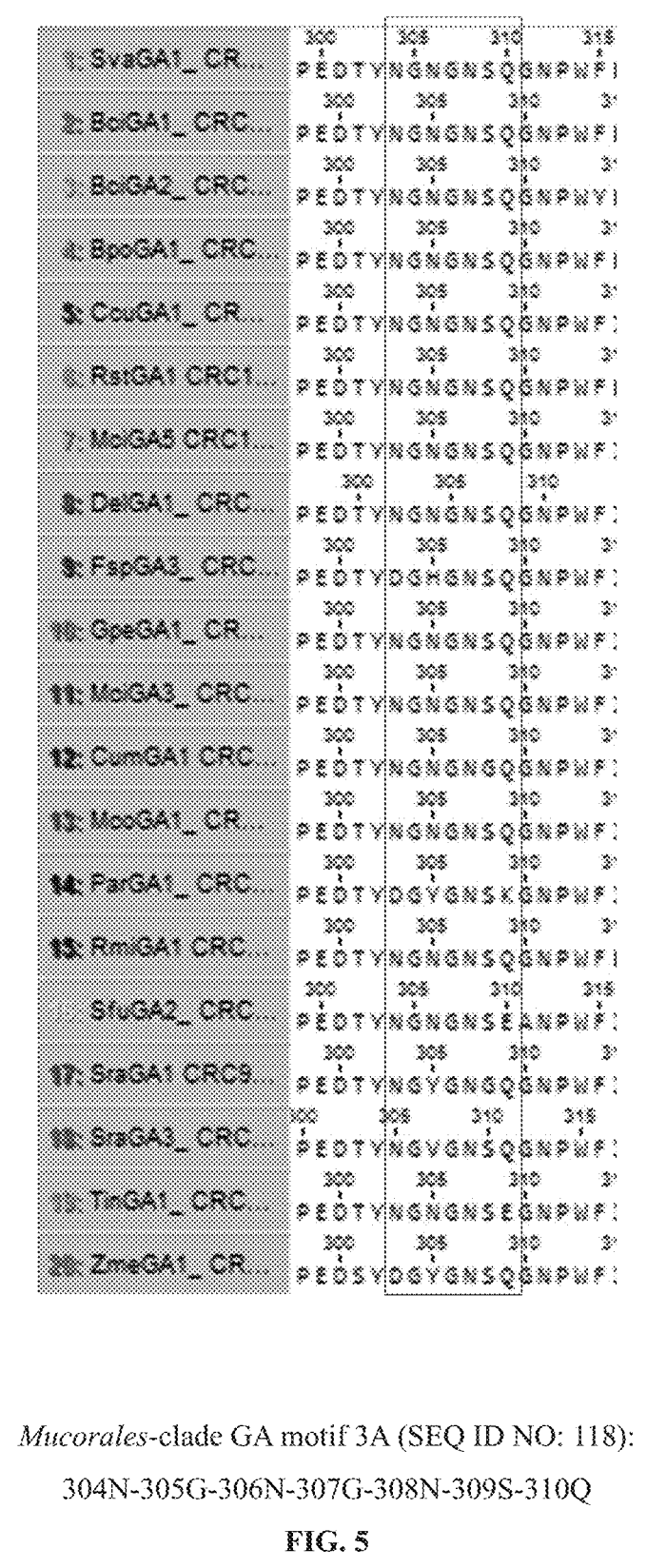

A series of insertions and deletions and high sequence variability regions were observed on the multiple sequence alignment shown on FIG. 1A, FIG. 1B, FIG. 1C, FIG. 1D, FIG. 1E, FIG. 1F, FIG. 1G, FIG. 1H, FIG. 1I, FIG. 1J and FIG. 1K. Several regions of high similarity among the Mucorales-clade glucoamylases become apparent and sequence motifs have been identified. FIGS. 3, 4 and 5 shows alignments of 3 different regions the Mucorales-clade glucoamylases catalytic domains and highlight the sequence motifs in common. FIG. 3 shows the alignment of Mucorales-clade GA amino acid sequences across the region spanning residues 50 to 70 (numbered according to SEQ ID NO: 81), highlighting the Mucorales-clade GA sequence motif 1 (SEQ ID NO: 113): $57Y\text{-}58X_a\text{-}59X_b\text{-}60T\text{-}61X\text{-}62X\text{-}63X_c\text{-}64X_d$, wherein X is any amino acid and $X_a$ is N or S; $X_b$ is T, S, or R; $X_c$ is G or N; and $X_d$ is D, N, or S. A further refined motif for this region is the Mucorales-clade GA motif 1A (SEQ ID NO: 114): 57Y-58N-59T-60T-61X-62A-63G-64D, wherein X is any amino acid. FIG. 4 shows the alignment of Mucorales-clade GA amino acid sequences (numbered according to SEQ ID NO: 81) across the region spanning residues 240 to 260, describing the Mucorales-clade GA sequence motif 2 (SEQ ID NO: 115): $244X_a\text{-}245X_b\text{-}246X_c\text{-}247X_e\text{-}248A\text{-}249A\text{-}250N\text{-}251X\text{-}252X_d$, wherein X is any amino acid and $X_a$ is S or A; $X_b$ is T, N, or V; $X_c$ is L or I; and $X_d$ is A or G. A further refined motif for this region is the Mucorales-clade GA sequence motif 2A (SEQ ID NO: 116): 244S-245T-246L-247I-248A-249A-250N-251X-252A, wherein X is any amino acid. FIG. 5 shows the alignment of Mucorales-clade GA amino acid sequences (numbered according to SEQ ID NO: 81) across region spanning residues 299 to 315, describing the Mucorales-clade GA sequence motif 3 (SEQ ID NO: 117): 304$X_a$-305G-306X-307G-308N-309$X_b$-310$X_c$, wherein X is any amino acid and $X_a$ is N or D; $X_b$ is S or G; and $X_c$ is Q, K, or E. A further refined motif for this region is the Mucorales-clade GA motif 3A (SEQ ID NO: 118): 304N-305G-306N-307G-308N-309S-310Q.

Example 6

Thermostability Evaluation of Glucoamylases

Stability Comparison at 60° C.

The thermostability of SvaGAv2 and SvaGA1v3 was compared with preincubations of the enzyme samples (20 ppm) at 60° C. for 10 min. The preincubation at 4° C. for 10 min was included and set as 100% activity of each glucoamylase sample. The residual activity of the glucoamylase after preincbuation was then measured using the same method as described in Example 4 except the pH was 4.5 and the incubation temperature was 60° C. As shown in Table 5, SvaGA1v3 retained 55% of its activity under these conditions.

TABLE 5

| SvaGA1v2 and SvaGA1v3 stability preincubated at 60° C. for 10 min followed by residual activity measurement 60° C. for 10 min at pH 4.5 | | |
| --- | --- | --- |
| Sample | 4° C. | 60° C. |
| SvaGA1v2 | 100% | 13% |
| SvaGA1v3 | 100% | 55% |

Tm Measurement Using DSC

Differential scanning calorimetry (DSC) measurements were carried out using an ultrasensitive MicroCal™ VP-Capillary DSC System (GE healthcare). Purified SvaGA1, SvaGA1v2 and SvaGA1v3 were diluted to a final concentration of 0.4 mg/mL in 100 mM pH 4.5 sodium acetate buffer. 400 μL of the enzyme solution, as well as a reference containing an identical amount of enzyme-free buffer, were added to a 96-well plate. The plate was then placed in the thermally controlled autosampler compartment kept at 10° C. The enzyme sample and the buffer reference were scanned respectively from 20 to 100° C. at a scan rate of 2° C. per minute. Tm was determined as the temperature at the peak maximum of the transition from the folded to unfolded state. Maximum variation in the Tm was ±0.2° C. The ORIGIN software package (MicroCal, GE Healthcare) was used for baseline subtraction and graph presentation of the data. The DSC result in Table 6 shows that the Tm of SvaGA1v3 is 3 degrees higher than that of SvaGA1v2.

TABLE 6

| Tm measurement of SvaGA1v2 and SvaGA1v3 using DSC. | |
| --- | --- |
| Sample | Tm (° C.) |
| SvaGA1 | 62 |
| SvaGA1v2 | 64 |
| SvaGA1v3 | 67 |

Example 7

Saccharification Activity Determination

The saccharification performance of SvaGA1v2 and SvaGA1v3 were evaluated at pH 4.5 and 60, 62, 65° C., respectively. All the incubation conditions were the same as described in Example 3, with the exception that the corn starch liquefact was purchased from Cargill. The pullulanase OPTIMAX™ L 1000 (a DuPont product) was dosed at 4 pig/gds, and the alpha-amylase *Aspergillus terreus* amylase (AtAA, described in, for example, International Patent Application Publication Nos. WO2017112635A1 and WO2014099415, incorporated by reference herein) was dosed at 1 μg/gds. The values shown in Table 7 reflect the peak area percentages of each DP(n) as a fraction of the total DP1 to DP3+. The DP1 generation and DP3+ hydrolysis by SvaGA1v3 indicate superior performance when compared to the reference GtGA enzyme under all the selected conditions.

TABLE 7

| Sugar composition results for glucoamylases incubated with corn starch liquefact at pH 4.5, 60° C., 62° C., and 65° C., for 24 h, 48 h, and 65 h, respectively. | | | | | | |
| --- | --- | --- | --- | --- | --- | --- |
| GA sample | Incubation temp. (° C.) | Incubation time (h) | DP1 % | DP2 % | DP3 % | DP3+ % |
| SvaGA1v2 | 60 | 24 | 94.5 | 2.6 | 0.9 | 1.9 |
| | | 48 | 96.7 | 2.2 | 0.7 | 0.4 |
| | | 65 | 96.5 | 2.4 | 0.7 | 0.4 |
| | 62 | 24 | 94.6 | 3.0 | 1.0 | 1.5 |
| | | 48 | 96.7 | 2.1 | 0.8 | 0.4 |
| | | 65 | 96.6 | 2.2 | 0.8 | 0.4 |
| | 65 | 24 | 88.5 | 6.2 | 1.0 | 4.3 |
| | | 48 | 91.1 | 5.8 | 1.1 | 2.0 |
| | | 65 | 92.6 | 4.8 | 1.1 | 1.5 |
| SvaGA1v3 | 60 | 24 | 92.9 | 3.4 | 0.9 | 2.7 |
| | | 48 | 96.7 | 2.2 | 0.7 | 0.3 |
| | | 65 | 96.6 | 2.5 | 0.6 | 0.3 |
| | 62 | 24 | 93.8 | 3.1 | 0.9 | 2.2 |
| | | 48 | 96.7 | 2.2 | 0.7 | 0.3 |
| | | 65 | 96.6 | 2.5 | 0.6 | 0.3 |

TABLE 7-continued

Sugar composition results for glucoamylases incubated with corn
starch liquefact at pH 4.5, 60° C., 62° C., and 65° C., for 24 h, 48 h,
and 65 h, respectively.

| GA sample | Incubation temp. (° C.) | Incubation time (h) | DP1 % | DP2 % | DP3 % | DP3+ % |
|---|---|---|---|---|---|---|
| | 65 | 24 | 92.9 | 3.4 | 1.0 | 2.7 |
| | | 48 | 96.3 | 2.2 | 0.8 | 0.6 |
| | | 65 | 96.5 | 2.2 | 0.8 | 0.5 |
| GtGA | 60 | 24 | 91.3 | 3.7 | 1.0 | 4.0 |
| | | 48 | 96.3 | 2.2 | 0.8 | 0.7 |
| | | 65 | 96.6 | 2.3 | 0.6 | 0.5 |
| | 62 | 24 | 92.2 | 3.4 | 1.0 | 3.4 |
| | | 48 | 96.3 | 2.2 | 0.7 | 0.8 |
| | | 65 | 96.3 | 2.5 | 0.7 | 0.5 |
| | 65 | 24 | 92.6 | 3.1 | 0.9 | 3.4 |
| | | 48 | 96.1 | 2.3 | 0.7 | 0.9 |
| | | 65 | 96.2 | 2.5 | 0.6 | 0.7 |

Example 8

Identification of Additional Homologous Mucorales-Clade Glucoamylases

A number of genes were identified in the genomes of Mucorales order organisms and the sequences were further analyzed. Genes encoding the Mucorales-clade glucoamylases were identified from the sources listed on Table 8, and are assigned the SEQ ID NOs shown on Table 9.

TABLE 8

Sequence source and SEQ ID NOs for *Mucorales*-clade glucoamylases evaluated in this study.

| Sample ID | SEQ ID NO | Gene sequence source *[://world wide web.ncbi.nlm.nih.gov/] | Organism |
|---|---|---|---|
| SobGA1 | 119 | *nuccore/JNEV01000736 | *Saksenaea oblongispora* B3353 |
| AosGA3 | 120 | *protein/KAF7727643 | *Apophysomyces ossiformis* NRRL A-21654 |
| AelGA1 | 121 | *nuccore/JNDQ01001334.1 | *Apophysomyces elegans* B7760 |
| AvaGA1 | 122 | *nuccore/MZZL01000409.1 | *Apophysomyces variabilis* NCCPF 102052 |
| AtrGA1 | 123 | *nuccore/JNDP01001364.1 | *Apophysomyces trapeziformis* B9324 |

The N-terminal signal peptides were predicted by SignalP software version 4.0 (Nordahl Petersen et al. (2011) Nature Methods, 8:785-786). The genes encoding the various Mucorales-clade glucoamylases were codon modified for expression in *Trichoderma reesei*. Based at least in part on this analysis, a new variant of SvaGA1, named SvaGA1v3, was made and assigned SEQ ID NO: 140 as showed in Table 9.

TABLE 9

Sequences of additional *Mucorales*-clade glucoamylases evaluated in this study. SEQ ID NOs for the nucleotide sequences of expression cassettes, predicted signal peptide and predicted mature polypeptide.

| | SEQ ID Nos | | |
|---|---|---|---|
| Sample ID | codon modified sequences used as expression cassettes | predicted signal peptide | predicted mature protein sequence |
| SobGA1 | SEQ ID NO: 124 | SEQ ID NO: 125 | SEQ ID NO: 126 |
| AosGA3 | SEQ ID NO: 127 | SEQ ID NO: 128 | SEQ ID NO: 129 |
| AelGA1 | SEQ ID NO: 130 | SEQ ID NO: 131 | SEQ ID NO: 132 |
| AvaGA1 | SEQ ID NO: 133 | SEQ ID NO: 134 | SEQ ID NO: 135 |
| AtrGA1 | SEQ ID NO: 136 | SEQ ID NO: 137 | SEQ ID NO: 138 |
| SvaGA1v3 | SEQ ID NO: 139 | SEQ ID NO: 41 | SEQ ID NO: 140 |

Example 9

Expression of Mucorales-Clade Glucoamylases in *Trichoderma reesei*

The polynucleotides (codon modified sequences used as expression cassettes) encoding the Mucorales-clade glucoamylases genes (SEQ ID NO: 124, SEQ ID NO: 127, SEQ ID NO: 130, SEQ ID NO: 133, SEQ ID NO: 136) were synthesized by Generay (Generay Biotech Co., Ltd, Shanghai, China) and inserted into the pGX256 expression vector, a derivative vector from pTTT (see, Published US Patent Application 20110020899).

All plasmids were transformed into a suitable *Trichoderma reesei* strain using protoplast transformation (Te'o et al., J. Microbiol. Methods 51:393-99, 2002). The transformants were selected and fermented by the methods described in WO 2016/138315. Supernatants from these cultures were used to confirm the protein expression by SDS-PAGE analysis.

Fungal cell cultures were grown in a defined medium as described by Lv et al (2012) in "Construction of teo vectors for gene expression in *Trichoderma reesei*". Plasmids 67:67-71. Clarified culture broth were collected after 96 hours by centrifugation. The Mucorales-clade glucoamylases were purified by methods known in the art. The column chromatography fractions containing the target protein were pooled, concentrated and equilibrated to 20 mM sodium acetate pH 5.0, 150 mM sodium chloride using an Amicon Ultra-15 device with 10 K MWCO. The purified samples were approximately 99% pure (by SDS-PAGE analysis) and were stored in 40% glycerol at −80° C. until use.

Example 10

Evaluation of Additional Homologous Mucorales-Clade Glucoamylases in Saccharification The saccharification performance of additional homologous Mucorales-clade glucoamylases were evaluated at pH 4.5, 60° C., 62° C., and 65° C., respectively, for 48 h. All the incubation conditions were the same as described in Example 7, except that the glucoamylase samples were dosed at 25 µg/gds. The values shown in Table 10 reflect the peak area percentages of each DP(n) as a fraction of the total DP1 to DP3+. The results of DP1 generation and DP3+ hydrolysis by the Mucorales-clade glucoamylases indicate superior performance when compared to the reference GtGA enzyme when evaluated at pH 4.5, 60° C. for 48 h. When the incubation temperature was increased to 62° C., all the Mucorales-clade GAs also showed better saccharification performance than GtGA enzyme. AtrGA1 could maintain its superior performance when the incubation temperature was raised to 65° C. while GtGA did not.

TABLE 10

Sugar composition results for glucoamylases incubated with corn starch liquefact at pH 4.5, 60, 62, and 65° C., respectively, for 48 h.

| Incubation temp, (° C.) | Sample | DP1% | DP2% | DP3% | DP3+ % |
|---|---|---|---|---|---|
| 60 | AosGA3 | 96.6 | 2.3 | 0.7 | 0.4 |
|  | AelGA1 | 96.6 | 2.2 | 0.7 | 0.4 |
|  | AvaGA1 | 96.6 | 2.2 | 0.8 | 0.4 |
|  | AtGA1 | 96.7 | 2.2 | 0.7 | 0.4 |
|  | SvaGA1 | 96.5 | 2.0 | 0.8 | 0.6 |
|  | GlGA | 95.9 | 7 7 | 0.8 | 1.0 |
| 62 | AosGA3 | 96.5 | 2.3 | 0.7 | 0.4 |
|  | AelGA1 | 96.4 | 2.3 | 0.8 | 0.5 |
|  | AvaGA1 | 96.5 | 2.3 | 0.8 | 0.4 |
|  | AtGA1 | 96.6 | 2.3 | 0.7 | 0.4 |
|  | SvaGA1 | 95.3 | 2 9 | 1.0 | 0.9 |
|  | GtGA | 96.3 | 2.1 | 0.8 | 0.8 |
| 65 | AosGA3 | 95.7 | 2.6 | 0.9 | 0.8 |
|  | AelGA1 | 88.1 | 7.6 | 1.4 | 2.9 |
|  | AvaGA1 | 95.0 | 3.0 | 1.0 | 1.0 |
|  | AtrGA1 | 96.4 | 2.3 | 0.7 | 0.5 |
|  | SvaGA1 | 77.1 | 13.1 | 3.0 | 6.7 |
|  | GtGA | 95.8 | 2 2 | 0.8 | 1.1 |

Example 11

Figure 7:
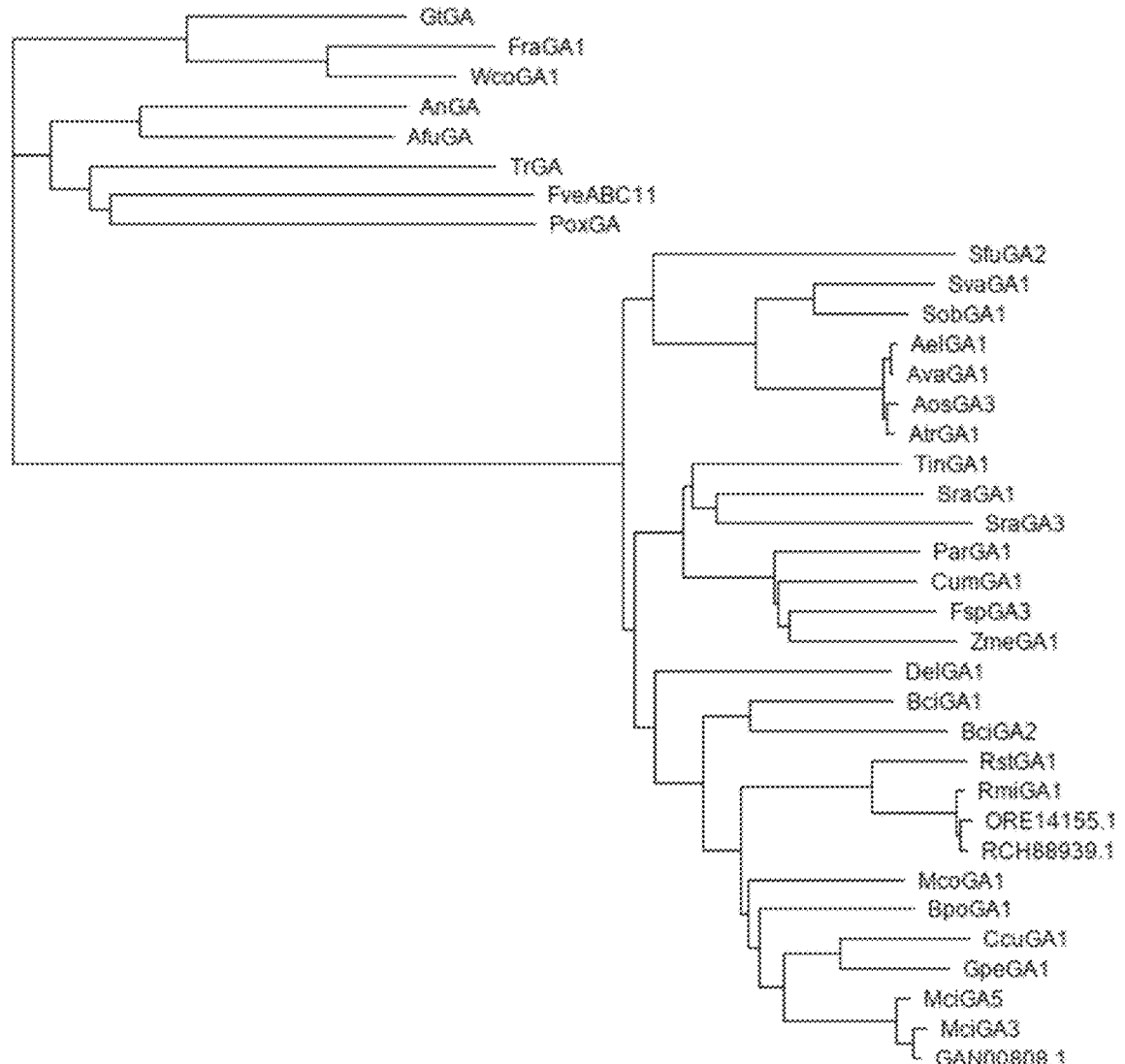
FIG. 7 provides a phylogenetic tree of additional Mucorales-clade glucoamylases and other fungal glucoamylases.

Sequence Analysis of Additional Homologous Mucorales-Clade Glucoamylase Sequences A multiple amino acid sequence alignment was constructed for the regions encompassing the catalytic domain of the Mucorales-clade glucoamylases: SvaGA1 SEQ ID NO:81, SobGA1 SEQ ID NO:119, AosGA3 SEQ ID NO:120, AelGA1 SEQ ID NO:121, AvaGA1 SEQ ID NO: 122, and AtrGA1 SEQ ID NO:123 as described in Example 5. These sequences were aligned using MUSCLE alignment tool within Geneious 10.2 software with the default parameters. In addition, the catalytic domains of other glucoamylases, not members of the Mucorales order of fungi, were included in the alignment: Aspergillus niger glucoamylase (AnGA) SEQ ID NO:105, Aspergillus fumigatus glucoamylase (AfuGA) SEQ ID NO:106, Fibroporia radiculosa TFFH 294 glucoamylase (FraGA1) SEQ ID NO:107, Fusarium verticillioides glucoamylase (FveABC11) SEQ ID NO:108, Gloeophyllum trabeum glucoamylase (GtGA) SEQ ID NO:109, Penicillium oxalicum glucoamylase (PoxGA) SEQ ID NO:110, Trichoderma reesei glucoamylase (TrGA) SEQ ID NO:111, and Wolfiporia cocos MD-104 SS10 glucoamylase (WcoGA1) SEQ ID NO: 12, in order to identify regions of sequence similarities and differences. The multiple sequence alignment is shown on FIG. 6A, FIG. 6B, FIG. 6C, FIG. 6D. The additional new homologs (SobGA1, AosGA3, AelGA1, AvaGA1, AtrGA1) fall within the motifs outlined in sequences SEQ ID NO: 113, SEQ ID NO: 15, and SEQ ID NO:117. A phylogenetic tree was generated using Geneious 10.2 software from the alignment of the following sequences: SvaGA1 SEQ ID NO:81, BciGA1 SEQ ID NO:82, BciGA2 SEQ ID NO:83, BpoGA1 SEQ ID NO:84, CcuGA1 SEQ ID NO:85, RstGA1 SEQ ID NO. 86, MciGA5 SEQ ID NO:87, DelGA1 SEQ ID NO:88, FspGA3 SEQ ID NO:89, GpeGA1 SEQ ID NO:90, MciGA3 SEQ ID NO:91, CumGA1 SEQ ID NO:92, McoGA1 SEQ ID NO:93, ParGA1 SEQ ID NO:94, RmiGA1 SEQ ID NO:95, SfuGA2 SEQ ID NO:96, SraGA1 SEQ ID NO:97, SraGA3 SEQ ID NO:98, TinGA1 SEQ ID NO:99, ZmeGA1 SEQ ID NO:100, GAN00808.1 SEQ ID NO:101, ORE14155.1 SEQ ID NO:102, and RCH88939.1 SEQ ID NO:103, Aspergillus niger glucoamylase (AnGA) SEQ ID NO:105, Aspergillus fumigatus glucoamylase (AfuGA) SEQ ID NO:106, Fibroporia radiculosa TFFH 294 glucoamylase (FraGA1) SEQ ID NO:107, Fusarium verticillioides glucoamylase (FveABC11) SEQ ID NO:108, Gloeophyllum trabeum glucoamylase (GtGA) SEQ ID NO:109, Penicillium oxalicum glucoamylase (PoxGA) SEQ ID NO:110, Trichoderma reesei glucoamylase (TrGA) SEQ ID NO:111, and Wolfiporia cocos MD-104 SS10 glucoamylase (WcoGA1) SEQ ID NO:112, SobGA1 SEQ ID NO:119, AosGA3 SEQ ID NO:120, AelGA1 SEQ ID NO:121, AvaGA1 SEQ ID NO: 122, and AtrGA1 SEQ ID NO:123, and is shown on FIG. 7.

What is claimed is:

1. An isolated recombinant host cell comprising a glucoamylase selected from the group consisting of:

a) a polypeptide having an amino acid sequence at least 90% identity to SEQ ID NO: 61 or SEQ ID NO: 142; and b) a polypeptide having at least 90% identity to SEQ ID NO: 81;

wherein the polypeptide comprises a substitution, deletion or addition at a position corresponding to position 102 of the polypeptide of SEQ ID NO: 61 and wherein the polypeptide comprises a substitution, deletion or addition at a position corresponding to position 66 of the polypeptide of SEQ ID NO: 61.

2. The isolated recombinant host cell of claim 1, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

3. The isolated recombinant host cell of claim 1, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

4. The isolated recombinant host cell of claim 1, wherein the polypeptide comprises SEQ ID NO:61, SEQ ID NO:81, or SEQ ID NO: 142.

5. The isolated recombinant host cell of claim 1, which is an ethanologenic microorganism.

6. The isolated recombinant host cell of claim 5, which is a yeast cell.

7. The isolated recombinant host cell of claim 1, wherein said host cell is not *Saksenaea vasiformis*.

\* \* \* \* \*